(12) United States Patent
Saadat et al.

(10) Patent No.: US 12,582,426 B2
(45) Date of Patent: Mar. 24, 2026

(54) APPARATUSES FOR REMOVING OBSTRUCTIVE MATERIAL FROM BODY LUMENS

(71) Applicant: Inquis Medical, Inc., Redwood City, CA (US)

(72) Inventors: Vahid Saadat, Atherton, CA (US); William Jason Fox, San Mateo, CA (US); Richard Christian Ewers, Fullerton, CA (US); Mojgan Saadat, Atherton, CA (US); Sherwin Llamido, Redwood City, CA (US); Chris Arnold Rothe, Atherton, CA (US); Max Niklas Rothe, Atherton, CA (US)

(73) Assignee: Inquis Medical, Inc., Menlo Park, CA (US)

( * ) Notice: Subject to any disclaimer, the term of this patent is extended or adjusted under 35 U.S.C. 154(b) by 0 days.

(21) Appl. No.: 18/555,859

(22) PCT Filed: Apr. 15, 2022

(86) PCT No.: PCT/US2022/024986
§ 371 (c)(1),
(2) Date: Oct. 17, 2023

(87) PCT Pub. No.: WO2022/221643
PCT Pub. Date: Oct. 20, 2022

(65) Prior Publication Data
US 2024/0197347 A1 Jun. 20, 2024

Related U.S. Application Data

(63) Continuation-in-part of application No. 17/393,618, filed on Aug. 4, 2021, now Pat. No. 11,376,028.
(Continued)

(51) Int. Cl.
*A61B 17/221* (2006.01)
*A61B 17/22* (2006.01)
*A61B 17/3207* (2006.01)

(52) U.S. Cl.
CPC .. *A61B 17/221* (2013.01); *A61B 2017/22079* (2013.01); *A61B 2017/2215* (2013.01);
(Continued)

(58) Field of Classification Search
CPC .......... A61B 17/221; A61B 17/320758; A61B 2017/22079; A61B 2017/2215; A61B 2017/320766; A61B 2017/320775
See application file for complete search history.

(56) References Cited

U.S. PATENT DOCUMENTS 4,368,730 A 1/1983 Sharrock
4,733,669 A 3/1988 Segal
(Continued)

FOREIGN PATENT DOCUMENTS

DE 212015000300 U1 9/2017
EP 1292244 B1 1/2007
(Continued)

OTHER PUBLICATIONS

Saadat et al.; U.S. Appl. No. 18/665,380 entitled "Directional aspiration," filed May 15, 2024.
(Continued)

*Primary Examiner* — Mohamed G Gabr
(74) *Attorney, Agent, or Firm* — Shay Glenn LLP

(57) ABSTRACT

Devices for the disruption and/or removal of obstructive material in a blood vessel. The device can comprise an elongated shaft having a proximal portion, a distal portion, and a lumen extending therebetween. The device can further comprise a capture structure carried by the distal portion of the elongated shaft and having a greater cross-sectional
(Continued)

dimension than a cross-sectional dimension of the elongated shaft. The capture structure can comprise an opening at a first end portion that is fluidly coupled to the lumen of the elongated shaft, a fluid impermeable sidewall enclosing an interior region, and an opening extending through a thickness of the sidewall. A portion of the sidewall surrounding the opening can be configured to deform towards or away from the interior region such that a cross-sectional dimension of the opening increases to receive the obstructive material therethrough.

13 Claims, 60 Drawing Sheets

Related U.S. Application Data

(60) Provisional application No. 63/303,004, filed on Jan. 25, 2022, provisional application No. 63/192,562, filed on May 24, 2021, provisional application No. 63/184,083, filed on May 4, 2021, provisional application No. 63/176,224, filed on Apr. 17, 2021.

(52) U.S. Cl.
CPC ............. *A61B 2017/320766* (2013.01); *A61B 2017/320775* (2013.01)

(56) References Cited

U.S. PATENT DOCUMENTS

| | | | |
|---|---|---|---|
| 4,828,543 | A | 5/1989 | Weiss et al. |
| 4,967,753 | A | 11/1990 | Haase et al. |
| 4,976,682 | A | 12/1990 | Lane et al. |
| 5,248,297 | A | 9/1993 | Takase et al. |
| 5,417,703 | A | 5/1995 | Brown et al. |
| 5,569,275 | A | 10/1996 | Kotula et al. |
| 5,603,703 | A | 2/1997 | Elsberry et al. |
| 5,662,671 | A | 9/1997 | Barbut et al. |
| 5,730,752 | A | 3/1998 | Alden et al. |
| 5,749,914 | A | 5/1998 | Janssen |
| 5,772,402 | A | 6/1998 | Goodman |
| 5,827,229 | A | 10/1998 | Auth et al. |
| 5,954,737 | A | 9/1999 | Lee |
| 6,027,450 | A | 2/2000 | Brown et al. |
| 6,059,745 | A | 5/2000 | Gelbfish |
| 6,089,235 | A | 7/2000 | Hastings et al. |
| 6,152,882 | A | 11/2000 | Prutchi |
| 6,428,551 | B1 | 8/2002 | Hall et al. |
| 6,589,227 | B2 | 7/2003 | Sønderskov Klint |
| 6,638,293 | B1 | 10/2003 | Makower et al. |
| 6,719,717 | B1 | 4/2004 | Johnson et al. |
| 6,719,718 | B2 | 4/2004 | Bonnette et al. |
| 6,849,068 | B1 | 2/2005 | Bagaoisan et al. |
| 6,979,318 | B1 | 12/2005 | McDonald et al. |
| 7,294,117 | B2 | 11/2007 | Provost tine et al. |
| 7,608,063 | B2 | 10/2009 | Le et al. |
| 7,655,016 | B2 | 2/2010 | Demarais et al. |
| 7,699,790 | B2 | 4/2010 | Simpson |
| 7,713,235 | B2 | 5/2010 | Torrance et al. |
| 7,734,332 | B2 | 6/2010 | Sher |
| 7,771,445 | B2 | 8/2010 | Heitzmann et al. |
| 7,854,740 | B2 | 12/2010 | Carney |
| 7,927,346 | B2 | 4/2011 | VanCamp et al. |
| 7,938,820 | B2 | 5/2011 | Webster et al. |
| 7,942,852 | B2 | 5/2011 | Mas et al. |
| 7,947,012 | B2 | 5/2011 | Spurchise et al. |
| 8,048,032 | B2 | 11/2011 | Root et al. |
| 8,133,214 | B2 | 3/2012 | Hayase et al. |
| 8,150,499 | B2 | 4/2012 | Gelbart et al. |
| 8,208,990 | B2 | 6/2012 | Maschke |
| 8,246,640 | B2 | 8/2012 | Rosenthal et al. |
| 8,252,020 | B2 | 8/2012 | Hauser et al. |
| 8,265,745 | B2 | 9/2012 | Hauck et al. |
| 8,273,023 | B2 | 9/2012 | Razavi |
| 8,298,252 | B2 | 10/2012 | Krolik et al. |
| 8,343,084 | B2 | 1/2013 | Nowakowski et al. |
| 8,366,615 | B2 | 2/2013 | Razavi |
| 8,409,237 | B2 | 4/2013 | Galdonik et al. |
| 8,430,837 | B2 | 4/2013 | Jenson et al. |
| 8,465,452 | B2 | 6/2013 | Kassab |
| 8,496,653 | B2 | 7/2013 | Steinke |
| 8,613,717 | B2 | 12/2013 | Aklog et al. |
| 8,771,289 | B2 | 7/2014 | Mohluddin et al. |
| 8,814,890 | B2 | 8/2014 | Miyata et al. |
| 8,920,402 | B2 | 12/2014 | Nash et al. |
| 8,920,448 | B2 | 12/2014 | To et al. |
| 9,050,126 | B2 | 6/2015 | Rivers et al. |
| 9,055,964 | B2 | 6/2015 | Cartier et al. |
| 9,060,895 | B2 | 6/2015 | Hartley et al. |
| 9,084,857 | B2 | 7/2015 | Cully et al. |
| 9,248,221 | B2 | 2/2016 | Look et al. |
| 9,254,140 | B2 | 2/2016 | Song et al. |
| 9,259,290 | B2 | 2/2016 | Jenkins et al. |
| 9,282,992 | B2 | 3/2016 | Levine et al. |
| 9,402,938 | B2 | 8/2016 | Aklog et al. |
| 9,415,188 | B2 | 8/2016 | He et al. |
| 9,433,427 | B2 | 9/2016 | Look et al. |
| 9,492,226 | B2 | 11/2016 | Fish et al. |
| 9,510,854 | B2 | 12/2016 | Mallaby |
| 9,655,633 | B2 | 5/2017 | Leynov et al. |
| 9,668,767 | B2 | 6/2017 | To et al. |
| 9,700,216 | B2 | 7/2017 | Razavi et al. |
| 9,801,527 | B2 | 10/2017 | Ferren et al. |
| 9,801,642 | B2 | 10/2017 | Thor et al. |
| 9,808,266 | B2 | 11/2017 | Ray et al. |
| 9,883,877 | B2 | 2/2018 | Look et al. |
| 10,130,386 | B2 | 11/2018 | Simpson et al. |
| 10,226,263 | B2 | 3/2019 | Look et al. |
| 10,226,268 | B2 | 3/2019 | Ulm |
| 10,238,456 | B2 | 3/2019 | Murphy et al. |
| 10,271,873 | B2 | 4/2019 | Steingisser et al. |
| 10,285,720 | B2 | 5/2019 | Gilvarry et al. |
| 10,383,983 | B2 | 8/2019 | Aklog et al. |
| 10,413,317 | B2 | 9/2019 | Whiseant |
| 10,517,617 | B2 | 12/2019 | Aklog et al. |
| 10,661,053 | B2 | 5/2020 | Yang et al. |
| 10,716,586 | B2 | 7/2020 | Krolik et al. |
| 10,722,238 | B2 | 7/2020 | Sutton et al. |
| 10,743,907 | B2 | 8/2020 | Bruzzi et al. |
| 10,751,159 | B2 | 8/2020 | Janardhan et al. |
| 10,835,257 | B2 | 11/2020 | Ferrera et al. |
| 10,888,337 | B2 | 1/2021 | Shen et al. |
| 10,912,482 | B2 | 2/2021 | Bozsak et al. |
| 10,945,758 | B1 | 3/2021 | Davis et al. |
| 11,013,523 | B2 | 5/2021 | Arad Hadar |
| 11,089,947 | B2 | 8/2021 | Govari |
| 11,096,712 | B2 | 8/2021 | Teigen et al. |
| 11,197,683 | B1 | 12/2021 | Teigen et al. |
| 11,253,277 | B2 | 2/2022 | Buck et al. |
| 11,259,821 | B2 | 3/2022 | Buck et al. |
| 11,376,028 | B1 | 7/2022 | Saadat et al. |
| 11,383,064 | B2 | 7/2022 | Garrison et al. |
| 11,395,665 | B2 | 7/2022 | Yang et al. |
| 11,400,255 | B1 | 8/2022 | Chou et al. |
| 11,464,528 | B2 | 10/2022 | Brady et al. |
| 11,510,577 | B2 | 11/2022 | Bozsak et al. |
| 11,568,990 | B2 | 1/2023 | Lebedev et al. |
| 11,730,924 | B2 | 8/2023 | Saadat et al. |
| 11,730,925 | B2 | 8/2023 | Saadat et al. |
| 11,779,238 | B2 | 10/2023 | Sweeney et al. |
| 11,849,963 | B2 | 12/2023 | Quick |
| 11,969,332 | B2 | 4/2024 | Merritt et al. |
| 12,076,036 | B2 | 9/2024 | Baron et al. |
| 2001/0049486 | A1 | 12/2001 | Evans et al. |
| 2002/0165575 | A1 | 11/2002 | Saleh |
| 2002/0177800 | A1 | 11/2002 | Bagaoisan et al. |
| 2003/0069549 | A1 | 4/2003 | MacMahon et al. |
| 2003/0191493 | A1 | 10/2003 | Epstein et al. |
| 2004/0019310 | A1 | 1/2004 | Hogendijk |
| 2004/0049225 | A1 | 3/2004 | Denison |
| 2006/0004325 | A1 | 1/2006 | Hamatake et al. |
| 2006/0122575 | A1 | 6/2006 | Wakabayashi |

(56) References Cited

U.S. PATENT DOCUMENTS

| | | | |
|---|---|---|---|
| 2006/0264988 A1 | 11/2006 | Boyle | |
| 2007/0060944 A1 | 3/2007 | Boldenow et al. | |
| 2007/0083195 A1 | 4/2007 | Werneth et al. | |
| 2007/0106211 A1 | 5/2007 | Provost Tine et al. | |
| 2007/0191812 A1 | 8/2007 | Nishide et al. | |
| 2008/0161840 A1 | 7/2008 | Osiroff et al. | |
| 2008/0228231 A1 | 9/2008 | Raphael et al. | |
| 2008/0243153 A1 | 10/2008 | Nguyen et al. | |
| 2009/0069828 A1 | 3/2009 | Martin et al. | |
| 2009/0177069 A1 | 7/2009 | Razavi | |
| 2009/0221957 A1 | 9/2009 | Bowman et al. | |
| 2010/0023033 A1 | 1/2010 | Mauch et al. | |
| 2010/0041984 A1 | 2/2010 | Shapland et al. | |
| 2010/0185048 A1 | 7/2010 | Lonky et al. | |
| 2010/0204712 A1 | 8/2010 | Mallaby | |
| 2010/0286708 A1 | 11/2010 | Rittman | |
| 2011/0130714 A1 | 6/2011 | Wells | |
| 2011/0137399 A1* | 6/2011 | Chomas | A61M 25/0075 |
| | | | 623/1.12 |
| 2011/0160740 A1 | 6/2011 | Makower et al. | |
| 2011/0230799 A1 | 9/2011 | Christian et al. | |
| 2012/0041474 A1* | 2/2012 | Eckhouse | A61B 17/221 |
| | | | 606/200 |
| 2012/0071838 A1 | 3/2012 | Fojtik | |
| 2013/0158578 A1 | 6/2013 | Ghodke et al. | |
| 2013/0178790 A1 | 7/2013 | Tekulve | |
| 2013/0268048 A1 | 10/2013 | Watson et al. | |
| 2013/0317589 A1 | 11/2013 | Martin et al. | |
| 2014/0046244 A1 | 2/2014 | Ray et al. | |
| 2014/0058294 A1 | 2/2014 | Gross et al. | |
| 2014/0094741 A1 | 4/2014 | Bellisario et al. | |
| 2014/0217030 A1 | 8/2014 | Meyer et al. | |
| 2014/0222049 A1 | 8/2014 | Fruland et al. | |
| 2014/0303658 A1 | 10/2014 | Bonnette et al. | |
| 2015/0005781 A1 | 1/2015 | Lund-Clausen et al. | |
| 2015/0011856 A1 | 1/2015 | Arevalos | |
| 2015/0250982 A1 | 9/2015 | Osypka | |
| 2015/0305765 A1 | 10/2015 | Fojtik et al. | |
| 2015/0327875 A1 | 11/2015 | Look et al. | |
| 2015/0374405 A1 | 12/2015 | Takuma | |
| 2016/0067464 A1 | 3/2016 | Kim et al. | |
| 2016/0089227 A1 | 3/2016 | Loh | |
| 2016/0113676 A1 | 4/2016 | Tada et al. | |
| 2016/0166265 A1 | 6/2016 | Nita | |
| 2016/0166266 A1 | 6/2016 | Nita | |
| 2016/0184562 A1 | 6/2016 | Ludin et al. | |
| 2016/0220298 A1 | 8/2016 | Paul et al. | |
| 2016/0278856 A1 | 9/2016 | Panescu et al. | |
| 2016/0310020 A1 | 10/2016 | Warnking et al. | |
| 2016/0346037 A1 | 12/2016 | Truckai et al. | |
| 2016/0354100 A1 | 12/2016 | Darian | |
| 2017/0035445 A1 | 2/2017 | Nguyen et al. | |
| 2017/0043137 A1 | 2/2017 | Felkins et al. | |
| 2017/0056581 A1 | 3/2017 | Deak et al. | |
| 2017/0065396 A1 | 3/2017 | Look et al. | |
| 2017/0224283 A1 | 8/2017 | Kassab et al. | |
| 2017/0258512 A1 | 9/2017 | Germain et al. | |
| 2017/0290598 A1 | 10/2017 | Culbert et al. | |
| 2018/0042623 A1 | 2/2018 | Batiste | |
| 2018/0206865 A1 | 7/2018 | Martin et al. | |
| 2018/0235644 A1* | 8/2018 | Jaffe | A61B 17/221 |
| 2018/0344248 A1 | 12/2018 | Zeng et al. | |
| 2018/0360479 A1 | 12/2018 | Hofmann et al. | |
| 2019/0142453 A1 | 5/2019 | Efremkin | |
| 2019/0167287 A1 | 6/2019 | Vale et al. | |
| 2019/0175210 A1 | 6/2019 | Wittens | |
| 2019/0192175 A1 | 6/2019 | Chida et al. | |
| 2019/0262031 A1 | 8/2019 | Efremkin | |
| 2019/0298396 A1 | 10/2019 | Gamba et al. | |
| 2019/0313941 A1 | 10/2019 | Radjabi | |
| 2019/0358387 A1 | 11/2019 | Elbrady et al. | |
| 2019/0365469 A1 | 12/2019 | Efremkin | |
| 2019/0380651 A1 | 12/2019 | Carreel et al. | |
| 2019/0388002 A1 | 12/2019 | Bozsak et al. | |
| 2020/0054432 A1 | 2/2020 | Martin | |

| | | | |
|---|---|---|---|
| 2020/0100839 A1 | 4/2020 | Efremkin | |
| 2020/0129202 A1 | 4/2020 | Schoenle et al. | |
| 2020/0129741 A1 | 4/2020 | Kawwas et al. | |
| 2020/0164117 A1 | 5/2020 | Culhane et al. | |
| 2020/0170666 A1 | 6/2020 | Trosper et al. | |
| 2020/0188016 A1 | 6/2020 | Miller et al. | |
| 2020/0205738 A1 | 7/2020 | Adawi et al. | |
| 2020/0246029 A1 | 8/2020 | Singleton et al. | |
| 2020/0253670 A1 | 8/2020 | Doisneau et al. | |
| 2020/0261112 A1 | 8/2020 | Jamous et al. | |
| 2020/0281612 A1 | 9/2020 | Kelly et al. | |
| 2020/0281648 A1 | 9/2020 | Schultheis et al. | |
| 2020/0297362 A1 | 9/2020 | Deville et al. | |
| 2020/0305900 A1 | 10/2020 | Vale et al. | |
| 2020/0323546 A1 | 10/2020 | Skujins et al. | |
| 2021/0007760 A1 | 1/2021 | Reisin | |
| 2021/0068852 A1 | 3/2021 | Spence | |
| 2021/0161544 A1 | 6/2021 | Casey | |
| 2021/0161545 A1 | 6/2021 | Bhogal et al. | |
| 2021/0220528 A1 | 7/2021 | Jalgaonkar et al. | |
| 2021/0236257 A1 | 8/2021 | Walzman | |
| 2021/0267613 A1* | 9/2021 | Follmer | A61B 17/221 |
| 2021/0353314 A1 | 11/2021 | Porter | |
| 2021/0361305 A1 | 11/2021 | Mogi et al. | |
| 2022/0001141 A1 | 1/2022 | Yourgenlow et al. | |
| 2022/0211429 A1 | 7/2022 | Taff et al. | |
| 2022/0226555 A1 | 7/2022 | Sunenshine et al. | |
| 2022/0233264 A1 | 7/2022 | Klem et al. | |
| 2022/0280171 A1 | 9/2022 | Teigen et al. | |
| 2022/0338887 A1 | 10/2022 | Nair et al. | |
| 2022/0339339 A1 | 10/2022 | Nair et al. | |
| 2022/0361901 A1 | 11/2022 | De Leon et al. | |
| 2022/0379084 A1 | 12/2022 | Look et al. | |
| 2022/0409223 A1 | 12/2022 | Saadat et al. | |
| 2023/0310751 A1 | 10/2023 | Merritt et al. | |
| 2023/0310804 A1 | 10/2023 | Saadat et al. | |
| 2023/0355125 A1 | 11/2023 | Wang et al. | |
| 2023/0364319 A1 | 11/2023 | Vale et al. | |
| 2023/0405273 A1 | 12/2023 | Saadat et al. | |

FOREIGN PATENT DOCUMENTS

| | | | |
|---|---|---|---|
| EP | 2138200 A1 | 12/2009 | |
| EP | 2782514 B1 | 12/2016 | |
| EP | 2787893 B1 | 2/2017 | |
| EP | 3244813 A1 | 11/2017 | |
| EP | 3311875 A1 | 4/2018 | |
| EP | 2231256 B1 | 5/2018 | |
| EP | 1617893 B1 | 6/2018 | |
| EP | 2299916 B1 | 8/2018 | |
| EP | 2309934 B1 | 11/2018 | |
| EP | 3705067 A2 | 9/2020 | |
| EP | 3787523 A1 | 3/2021 | |
| EP | 2908901 B1 | 5/2021 | |
| EP | 4119069 A1 | 1/2023 | |
| FR | 2903292 A1 | 1/2008 | |
| JP | 2019187457 A | 10/2019 | |
| JP | 2022062169 A | 4/2022 | |
| JP | 2023022170 A | 2/2023 | |
| KR | 20160026345 A | 3/2016 | |
| WO | WO98/38929 A1 | 9/1998 | |
| WO | WO2014/147815 A1 | 9/2014 | |
| WO | WO2015/003134 A1 | 1/2015 | |
| WO | WO2017/072663 A1 | 5/2017 | |
| WO | WO2017/154748 A1 | 9/2017 | |
| WO | WO2017/161204 A1 | 9/2017 | |
| WO | WO2019/070782 A1 | 4/2019 | |
| WO | WO2020/160179 A1 | 8/2020 | |
| WO | WO2021/016213 A1 | 1/2021 | |
| WO | WO2021/180826 A1 | 9/2021 | |
| WO | WO2021/263033 A1 | 12/2021 | |
| WO | WO2022/157270 A1 | 7/2022 | |
| WO | WO2022/221643 A1 | 10/2022 | |
| WO | WO2022/261448 A1 | 12/2022 | |
| WO | WO2023/278495 A2 | 1/2023 | |

(56)          References Cited

FOREIGN PATENT DOCUMENTS

WO      WO2023/020961 A1      2/2023
WO      WO2023/205815 A2      10/2023

OTHER PUBLICATIONS

Saadat et al.; U.S. Appl. No. 18/671,981 entitled "Apparatuses and methods for tracking obstructive material within a suction catheter," filed May 22, 2024.
Saadat et al.; U.S. Appl. No. 18/720,594 entitled "Clot sending methods and apparatuses," filed Jun. 14, 2024.
Childs et al.; U.S. Appl. No. 18/859,162 entitled "Aspiration apparatuses for clot removal," filed Oct. 22, 2024.
Saadat et al.; U.S. Appl. No. 18/859,162 entitled "Apparatuses and methods for tracking obstructive material within a suction catheter," filed Nov. 1, 2024.
PCR Online; First-in-human data for sensome clot-sensing guidewire used in ischemic stroke treatment demonstrate ability to automate clot characterization with no safety issues; 4 pages; retrieved from the internet (https://www.pcronline.com/News/Press-releases/2024/First-in-human-data-for-Sensome-clot-sensing-guidewire-used-in-ischemic-stroke-treatment-demonstrate-ability-to-automate-clot-characterization-with-no-safety-issues?utm_source=chatgpt.com) on Feb. 18, 2025.
PCR Online; Sensome announces data from two new studies showing clot-sensing guidewire successfully identifies fresh clot to support decision-making in peripheral artery disease treatment; 4 pages; retrieved from the internet (https://www.pcronline.com/News/Press-releases/2024/Sensome-announces-data-from-two-new-studies-showing-clot-sensing-guidewire-successfully-identifies-fresh-clot-to-support-decision-making-in-peripheral-artery-disease-treatment?utm_source=chatgpt.com) on Feb. 18, 2025.
Rice et al.; CLOTILD a smart guidewire sensing clot characteristics during the mechanical thrombectomy procedure—results from the CLOT OUT study; 1 page; retrieved from the internet (https://www.sensome.com/_files/ugd/9575e7_0370965f17994ee193753e4b4df10e1a.pdf) on Feb. 18, 2025.
Childs et al.; U.S. Appl. No. 19/192,303 entitled "Aspiration apparatuses for clot removal," filed Apr. 28, 2025.
Santilli et al.; Superficial femoral popliteal vein: an anatomic study; Journal of vascular surgery; 31(3); pp. 450-455; Mar. 1, 2000.
Pare et al.; U.S. Appl. No. 19/200,621 entitled "Thrombectomy methods," filed May 6, 2025.
Fox et al.; U.S. Appl. No. 19/200,626 entitled "Methods for removing clot material from a patient," filed May 6, 2025.
Nauleau et al.; U.S. Appl. No. 19/200,634 entitled "Apparatus for removing clot material," filed May 6, 2025.
Saadat et al.; U.S. Appl. No. 19/253,642 entitled "Apparatuses and methods for tracking obstructive material within a suction catheter," filed Jun. 27, 2025.

* cited by examiner

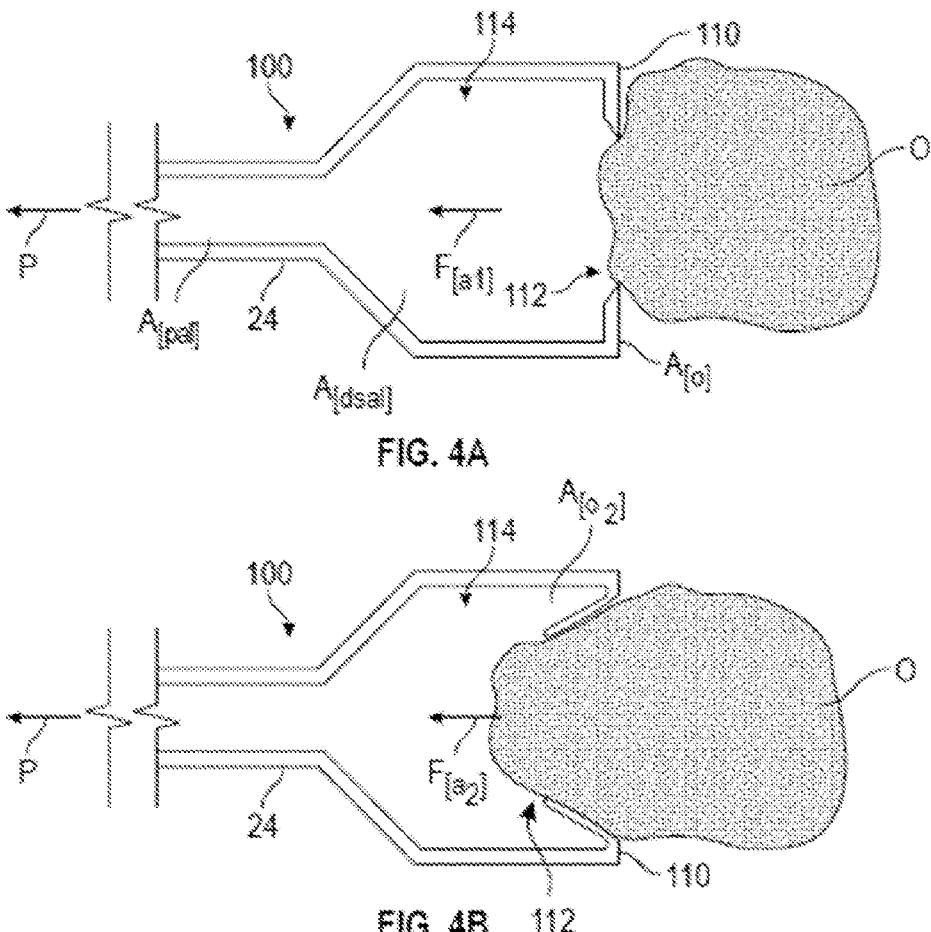
FIG. 4A
FIG. 4B
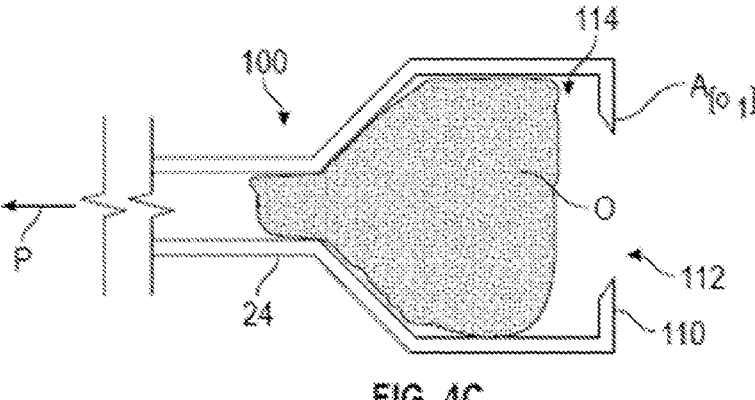
FIG. 4C

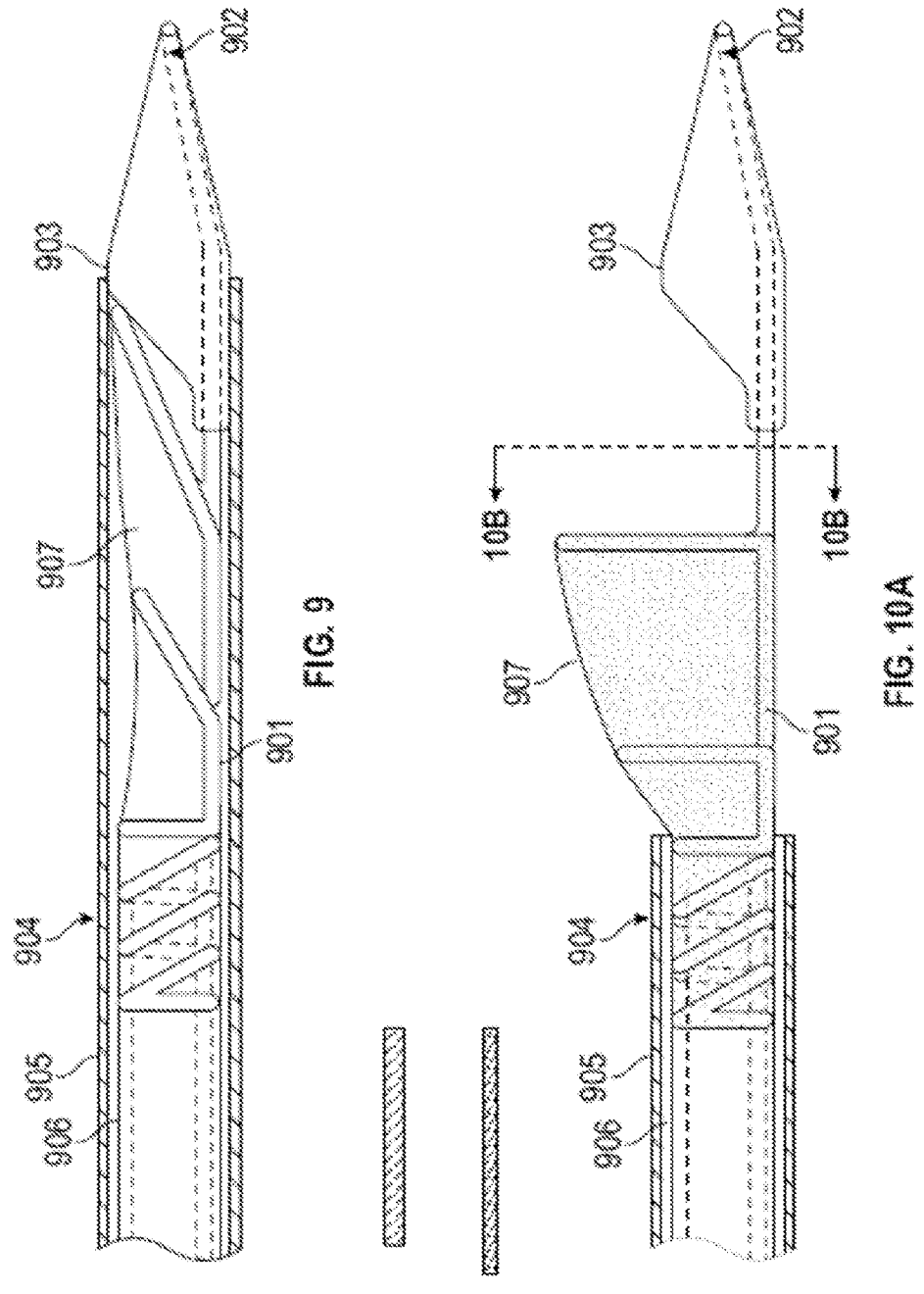

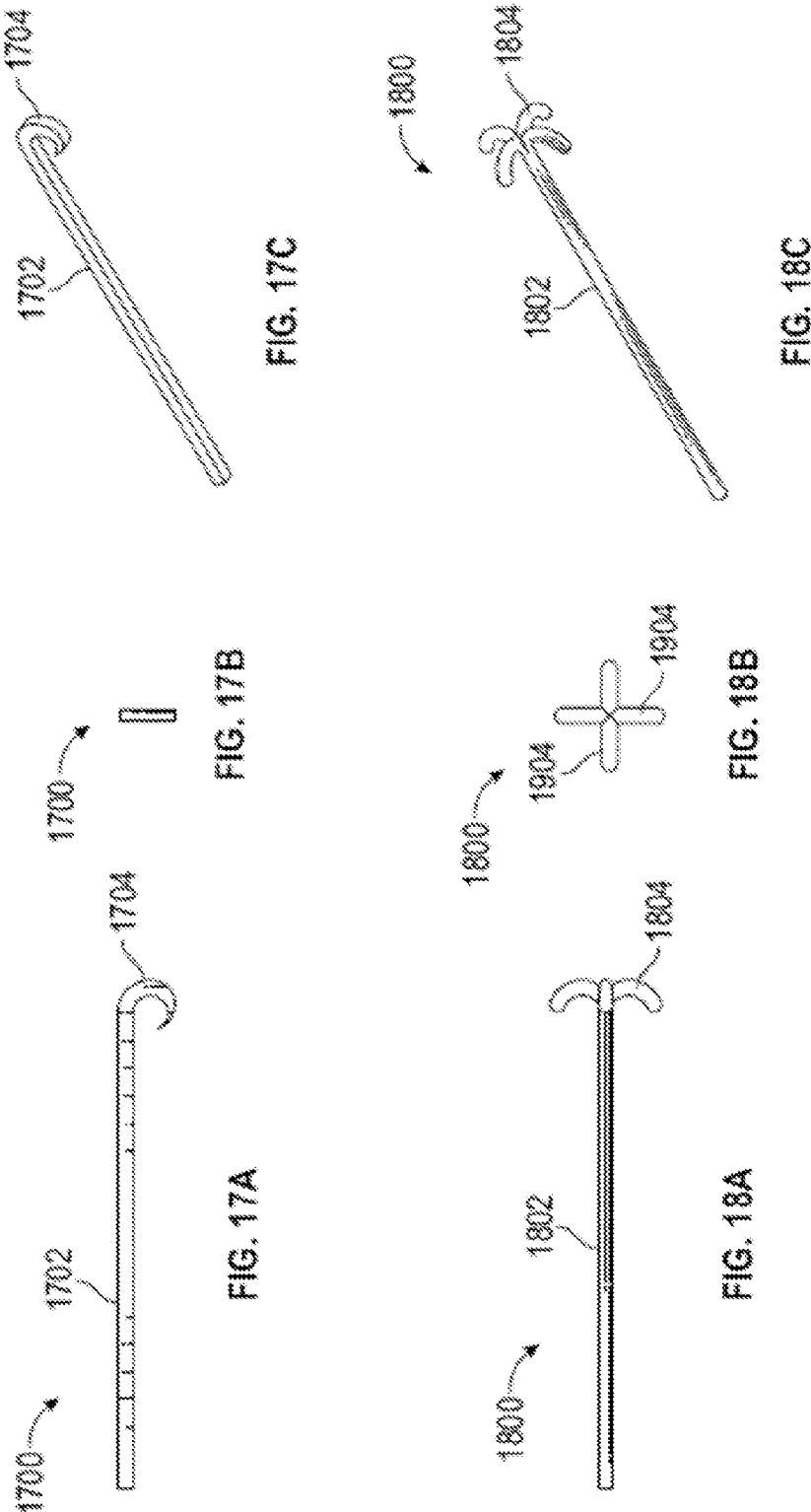

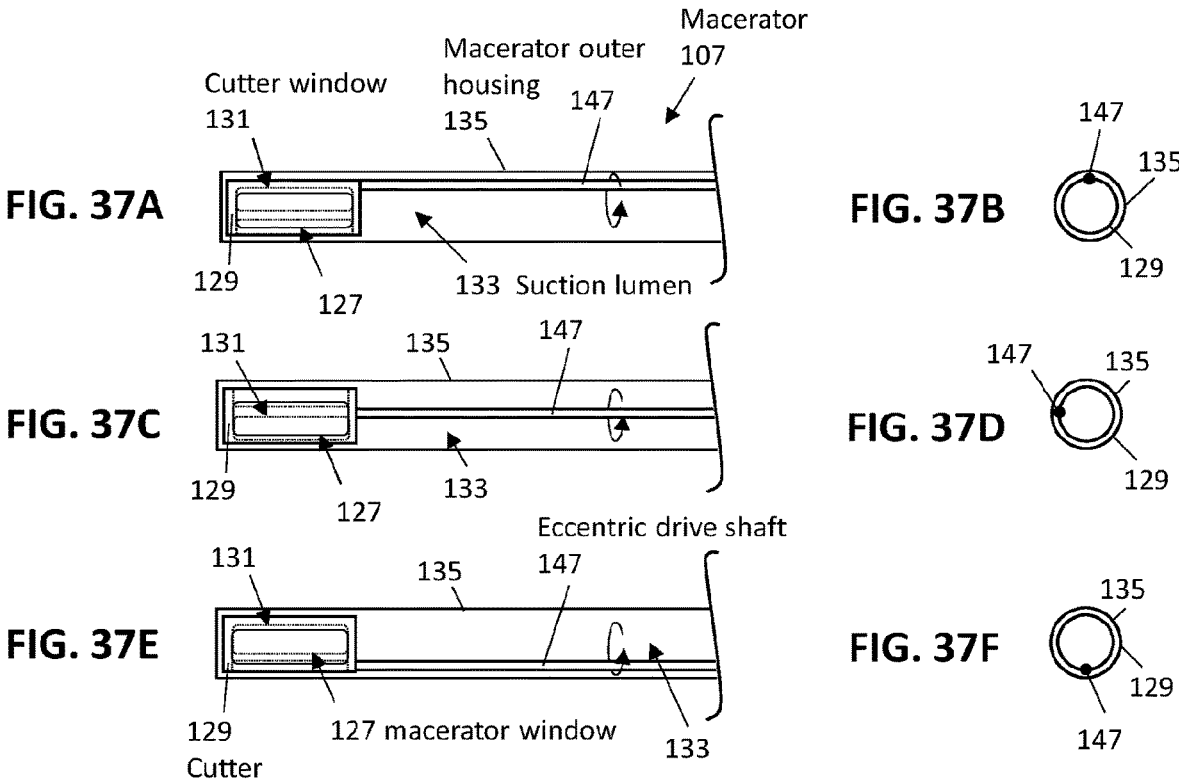
FIG. 37A
FIG. 37B
FIG. 37C
FIG. 37D
FIG. 37E
FIG. 37F
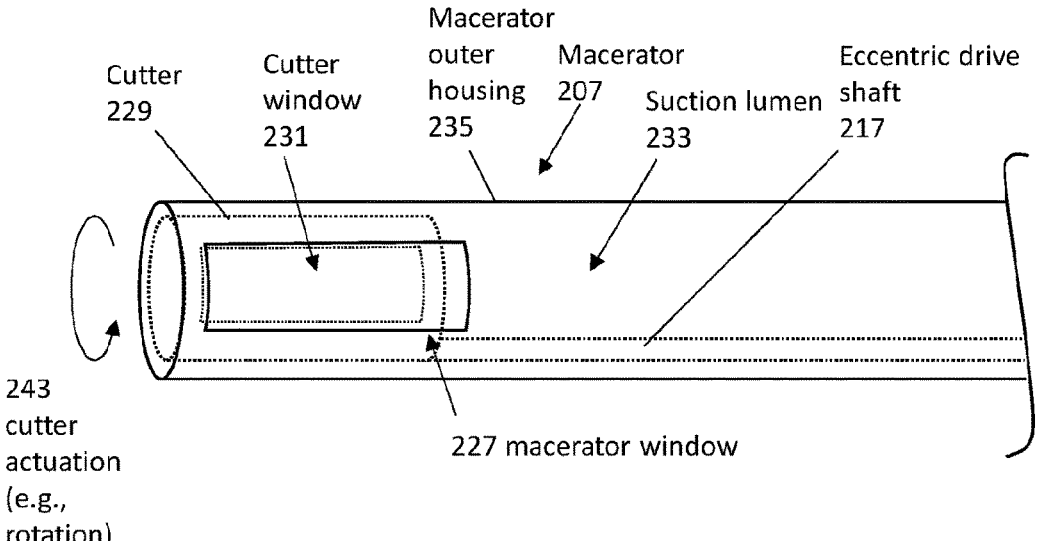
FIG. 38

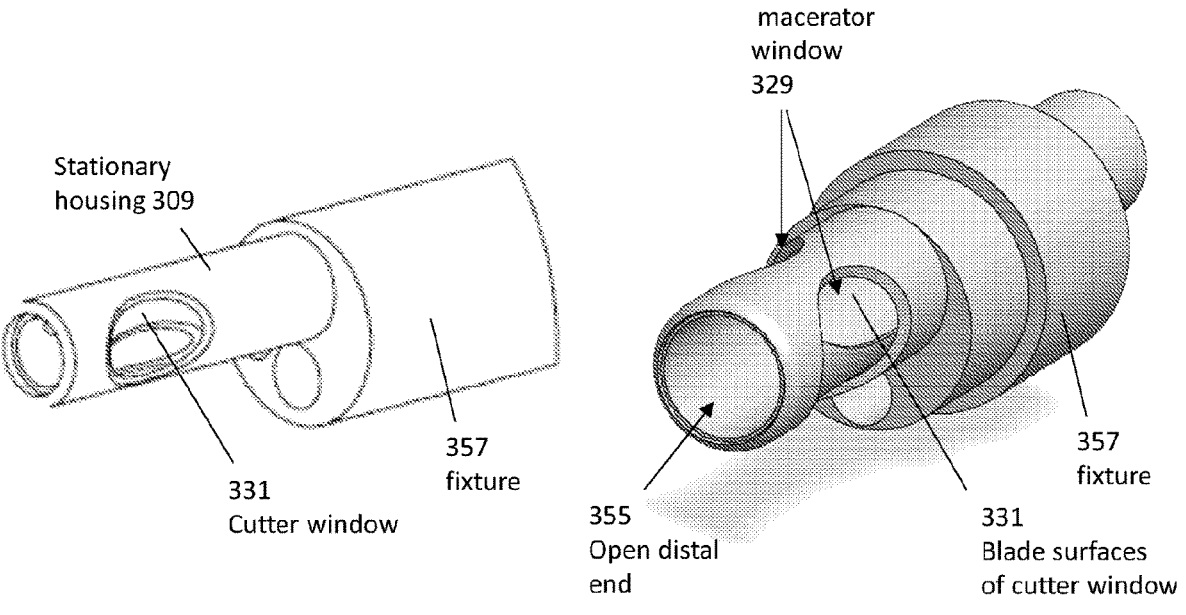
FIG. 39A
FIG. 39B
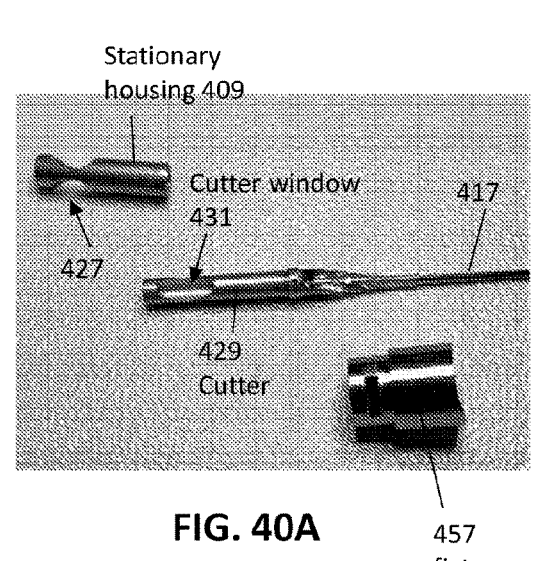
FIG. 40A
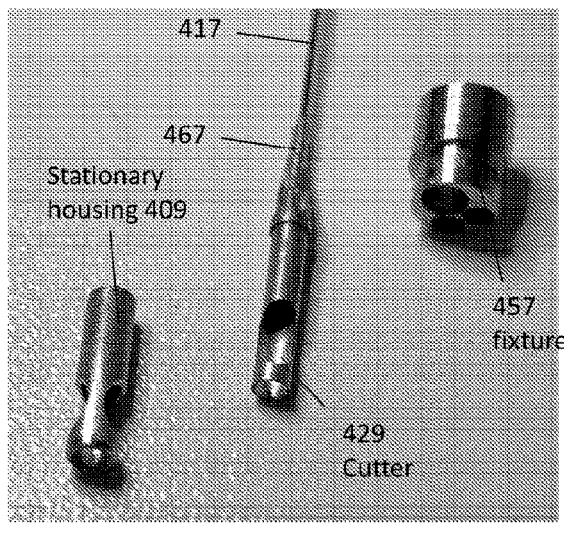
FIG. 40B

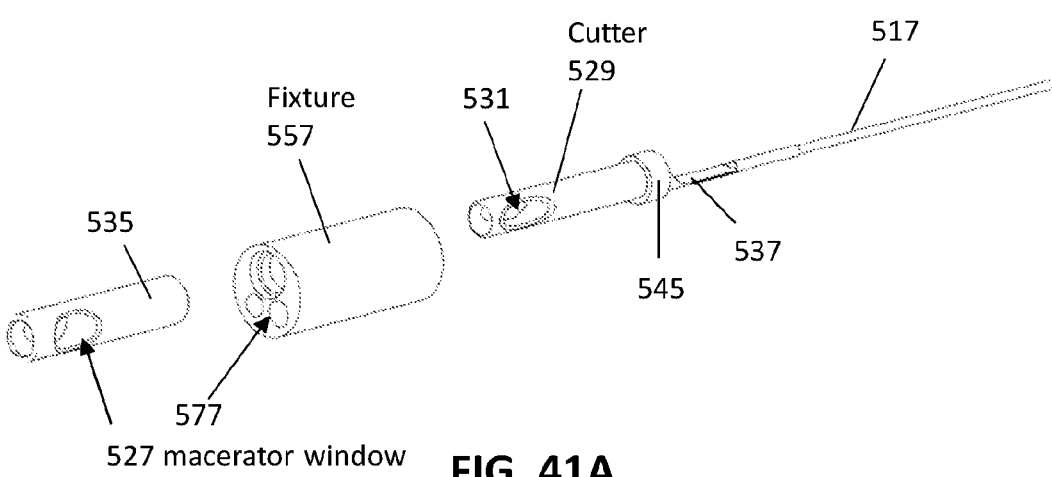
Cutter
529
Fixture
557    531    517
535    537
545
577
527 macerator window    FIG. 41A
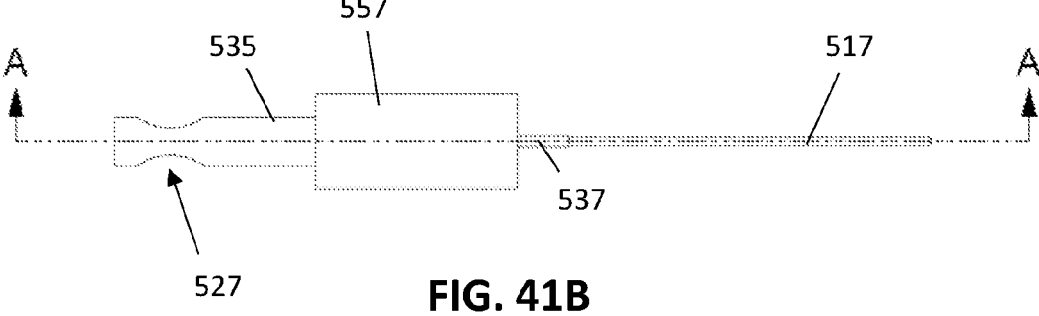
557
535    517
A    A
537
527    FIG. 41B
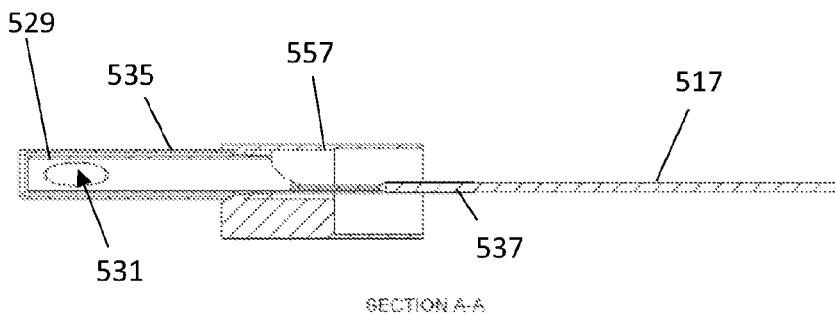
529
535    557    517
531    537
SECTION A-A
FIG. 41C

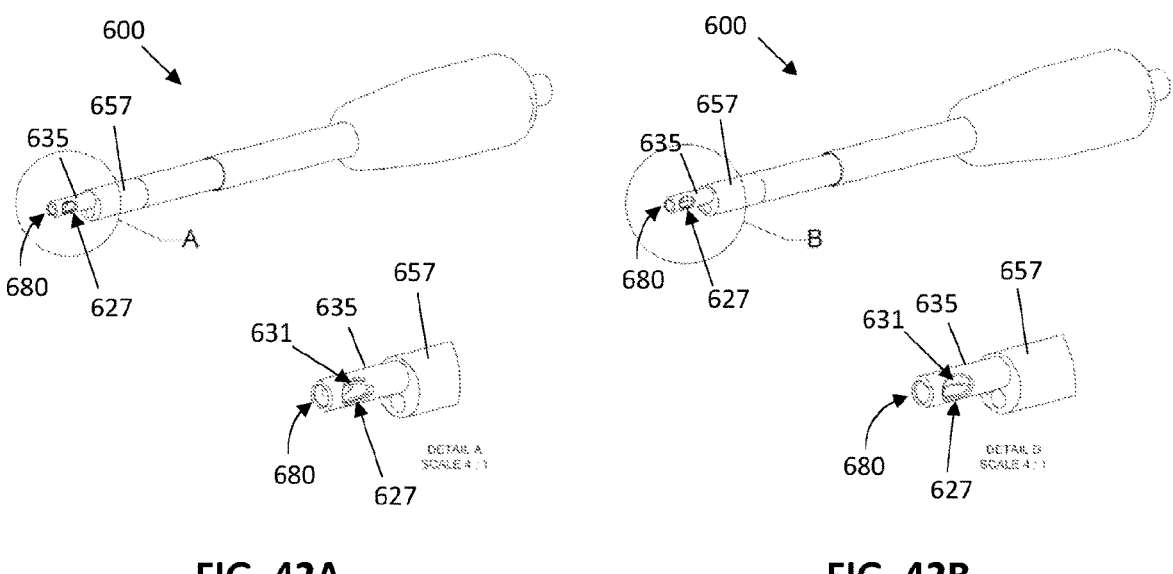
FIG. 42A        FIG. 42B
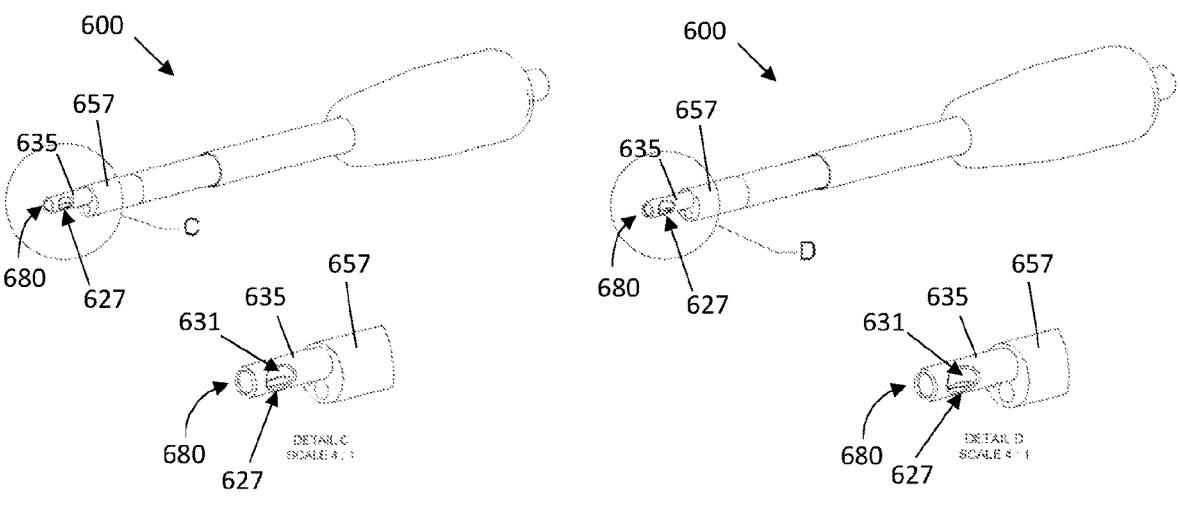
FIG. 42C        FIG. 42D

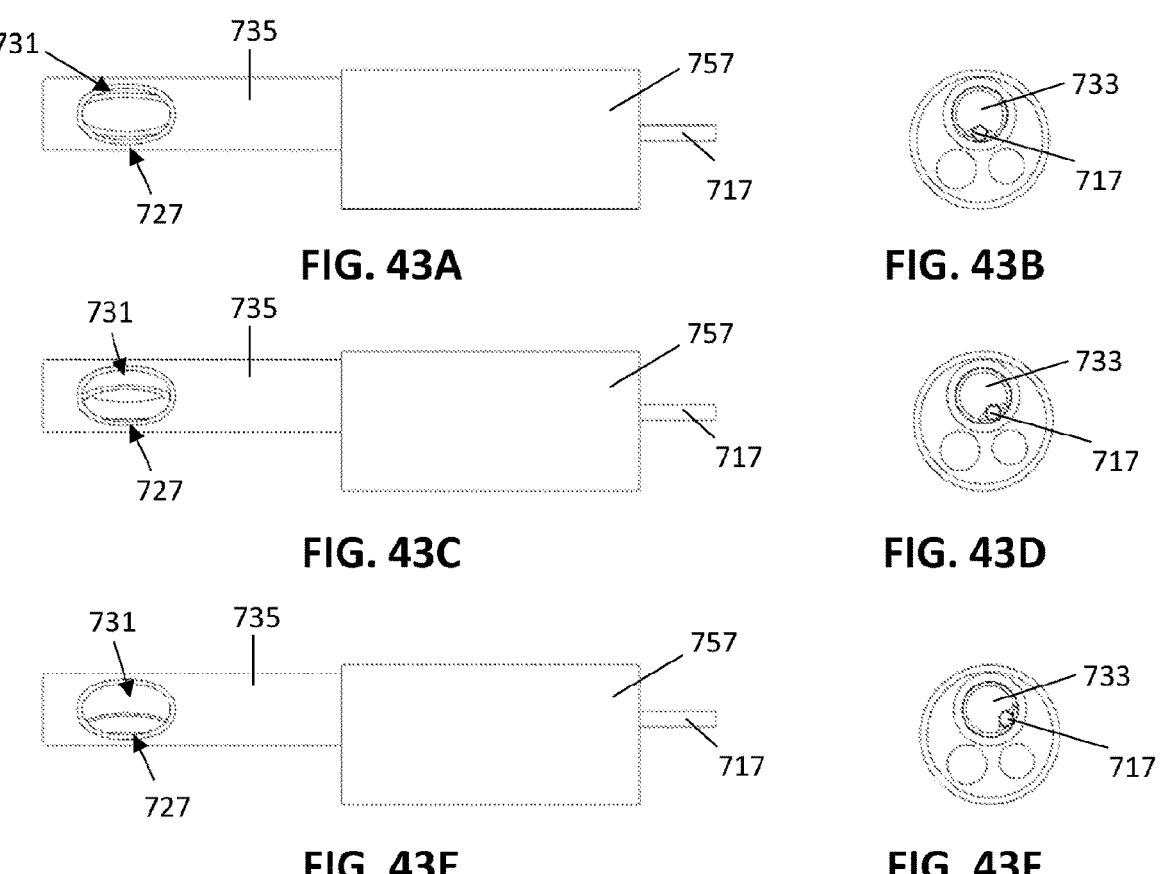
FIG. 43A
FIG. 43B
FIG. 43C
FIG. 43D
FIG. 43E
FIG. 43F
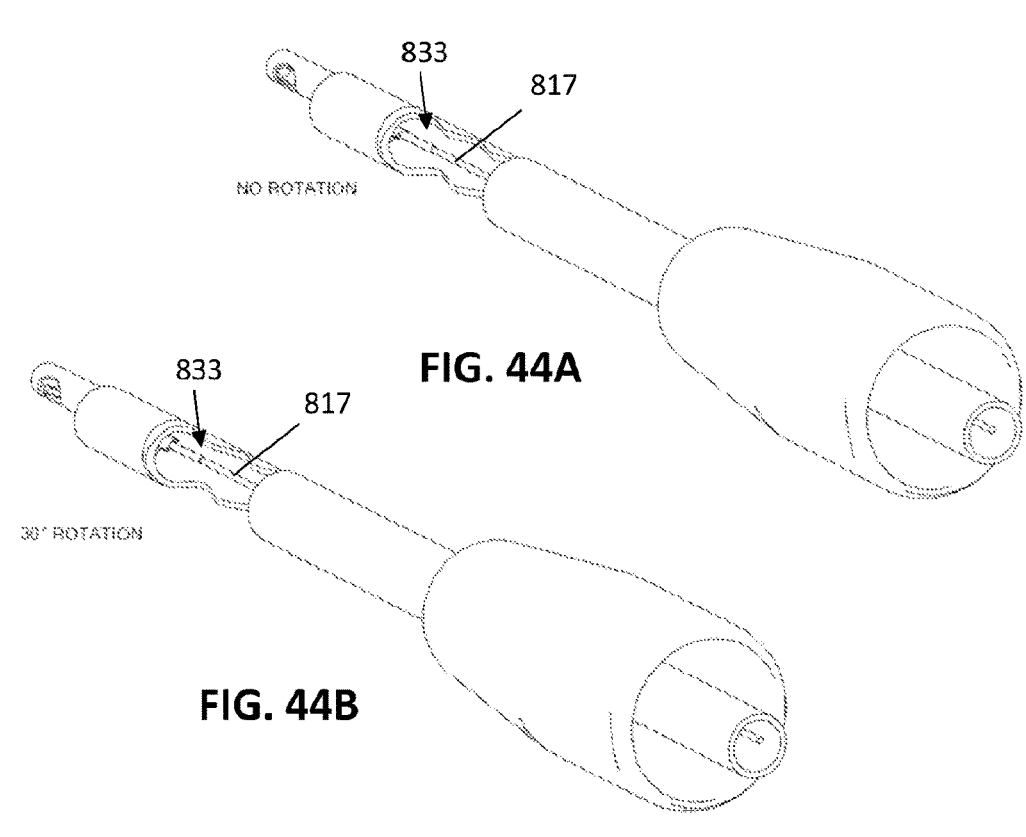
NO ROTATION
FIG. 44A
30° ROTATION
FIG. 44B

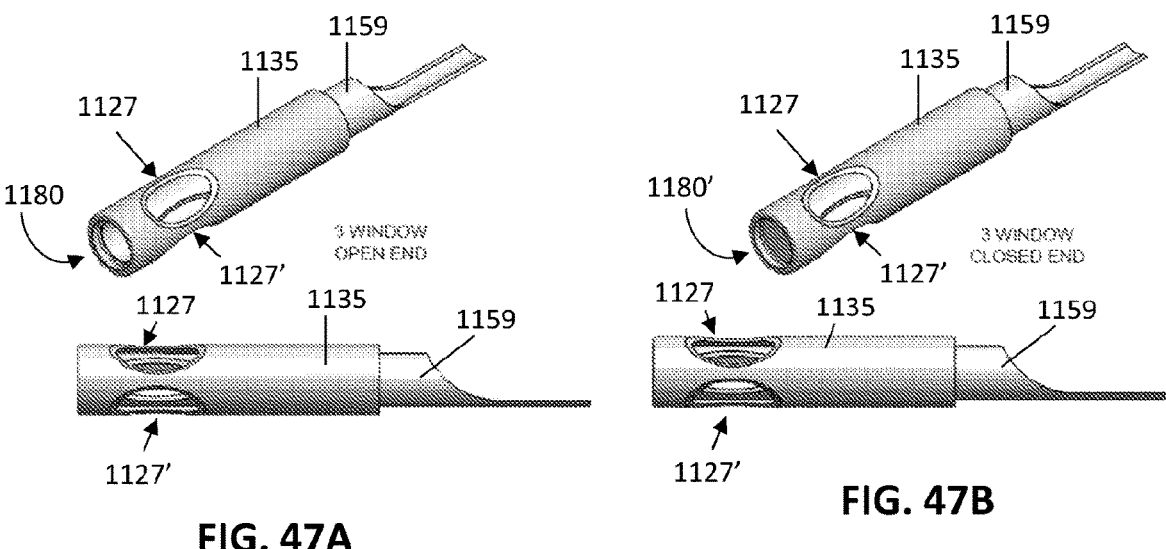
FIG. 47A
FIG. 47B
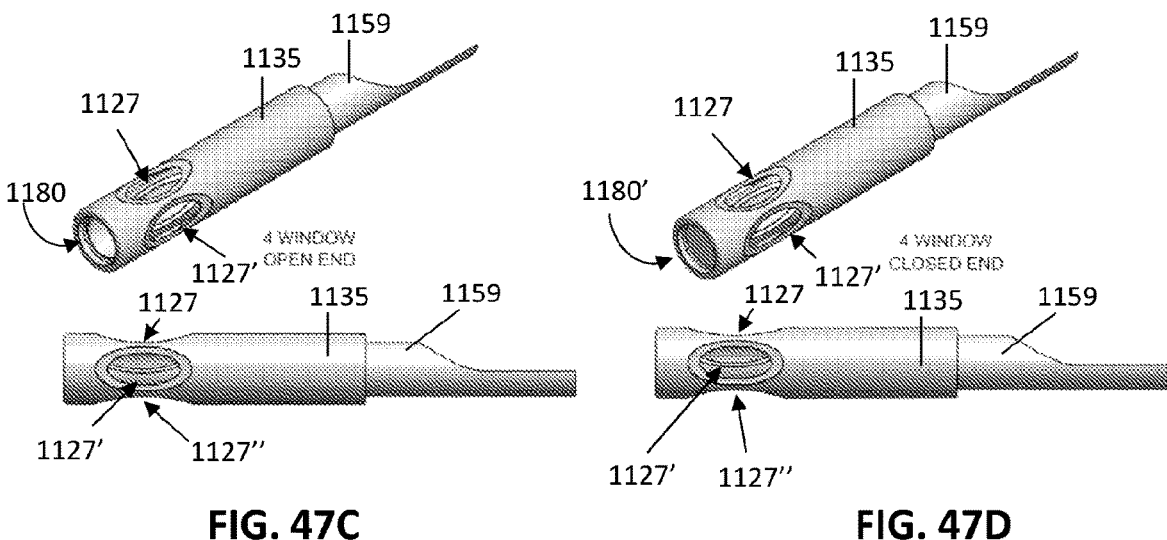
FIG. 47C
FIG. 47D

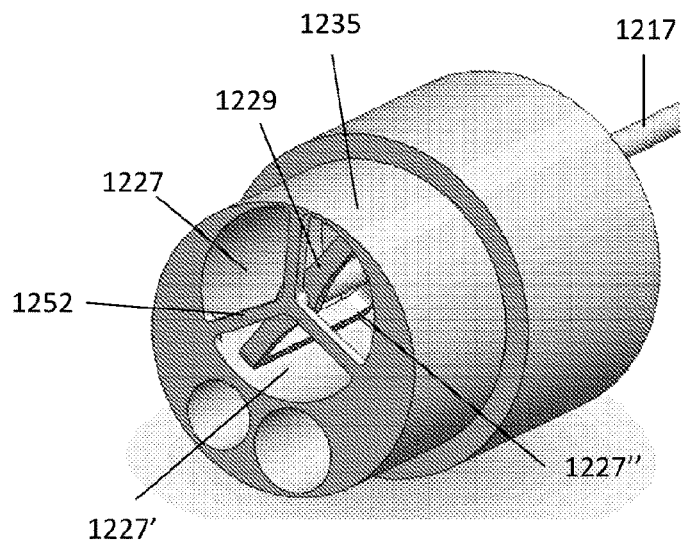
FIG. 48
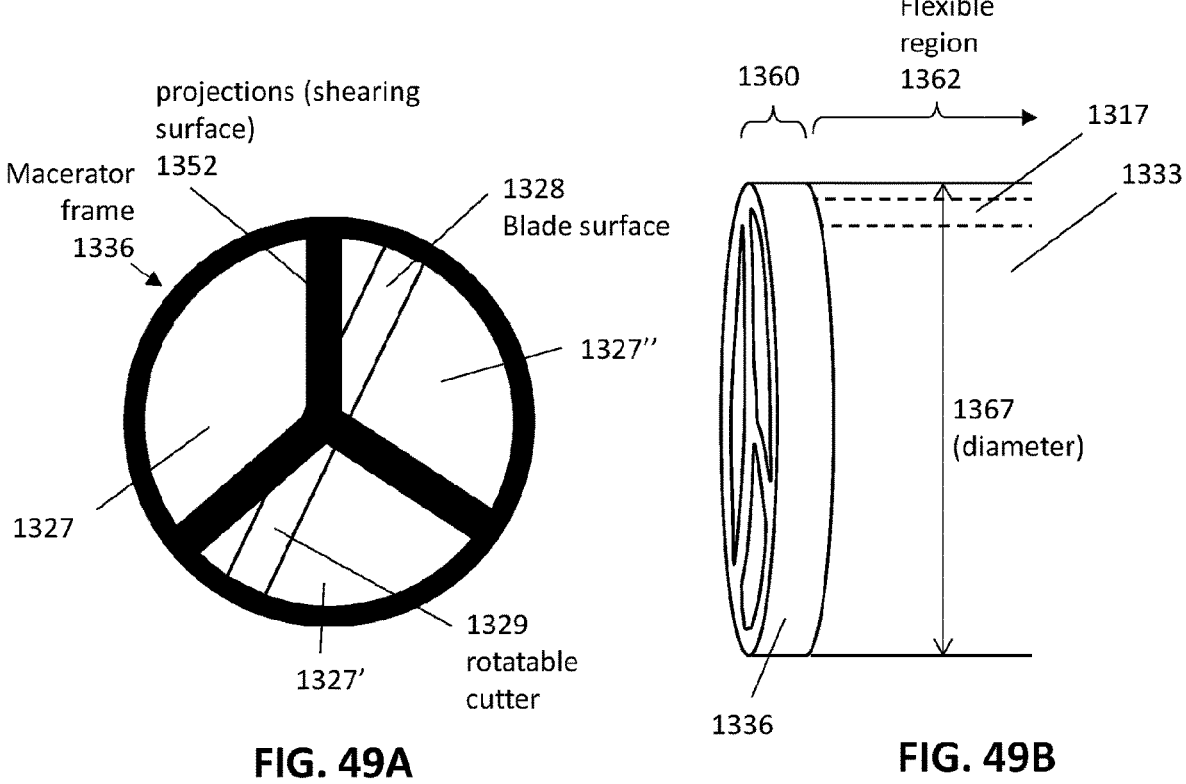
FIG. 49A
FIG. 49B

1435

1487

1452

1428'

1417

1595

1587

1552

1517

1529

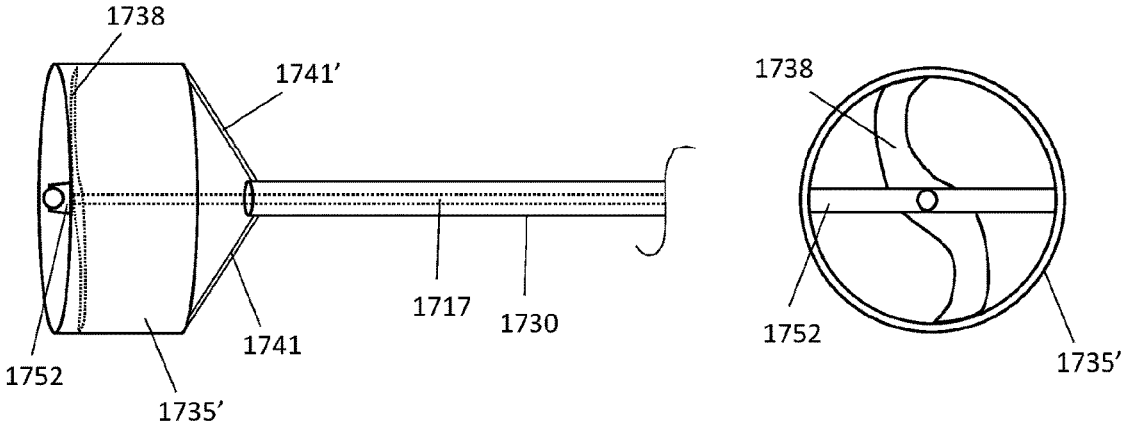
FIG. 53A
FIG. 53B
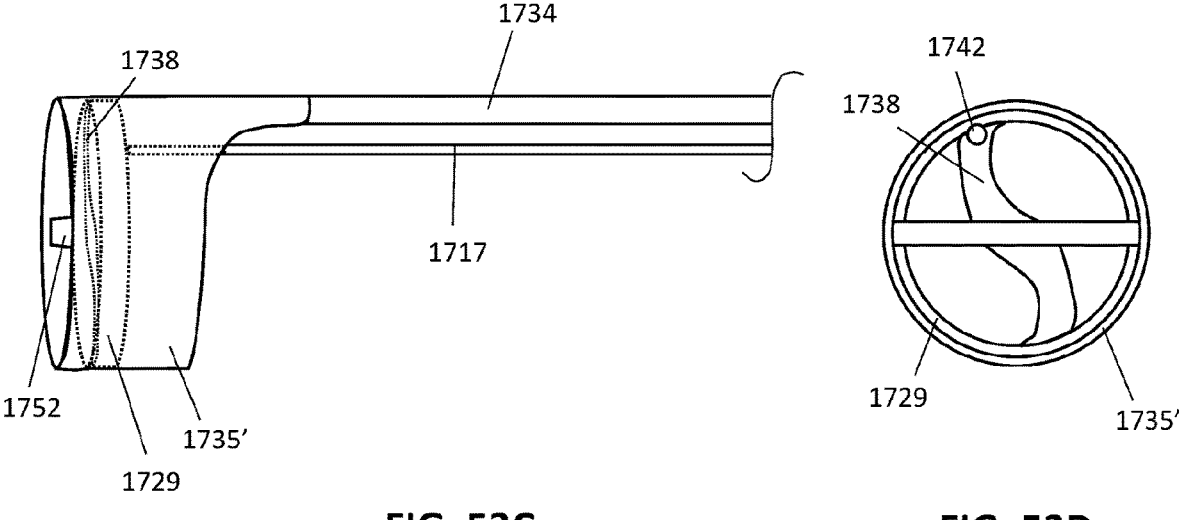
FIG. 53C
FIG. 53D

This works just like an interlock on
an Class IV Laser enclosure

Safety switch
Normally closed
and when $E_m$ Contacts $E_A$
switch opens

APPARATUSES FOR REMOVING OBSTRUCTIVE MATERIAL FROM BODY LUMENS

PRIORITY CLAIM

The present application is a national phase application under 35 U.S.C. 371 of International Patent Application No. PCT/US2022/024986, titled "DEVICES, SYSTEMS, AND METHODS FOR REMOVING OBSTRUCTIVE MATE- RIAL FROM BODY LUMENS," filed Apr. 15, 2022, now International Patent Application Publication No. WO 2022/ 221643, which claims priority to each of the following patent applications: U.S. provisional patent application No. 63/176,224, titled "METHODS AND SYSTEMS FOR REMOVAL OF THROMBUS FROM BLOOD VESSELS," filed Apr. 17, 2021; U.S. provisional patent application No. 63/184,083, titled "METHODS AND SYSTEMS FOR REMOVAL OF THROMBUS FROM BLOOD VESSELS," filed May 4, 2021; U.S. provisional patent application No. 63/192,562, titled "DEVICES, SYSTEMS, AND METH- ODS FOR REMOVING OBSTRUCTIVE MATERIAL FROM BODY LUMENS," filed May 24, 2021; and U.S. provisional patent application No. 63/303,004, titled "MAC- ERATOR APPARATUS AND METHODS," and filed on Jan. 25, 2022. International Patent Application No. PCT/ US2022/024986 also claims priority as a continuation-in- part of U.S. patent application Ser. No. 17/393,618, titled "DEVICES, SYSTEMS, AND METHODS FOR REMOV- ING OBSTRUCTIVE MATERIAL FROM BODY LUMENS" filed Aug. 4, 2021, now U.S. Pat. No. 11,376, 028, each of which is herein incorporated by reference in its entirety.

TECHNICAL FIELD

The present technology relates to devices, systems, and methods for removing obstructive material from body lumens. In particular embodiments, the present technology relates to devices, systems, and methods for removing clot material from blood vessel lumens.

BACKGROUND

Venous thromboembolism (VTE) is the third leading vascular diagnosis after heart attack and stroke, affecting between 300,000 to 600,000 people in the US each year. There are two types of VTE which are Deep Vein Throm- bosis (DVT) and Pulmonary Embolism (PE). DVT is a clot in a deep vein, usually in the leg. PE occurs when a deep vein thrombus breaks free from the vein, travels through the heart, into the lungs and then blocks some or all the blood supply to the lungs. Venous thrombosis is known to be associated with considerable short-term morbidity and mor- tality having a 20% mortality rate within a year of a venous thrombosis event and a two to four times higher mortality rate for patients with PE within three months after the event.

The recommended treatment for VTE according to the American Society of Hematology guidelines is the use of thrombolytic therapy and direct oral anticoagulants. Throm- bolytic therapy includes intravenous or local delivery of tissue Plasminogen Activator (tPA) which is an enzyme designed to dissolve the blood clot that is blocking the blood flow. The thrombolytic therapy has been shown to be effective, but the treatment takes hours and involves the risk of hemorrhaging elsewhere in the body. In some cases, the thrombus is surgically removed from the vessel via an open surgical procedure. More recently, the thrombus or emboli is mechanically removed using a thrombectomy device via a percutaneous procedure with access through a distal or proximal vein. The current thrombectomy devices on the market use expandable cages, shape memory wires, and compliant balloons to physically grab and/or scrape off and extract the thrombus from the blood vessel. Several existing thrombectomy devices also aspirate the thrombus, with and without mechanically engaging and securing the clot. The use of aspiration for thrombus extraction has produced promising results. However, current PE thrombectomy devices require electrically powered suction systems or large profile catheters to generate sufficient aspiration power to aspirate the large pulmonary emboli in the pulmonary arteries. The use of such larger diameter aspiration catheters can cause safety concerns, such as access site complications, excessive blood loss, and damage to the vessel wall or the valves of the heart. These current technologies also require multiple passes and repositioning steps to completely remove the large pulmonary emboli. For DVT removal, mechanical scraping of thrombus from the vessel wall and removal with aspiration has been shown to increase blood flow within the vessel. However risk of damaging the vessel wall or valves remains high. Accordingly, there is a need for improved systems and methods for removing thrombus from the vascular anatomy as described herein.

Thrombectomy catheters have been used to continuously aspirate a blood clot from a blood vessel into the catheter lumen so as to remove the blood clot from the blood vessel. If the diameter of the thrombus is greater than the inner diameter of the catheter lumen, the catheter lumen may be blocked by the thrombus. One solution is to use a cutting device to break the clot into smaller portion that may be individually removed. However, this has proven challeng- ing, as clot material may have a variety of different textures and may be resistant to cutting. In addition, breaking clot into smaller portions may cause emboli, irregular heartbeats, and potential death due to vessel dissection. Thus, not all cutting devices function well, or are well suited for cutting within the lumen of the vessel.

In addition, a cutting device may add stiffness when used with a catheter which severely limits the ability of the catheter to access difficult to reach regions of the vascula- ture. Further, when used in conjunction with an aspiration catheter, the cutter device, including the drive shaft portion of the cutting device, may take up a large portion of the volume of the catheter.

Thus, there is a need for a robust and effective cutter (e.g., macerator) that may be used as part of or in conjunction with an aspiration catheter that minimally impacts the flexibility of the catheter. The apparatuses and methods described herein may address this need.

SUMMARY

The present technology provides devices, systems, and methods for disrupting and/or removing obstructive material from a blood vessel. The subject technology is illustrated, for example, according to various aspects described below, including with reference to FIGS. 1-36. Various examples of aspects of the subject technology are described as numbered clauses (1, 2, 3, etc.) for convenience. These are provided as examples and do not limit the subject technology.

For example, descried herein are devices for the disrup- tion and/or removal of obstructive material in a blood vessel, the device comprising: an elongated shaft having a proximal portion, a distal portion, and a lumen extending therebetween, wherein the distal portion of the elongated shaft is configured to be positioned at a treatment site within the blood vessel proximate the obstructive material; and a capture structure carried by the distal portion of the elongated shaft and having a greater cross-sectional dimension than a cross-sectional dimension of the elongated shaft, the capture structure comprising (a) a first end portion, a second end portion, and a longitudinal axis extending therebetween, (b) an opening at the first end portion that is fluidly coupled to the lumen of the elongated shaft, (c) a fluid impermeable wall enclosing an interior region, and (d) an opening extending through a thickness of the wall, and wherein a portion of the wall surrounding the opening is configured to deform towards or away from the interior region, thereby increasing a cross-sectional dimension of the opening.

A proximal portion of the elongated shaft may be configured to be fluidly coupled to a negative pressure source to apply a negative pressure within the capture structure. The portion of the wall may be configured to deform in response to the application of negative pressure.

Any of these apparatuses may include a disruptor configured to be positioned within the interior region of the capture structure, wherein the disruptor is configured to break up obstructive material received through the opening in the wall. The wall may have (a) a first region extending longitudinally between the opening and the second end portion, and (b) a second region extending radially inwardly from the first region.

The opening may be a slit. The capture structure may be configured to transform between (a) a collapsed state in which the capture structure has a first cross-sectional dimension, and (b) an expanded state in which the capture structure has a second cross-sectional dimension greater than the first cross-sectional dimension.

Also described herein are devices for the disruption and/or removal of obstructive material in a blood vessel, the device comprising: an elongated shaft having a proximal portion, a distal portion, and a lumen extending therebetween, the lumen having a cross-sectional dimension, wherein the distal portion of the elongated shaft is configured to be positioned at a treatment site within the blood vessel proximate the obstructive material; a capture structure carried by the distal portion of the elongated shaft and defining an interior cavity in fluid communication with the lumen of the elongated shaft, the interior cavity having a cross-sectional dimension and configured to receive the obstructive material therein, wherein a cross-sectional dimension of the interior cavity is greater than the cross-sectional dimension of the lumen; and an engagement wall extending radially inwardly from a distal end of the capture structure and having an opening therethrough that is in fluid communication with the cavity, wherein the opening has a cross-sectional dimension less than the cross-sectional dimension of the interior cavity of the capture structure.

The opening in the engagement wall may have a cross-sectional dimension greater than the cross-sectional dimension of the lumen of the elongated shaft. The opening in the engagement wall may have a cross-sectional dimension less than the cross-sectional dimension of the lumen of the elongated shaft.

Also described herein are devices for the disruption and/or removal of obstructive material in a blood vessel, the device comprising: an elongated shaft having a proximal portion, a distal portion, and a lumen extending therebetween, wherein the distal portion of the elongated shaft is configured to be positioned at a treatment site within the blood vessel proximate the obstructive material; a capture structure carried by the distal portion of the elongated shaft and defining an interior cavity in fluid communication with the lumen of the elongated shaft, the interior cavity having a cross-sectional dimension and configured to receive the obstructive material therein; and an engagement wall extending radially inwardly from a distal end of the capture structure and having an opening therethrough, the opening in fluid communication with the cavity, wherein the opening has a cross-sectional dimension less than the cross-sectional dimension of the interior cavity of the capture structure, wherein the engagement wall is configured to deform in response to engagement with the obstructive material to increase the cross-sectional dimension of the opening.

Also described herein are devices for the disruption and/or removal of obstructive material in a blood vessel, the device comprising: an elongated shaft having a proximal portion, a distal portion, and a lumen extending therebetween, wherein the distal portion of the elongated shaft is configured to be positioned at a treatment site within the blood vessel proximate the obstructive material; a capture structure carried by the distal portion of the elongated shaft and defining an interior cavity in fluid communication with the lumen of the elongated shaft, the interior cavity having a cross-sectional dimension and configured to receive the obstructive material therein; and an engagement wall extending radially inwardly from a distal end of the capture structure and having an opening therethrough that is in fluid communication with the cavity, wherein the opening has a cross-sectional dimension less than the cross-sectional dimension of the interior cavity of the capture structure, wherein, when the engagement wall is pushed up against the obstructive material so that the obstructive material is in contact with an edge of the engagement wall surrounding the opening, the engagement wall deforms around the obstructive material such that the opening is stretched to an increased cross-sectional dimension.

The portion of the engagement wall defining the opening may be configured to apply a radially compressive force on obstructive material positioned within the opening. The edge of the engagement wall surrounding the opening may be configured to apply a radially compressive force on obstructive material positioned within the opening. The proximal portion of the elongated shaft may be configured to be coupled to a negative pressure source to apply a negative pressure in the interior cavity. The capture structure may comprise a sidewall that is substantially impermeable to fluids. The portion of the engagement wall surrounding the opening may be substantially impermeable to fluids. The cross-sectional dimension of the interior cavity of the capture structure increases or remains substantially constant in a direction towards the distal end of the capture structure. In any of these devices, a maximum cross-sectional dimension of the interior cavity of the capture structure may be at least two times greater than the cross-sectional dimension of the lumen of the elongated shaft.

The elongated shaft may have an outer diameter of about 30 French or less, about 24 French of less, about 20 French or less, about 18 French of less, or about 16 French or less. The interior cavity of the capture structure may be configured to receive a disruptor, and wherein the disruptor is configured to mechanically engage and break up obstructive material received at least partially within the interior cavity.

Also described herein are devices for the disruption and/or removal of obstructive material in a blood vessel, the device comprising: an elongated shaft having a proximal portion, a distal portion, and a lumen extending therebetween, wherein the distal portion of the elongated shaft is configured to be positioned at a treatment site within the blood vessel proximate the obstructive material; and a distal housing carried by the distal portion of the elongated shaft, the distal housing comprising (a) a sidewall extending between a first end portion fluidly coupled to the lumen of the elongated shaft and a second end portion, and (b) a distal wall extending across the second end portion and including an opening configured to receive the obstructive material therethrough, wherein the sidewall and the distal wall together enclose an interior region, and wherein the distal surface is configured such that advancement of the distal wall onto and/or over the obstructive material increases a cross-sectional dimension of the opening.

The opening of the distal surface may have a cross-sectional dimension greater than the cross-sectional dimension of the lumen of the elongated shaft. A cross-sectional dimension of the opening may be greater than a cross-sectional dimension of the lumen of the elongated shaft. A cross-sectional dimension of the sidewall at the first end portion may be less than a cross-sectional dimension of the sidewall at the second end portion. A cross-sectional dimension of the interior region of the sidewall at the first end portion may be less than a cross-sectional dimension of the interior region at the second end portion. The portion of the distal wall defining the opening may be configured to apply a radially compressive force on obstructive material positioned within the opening. The proximal portion of the elongated shaft may be configured to be fluidly coupled to a negative pressure source to apply a negative pressure in the interior region of the distal housing. The sidewall may be substantially impermeable to fluids. The portion of the distal wall surrounding the opening may be substantially impermeable to fluids. The elongated shaft may have an outer diameter of about 30 French or less, about 24 French of less, about 20 French or less, about 18 French of less, or about 16 French or less. The interior region of the distal wall may be configured to receive a disruptor, and wherein the disruptor is configured to mechanically engage and break up obstructive material received at least partially within the interior region.

Also described herein are methods for treating a blood vessel of a human patient, the method comprising: positioning a distal portion of a treatment device in the blood vessel at a treatment site proximate obstructive material, the treatment device comprising an elongated shaft and a capture structure disposed at a distal portion of the elongated shaft and enclosing an interior region, wherein a surface of the capture structure has an opening therethrough with a cross-sectional dimension less than a cross-sectional dimension of the interior region of the capture structure; engaging the obstructive material with the surface of the capture structure such that at least a portion of the obstructive material is positioned in and/or through the opening, thereby increasing a cross-sectional dimension of the opening; and removing at least the portion of the obstructive material from the patient's body. Engaging the obstructive material may causes the surface to deform around the obstructive material, thereby stretching the opening. In some examples, engaging the obstructive material comprises creating a seal between the obstructive material and an edge of the surface surrounding the opening. Engaging the obstructive material may comprise pushing the surface onto and/over a portion of the obstructive material.

Any of these methods may include applying negative pressure to the interior region of the capture structure before, during, and/or after engaging the obstructive material, thereby pulling the obstructive material through the surface opening and into the interior region. The methods may include increasing a proximally-directed force on the obstructive material without increasing the negative pressure. In some examples, the method may include positioning a disrupting element within the interior region of the capture structure before, during, and/or after engaging the obstructive material.

Any of these methods may include breaking up the portion of the obstructive material positioned within the interior region with the disrupting element. The methods may include comprising mechanically engaging the obstructive material with the disrupting element and pulling the obstructive material into the interior region of the capture structure with the disrupting element. In some examples the method includes removing the disrupting element from the patient's body while holding the capture structure at the treatment site. The method may include applying negative pressure to the interior region of the capture structure before, during, and/or after engaging the obstructive material, and/or breaking up the portion of the obstructive material positioned within the interior region with a disrupting element positioned within the interior region, wherein applying the negative pressure and breaking up the obstructive material occur at different times. In some examples the methods may include applying negative pressure to the interior region of the capture structure before, during, and/or after engaging the obstructive material, and breaking up the portion of the obstructive material positioned within the interior region with a disrupting element positioned within the interior region, wherein at least some of the application of negative pressure occurs while the disrupting element is breaking up the obstructive material, or vice versa.

Also described herein are devices for the disruption and/or removal of obstructive material in a blood vessel, the device comprising: an elongated shaft having a proximal portion, a distal portion, and a lumen extending therebetween, wherein the distal portion of the elongated shaft is configured to be positioned at a treatment site within the blood vessel proximate the obstructive material; and a distal housing carried by the distal portion of the elongated shaft and having a greater cross-sectional dimension than a cross-sectional dimension of the elongated shaft, the distal housing comprising (a) a sidewall extending between an opening at a first end portion and a second end portion, the opening fluidly coupled to the lumen of the elongated shaft, (b) an engagement wall extending across the second end portion of the sidewall, and (c) an aperture extending through the sidewall and/or engagement wall, the aperture configured to receive the obstructive material therethrough, wherein the sidewall and the engagement wall together enclose an interior region, and wherein the engagement wall is configured to deform towards or away from the interior region such that a cross-sectional dimension of the opening increases.

For example, a method of removing material from the vascular anatomy may include: advancing a distal section of a catheter with central lumen adjacent to unwanted material within vascular anatomy in a first radial profile; expanding the distal section of a catheter with a central lumen to a second radial profile greater than the first radial profile; engaging material with distal end of distal section of catheter; applying negative pressure within central lumen of catheter onto the material causing at least a portion of material to enter distal section of catheter; agitating material within the distal section of catheter while maintaining negative pressure within catheter; aspirating at least a portion of the material from the vascular anatomy where the portion has a greater cross-sectional area than the cross-sectional area of the central lumen.

An extraction system may include; an elongated catheter, having a proximal end, a proximal section, an expandable articulating distal section, an expandable distal orifice, a central lumen, and an agitating element within the central lumen, wherein the distal section first radial profile cross sectional area is less than or equal to proximal section profile cross-sectional area and the second radial profile cross-sectional area is greater than the proximal section profile area and has an axial length greater than 5 mm and a taper transition to the proximal section profile, and wherein the cross-sectional area of the distal section in the second radial profile maintains an area greater than the proximal section profile when negative pressure is applied within the central lumen.

A method for treating a blood vessel of a human patient may include: positioning a distal portion of a treatment device in the blood vessel at a treatment site proximate obstructive material, the treatment device comprising an elongate shaft and a capture structure disposed at a distal portion of the elongate shaft and enclosing an interior region; positioning the obstructive material within the interior region of the capture structure; macerating the obstructive material within the interior region of the capture structure with a disrupting element positioned within the interior region of the capture structure; and applying aspiration to pull the processed portion of the obstructive material from the patient's body. Macerating the obstructive material may occur without aspiration.

Also described herein are methods for treating a blood vessel of a human patient, the method comprising: positioning a distal portion of a treatment device in the blood vessel at a treatment site proximate obstructive material, the treatment device comprising an elongated shaft and a capture structure disposed at a distal portion of the elongated shaft and enclosing an interior region, wherein a surface of the capture structure has an opening therethrough with a cross-sectional dimension less than a cross-sectional dimension of the interior region of the capture structure; engaging the obstructive material with the surface of the capture structure such that at least a portion of the obstructive material is positioned in and/or through the opening, thereby increasing a cross-sectional dimension of the opening; and removing at least the portion of the obstructive material from the patient's body. Engaging the obstructive material may cause the surface to deform around the obstructive material, thereby stretching the opening. Engaging the obstructive material may comprise creating a seal between the obstructive material and an edge of the surface surrounding the opening. In some examples, engaging the obstructive material comprises pushing the surface onto and/over a portion of the obstructive material. Any of these methods may include applying negative pressure to the interior region of the capture structure before, during, and/or after engaging the obstructive material, thereby pulling the obstructive material through the surface opening and into the interior region.

Described herein are apparatuses (e.g., devices and systems, including macerators) that may be used to remove tissue from within a vessel, and in particular, may be used to remove clot material (e.g., embolus). In general, these apparatuses may be used with an aspiration catheter, and in particular may be used within an enclosed or partially enclosed aspiration chamber. The apparatuses described herein may have a distal-facing and/or multiple side-facing windows. Any of these apparatuses may be driven by a wire drive shaft that may be eccentrically rotated. The apparatuses and methods described herein may be configured to extend the macerator out of the distal end of an aspiration catheter; in some examples, the macerator may be controlled automatically, manually or semi-automatically based on where in the aspiration catheter it is positioned. Methods of controlling the operation of the macerator are also described.

In general, the apparatuses described herein may be use in the vascular system, preferably in the venous system. For example, these apparatuses may be used within a pulmonary artery to remove pulmonary embolism material. The apparatuses described herein may remove material (e.g., emboli) from a naturally occurring or surgically created body lumen or cavity. In some examples, these apparatuses may remove plaque material, such as (but not limited to) acute or chronic blood clot material. These apparatuses may be used for (and may be configured for use for) removal of other tissues, such as tumor tissue or polyps.

In some examples, the methods described herein may be used to clear or unclog, or otherwise enhance operation of an aspiration catheter. For example, a macerator may be used within an aspiration catheter anywhere along the length of the aspiration catheter. In some examples the macerators described herein may be used within a particular region (e.g., a distal maceration chamber) of the aspiration catheter. Thus, these apparatuses and methods may be used inside of a body (as part of a surgical procedure) or may be used separately, outside of a patient's body, for preparing an aspiration catheter (e.g., driving the macerator within the lumen of the aspiration catheter).

The apparatuses described herein may be used with one or more catheters (e.g., aspiration catheters) and/or introducers and may be used as part of a minimally invasive procedure, e.g., through a laparoscopic or percutaneous access site. In some examples, these apparatuses may be used through a right femoral percutaneous access. The apparatus may be configured to have a crossing profile, length, and flexibility appropriate to reach the target location. Imaging may be used to position and manipulate these apparatuses, and the apparatuses described herein may be adapted for use with any appropriate form of imaging. For example, these apparatuses may be place with combined direct vision angioscopy, ultrasound, MRI, impedance mapping (NavX). For example, an apparatus as described herein may be placed with fluoroscopic imaging and may include one or more radioopaque markers or may be formed in part by a radioopaque material. The apparatuses described herein may be navigated by the user with push/pull and rotation, and in some examples may be placed alongside or over a preplaced guidewire. For example, any of these apparatuses may be positioned in a pulmonary artery (e.g., the main branch, right or left branches, secondary branches, tertiary branches) and used to remove an embolism. A macerator (e.g., agitator/cutter) apparatus may be used in conjunction with aspiration to engage, disrupt then suck material through the device shaft and out of the body.

The macerator apparatuses described herein may be configured to macerate and/or cut by shearing. For example, any of these apparatuses may include one or more apertures having a shearing surface forming an edge of the aperture, against with a rotating member may be driven. Macerating or cutting by shearing against one or more shearing surfaces, which may be static or moving counter to the rotatable cutter, may be particularly advantageous for macerating non-adherent thrombus material that has been driven into a suction lumen. Unlike cutters that drill or core into clot material (particularly adherent clot material) shearing as described herein, including shearing clot material that is already drawn into the aspiration catheter, may more efficiently and effectively macerate clot material without risk damaging the vessel wall.

Any of these apparatuses and methods may include a rotating cutter as part of the macerator. The rotating cutter may be rotated at a distal end of the macerator, within the suction lumen of the macerator. The rotating cutter may be rotated concentrically, e.g., by driving rotation of the cutter from a central axis region, or non-concentrically, e.g., by driving rotation of the cutter from a side region of the cutter, off-axis, that is not the same as the axis of rotation of the cutter (e.g., "off-axis" in reference to the axis of rotation of the cutter). Surprisingly non-concentric cutting may be preferred in some examples and may provide advantages over more traditional concentric rotation. Driving the rotating cutter off-axis (e.g., by coupling a flexible drive shaft to a side or peripheral region of the cutter, that is off-axis relative to the cutter's axis of rotation) may prevent the flexible drive shaft from occluding the region immediately proximal to the shearing surfaces of the opening(s) into the suction lumen. This configuration may also result in a vibration and/or sound when rotating the drive shaft, which may be provide immediate tactile feedback to the user holding the apparatus. Finally, driving the rotating cutter off-axis may allow further maceration by the drive shaft itself as it is driven around (and in some cases across) the periphery of the suction lumen of the macerator; this may also prevent clogging of the macerator.

For example, described herein are macerator apparatuses comprising: an elongate body having a suction lumen extending a length of the elongate body; an opening through a distal end region of the elongate body into the suction lumen; a rotatable cutter including one or more blade surfaces, wherein the rotatable cutter is rotatably mounted to the elongate body so that the one or more blade surfaces is configured to traverse the opening to generate a shearing force between an edge of the opening and the one or more blade surfaces when the rotatable cutter is rotated; and a flexible drive shaft coupled to the rotatable cutter and extending within the suction lumen, wherein the drive shaft is configured to rotate eccentrically within the suction lumen to drive rotation of the rotatable cutter.

As mentioned, the flexible drive shaft is configured to further macerate material within the suction lumen as it rotates eccentrically within the suction lumen. For example, the outer surface of the flexible drive shaft may be textured to assist in maceration. The flexible drive shaft may be configured to rotate around and against the sidewall of the suction lumen of the macerator.

The distal end region of the elongate body may include a plurality of openings through the distal end region, wherein the one or more blade surfaces are configured to traverse each of the plurality of openings to generate a shearing force. Alternatively or additionally, the opening may be or may include a distal-facing opening at a distal end of the elongate body. In some examples the apparatus may include a distal opening that divided up into multiple openings (all distally facing) forming shearing surfaces against which the cutter may rotate to generate shear. As used herein, when the rotating cutter (e.g., cutting edge(s) or surface(s) of the rotating cutter) shear against the shearing surface(s) of the cutter, the cutting edge(s)/surface(s) may be separated from the shearing surface by a controlled distance (e.g., between about 0.1 mm and about 1 mm, between about 0.1 mm and about 0.8 mm, etc.) and are not necessarily touching. Thus, any of these apparatuses may be configured to maintain the spacing between the shearing surface and the cutting edge or surface of the rotating cutter.

In some examples the macerator opening comprises one or more side-facing openings on a lateral side of the distal end region of the macerator. Side-facing openings may be arranged around a perimeter of the distal end of the macerator. As will be described in more detail below, in general, these apparatuses may be configured so that the cutter does not ever fully occlude (and/or does not mostly occlude) the opening(s) of the macerator at any point during rotation of the cutter. This may allow the macerator to be operated as just a smaller-bore aspirator/suction device. This may also prevent variations in the suction due to rapidly opening/closing the openings.

In any of these apparatuses, the flexible drive shaft may be eccentrically coupled to the rotatable cutter, which may result in the eccentric rotation of the cutter. The flexible drive shaft may be coupled direction (e.g., by welding, crimping, etc.) to the rotatable cutter or it may be coupled through a flexible cutter, such as a spring, or more elastic member. This may reduce strain on the cutter, the drive shaft, and/or on the connection between the cutter and the flexible drive shaft. The flexible drive shaft may be affixed axially on the distal end so that the cutting blades dimensional relationship is fixed and rotatably affixed to the driving element on the proximal end allowing for the driving element to apply torque to at least one cutting blade via the drive shaft as well as axial movement of the flexible drive shaft to accommodate the axial changes of the drive shaft as it tracks through tortious regions of the vasculature.

In general, the elongate body of the macerator may be flexible. The elongate body may be formed of a flexible polymeric material that maintains the patency of the suction lumen (including during the application of suction) while permitting the macerator to navigate through tortious regions of the vasculature. In some examples the elongate body may be reinforced, e.g., by including a coil, for example, that allows it to maintain a high degree of flexibility while preventing collapse. In some examples the elongate body may include a hypotube that has been cut (e.g., laser cut) to enhance flexibility. The elongate body may be coated or covered with a material to maintain the seal (so that vacuum may be applied out of the opening(s) at the distal end.

The one or more blade surfaces may be sharpened and/or may include a cutting edge. The shearing surface(s) of the openings may comprise one or more skived windows. Alternatively or additionally, the cutter may include one or more openings that are configured as skived windows.

In some examples the rotatable cutter comprises a tube having an open distal end. As mentioned, the rotatable cutter may be a tube having one or more cutting windows that are configured to shear against the opening(s) of the distal end region.

The rotatable cutter may be configured to rotate within the distal end region of the elongate body. For example, the rotatable cutter may be configured to be housed within the distal end region of the macerator (in communication with the suction lumen) and may fit within a track or channel to guide rotation. Alternatively the cutter may be configured so that it rotates at or within the distal end region without contacting the walls of the apparatus. In some examples the rotatable cutter is secured within the distal end region of the elongate body by a proximal retaining ring.

Any appropriate drive shaft (e.g., flexible drive shaft) may be used. For example, the drive shaft may comprise a metal or polymeric wire(s).

In general, any of the macerator apparatuses described herein may be used as part of a system including an aspiration catheter. For example, any of the macerators described herein may be configured as part of a suction catheter (e.g., may be used within and/or with a suction catheter). The macerator apparatus may be applied through the suction lumen of the aspiration catheter, or it may be applied (e.g., inserted) through a separate lumen. Suction may be directed through both the aspiration catheter lumen and/or through the macerator suction lumen. In some examples the apparatus may control switching between the macerator suction lumen and the aspiration catheter lumen.

In some examples the macerator includes a housing or distal end region at a distal end of the elongate body. For example, the distal end region of the elongate body may comprise a cylindrical housing. The cutter assembly may be housed within the cylindrical housing.

Also described herein are methods of using the apparatuses described herein. For example, described herein are methods or removing clot from a vessel that include: applying suction through an elongate body having a suction lumen extending therethrough; and rotating a flexible drive so that the drive shaft rotates eccentrically within the suction lumen and rotates a cutter at a distal end of the elongate body so that one or more blade surfaces of the cutter traverse an opening into suction lumen so that a clot material is drawn from the vessel into the opening and is cut by a shearing force between an edge of the opening and the one or more blade surfaces. Any of these methods may include macerating the clot material within the lumen with the suction lumen by the flexible drive shaft as rotates eccentrically within the suction lumen.

The macerators described herein may include multiple openings into the suction lumen of the macerator into which clot material may be drawn. The macerator may be configured so that the cutter assembly does not prevent or substantially reduce suction into the suction lumen, even when the cutter is stopped in front of the opening(s). For example, described herein are macerator apparatuses including: an elongate body having a suction lumen extending a length of the elongate body; a plurality of openings through a distal end region of the elongate body into the suction lumen; a rotatable cutter including one or more blade surfaces, wherein the rotatable cutter is rotatably mounted to the elongate body so that the one or more blade surfaces is configured to traverse each of the openings to generate a shearing force between an edge of each opening and the one or more blade surfaces when the rotatable cutter is rotated; and a flexible drive shaft coupled to the rotatable cutter and extending the length of the elongate body, wherein at any rotational position of the one or more blade surfaces of the rotatable cutter the plurality of openings remain sufficiently unobstructed by the rotatable cutter.

The rotatable cutter may occlude, for example, less than x % of the opening(s) into the suction lumen (e.g., the open area into the suction lumen), such as, e.g., 90% or less, 60% or less, 50% or less, 45% or less, 40% or less, 35% or less, 30% or less, etc., of the plurality of openings at any rotational position of the one or more blade surfaces of the rotatable cutter. In some examples, the blade surfaces of the rotatable cutter may be minima; for example, the blades may be a wire or wires extending across the rotatable cutter frame. For example, the "blades" may be one or more wires held in tension across the cutter frame. The wire may be, e.g., a tungsten wire.

The rotatable cutter and the one or more blades may be configured so that as the rotatable cutter is rotated, the plurality of openings remain sufficiently unobstructed by the cutter to maintain an aggregate open area into the suction lumen that is greater than at least a percentage (e.g., 50% or more, 60% or more, 70% or more, 80% or more, 85% or more, 90% or more, 100% or more, 110% or more, 120% or more, etc.) of a cross-sectional area of the suction lumen.

The rotatable cutter and the one or more blades may be configured so that as the rotatable cuter is rotated, the plurality of openings remains sufficiently unobstructed by the cutter to maintain the aggregate open area into the suction lumen that is greater than or equal to the cross-sectional area of the suction lumen. The plurality of openings may be arranged circumferentially around the distal end region of the elongate body. In some examples the distal end region of the elongate body may comprise a cylindrical housing.

The flexible drive shaft may be configured to rotate eccentrically within the suction lumen. The flexible drive shaft may be eccentrically coupled to the rotatable cutter.

In some examples, one of the openings of the plurality of openings is a distal-facing opening at a distal end of the elongate body. In some examples, the distal-facing end of the macerator may include multiple openings, including a large opening that is divided up into multiple openings, by one or more shearing surfaces (e.g., a strut, support, beam, crosspiece, etc.).

Any of these apparatuses may include a distal-facing opening at a distal end of the elongate body, wherein the area of the distal-facing opening is included in the aggregate open area. In some examples the distal-facing end of the macerator is always open.

The plurality of openings may include a plurality of side-facing openings on a lateral side of the distal end region.

In general, the elongate body may be a flexible elongate body.

The one or more blade surfaces may include one or more skived windows. For example, the cutter may be a cylindrical cutter assembly that includes one or more openings that may shear relative to the openings in the plurality of openings through a distal end region of the elongate body. Thus, the rotatable cutter may comprise a tube. In some examples the rotatable cutter is configured to rotate within the distal end region of the elongate body. The rotatable cutter may be secured within the distal end region of the elongate body by a proximal retaining ring.

Also described herein are apparatuses in which the rotatable cutter is configured to have a minimal elongated (longitudinal) width or thicknesses as it extends down the proximal-to-distal axis of the macerator. This may help maintain the flexibility of the macerator, which may be particularly helpful as the macerator (or macerator and an aspiration catheter within which the macerator is inserted) navigates through the often tortious regions of the vasculature. For example, any of these macerator apparatuses described herein may include a distal-facing shearing cutter (cutter assembly) having a narrow length (e.g., longitudinal length or equivalently longitudinal width). For example, the cutter assembly may have a longitudinal width that is short, such as less than about 0.8 times the diameter of the suction lumen (e.g., about 0.9 times or less than the diameter, about 0.8 times or less than the diameter of the suction lumen, about 0.75 times or less than the diameter of the suction lumen, about 0.7 times or less than the diameter of the suction lumen, about 0.65 times or less than the diameter of the suction lumen, etc.).

In general, any of these apparatuses may be distal-facing macerators, so that the one or more openings into the macerator are distal facing and may be sheared by a rotating cutter that is oriented for distal-facing cutting. For example, a rotating blade or blades may be oriented distally. The one or more cutters (e.g., blades) may be pinned distally so that they may spin within the distal end region to shear any clot material that enters into the distal facing openings. As described, the cutter assembly at the distal end region may be relatively small (e.g., approximately the diameter of the suction lumen or smaller) thus, the overall macerator, including the distal end region may remain highly flexible, allowing it to navigate through a tortious path, including within an aspiration lumen of an aspiration catheter.

For example, a macerator apparatus may include: an elongate body having a suction lumen extending a length of the elongate body, wherein the suction lumen is flexible; an opening at a distal end of the elongate body into the suction lumen; one or more projections extending at least partially across the opening forming a shearing surface; a rotatable cutter including one or more blade surfaces, wherein the rotatable cutter is rotatably mounted to the elongate body so that the one or more blade surfaces are configured to rotate relative to the one or more projections to generate a shearing force between the shearing surfaces and the one or more blade surfaces when the rotatable cutter is rotated, wherein the rotatable cutter has a longitudinal thickness that is less than 90% of the diameter of the suction lumen; and a flexible drive shaft coupled to the rotatable cutter and extending within the suction lumen.

The rotatable cutter may be coupled to the distal end of the macerator (e.g., the macerator elongate body) in communication with the one or more openings) to that it may rotate the cutter assembly (e.g., blades) while the elongate body, including the distal end region is curved or bent, while minimizing the strain on the connection between the drive shaft (e.g., wire) and the cutter assembly (e.g., rotatable cutter). In some examples the rotatable cutter may be coupled to the drive shave via an elastic joint, or a spring joint (e.g., a helical spring), permitting bending, while maintain the torsional stiffness to permit rotation, which may also be referred to as an "elastic" joining section. The distal end of the drive shaft may be mounted to the cutter and/or to the distal end region of the macerator body via a flexible joint, such as a ball joint. Thus the drive shaft may be configured to angulate slightly relative to the distal end region (e.g., shearing surface and/or rotatable cutter). For example, the rotatable cutter may be coupled to the flexible drive shaft via a ball connector. In some examples the flexible drive shaft may be coupled to the rotatable cutter via a spring connection.

The longitudinal thickness of the rotatable cutter (cutter assembly) may be, e.g., less than half of the diameter of the suction lumen. The flexible drive shaft may be configured to rotate eccentrically within the suction lumen. In some examples, the flexible drive shaft may be eccentrically coupled to the rotatable cutter.

As mentioned, the flexible drive shaft may comprise a metal wire (e.g. a stainless steel wire).

Any of these macerators described herein may be used with and/or may be part of a system including an aspiration catheter. In some cases the aspiration catheter may include a maceration chamber. For example, described herein are apparatuses comprising: an elongate body comprising a lumen extending from a proximal end to a distal end region; a maceration chamber at the distal end region of the elongate body and in fluid communication with the lumen, and further wherein the maceration chamber has a distal-facing end that is at least partially closed; an aperture on the distal-facing end of the maceration chamber that is configured to open; and a macerator positioned within the maceration chamber, the macerator having a suction lumen extending therethrough and a distal rotatable cutter, wherein the macerator is configured suck a clot from within the maceration chamber through the distal rotatable cutter to macerate the clot, and to suck the macerator clot through the suction lumen. The distal-facing end may be configured to deform to open the aperture. For example, the distal-facing end may be formed of an elastomeric material.

Any of these apparatuses may include a control configured to apply suction to either or both the lumen of the elongate body and the suction lumen of the macerator. Any of these apparatuses may include a guide lumen extending adjacent to the suction lumen, wherein the guide lumen extends distal of the distal-facing end of the maceration chamber. The aperture may provide exclusive access into the maceration chamber from a body lumen into which the apparatus is inserted.

The aperture may be further configured to exert a radially inward gripping force to hold clot material in the aperture. The distal-facing end of the maceration chamber may be tapered as it extends distally. The maceration chamber may be formed of a fluid-impermeable material. In some examples the maceration chamber is larger in diameter than the inner diameter of the lumen of the elongate body. In some examples the maceration chamber is configured to self-expand radially outwards into a deployed configuration.

As described above, the macerator may comprise a rotatable cutter including one or more blade surfaces, wherein the rotatable cutter is rotatably mounted to a body in fluid communication with an opening into the suction lumen so that the one or more blade surfaces of the cutter are configured to traverse the opening to generate a shearing force between an edge of the opening and the one or more blade surfaces when the rotatable cutter is rotated. The macerator may be coupled to a rotatable drive shaft extending within the suction lumen. In some examples the rotatable drive shaft is configured to eccentrically rotate within the suction lumen. A distal end of the macerator within the maceration chamber may be enclosed by a cover having one or more lateral openings into the suction lumen.

Also described herein are methods of removing clot from a body vessel using any of these apparatuses. For example, a method may include: positioning a distal-facing end of a maceration chamber of a device so that an aperture though the distal-facing end of the maceration chamber is adjacent to a clot material; applying suction from a suction lumen within the maceration chamber to draw the clot material into the maceration chamber through the aperture, so that the aperture elastically deforms around the clot material to hold the clot material within the maceration chamber; and macerating the clot material within the maceration chamber and removing macerated clot material from the maceration chamber through the suction lumen.

Also described herein are methods of removing material from within a suction lumen of the elongate body (e.g., of an aspiration catheter). For example, a method may include: advancing a macerator distally within a first suction lumen, wherein the macerator comprises an elongate body having a second suction lumen extending a length of the elongate body, an opening at a distal end of the elongate body into the suction lumen, one or more projections extending at least partially across the opening forming a shearing surface and a rotatable cutter including one or more blade surfaces, driving a flexible drive shaft coupled to the rotatable cutter to rotate the rotatable cutter so that the one or more blade surfaces rotate relative to the one or more projections to generate a shearing force between the shearing surfaces and the one or more blade surfaces to macerate any clot within the first suction lumen; and sucking macerator clot through the second suction lumen.

Advancing the macerator distally may include advancing the macerater into a maceration chamber at a distal end of the first suction lumen. Driving the flexible drive shaft coupled to the rotatable cutter to rotate the rotatable cutter may comprise driving a distal-facing rotatable cutter. Driving the flexible drive shaft may comprise driving the drive shaft off-axis within the section suction lumen. Any of these methods may include automatically turning off driving of the drive shaft when a distal end of the macerator extends distally out of the first suction lumen.

Any of these methods may include apply suction through the second suction lumen while advancing the macerator distally and concurrently driving the flexible drive shaft to rotate the rotatable cutter. For example, these methods may include applying suction through both the first and second suction lumen. In some examples the method may include turning off suction through the first suction lumen when applying suction through the second suction lumen.

All of the methods and apparatuses described herein, in any combination, are herein contemplated and can be used to achieve the benefits as described herein.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

In FIG. 2E, the cover has been removed from the capture structure to better view the frame.

FIGS. 4A-4C show a method for engaging clot material

FIGS. 9 and 10A show a distal portion of a treatment system in a collapsed state and an expanded state, respectively, in accordance with several embodiments of the present technology.

FIGS. 17A-17C are various views of a disrupting element configured in accordance with several embodiments of the present technology.

FIGS. 18A-18C are various views of a disrupting element configured in accordance with several embodiments of the present technology.

FIGS. 37A-37F schematically illustrate one example of a macerator apparatus.

FIG. 38 shows a schematic of a distal end of a macerator.

FIGS. 39A-39B show examples of a portion of a macerator.

FIGS. 40A-40B illustrate component portions of one example of a macerator.

FIGS. 41A-41C show an exploded view, a side perspective view and a section of an example of a cutter assembly of a macerator.

FIGS. 42A-42D illustrate operation of one example of a macerator.

FIGS. 43A-43F illustrate operation of an example of a macerator.

FIGS. 44A-44B illustrate examples of a macerator with a region removed to show the suction lumen and drive member.

FIGS. 47A-47D illustrate another example of a macerator having three open lateral macerator windows (FIGS. 47A and 47B) or four open lateral macerator windows (FIGS. 47C and 47D).

FIG. 48 shows an example of a portion of a distal-facing macerator.

FIGS. 49A-49B shows an example of a distal-facing macerator apparatus.

FIGS. 53A and 53B show an example of a macerator that does not include a suction lumen but may be used within the suction lumen of an aspiration catheter. FIG. 53A shows a side perspective view and FIG. 53B shows a distal end view.

FIGS. 53C and 53D show another example of a macerator that does not include a suction lumen but may be used within the suction lumen of an aspiration catheter. FIG. 53C shows a side perspective view and FIG. 53D shows a distal end view.

FIG. 54A shows a perspective view.

DETAILED DESCRIPTION

Figure 1:
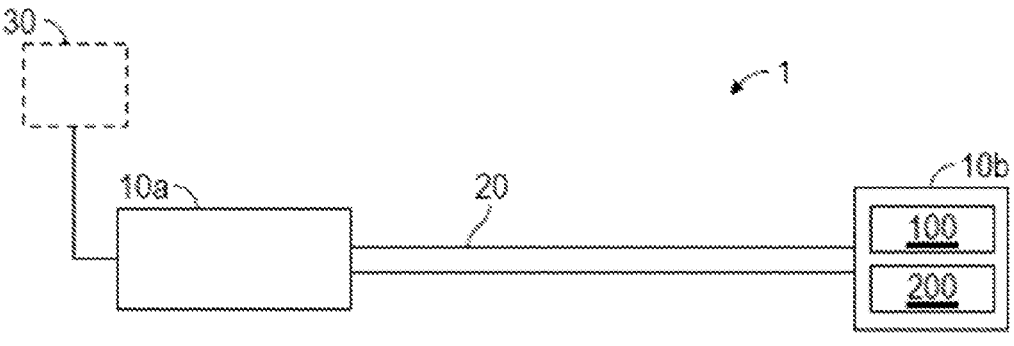
FIG. 1 schematically depicts a treatment system configured in accordance with several embodiments of the present technology.

FIG. 1 schematically depicts a treatment system 1 (also referred to herein as "the system 1") configured in accordance with the present technology. The treatment system 1 is configured to access a blood vessel (such as a vein or an artery) and disrupt, capture, and/or remove obstructive material from the blood vessel lumen. As used herein, "obstruction" or "obstructive material" can comprise, for example, clot material, atherosclerotic plaque, and/or other flow-obstructing structures, including those derivative of clot material, such as fibrotic clot material. Moreover, as used herein, the act of "disrupting" obstructive material includes breaking the material into smaller pieces, modifying the shape of the material, stretching and/or elongating the material, compressing the material, permanently or temporarily repositioning all or a portion of the material, extracting all or a portion of the material, macerating the material, morcellating the material, and/or any other action that modifies the obstructive material.

As shown in FIG. 1, the system 1 may comprise a proximal portion 10a configured to be positioned outside of the patient's body during the procedure, a distal portion 10b configured to be positioned at a treatment site within a blood vessel, and one or more elongated shafts 20 extending between the proximal portion 10a and the distal portion 10b. The proximal portion 10b can comprise one or more handles, actuators, and/or connectors that are coupled to a proximal end region of the elongated shaft(s) 20 to facilitate delivery and/or removal of fluids and other material from the treatment site, as well as to provide a means for manipulating the distal portion 10b of the system 1. In some embodiments, the system 1 further comprises a negative pressure source 30 configured to be fluidly coupled to the distal portion 10*b* via the one or more handles and the elongated shaft(s) 20.

The distal portion 10*b* of the system 1 can include a capture structure 100 and a disrupting element 200 that work synergistically to engage and process obstructive material at the treatment site to enable removal of the obstructive material through the elongated shaft(s) 20. The capture structure 100 can be any of the capture structures disclosed herein, and the disrupting element 200 can be any of the disrupting elements and/or disruptors disclosed herein. In some embodiments of the treatment system 1, the distal portion 10*b* includes only the capture structure 100 and does not include a disrupting element 200.

The capture structure 100 can be carried by a distal end region of the elongated shaft(s) 20 and is configured to engage and capture obstructive material at the treatment site. In some embodiments the capture structure 100 is integral with the elongated shaft(s) 20, and in some embodiments the capture structure 100 is a separate component that is coupled to a distal end region of the elongated shaft(s) 20. The capture structure 100 can be configured to transform between a collapsed or low-profile state for navigation through the vasculature and an expanded state for engaging the obstructive material. In some embodiments, the capture structure 100 has an outer cross-sectional dimension in the collapsed state that is substantially the same as or less than that of the elongated shaft(s) 20, and an outer cross-sectional dimension in the expanded state that is greater than that of the elongated shaft(s) 20. The elongated shaft(s) 20 and/or collapsed capture structure 100 can have an outer cross-sectional dimension of 24 Fr or less, 20 Fr or less, or 16 Fr or less, and the expanded capture structure 100 can have an outer cross-sectional dimension of greater than 24 Fr, including 28 Fr or greater, 36 Fr or greater, 40 Fr or greater, or 45 Fr or greater. The versatile profile of the capture structure 100 confers the delivery advantages associated with a smaller profile catheter, such as improved trackability and reduced risk of damaging a vessel wall or heart structure, as well as the therapeutic benefits of a larger diameter capture structure, such as the ability to engage, hold on to, and remove large volumes of obstructive material efficiently. Efficient material removal reduces the number of passes required to remove all of the obstructive material from the treatment site, which reduces the amount of blood loss and procedure time.

In the expanded state, the capture structure 100 may comprise a fluid impermeable housing that provides a substantially enclosed working space that is configured to receive obstructive material for further processing and extraction from the body. The capture structure 100 can include a small orifice in the housing that is configured to engage and receive the obstructive material. The portion of the capture structure 100 defining the orifice can comprise a material configured to deform in response to negative pressure and/or engagement with the obstructive material, thereby enlarging the orifice. According to several embodiments, if no obstructive material is positioned against the orifice when aspiration is applied, the orifice may deform slightly but the change will be relatively small (i.e., less than 20% of the orifice's original cross-sectional dimension, less than the cross-sectional dimension of the interior region of the capture structure 100, etc.) until the obstructive material is engaged. Limiting the size of the orifice in this way advantageously reduces blood loss during aspiration.

The interior region of the capture structure 100 can be fluidly coupled to the negative pressure source 30 via the elongated shaft 24, and negative pressure can be applied to the capture structure 100 to draw obstructive material through the orifice and continue pulling the material proximally through the elongated shaft(s) 20 to a location outside of the patient's body. Instead of or in addition to applying aspiration to engage the obstructive material and/or pull the obstructive material into the capture structure 100, the operator can advance the capture structure 100 onto and over the obstructive material to force the obstructive material through the orifice. Engagement of the obstructive material in this manner deforms the wall surrounding the opening, thereby enlarging the opening to receive larger volumes of obstructive material and increasing the aspiration force applied at the orifice.

Once all or a portion of the obstructive material is disposed within the capture structure 100, the disrupting element 200 can be activated (if necessary) to disrupt the obstructive material so that the obstructive material is in a form conducive to aspiration through the elongated shaft(s) 20. In some embodiments, the disrupting element 200 disrupts the obstructive material as it enters the interior region of the capture structure 100 and/or a lumen of the elongated shaft(s) 20.

I. Selected System Embodiments

Figure 2A:
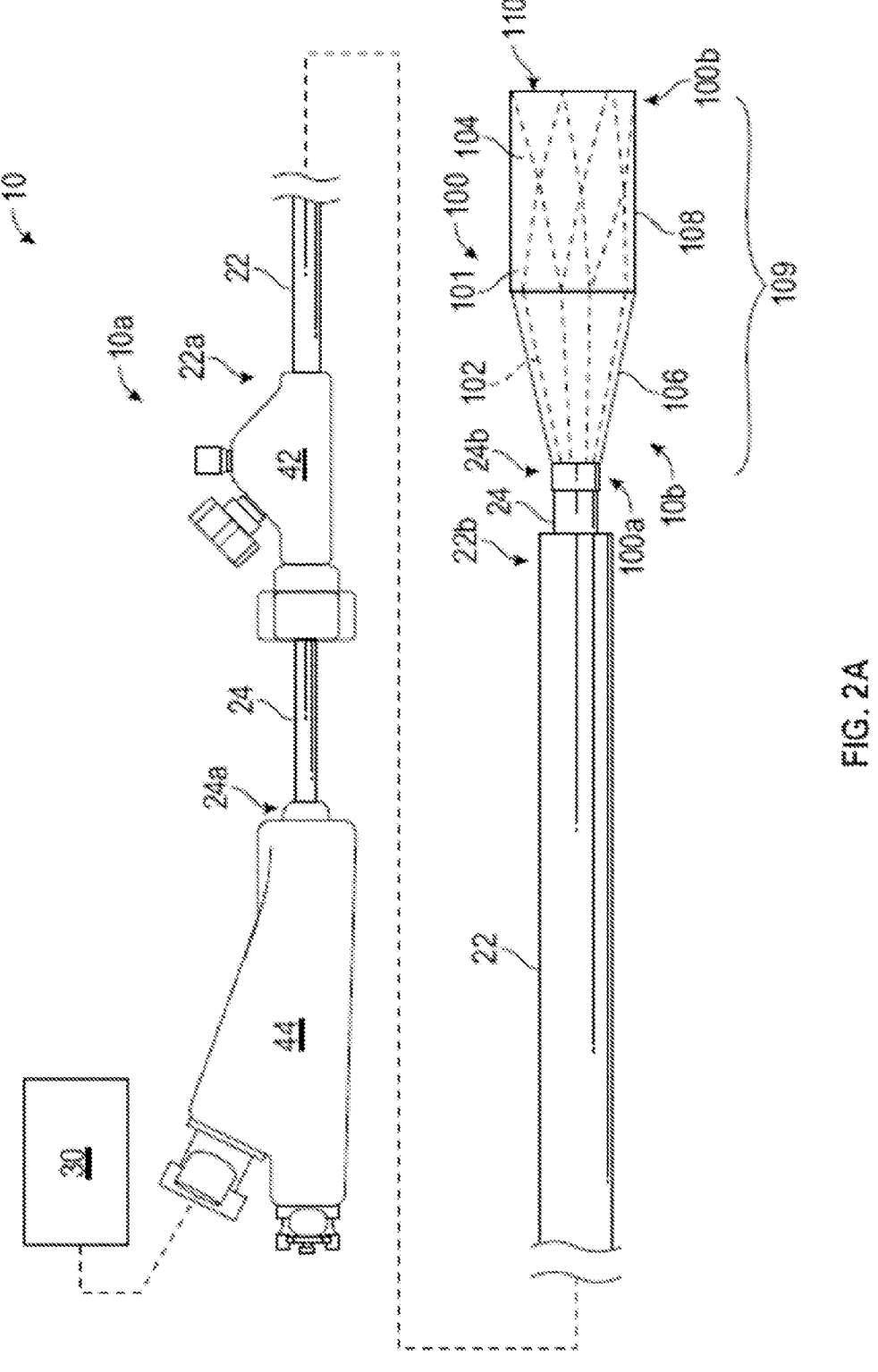
FIG. 2A shows a treatment system configured in accordance with several embodiments of the present technology.

FIG. 2A shows a treatment system 10 configured in accordance with several embodiments of the present technology. The treatment system 10 includes a proximal portion 10*a* configured to be extracorporeally positioned during a procedure and a distal portion 10*b* configured to be intravascularly delivered to a treatment site within a blood vessel. The distal portion 10*b* can comprise a capture structure 100 configured to engage, capture, and/or process obstructive material to facilitate removal of the obstructive material from the patient's body. The capture structure 100 can have a collapsed or low-profile state for delivery through the vasculature to the treatment site, and an expanded state (shown in FIG. 2A) for engaging with the obstructive material.

As shown in FIG. 2A, the treatment system 10 can include a sheath 22 and an elongated shaft 24 extending between the proximal and distal portions 10*a*, 10*b* of the system 10. The sheath 22 can be a generally tubular member having a proximal end portion 22*a*, a distal end portion 22*b*, and a lumen extending therethrough. The elongated shaft 24 can also be a generally tubular member having a proximal end portion 24*a*, a distal end portion 24*b*, and a lumen extending therethrough. The elongated shaft 24 can be configured to be slidably positioned through the lumen of the sheath 22. In some embodiments, the capture structure 100 is carried by a distal end portion 24*b* of the elongated shaft 24, and both the elongated shaft 24 and the capture structure 100 are configured to be slidably disposed within the sheath's lumen. In those embodiments where the capture structure 100 is self-expanding, the sheath 22 can be configured to radially constrain the capture structure 100 during delivery of the distal portion 10*b* and release the capture structure 100 to self-expand into the expanded state upon proximal withdrawal of the sheath 22.

The proximal portion 10*a* of the system 10 can include a first hub 42 and a second hub 44 configured to be positioned external to the patient. A distal region of the first hub 42 can be secured to the proximal end portion 22*a* of the sheath 22, and a proximal region of the first hub 42 can include an opening configured to slidably receive the elongated shaft 24 therethrough. A distal region of the second hub 44 can be secured to the proximal end portion 24a of the elongated shaft 24, and a proximal region of the second hub 44 can include an opening configured to receive a guidewire and/or another interventional device therethrough (such as a disrupting element, as discussed in greater detail herein). In some embodiments, the system 10 can include a manipulation member (not shown) having a first end coupled to an actuator at a hub (such as first hub 42 and/or second hub 44) and a second end coupled to a distal portion of the corresponding elongated shaft 24 and/or sheath 22. The manipulation member is configured to bend, flex, and/or otherwise articulate a distal portion of the corresponding elongated shaft 24 and/or sheath 22 when actuated by the operator.

The first and/or second hubs 42, 44 can include a hemostatic adaptor, a Tuohy Borst adaptor, and/or other suitable connectors, valves and/or sealing devices. For example, in some embodiments, the second hub 44 includes a connector configured to be coupled to a negative pressure source 30 (shown schematically), such as a syringe or a vacuum pump, for applying a negative pressure through a lumen of the elongated shaft 24. Additionally or alternatively, the first hub 42 can include a connector configured to be coupled to a negative pressure source 30 for applying a negative pressure through a lumen of the sheath 22. In some embodiments, the first and/or second hub 42, 44 can include a port configured to be coupled to a fluid source for delivering one or more fluids to the treatment site before, during and/or after the procedure (e.g., contrast, saline, etc.). Additionally or alternatively, the first and/or second hubs 42, 44 can include one or more ports configured to be coupled to a collection chamber for receiving and containing aspirated material from the treatment site. In some embodiments, the first and/or second hub 42, 44 includes one or more actuators that enable the operator to manipulate the distal portion 10b of the system 10. For example, the second hub 44 can include an actuator for controlling the curvature of an articulating region of the elongated shaft 24, as discussed in greater detail herein.

Figures 2B, 2C, 2D:
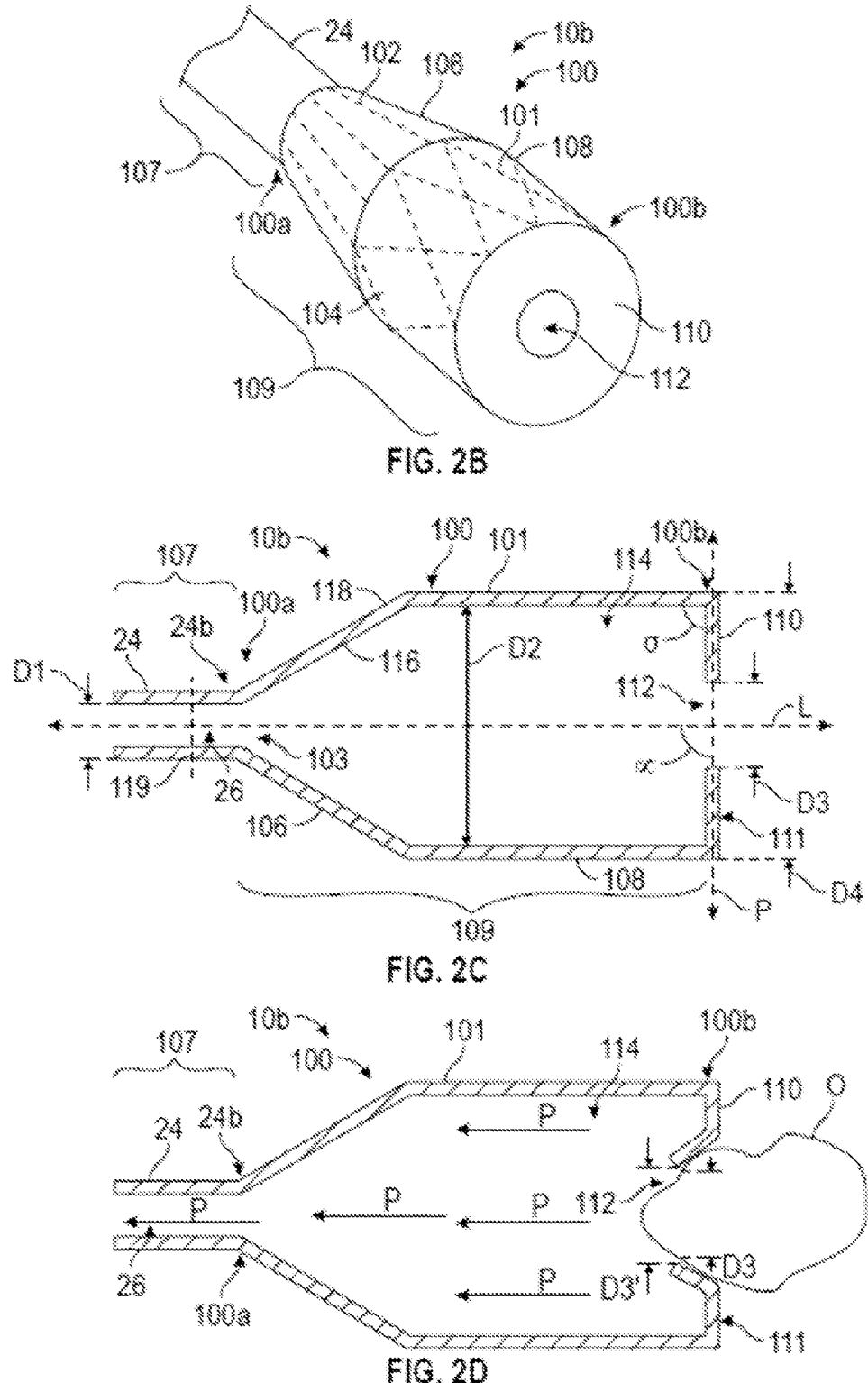
FIG. 2B is an isometric view of a distal portion of the treatment system shown in FIG. 2A.
FIG. 2C is a partially schematic cross-sectional side view of the distal portion of the treatment system shown in FIGS. 2A and 2B.
FIG. 2D schematically depicts the capture structure shown in FIG. 2C engaging obstructive material.

At least in the expanded state, the capture structure 100 can enclose an interior region 114 (see FIG. 2C) that is configured to receive and process obstructive material from the treatment site to facilitate removal of the obstructive material from the patient's body. As shown in FIGS. 2A and 2B, the capture structure 100 can have a proximal end portion 100a, a distal end portion 100b, and a longitudinal axis L (FIG. 2C) extending therebetween. The proximal end portion 100a of the capture structure 100 defines a proximal opening 103 (see FIG. 2C) and is coupled to the distal end portion 24b of the elongated shaft 24. As such, the interior region 114 of the capture structure 100 is fluidly coupled to the lumen of the elongated shaft 24 such that negative pressure applied to the lumen of the elongated shaft 24 is also applied to the interior region 114 of the capture structure 100. The lumen of the elongated shaft 24 and the interior region 114 of the capture structure 100 can be referred to together as "the aspiration lumen."

The wall of the capture structure 100 can comprise a tubular sidewall 109 extending longitudinally between the first and second end portions 100a, 100b and an engagement wall and/or surface 110 extending across a distal end of the sidewall 109. The tubular sidewall 109 can extend between a proximal opening and a distal opening, and can comprise a tapered portion 106 and a substantially cylindrical portion 108. In some embodiments, the sidewall 109 and/or capture structure 100 comprises a neck portion 107 at the proximal end of the tapered portion 106 that is configured to be coupled to the distal end portion 24b of the elongated shaft

24. The neck portion 107 can have a cross-sectional dimension less than a cross-sectional dimension of the main body of the capture structure 100. All or a portion of the neck portion 107 can be positioned over or within the distal end portion 24b of the elongated shaft 24, or the capture structure 100 and/or neck portion 107 can be joined end-to-end. In some embodiments, the capture structure and/or sidewall 109 do not include a neck portion 107 and the proximal end of the tapered portion 106 is coupled to the distal end portion 24b of the elongated shaft 24.

The engagement wall 110 can extend across and cover a portion of the sidewall 109. In the example shown in FIGS. 2A-2C, the sidewall 109 has an annular distal surface and the engagement wall 110 extends across that surface, thereby forming a distal face of the capture structure 100. In those embodiments where the opening 112 and/or engagement wall 110 are disposed at another portion of the capture structure 100 (as detailed below), such as along the substantially cylindrical portion 108 or tapered portion 106, the engagement wall 110 does not comprise the distal face of the capture structure 100. The engagement wall 110 includes an outer engagement surface 111 configured to contact obstructive material at the treatment site and an opening 112 configured to receive obstructive material therethrough. In some embodiments, the engagement wall 110 coincides with and/or comprises the distal-most portion of the capture structure 100, at least when the capture structure 100 is in a resting state.

Figures 5A, 5B, 5C:
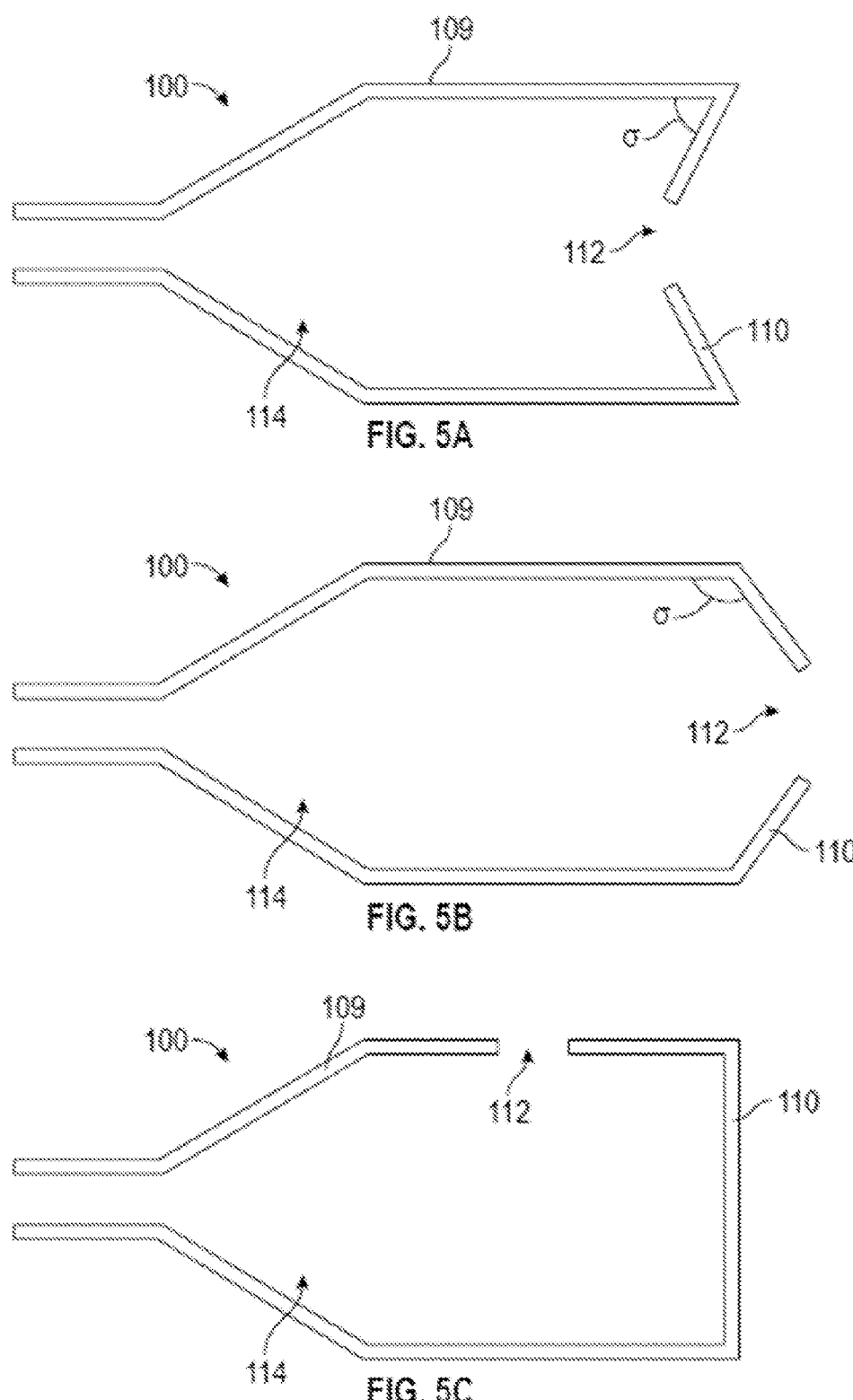
FIGS. 5A-5I depict different capture structure configurations in accordance with the present technology.
Figures 5D, 5E, 5F:
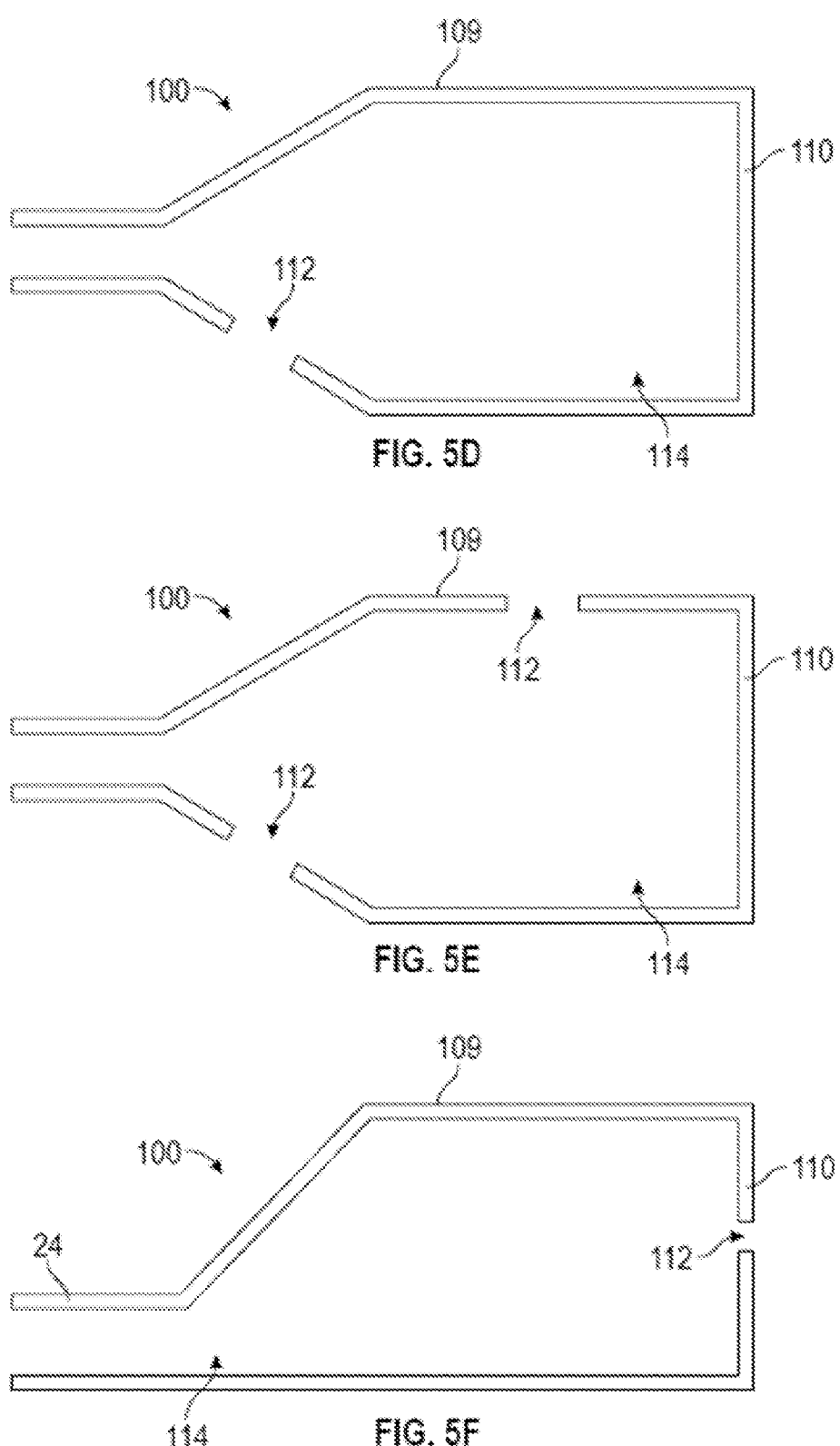

According to several aspects of the present technology, all or a portion of the engagement wall 110 and/or opening 112 is disposed proximal of the distal-most portion of the capture structure 100. For example, the engagement wall 110 and/or opening 112 can be disposed at and/or along the sidewall 109 (for example, as shown in FIGS. 5C and 5D). In such embodiments, the distal face of the capture structure 100 can be closed (e.g., does not include an opening 112). A laterally-positioned engagement wall 110 and/or opening 112 can be beneficial for engaging obstructive material positioned laterally of the capture structure 100 within the blood vessel. In these and other embodiments, the engagement wall 110 can extend toward the interior region 114 such that at least the portions of the engagement wall 110 surrounding the opening 112 are proximal of the distal terminus of the capture structure 100, even in the resting state.

Figures 5G, 5H, 5I:
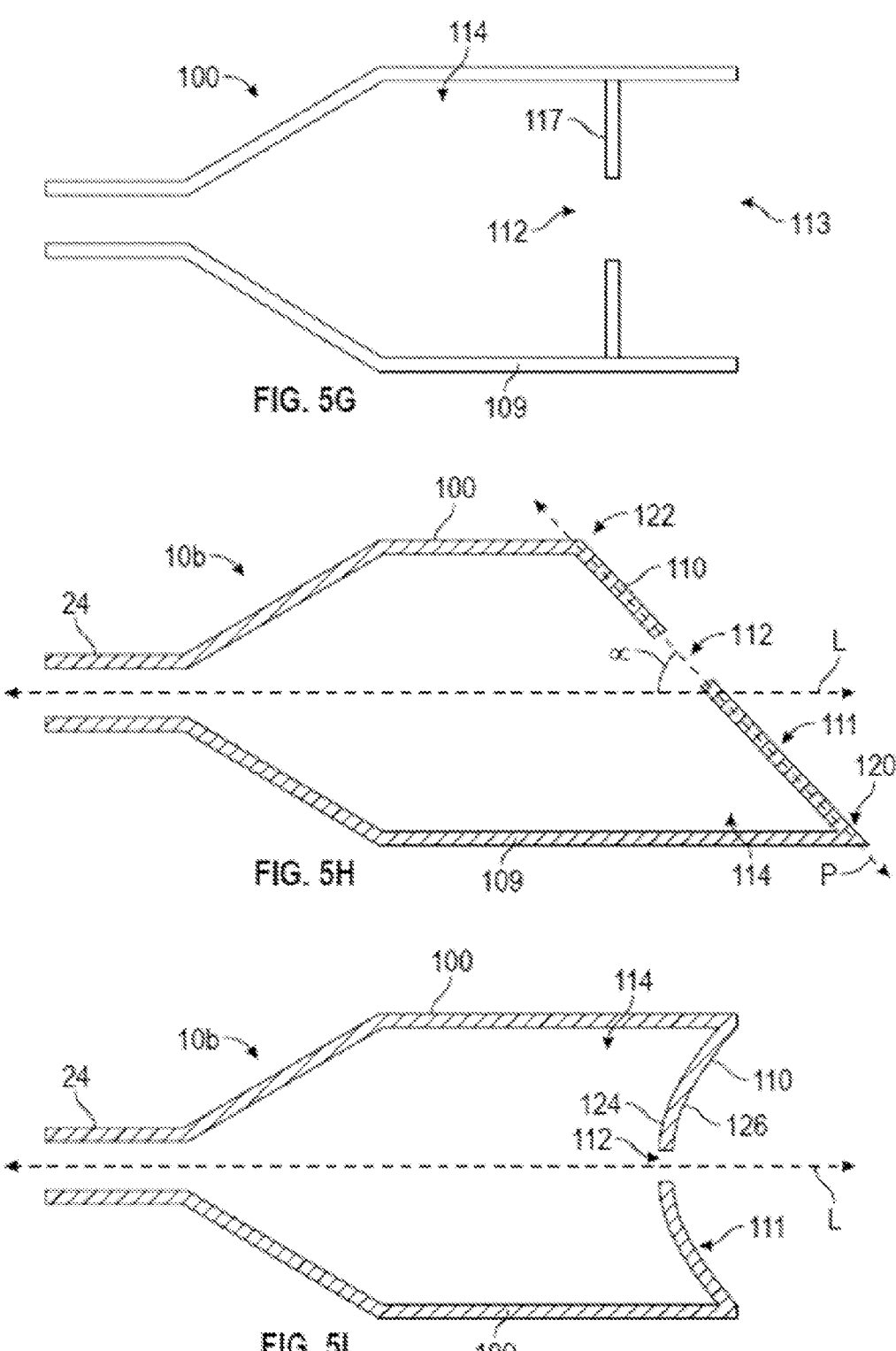

As best shown in FIGS. 2B and 2C, the engagement wall 110 can extend radially inwardly from the annular distal end of the sidewall 109. The engagement wall 110 can lie in a plane P that is substantially perpendicular to a longitudinal axis L of the capture structure 100 (as shown in FIGS. 2A-2D), or the engagement wall 110 may extend radially inwardly from the sidewall 109 in a proximal direction (as shown in FIG. 5A), or may extend radially inwardly from the sidewall 109 in a distal direction (as shown in FIG. 5B). In some embodiments, for example as shown in FIG. 5H, the engagement wall 110 lies within a plane P that is angled relative to the longitudinal axis L of the capture structure 100. In such embodiments, the engagement wall 110 can have a more distal leading edge 120 and a more proximal trailing edge 122. Such a configuration can be beneficial for locating an orifice 112 in the engagement wall 110 at or adjacent to the obstructive material, dislodging obstructive material from a vessel wall, and/or receiving the obstructive material within the interior region 114 of the capture structure 100. For example, the capture structure 100 can be rotated about its longitudinal axis L to align the orifice 112 with obstructive material located at various circumferential locations within a blood vessel. Such a configuration can also enhance collapsibility of the capture structure 100.

The engagement wall 110 can have an orifice 112 configured to receive obstructive material therethrough. As shown in the partially schematic cross-sectional view of the capture structure 100 in FIG. 2C, the orifice 112 can have a resting cross-sectional dimension D3 that is less than a cross-sectional dimension D2 of the interior region 114 of the capture structure 100 in the expanded state. As such, the capture structure 100 initially presents a smaller aspiration area (as compared to a capture structure without the engagement wall 110), which can be especially beneficial when aspirating obstructive material smaller than an inner cross-sectional dimension of the capture structure 100. The engagement wall 110 and orifice 112 provide a reduced cross-sectional aspiration area during initial aspiration that reduces the unintended collateral aspiration of blood and thus helps limit unnecessary blood loss during the procedure.

In any of the embodiments disclosed herein, the resting cross-sectional dimension D3 of the orifice 112 can be of from about 1 mm to about 10 mm. In those embodiments in which the orifice 112 comprises a slit or puncture in the engagement wall 110, the resting cross-sectional dimension D3 of the orifice 112 is effectively zero. Additional details regarding slits and punctures are discussed below with reference to FIGS. 6A-6D.

In some embodiments, the resting cross-sectional dimension D3 of the orifice 112 can be less than an inner cross-sectional dimension D2 of the capture structure 100 but greater than an inner cross-sectional dimension D1 of the elongated shaft 24. In such embodiments, the capture structure 100 is configured to provide an aspiration cross-sectional area and force that is greater than the aspiration cross-sectional area and force would be if aspiration were applied only through the opening at the distal end of the elongated shaft 24. According to some embodiments, the resting cross-sectional dimension D3 of the orifice 112 can be less than an inner cross-sectional dimension D2 of the capture structure 100 and less than an inner cross-sectional dimension D1 of the elongated shaft 24. Reducing the size of the orifice 112 can be desirable for containing captured obstructive material within the interior region 114 of the capture structure 100 and limiting egress of captured material through the orifice 112.

In some embodiments, the engagement wall 110 can comprise a material configured to deform in response to negative pressure and/or engagement with the obstructive material. The engagement wall 110, for example, can be configured to stretch and/or bend proximally in response to proximally-directed negative pressure. The engagement wall 110 can also be configured to stretch and/or bend to accommodate progressively larger portions of obstructive material urged into contact with the opening. With or without aspiration, the capture structure 100 can be urged distally against obstructive material, which can exert an opposing force on the engagement wall 110. As depicted in FIG. 2D, for example, the engagement wall 110 can stretch, bend, and/or otherwise deform to adapt to the size of the obstructive material and enlarge a cross-sectional dimension D3 of the orifice 112 (from D3 to D3'). The increased cross-sectional area of the orifice 112, in turn, simultaneously allows more material to be aspirated and increases an aspiration force applied on the obstructive material (described in greater detail below with reference to FIGS. 4A-4C). While the obstructive material is positioned through the orifice 112, the portion of the engagement wall 110 surrounding the orifice

112 can elastically constrict the obstructive material and thus secure the obstructive material in the absence or reduction of aspiration engagement. In such cases, the radially inward force applied to the material by the portion of the engagement wall 110 surrounding the orifice 112 can be greater than the force generated by the blood acting on the material hanging outside of the capture structure 100 but less than the force generated by the negative pressure source through the elongated shaft 24. As such, the orifice 112 is configured to engage the obstructive material in such a way that prevents the obstructive material from escaping the capture structure 100 yet still allows the material to continue to advance through the lumen of the elongated shaft 24 to a location outside of the body.

Figure 2E:
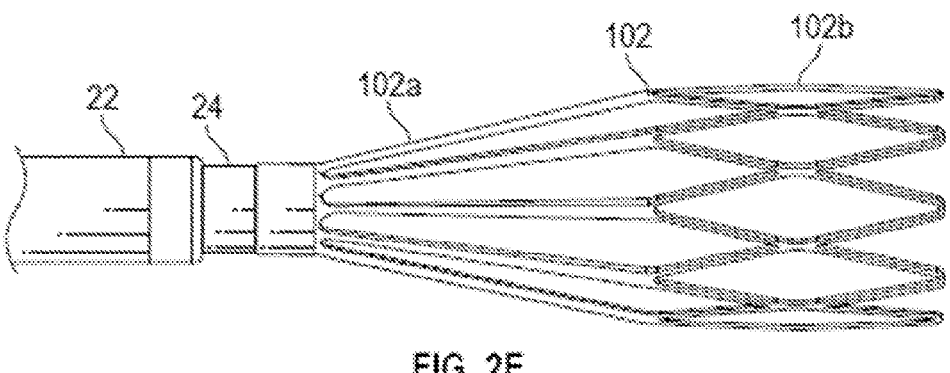
FIG. 2E is an enlarged side view of the distal portion shown in FIGS. 2A and 2B.
Figure 2F:
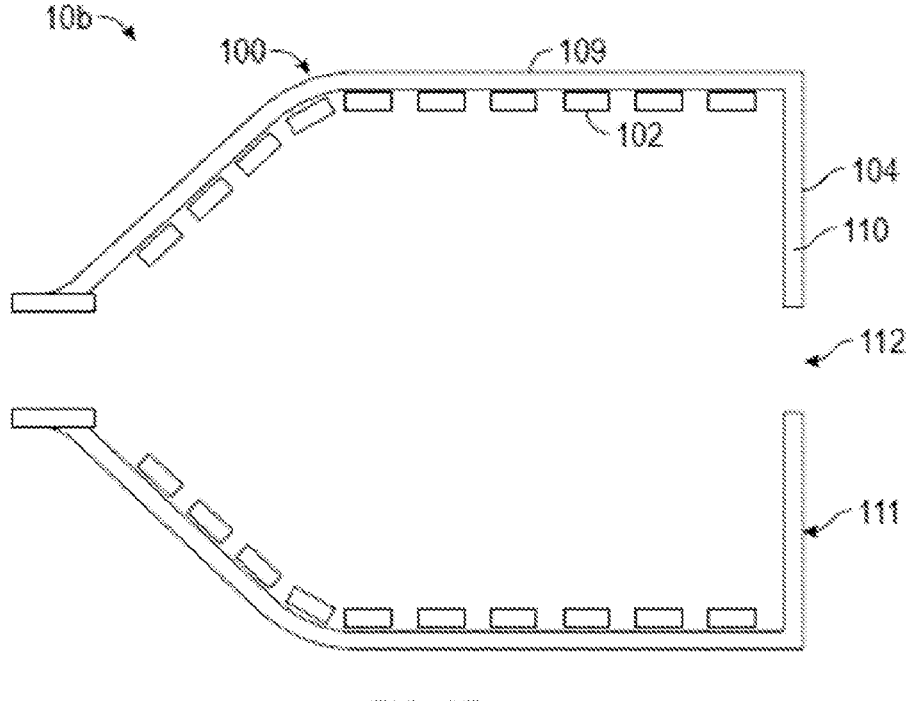
FIG. 2F is a partially schematic cross-sectional side view of the distal portion of the treatment system shown in FIGS. 2A-2E.

In some embodiments, the wall defining the capture structure 100 comprises a frame and a cover. For example, the wall of the capture structure 100 can comprise a frame 102 and a cover 104 disposed on the frame 102. FIG. 2E shows the capture structure 100 with the cover 104 removed for better visualization of the frame 102. FIG. 2F is a partially schematic cross-sectional view of the capture structure 100 showing the frame 102 and the cover 104. The frame 102 is configured to provide structural support to the capture structure 100 while the cover 104 provides a fluid impermeable layer that protects the interior region 114 and enables creation of an aspiration lumen within the interior region 114.

Figure 3:
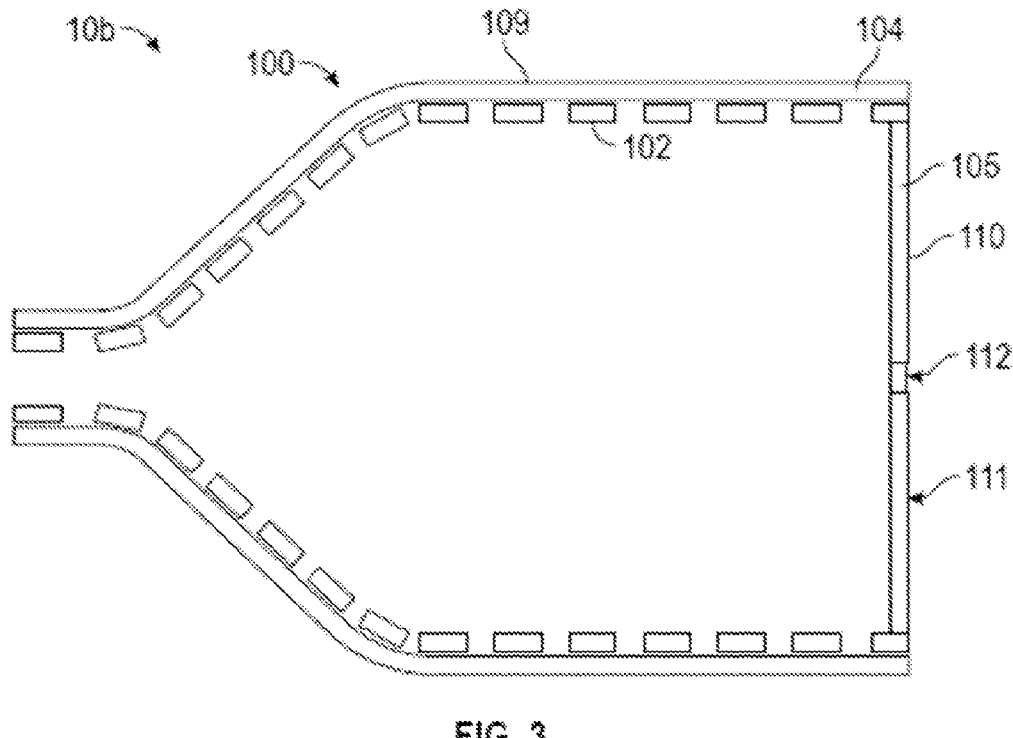
FIG. 3 is a partially schematic cross-sectional side view of a distal portion of a treatment system configured in accordance with several embodiments of the present technology.

Referring to FIGS. 2E and 2F, the cover 104 can be positioned within a lumen of the frame 102 (not shown), on an outer surface of the frame 102, and/or within a thickness of the frame 102 (e.g., extending between pores of the frame 102 at a radial location that does not extend beyond the abluminal and luminal surfaces of the frame 102) (not shown). In some embodiments, the portion of the cover 104 of the tubular sidewall 109 is monolithic and/or integral with the portion of the cover 104 of the engagement wall 110. For example, the cover 104 can have an open proximal end and a closed distal end such that, when the cover 104 is positioned over the frame of the tubular sidewall 109, the closed distal end of the cover 104 forms the engagement wall 110. In some embodiments, the engagement wall 110 can be formed separately from the frame and/or cover forming the tubular sidewall 109 (for example, as shown in FIG. 3).

The engagement wall 110 can comprise the same material as the frame 102 and/or cover 104 or can comprise a different material from the frame 102 and/or cover 104. In some embodiments, engagement wall 110 can be formed separately from the tubular sidewall 109 and secured to the sidewall 109 during assembly of the capture structure 100. The cover and/or the material forming the engagement wall 110, if distinct from the cover, can comprise at least one of a film, a coating, a foil, or a sheet. The cover and/or the material forming the engagement wall 110 can comprise a polymer, an elastomer, and/or a rubber. For example, the cover and/or the material forming the engagement wall 110 can comprise a latex or a silicone rubber. The cover and/or the material forming the engagement wall 110 can be configured to elongate, stretch, and/or expand between about 100% and about 1500%. In some embodiments, the cover and/or the material forming the engagement wall 110 can have a durometer of between about 10 on the Shore 00 hardness scale to about 60 on the Shore A hardness scale, about 0 on the Shore A hardness scale to about 40 on the Shore A hardness scale, or about 10 on the Shore A hardness scale to about 30 on the Shore A hardness scale. The cover and/or the material forming the engagement wall 110 can have a thickness of less than about 0.5 mm, less than about 0.4 mm, less than about 0.3 mm, less than about 0.2 mm, less than about 0.1 mm, less than about 0.05 mm, less than about 0.01 mm, less than about 5 μm, less than about 1 μm, less than about 0.5 μm, or less than about 0.1 μm.

The engagement wall 110 can comprise a portion of the cover 104 (discussed in greater detail below) or may be a separate component that is joined to the frame 102 and/or cover 104. For example, in the more detailed view shown in FIG. 2F, the cover 104 can extend across a break in the frame 102 and form the engagement wall 110. In some embodiments, the engagement wall 110 comprises a separate component from the cover 104 and the frame 102. FIG. 3, for example, shows a capture structure 100 having a frame 102, a cover 104, and an engagement wall 110 comprising a separate material 105 coupled to the distal portions of the frame 102 and cover 104. In some embodiments the engagement wall 110 includes a portion of the frame 102, and in some embodiments the engagement wall 110 comprises only the cover 104. In some embodiments, substantially all of the wall includes both the frame 102 and the cover 104. According to several embodiments, the frame 102 is only positioned at the sidewall 109 and/or neck portion 107 and not along the engagement wall 110. Said another way, in such embodiments the engagement wall 110 comprises only the cover 104 and does not include the frame 102. In some embodiments, the wall of the capture structure 100 comprises a single structure that provides both the structural support and the fluid impermeable cover. For example, in some embodiments the capture structure 100 comprises a resilient polymer structure.

The frame 102 can have any suitable shape or cross-sectional dimension. In some embodiments, the shape of the capture structure 100 substantially follows the shape of the frame 102. The frame 102 can comprise a single continuous structure, or may comprise a plurality of separate structures. In some embodiments, the frame 102 comprises a mesh structure formed of a resilient and/or superelastic material configured to self-expand when released from the sheath 22 or other radially constraining structure of the system. According to several embodiments, the mesh structure comprises a laser-cut tube or sheet of material. The material, for example, can comprise a resilient, elastic, and/or superelastic metal alloy or polymer. In such embodiments, the frame 102 can comprise a plurality of interconnected struts defining a plurality of cells therebetween. In some embodiments, the mesh structure comprises a plurality of braided wires (e.g., filaments, threads, sutures, fibers or the like) that have been interwoven to form a structure having openings. In some embodiments, the mesh structure is formed of a single braided or woven wire. The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate (PET), polylactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium, or alloys of any of these metals. In certain embodiments including at least metal, some or all of the surface of the frame 102 may be highly polished and/or surface treated to further improve its hemocompatibility. The frame 102 can be constructed solely from metallic materials without the inclusion of any polymer materials, solely from polymer materials without the inclusion of any metallic materials, or a combination of polymer and metallic materials.

In those embodiments where the frame 102 comprises a braided structure, some or all of the wires forming the braided structure can be drawn-filled tube ("DFT") wires having a radiopaque core (e.g., platinum, tantalum, gold, tungsten, etc.) surrounded by an elastic or superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. Moreover, some or all of the wires may have a wire diameter of about 0.003 inches to about 0.015 inches (e.g., 0.008 inches, 0.009 inches, 0.01 inches, etc.). In some embodiments, all of the wires have the same diameter, and in other embodiments some of the wires have different diameters.

The cover 104 can comprise a polymeric coating, a thin film, a membrane, or other fluid impermeable material. Additionally or alternatively, the cover 204 can comprise a stretchable material such as a low durometer polymer or silicone. The cover 104 can be configured to deform during aspiration and/or in response to forces applied by the obstructive material. As used herein, "deform" can refer to stretching, bending, or both. In some embodiments, the engagement wall 110 comprises a separate material and/or component from the cover 104.

In order to optimize the volume of the interior region 114 of the capture structure 100, the capture structure 100 can have the lowest wall thickness required to withstand a desired negative pressure. For example, in some embodiments the capture structure 100 has a wall thickness that is from about 0.1 mm to about 0.5 mm, less than 0.3 mm, or less than 0.5 mm, and is configured to withstand a negative pressure of from about 0 mmHg to about 760 mmHg, about 100 mmHg to about 600 mmHg, about 100 mmHg to about 500 mmHg, about 100 mmHg to about 450 mmHg, about 0 mmHg to about 500 mmHg, about, about 0 mm Hg to about 200 mm Hg, about 10 mmHg to about 500 mmHg, about 100 mmHg to about 500 mmHg, at least 100 mmHg, at least 200 mmHg, at least 300 mmHg, or at least 400 mmHg. The wall of the capture structure 100 can have a substantially constant thickness or may have a varying thickness. For example, in some embodiments the wall of the capture structure 100 is thicker along the sidewall 109 and thinner along the engagement wall 110. According to several embodiments, the wall of the capture structure 100 is thinner along the sidewall 109 and thicker along the engagement wall 110.

The capture structure 100 may be configured to self-expand from the low-profile state to the expanded state upon release of a radial constraint (such as withdrawal of a sheath), or may be actively expandable by an operator, such as via a pull-wire or other expansion mechanism. In some embodiments, the capture structure 100 can be configured to be deployed via both self-expansion and actuation. In some embodiments the capture structure 100 can be expanded via one or more pull-wires, cinching elements, and/or other actuation mechanisms. In some embodiments, the capture structure 100 can be radially expanded and collapsed via axial elongation and compression. For example, in some embodiments the distal end portion of the capture structure 100 structure is coupled to a first elongated member and the proximal end portion of the capture structure 100 is coupled to a second elongated member. The proximal ends of the first and second elongated members can be moved axially relative to one another to expand and collapsed the capture structure 100 as desired. In some embodiments, the capture structure 100 is expandable using hydrostatic pressure via a balloon catheter. According to several embodiments, the capture structure 100 is an inflatable structure and can be expanded via fluid delivery. In any case, in the expanded state, the maximum cross-sectional dimension of the capture structure 100 can be 150% to 300% larger than the cross-sectional dimension of the capture structure 100 in its low-profile state.

In some embodiments, the capture structure 100 has an outer cross-sectional dimension no greater than the outer cross-sectional dimension of the elongated shaft 24. According to several embodiments, the capture structure 100 has an outer cross-sectional dimension in the collapsed state that is no greater than 24 Fr. In some embodiments, the capture element 100 has an outer cross-sectional dimension in the collapsed state that is no greater than 22 Fr, no greater than 20 Fr, no greater than 19 Fr, no greater than 18 Fr, no greater than 17 Fr, no greater than 16 Fr, no greater than 15 Fr, or no greater than 14 Fr. In other embodiments, the outer cross-sectional dimension of the capture structure 100 in the expanded state is three times that of outer cross-sectional dimension of the elongated shaft 24. In some embodiments, the outer cross-sectional dimension of the capture structure 100 in the expanded state is greater than 8 mm and the outer cross-sectional dimension in the collapsed state is less than 8 mm. In some embodiments, a cross-sectional area of the capture structure 100 in the expanded state is greater than or equal to 50% of the diameter of the main right or left pulmonary artery. In some embodiments, the capture structure 100 has additional cross-sectional dimensions.

In some embodiments, an outer cross-sectional dimension of the capture structure 100 in the expanded state is substantially the same as or slightly larger than a diameter of the blood vessel at the treatment site. In such embodiments, the capture structure 100 can be configured to expand into apposition with the blood vessel wall. Contact between the capture structure 100 and the blood vessel wall can help anchor the capture structure 100 in place during the procedure, and can help force the obstructive material into the capture structure 100.

The shape of the capture structure 100 can be configured to facilitate engagement, capture, and containment of the obstructive material. In some instances, the shape of the capture structure 100 can help in shaping, transitioning, forming, compressing, and/or guiding the clot material into the elongated shaft 24. The shape of the capture structure 100 is also configured to provide a therapeutic working space shielded from the surrounding anatomy. In some embodiments, for example as shown in FIGS. 2A-2D, the capture structure 100 has a tapered proximal portion 106 and substantially cylindrical distal portion 108. In some embodiments, the capture structure 100 has a tapered proximal portion, a substantially cylindrical mid-portion, and a distally-tapering distal portion. According to several embodiments, the capture structure 100 has an outer cross-sectional dimension D4 (see FIG. 2D) and/or an inner cross-sectional dimension D2 that remains substantially constant along its entire length. According to several embodiments, the capture structure 100 has an outer cross-sectional dimension D4 and/or an inner cross-sectional dimension D2 that varies along all or a portion of the entire length.

The capture structure 100 can be generally symmetric about its longitudinal axis, or it may be eccentric (for example, as shown in FIG. 5F). The capture structure 100 can have an overall length greater than about 1 cm and less than about 30 cm. In some embodiments the capture structure 100 has an overall length of from about 5 cm to about 20 cm.

FIGS. 4A-4C illustrate how the deformable engagement wall 110 and orifice 112 can respond as an obstructive material (such as a thrombus) enters into the interior region of the capture structure 100. FIGS. 4A-4C show a distal portion of the system 10 having a proximal aspiration lumen area A[pal] (i.e., a cross-sectional area of an inner diameter of the elongated shaft 24), a capture structure aspiration lumen area A[dsal], and an orifice area adjacent to thrombus O. In this embodiment, the initial orifice area A[o1] is greater than the proximal aspiration lumen area A[pal] and less than the distal section aspiration lumen area A[dsal]. In some embodiments, the initial orifice area is less than or equal to the proximal aspiration lumen and can even have an initial orifice area close to zero when no forces are being applied on the orifice. Once the orifice 112 is adjacent to the thrombus O, a negative pressure P is applied to the lumen of the elongated shaft 24 and creates an initial aspiration force F[a1], as shown in FIG. 4A. As the thrombus O engages with the portion of the engagement wall 110 surrounding the orifice 112, the engagement wall 110 deforms such that the orifice 112 increases to a second orifice area which increases the aspiration force on the thrombus as the negative pressure stays constant, as shown in FIG. 4B. In FIG. 4B, the second orifice area and aspiration force are depicted as A[o2] and F[a2], respectively. This increase in force continues until the orifice area A[o] reaches the size of the capture structure aspiration lumen area A[dsal] or the thrombus passes through the orifice at which point the orifice area will return to the initial orifice area as shown FIG. 4C. By way of example for this embodiment, the initial orifice area A[o1] is 0.02-in2 and a negative pressure of 2-psi is applied to the central lumen of the flexible body generating an initial aspiration force F[a1] of 0.04-lbs. As the thrombus enters the distal section, the new orifice area A[o2] is 0.08 applying an increased aspiration force F[a2] of 0.16-lbs.

Figures 6A, 6B, 6C, 6D:
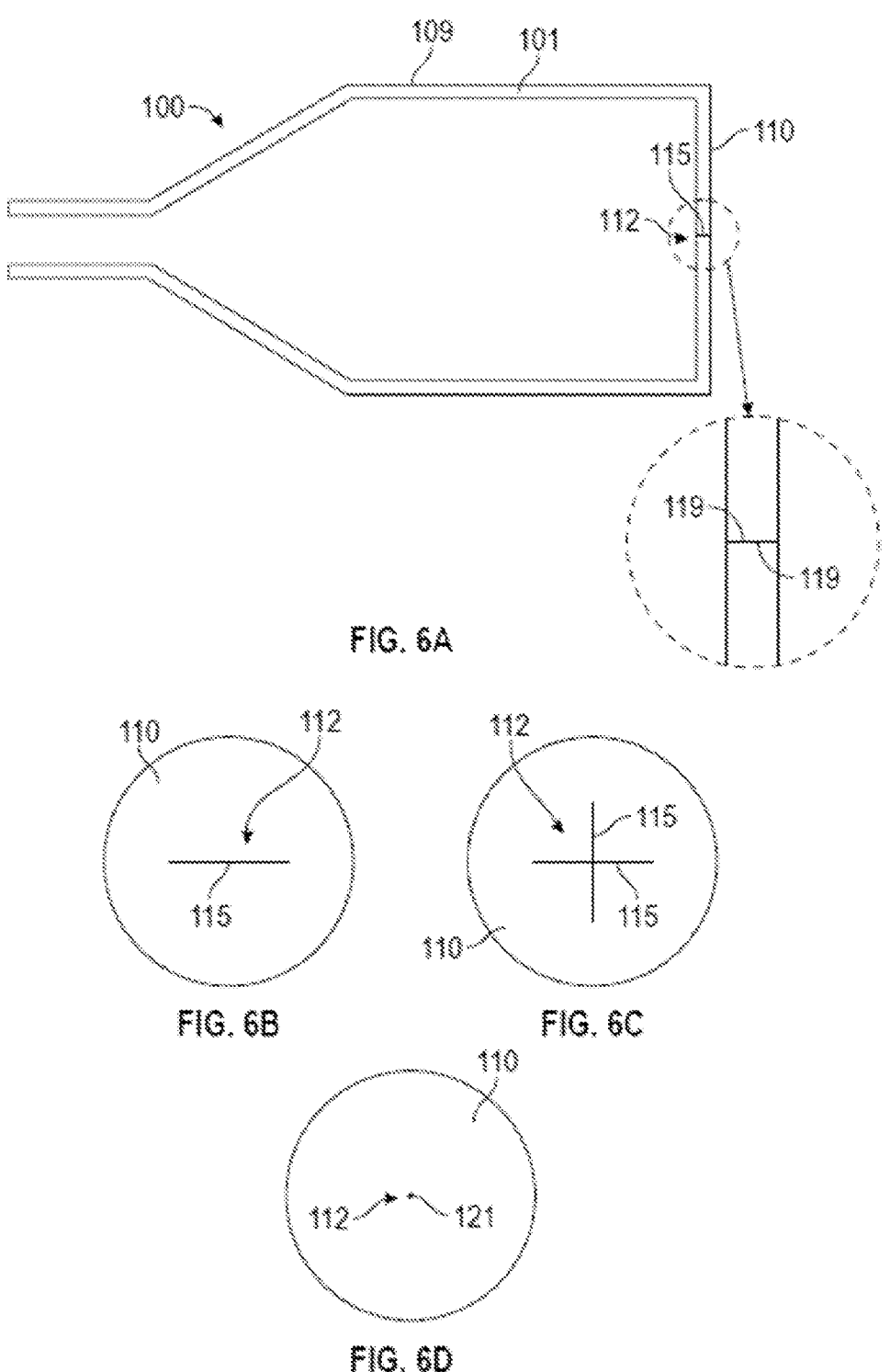
FIG. 6A is a partially schematic cross-sectional side view of a capture structure configured in accordance with the present technology.
FIGS. 6B-6D show different slit configurations for use with the capture structures of the present technology.

FIGS. 5A-5G illustrate different capture structure 100 configurations in accordance with the present technology. For example, as shown in FIG. 5A, in some embodiments the engagement wall 110 of the capture structure 100 can be angled inwardly, towards an interior region 114 of the capture structure 100. As shown in FIG. 5B, in some embodiments the engagement wall 110 of the capture structure 100 can be angled outwardly, away from an interior region 114 of the capture structure 100. As shown in FIGS. 5C and 5D, in some embodiments the orifice 112 and deformable wall can be disposed along a distal portion of the sidewall 109 or a proximal portion of the sidewall, respectively. Placement of an orifice at the sidewall 109 can be advantageous when attempting to engage and/or capture obstructive material positioned laterally of the capture structure 100. As illustrated by the capture structure 100 shown in FIG. 5E, in some embodiments the capture structure 100 can have multiple orifices 112/deformable wall portions. In such embodiments, the orifices 112 can be positioned anywhere along the sidewall 109 and/or engagement wall 110. The capture structure 100 can include two, three, four, five, six or any number of orifices. As illustrated by the capture structure 100 shown in FIG. 5F, in some embodiments the capture structure 100 can be asymmetric and/or the orifice 112 can be offset from the lumen of the elongated shaft 24. As shown in FIG. 5G, in some embodiments the orifice 112 and supporting wall 117 can be inset from a distal end of the sidewall 109 such that the capture structure 100 has a distal opening 113 and the wall 117 is proximal of the distal opening 113. As shown in FIG. 5H, in some embodiments the engagement wall 110 is beveled. As shown in FIG. 5I, in some embodiments all or a portion of the engagement wall 110 is curved. In such embodiments, the engagement wall 110 can have (a) an inner surface 124 that is convex towards the interior region 114, at least when the engagement wall 110 is in a resting state, and (b) an outer surface 126 (or engagement surface 111) that is concave towards an exterior of the capture structure 100 and/or obstructive material, at least when the engagement wall 110 is in a resting state FIG. 6A is a cross-sectional side view of a capture structure 100 having an orifice 112 comprising a slit 115. An end view of the slit 115 is shown in FIG. 6B. The slit 115 can comprise an elongated break in the continuity of the engagement wall 110 and/or any wall of the capture structure 100. In some embodiments, the adjacent surfaces 119 of the wall defining the slit 115 abut and/or are in contact with one another when the wall 110 is in an unstretched state and/or only a nominal clearance exists between the surfaces 119. For example, the portions of the wall defining the slit 115 and/or opening can be in contact but moveable relative to one another. As such, the engagement wall 110 comprising a slit 115 presents a substantially closed, fluid impermeable surface when the engagement wall 110 is not being deformed by aspiration and/or engagement with obstructive material. The cross-sectional dimension of the slit 115 in this resting state is approximately zero. When aspiration is applied within the capture structure 100 and/or when the engagement wall 110 is pushed up against the obstructive material, the engagement wall 110 deforms, causing the distance between the abutting surfaces defining the slit 115 to move apart from one another, thereby increasing the cross-sectional dimension to a value greater than zero and enabling the obstructive material to move through the slit into the interior region 114 of the capture structure 100.

In some embodiments, the orifice 112 can comprise a plurality of intersecting slits 115, for example as shown in FIG. 6C. According to several embodiments, the orifice 112 can comprise a single puncture 121 and/or pinhole in the engagement wall 110 and/or any wall of the capture structure 100. In some embodiments, the orifice 112 can comprise multiple punctures in the engagement wall 110 and/or any wall of the capture structure 100.

For any of the treatment systems disclosed herein, the system and/or any component thereof (such as elongated shaft 24, sheath 22, a disrupting device, etc.) can have an overall length of 80 cm or greater. For example, when separate elongated members are used for control of the sheath, the capture structure, and the disrupting device, any one of the individual elongated members can have a length 80 cm or greater. Any of the elongated members and/or elongated shafts disclosed herein can have a length less than or greater than 80 cm. Moreover, any of the elongated member and/or members disclosed herein (such as the elongated shaft 24, the sheath 22, a disrupting device, etc.) can have a flexibility that progressively increases in a proximal to distal direction such that the proximal portion of the respective elongated member has a greater column strength (for improved pushability) and the distal portion has better maneuverability. In some embodiments, one, some, or all of the elongated members have a substantially constant flexibility along their respective lengths.

According to some embodiments, a method for treating a blood vessel of a human patient, such as a pulmonary blood vessel, comprises positioning a distal portion of a treatment device in the blood vessel at a treatment site proximate obstructive material, the treatment device comprising an elongate shaft and a capture structure (such as any of the capture structures disclosed herein) disposed at a distal portion of the elongate shaft and enclosing an interior region. In some embodiments, the capture structure and elongated shaft are delivered through a delivery sheath. In some embodiments, the capture structure and elongated shaft are not delivered through a delivery sheath. The method can include engaging the obstructive material with the distal face of the capture structure such that at least a portion of the obstructive material is positioned in and/or through the orifice, thereby increasing a cross-sectional dimension of the orifice. The method can further include removing at least the portion of the obstructive material from the patient's body.

Negative pressure can be applied to the interior region of the capture structure before, during, and/or after engaging the obstructive material, thereby pulling the obstructive material through the orifice and into the interior region. In some cases, negative pressure is only applied once the obstructive material is engaged and/or while the obstructive material is moving through the opening, thereby reducing the volume of blood aspirated during a typical procedure (as compared to conventional thrombectomy systems that utilize aspiration).

In some embodiments, the method comprises increasing a proximally-directed force on the obstructive material without increasing the negative pressure. For example, in some embodiments, engaging the obstructive material comprises pushing the engagement wall onto and/over a portion of the obstructive material. Forcible contact between the engagement wall and the obstructive material can cause the engagement wall to deflect inwardly, toward the interior region. This inward deflection stretches the engagement wall, which enlarges the opening and enables a greater volume of obstructive material to enter the interior region of the capture structure. In those embodiments where aspiration is being applied while the obstructive material is engaged with the opening and/or engagement wall, enlarging the opening increases the aspiration force on the obstructive material. In several embodiments, engaging the obstructive material comprises creating a seal between the obstructive material and an edge of the engagement wall surrounding the orifice.

In some embodiments, the method comprises positioning a disruptor within the interior region of the capture structure before, during, and/or after engaging the obstructive material. The disruptor can break up the portion of the obstructive material positioned within the interior region of the capture structure to facilitate removal through the aspiration lumen. In some embodiments, the disruptor mechanically engages the obstructive material and pulls the obstructive material into the interior region of the capture structure 100. According to several methods, the disrupting device can be removed from the patient's body while holding the capture structure at the treatment site.

In some embodiments, the method comprises applying negative pressure to the interior region of the capture structure before, during, and/or after engaging the obstructive material, and breaking up the portion of the obstructive material positioned within the interior region with a disrupting element positioned within the interior region. In these and other embodiments, applying the negative pressure and breaking up the obstructive material occur at different times.

In some embodiments, the method comprises applying negative pressure to the interior region of the capture structure before, during, and/or after engaging the obstructive material, and breaking up the portion of the obstructive material positioned within the interior region with a disrupting element positioned within the interior region. In these and other embodiments, at least some of the application of negative pressure occurs while the disrupting element is breaking up the obstructive material, or vice versa.

In some embodiments, the method comprises engaging the obstructive material such that all or a portion of the obstructive material extends through the opening and is positioned within the interior region of the capture structure. During engagement, aspiration may or may not be applied. Once the obstructive material (or a portion thereof) is positioned within the interior region, the disrupting element can be activated to disrupt the obstructive material so that the obstructive material can be pulled (or more easily pulled) through the lumen of the elongated shaft. It may be beneficial to cease aspiration (if aspiration was being used prior to activation of the disrupting element) during the disrupting of the obstructive material by the disrupting element in order to limit the volume of blood pulled from the patient's body during the procedure. Once the obstructive material is sufficiently processed, aspiration can be started again to pull the processed obstructive material through the elongate shaft to a proximal portion of the system. The steps of pulling or otherwise forcing all or a portion of the obstructive material into the capture structure, disrupting the obstructive material that is within the capture structure with the disrupting element without any aspiration, then aspirating the processed obstructive material can be repeated as many times as necessary to remove the desired obstructive material.

II. Selected Embodiments of Capture Structures

Figure 7A:
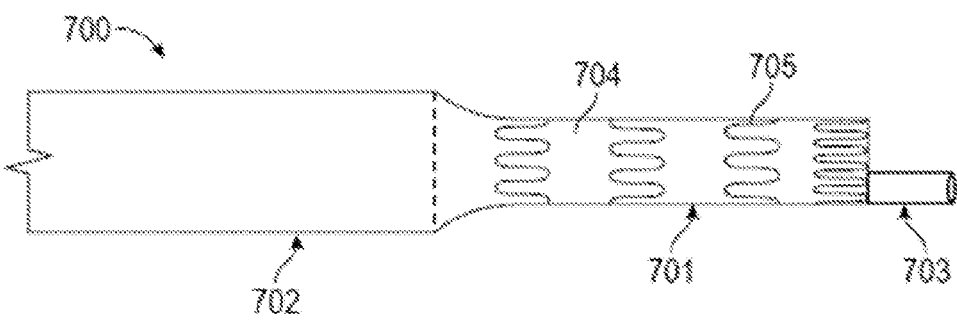
FIGS. 7A-7C show a capture structure configured in accordance with several embodiments of the present technology in different configurations.
Figure 7B:
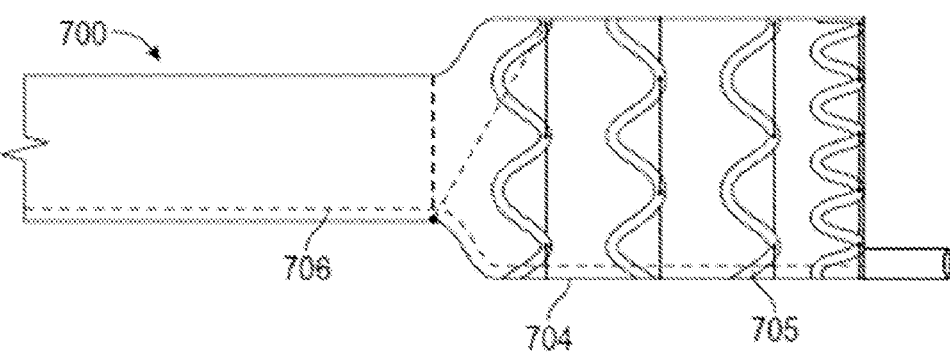
Figure 7C:
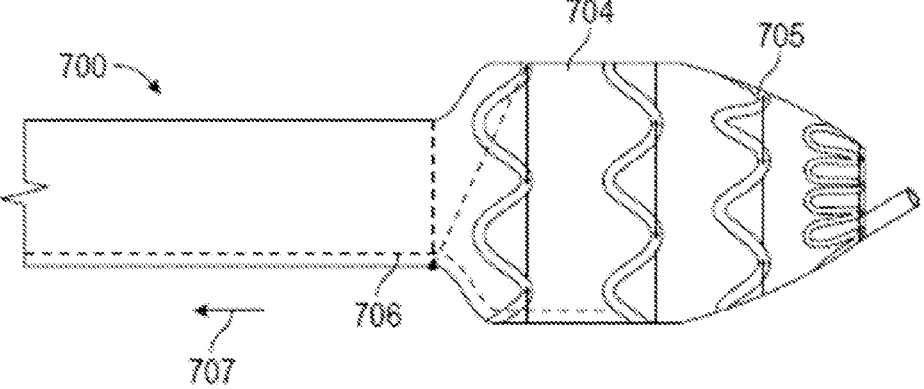

FIGS. 7A-11E show and describe examples of capture structures configured for use with any of the treatment systems and/or disrupting devices disclosed herein. FIGS. 7A-7C, for example, show a distal portion of a treatment system 700 with a capture structure 701 in various configurations in accordance with several embodiments of the present technology. The system 700 can comprise an elongated shaft 702, a capture structure 701 carried by a distal region of the elongated shaft 702, and a guidewire shaft 703 radially offset from the central longitudinal axis of the shaft 702 and/or system 700. In some embodiments, the guidewire shaft 703 can be coupled to all or a portion of an inner surface of the sidewall of the elongated shaft 702 and/or capture structure 701. The system 700 can further include a deployment member 706 coupled to the capture structure 701 and configured to retain the capture structure 701 in a low-profile and/or constrained state, as shown in FIG. 7A. The deployment member 706 can be a wire, thread, suture, coil, and/or other flexible member.

Figures 8A, 8B:
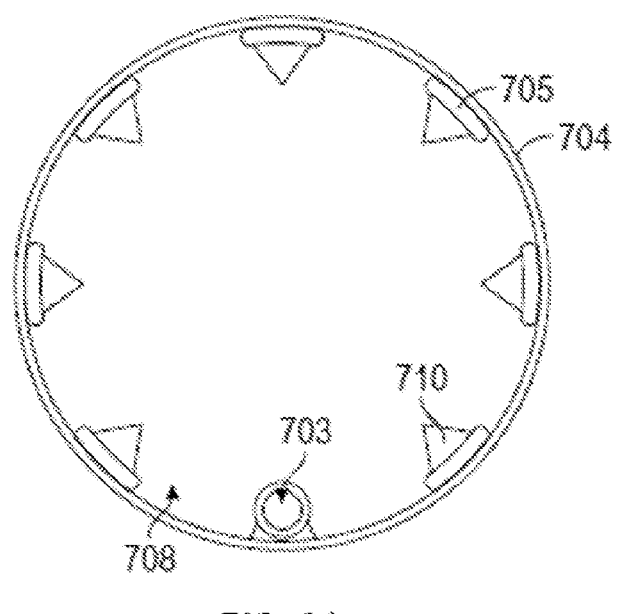
FIGS. 8A and 8B are cross-sectional end views taken of the capture structure as depicted in FIG. 7B and FIG. 7C, respectively.

The system 700 is configured such that a user can manipulate the tension in the deployment member 706 to increase or decrease a diameter and/or length of the capture structure 701. For example, in some embodiments the capture structure 701 can be expanded to a radial profile greater than the elongated shaft 702 by releasing the deployment member 706. When the deployment member 706 is released, the frame 705 of the capture structure 701 expands and the capture structure film 704 stretches and expands with the scaffolding rings. The scaffolding rings 705 are axially held in place with metallic connector shafts (not shown) positioned on the top and bottom sides of the capture structure. The scaffolding rings are thermally bonded or sutured to the film 704 creating a fluid tight central lumen that runs throughout the elongated system 700. The scaffolding rings 705 can be made out of cobalt-chromium, shaped memory alloy that has a transition temperature near body temperature, or super elastic nitinol material. The film 704 is made from a thermoplastic elastomer or polyurethane. The guidewire lumen 703 has a lubricious inner liner that accommodates guidewires between 0.020-0.038 in. The guidewire lumen also has the cross section area sufficient to allow the user to inject contrast media through the lumen to perform an angiography image to confirm location of the device and the thrombus. The guidewire lumen 703 is positioned axially to the system 700 but off the centerline to not obstruct the aspiration lumen during the digesting of large thrombus also having a guidewire lumen integrated into the central lumen provides the guidewire more support and helps the system follow the guidewire because of the inner diameter of the guidewire lumen 703 and the outer diameter of the guidewire. When the system 700 needs to be repositioned or has started to ingest a large volume of thrombus, the deployment wire 706 is pulled using an axial force 707 causing the capture structure to collapse distal to proximal. If this collapsing is performed when thrombus is present, the collapsing movement assists in advancing the thrombus through the central lumen 708 proximally. Also as shown in FIGS. 8A and 8B, the frame 705 can have sharp barbs or blades 710 pointing radially inwardly (toward the lumen 708) to assist in morcellating the thrombus to ease in digesting the thrombus.

Figure 10B:
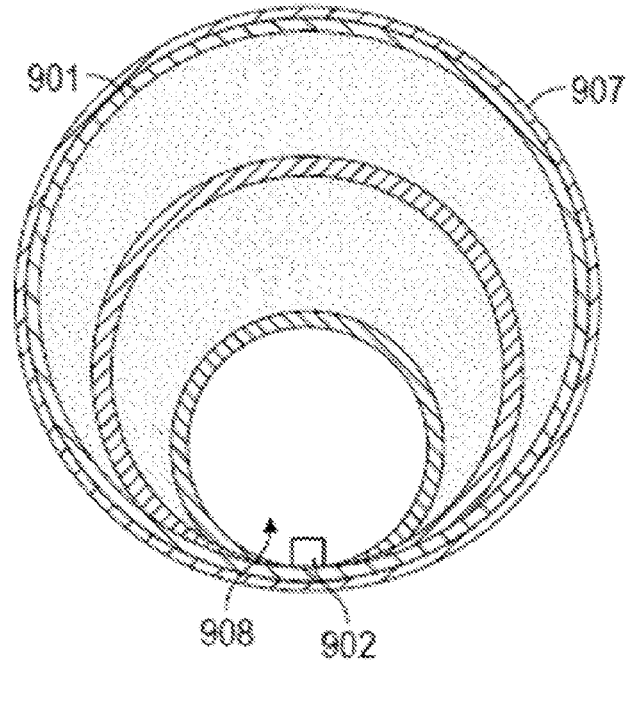
FIG. 10B is a cross-sectional end view taken along line 10B-10B in FIG. 10A.
Figures 11A, 11B, 11C, 11D, 11E:
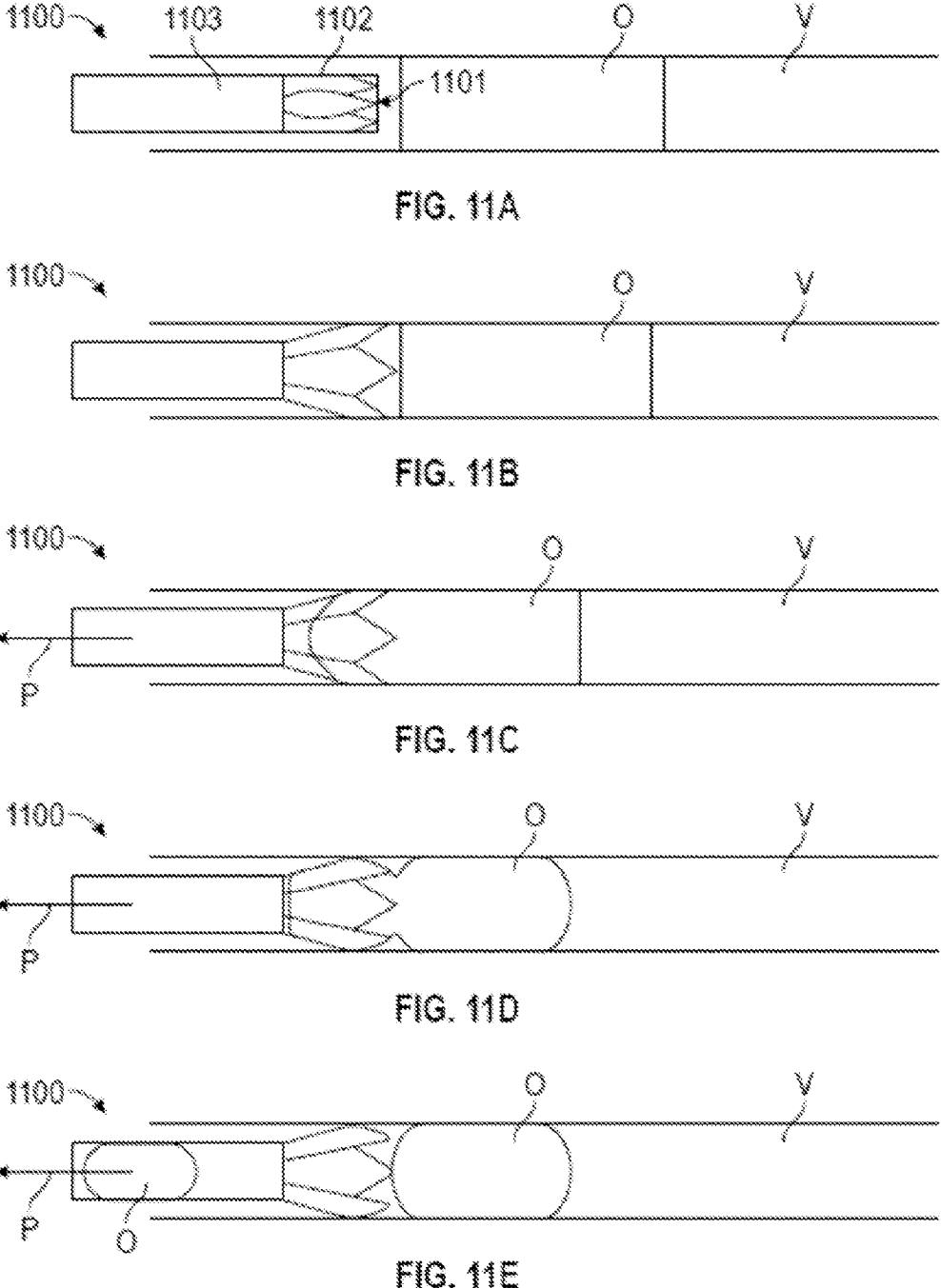
FIGS. 11A-11E show a method for disrupting and/or removing obstructive material using a treatment system configured in accordance with the present technology.

FIGS. 9, 10A, and 10B show a capture structure 900 configured in accordance with several embodiments of the present technology. the system has a funnel scaffolding 901, funnel film 907, an off-axis guidewire lumen 902 throughout the central lumen 908 of the system 900 that returns to the centerline axis of the system through the atraumatic distal tip 903. The system 900 also has a flexible neck 904, an outer sheath 905 and a proximal member 906. The expandable capture structure is deployed by advancing the proximal member 906 or by retracting the outer sheath 905. The expandable capture structure of the system 900 created by one heat shaped filament. The funnel scaffolding is optimally wound and heat set into the funnel shape and flexible neck that is desired and then the scaffolding 901 is covered with a film 907. The funnel is then collapsed by using an outer sheath 905. When collapsed the scaffolding funnel loops that are larger than the inner diameter of the outer sheath 905 are angled distally when collapsed to make repositioning easier.

FIGS. 11A-11E illustrate an example method of use of a treatment system 1100 configured in accordance with the present technology. The treatment system 1100 can comprise an elongated shaft 24, a capture structure 100 carried by the distal portion of the elongated shaft 24, and an orifice 112 extending through the capture structure 100. The capture structure 100 can be advanced distally through the vasculature V until it is positioned proximal to the thrombus O. Once in location, the capture structure 100 can be expanded (FIG. 11B) and negative pressure P can be applied (FIG. 11C) to draw a portion of the thrombus O into the capture structure 100. Once the thrombus O stops advancing into the capture structure 100, the operator can pull a biting wire (as described elsewhere herein) to cause the orifice 112 to collapse and pinch off a portion of thrombus O. The system 1100 digests that portion of the thrombus and an operator can repeat these steps until the thrombus is removed and blood flow within the lumen is increased.

III. Selected Embodiments of Disrupting Devices

Figure 12:
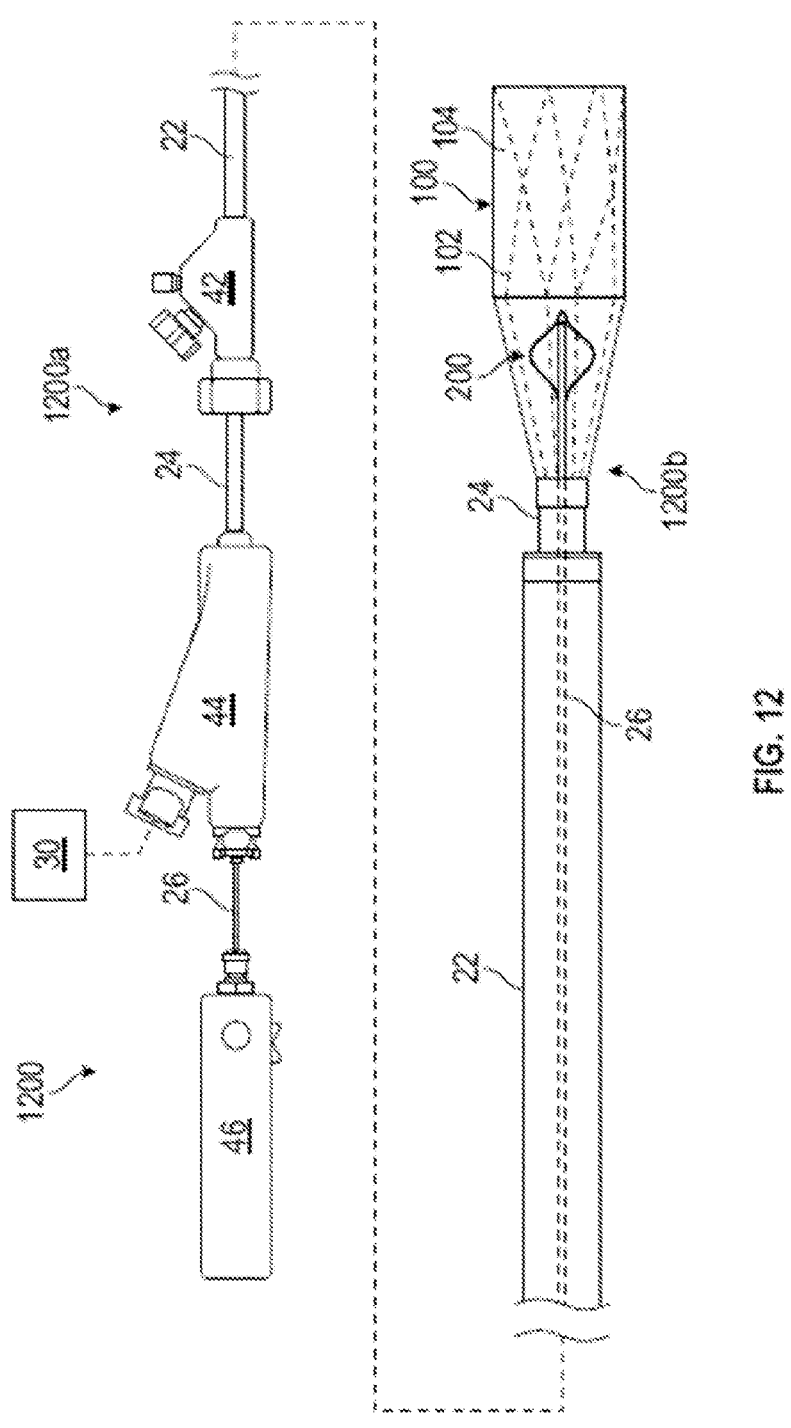
FIG. 12 shows a treatment system configured in accordance with several embodiments of the present technology.

FIG. 12 shows a treatment system 1200 configured in accordance with several embodiments of the present technology. Treatment system 1200 can be generally similar to treatment system 10, except treatment system 1200 further includes a removable disrupting device. "Disrupting device," "disruptor," and "disrupting element" can be used synonymously throughout the present application. The treatment system 1200 can include a proximal portion 1200a configured to be extracorporeally positioned during a procedure and a distal portion 1200b configured to be intravascularly delivered to a treatment site within a blood vessel. The distal portion 1200b can comprise a capture structure 100 and a disruptor 200 removably positioned within an interior region of the capture structure 100. The capture structure 100 and disruptor 200 can be configured to work synergistically to capture and process obstructive material so that the obstructive material can be removed from the patient through the system 1200.

As shown in FIG. 12, the treatment system 1200 can further include a sheath 22, an elongated shaft 24, and an elongated member 26 extending between the proximal and distal portions 1200a, 1200b of the system 1200. The sheath 22 can be a generally tubular member having a proximal end portion, a distal end portion, and a lumen extending therethrough. The elongated shaft 24 can also be a generally tubular member having a proximal end portion, a distal end portion, and a lumen extending therethrough. The elongated member 26 can be a generally tubular member or a solid member having a proximal end portion and a distal end portion. The elongated shaft 24 can be configured to be slidably positioned through the lumen of the sheath 22, and the elongated member 26 can be configured to be slidably positioned within the lumen of the elongated shaft 24.

In some embodiments, the capture structure 100 is carried by a distal end portion 24b of the elongated shaft 24, and both the elongated shaft 24 and the capture structure 100 are configured to be slidably disposed within the sheath's lumen. In those embodiments where the capture structure 100 is self-expanding, the sheath 22 can be configured to radially constrain the capture structure 100 during delivery of the distal portion 10b and release the capture structure 100 to self-expand into the expanded state upon proximal withdrawal of the sheath 22. Moreover, the disruptor 200 can be carried by a distal portion of the elongated member 26.

The proximal portion 1200a of the system 1200 can include a first hub 42, a second hub 44, and a third hub 46 configured to be positioned external to the patient. A distal region of the first hub 42 can be secured to the proximal end portion of the sheath 22, and a proximal region of the first hub 42 can include an opening configured to slidably receive the elongated shaft 24 therethrough. A distal region of the second hub 44 can be secured to the proximal end portion of the elongated shaft 24, and a proximal region of the second hub 44 can include an opening configured to receive the elongated member 26 of the interventional device therethrough. A distal region of the third hub 46 can be secured to the proximal end portion of the elongated member 26.

The first and/or second hubs 42, 44 can include a hemostatic adaptor, a Tuohy Borst adaptor, and/or other suitable connectors, valves and/or sealing devices. For example, in some embodiments, the second hub 44 includes a connector configured to be coupled to a negative pressure source 30 (shown schematically), such as a syringe or a vacuum pump, for applying a negative pressure through a lumen of the elongated shaft 24. Additionally or alternatively, the first hub 42 can include a connector configured to be coupled to a negative pressure source 30 for applying a negative pressure through a lumen of the sheath 22. In some embodiments, the first and/or second hub 42, 44 can include a port configured to be coupled to a fluid source for delivering one or more fluids to the treatment site before, during and/or after the procedure (e.g., contrast, saline, etc.). Additionally or alternatively, the first and/or second hubs 42, 44 can include one or more ports configured to be coupled to a collection chamber for receiving and containing aspirated material from the treatment site.

In some embodiments, the first, second, and/or third hubs 42, 44, 46 include one or more actuators that enable the operator to manipulate the distal portion 1200b of the system 1200. The third hub 46, for example, can comprise a motor coupled to the elongated member 26 and configured to translate, rotate, and/or otherwise agitate the disruptor 200 (via the elongated member 26) when activated. The third hub 26 can include an actuator, such as one or more levers, switches, knobs, buttons, etc., that, when actuated by the operator, turn on the motor and cause the disruptor 200 to begin engaging and/or disrupting obstructive material within the capture structure 100.

FIGS. 13A-30 show and describe examples of disruptors and/or disrupting devices configured for use with any of the treatment systems and/or any of the capture structures disclosed herein. Whether the system is engaging obstructive material by aspiration, mechanical means, or both, there is a possibility that the obstructive material is too large and/or too firm, fibrous, and/or organized to enter into and/or move through the lumen of the elongated shaft and/or aspiration lumen of the system. Accessory tools, such as the disrupting devices of the present technology and others, can be used in conjunction with the capture structure 100 to assist in the withdrawal of the obstructive material via aspiration and/or mechanical means. For example, in some cases, all or a portion of the obstructive material may become immovable or otherwise stuck within the capture structure and/or aspiration lumen. The disrupting devices of the present technology can be used to help release and/or dislodge such blockages of obstructive material. In some embodiments, the disrupting devices can be pre-positioned in the elongated shaft and/or sheath. In some embodiments, the disrupting devices can be integral with the elongated shaft and/or sheath. According to several embodiments, the disrupting devices can be inserted as needed into the elongated shaft and/or sheath. The disrupting devices of the present technology are configured to be advanced into and/or through lodged obstructive material and manipulated by translation, rotation, or both to disrupt lodged obstructive material. Such disruption can be conducted simultaneously with aspiration and/or without aspiration. The disruptor could be used intermittently with aspiration.

The disrupting devices of the present technology can disrupt the obstructive material in a variety of ways. In some embodiments, the disrupting device provides a break-away force to free up stuck obstructive material held in an equilibrium condition. In some embodiments, the disrupting device engages the obstructive material for forward or back translation and/or rotation to free stuck obstructive material held in an equilibrium condition. In some embodiments, the disrupting device breaks a stuck obstructive material into finer pieces or segments that can fit through the sheath lumen without becoming lodged. The breaking of obstructive material can be mechanical disruption (blunt dissection) or it could be slicing. The motion of the disrupting device can be generated by a user applying motion to an elongated member of the disrupting device that extends to an extracorporeal location. In some embodiments, a proximal end portion of the disrupting device extends through a seal that maintains hemostasis and vacuum pressures even during motion of the disrupting device. The motion of the disrupting device can be imparted through a mechanical means, such as a handle with linkages or rack and pinions to cause movement of the disrupting device through the squeeze, push, and/or pull of a handle comprising a housing and an actuator. In these and other embodiments, the motion of the disrupting device could be imparted through an electro-mechanical or pneumatic counsel.

Any of the embodiments of disrupting devices herein can be configured to engage with a guidewire coaxially or as rapid exchange. Any of the disruptors could have atraumatic filiform tips. Any of the disruptors could be configured to dispense contrast fluid through the elongated shaft. Certain embodiments of the disruptors could be used to help deploy and/or maintain the vacuum patency of the expandable capture structure.

In some embodiments, the disrupting device mechanically modulates the negative pressure within the central lumen of the catheter. In some embodiments, the disrupting element mechanically macerates the thrombus as it enters the central lumen. In some embodiments, the disrupting element mechanically engages and pulls the thrombus through the central lumen. In some embodiments, the thrombus is advanced within the central lumen of the distal section through the distal orifice prior to the negative pressure being applied.

Figures 13A, 13B, 13C:
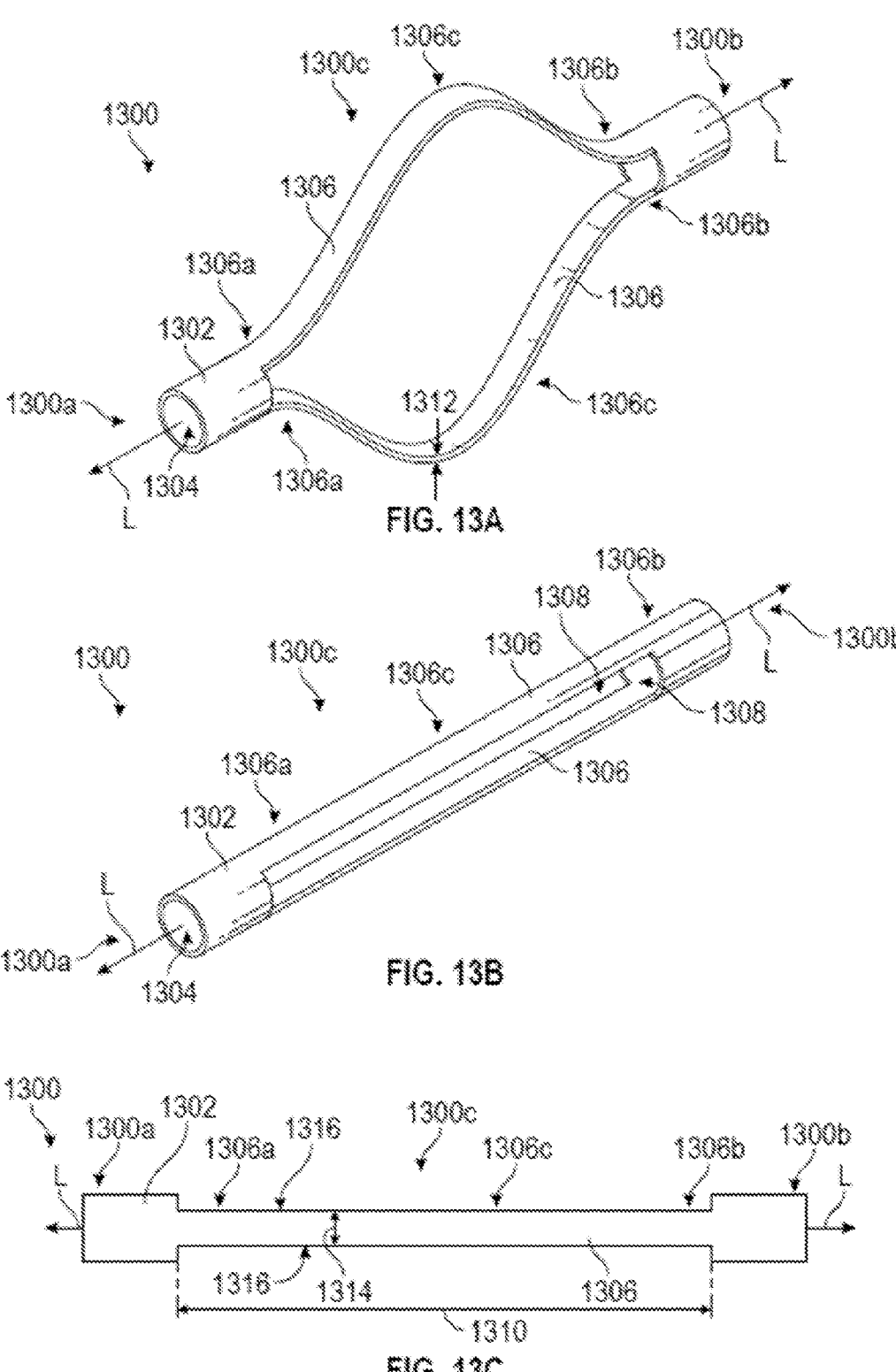
FIGS. 13A-13E are various views of a disrupting element configured in accordance with several embodiments of the present technology.

FIGS. 13A-13C depict a disruptor 1300 in accordance with several embodiments of the present technology. FIG. 13A is an isometric view of the disruptor 1300 in an expanded state and FIGS. 13B and 13C are isometric and top views, respectively, of the disruptor 1300 in a collapsed state. As shown in FIG. 13B, in the collapsed state the disruptor 1300 can have a substantially tubular shape. The disruptor 1300 can have a first end portion 1300a, a second end portion 1300b opposite the first end portion 1300a along a longitudinal axis L of the disruptor 1300, an intermediate portion 1300c between the first and second end portions 1300a, 1300b. The disruptor 1300 can have a sidewall 1302 defining a lumen 1304 extending from the first end portion 1300a to the second end portion 1300b. The disruptor 1300 can have a first cross-sectional dimension (e.g., a diameter, a radius, etc.) in the collapsed state and a second cross-sectional dimension in the expanded state. According to various embodiments, the second cross-sectional dimension of one or more portions of the disruptor 1300 can be larger than the first cross-sectional dimension of a corresponding portion of the disruptor 1300. In some embodiments, a maximum cross-sectional dimension of the disruptor 1300 can be less than, greater than, or substantially equivalent to a corresponding cross-sectional dimension of a lumen of an elongated shaft configured to receive the disruptor 1300 for delivery of the disruptor 1300. The disruptor 1300 can be heat set such that the disruptor 1300 is configured to self-expand from the collapsed state to the expanded state.

In some embodiments, for example as shown in FIGS. 13A-13C, the first end portion 1300a and/or the second end portion 1300b of the disruptor 1300 are circumferentially continuous. Additionally or alternatively, the intermediate portion 1300c of the disruptor 1300 can be circumferentially discontinuous. For example, as shown in FIGS. 13A and 13B, the intermediate portion 1300c can comprise one or more struts 1306. In some embodiments, the disruptor 1300 comprises a tube defining one or more openings 1308. For example, the disruptor 1300 can comprise a tube defining two openings 1308 comprising longitudinal slots such that the portions of the sidewall 1302 between the openings 1308 form the longitudinal struts 1306 (see, for example, FIGS.

13A-13C). As described herein, the tube can comprise a metal such as, for example, any superelastic or resilient metal (e.g., nitinol, a cobalt-chromium alloy, etc.).

Each of the struts 1306 can have a first end portion 1306a, a second end portion 1306b opposite the first end portion 1306b along the longitudinal axis L of the disruptor 1300, and an intermediate portion 1306c between the first and second end portions 1306a, 1306b. In the expanded state, one or more of the struts 1306 can extend radially outwardly from the first end portion 1306a to the intermediate portion 1306c and/or radially inwardly from the intermediate portion 1306c to the second end portion 1306b. Accordingly, the intermediate portion 1306c of the strut 1306 can comprise a radial peak and the first and second end portion 1306a, 1306b of the strut 1306 can converge towards the longitudinal axis L of the disruptor 1300.

Each of the struts 1306 of the disruptor 1300 can have a length 1310 defined along the longitudinal axis L of the disruptor 1300, a thickness 1312 defined between an abluminal surface of the disruptor 1300 and a luminal surface of the disruptor 1310, and a width 1314 defined as a circumferential distance between two edges 1316 of a strut 1306 of the disruptor 1300. In some embodiments, the length 1310 of one or more of the struts 1306 can be less than an overall length of the disruptor 1300. It may be advantageous for the width 1314 of each of the struts 1306 to be above a predetermined threshold and/or maximized in order to enhance durability of the struts 1306. However, it may also be desirable for a cross-sectional dimension of the disruptor 1300 to be below a predetermined threshold and/or minimized to prevent or limit obstruction of a lumen of an elongated shaft that the disruptor 1300 is positioned within. Accordingly, it may be advantageous for a disruptor 1300 to comprise fewer struts 1306 having larger widths 1314. For example, as shown in FIGS. 13A-13C, the disruptor 1300 can comprise two struts 1306. In these and other embodiments, each strut 1306 can have a width 1314 spanning a circumferential distance of no more than 180 degrees, no more than 150 degrees, no more than 120 degrees, no more than 90 degrees, no more than 60 degrees, no more than 30 degrees, about 170 degrees, about 160 degrees, about 150 degrees, about 140 degrees, about 130 degrees, about 120 degrees, about 110 degrees, about 100 degrees, about 90 degrees, about 80 degrees, about 70 degrees, about 60 degrees, about 50 degrees, about 40 degrees, about 30 degrees, about 20 degrees, about 10 degrees, or about 5 degrees.

In some embodiments, the disruptor 1300 is configured to rotate such that edges 1316 of the struts 1306 engage obstructive material and mechanically disrupt the obstructive material. The edges 1316 of the struts 1306 can be blunt or sharp. When the disruptor 1300 is rotated in a first direction (e.g., clockwise, counterclockwise, etc.) to disrupt obstructive material, a first one of the edges 1316 of each strut 1306 can be a leading edge that contacts the obstructive material before a second one of the edges 1316 of the strut 1306 contacts the obstructive material. In some embodiments, for example when the disruptor 1300 is configured to be rotated in a single direction, only the leading edges 1316 of the struts 1306 are sharpened. Additionally or alternatively, both edges 1316 of the struts 1306 can be sharpened, which may be advantageous if the disruptor 1300 is configured to be rotated in two opposing directions.

Figures 13D, 13E:
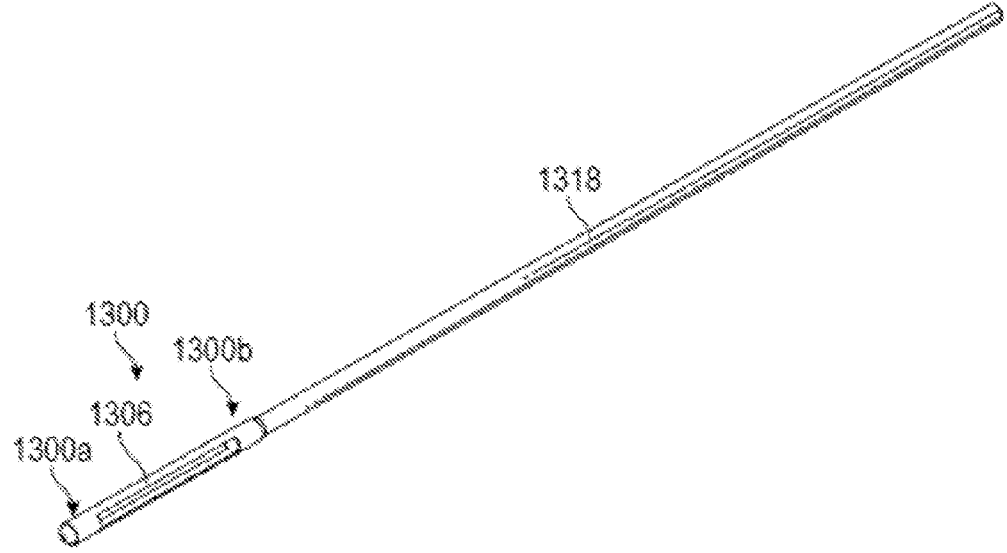

FIGS. 13D and 13E depict the disruptor 1300 of FIGS. 13A-13C in the collapsed configuration and the expanded configuration, respectively. As shown in FIGS. 13D and 13E, the disruptor 1300 can be positioned on, carried by, or otherwise secured to an elongated member 1318. The elongated member 1318 can be similar to any other elongated members disclosed herein (e.g., elongated member 26, etc.). In some embodiments the elongated member 1318 is positioned within the lumen 1304 of the disruptor 1300. The elongated member 1318 can have superelastic and/or shape memory properties. In some embodiments, the elongated member 1318 comprises a wire and/or a hypotube formed from Nitinol or another suitable metal. The elongated member 1318 can have a length between about 50 cm and about 200 cm, between about 60 cm and about 190 cm, between about 70 cm and about 180 cm, between about 80 cm and about 170 cm, between about 90 cm and about 160 cm, between about 100 cm and about 150 cm, between about 110 cm and about 140 cm, between about 120 cm and about 130 cm, less than 50 cm, about 50 cm, about 50 cm, about 60 cm, about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, about 200 cm, or greater than 200 cm. The elongated member 1318 can have a greatest cross-sectional diameter of between about 0.01 in and about 0.05 in, between about 0.015 in and about 0.045 in, between about 0.02 in and about 0.04 in, between about 0.025 in and about 0.035 in, less than 0.01 in, about 0.01 in, about 0.015 in, about 0.02 in, about 0.025 in, about 0.03 in, about 0.035 in, about 0.04 in, about 0.045 in, about 0.05 in, or greater than 0.05 in. In some embodiments, the elongated member 1318 has an outer diameter substantially equivalent to an inner diameter of a sleeve configured to receive the elongated member 1318 (e.g., elongated shaft 24).

In some embodiments, the first end portion 1300a of the disruptor 1300 is configured to be fixedly secured to the elongated member 1318 while the second end 1300b portion of the disruptor 1300 is configured to be slidably positioned over the elongated member 1318. The second end portion 1300b can be moved over the elongated member 1318 and away from the first end portion 1300a along the longitudinal axis L of the disruptor 1300 such that the disruptor 1300 elongates and radially compresses to assume the collapsed configuration. Conversely, the second end portion 1300b can be moved over the elongated member 1318 and towards the first end portion 1300a along the longitudinal axis L of the disruptor 1300 such that the disruptor 1300 shortens and radially expands to assume the expanded configuration. Additionally or alternatively, the second end portion 1300b of the disruptor 1300 can be configured to be fixedly secured to the elongated member 1318 while the first end 1300a portion of the disruptor 1300 is configured to be slidably positioned over the elongated member 1318 such that movement of the first end portion 1300a relative to the second end portion 1300b causes radial expansion or radial compression of the disruptor 1300. In some embodiments, the first end portion 1300a and/or the second end portion 1300b can be configured to move relative to the elongated member 1318 by a predetermined amount.

Figures 14A, 14B, 14C:
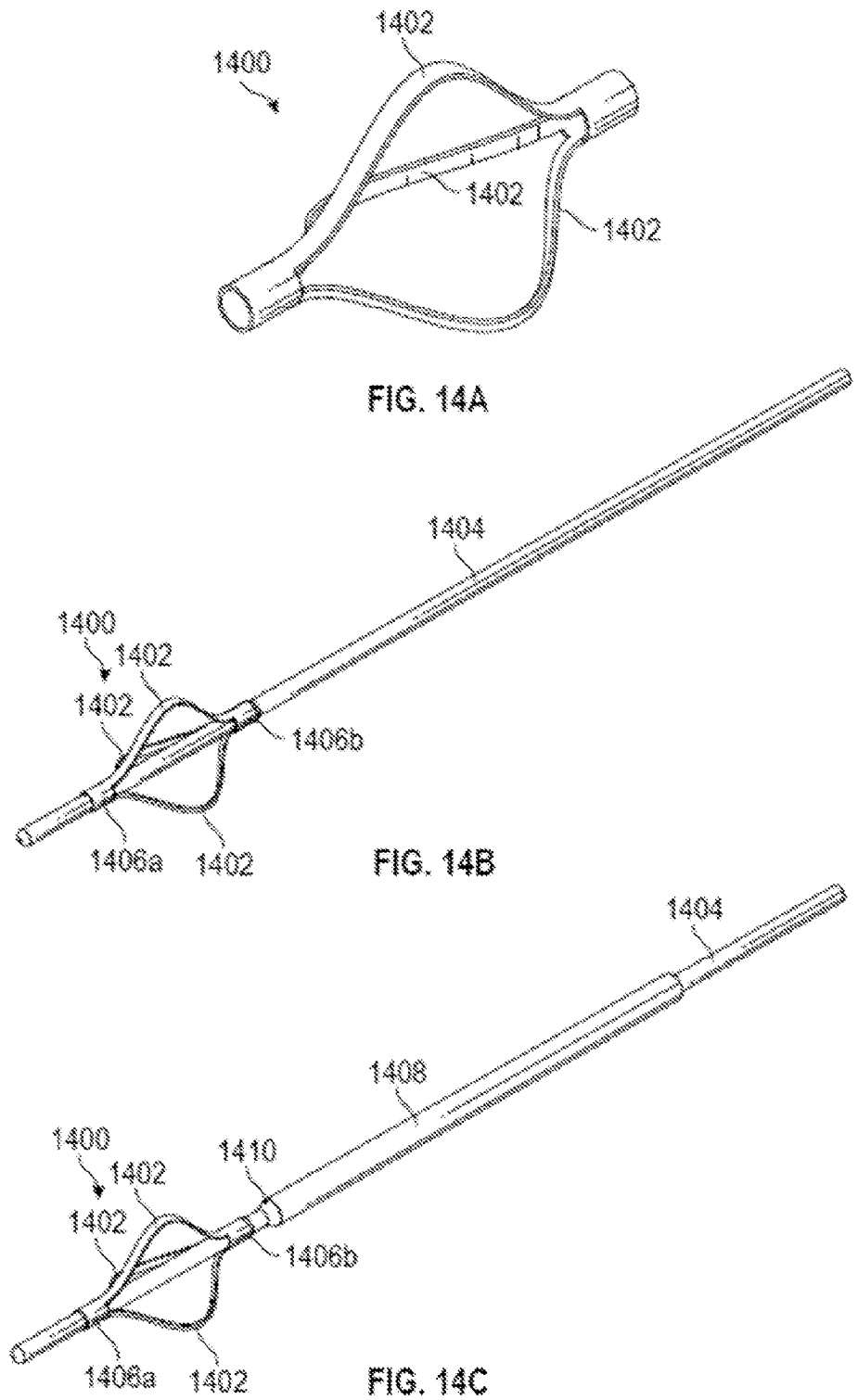
FIGS. 14A-14C are various views of a disrupting element configured in accordance with several embodiments of the present technology.

Although FIGS. 13A-13E depict the disruptor 1300 having two struts 1306, other numbers of struts 1306 are possible. As previously described, it may be advantageous for a disruptor to comprise a small number of wide struts. In some embodiments, it may be advantageous for a disruptor to have a specific number of struts and/or to maximize the number of struts. For example, as previously described, a disruptor can be configured to rotate such that edges of struts of the disruptor engage and disrupt obstructive material. In these and other embodiments, a disruptor with more struts has more edges to engage the obstructive material upon each rotation of the disruptor relative to a disruptor with fewer struts. As but one example, FIGS. 14A-14C show a disruptor 1400 having three struts 1402. A disruptor in accordance with the present technology can have one strut, two struts, three struts, four struts, five struts, six struts, seven struts, eight struts, nine struts, ten struts, or more than ten struts.

In some embodiments, the struts 1402 can be evenly distributed about a circumference of the disruptor 1400 such that an angular spacing between a pair of adjacent struts 1402 is substantially the same as angular spacing between one or more other pairs of adjacent struts 1402. For example, adjacent ones of the three struts 1402 shown in FIGS. 14A-14C can be spaced apart by about 120 degrees. In some embodiments, the struts 1402 can be unevenly spaced about a circumference of the disruptor 1400. For example, a first angular spacing between a first pair of adjacent struts 1402 can be different than a second angular spacing between a second pair of adjacent struts 1402.

As shown in FIG. 14B, the disruptor 1400 can be configured to be positioned on, carried by, or otherwise secured to an elongated member 1404. The disruptor 1400 can comprise a proximal collar 1406a and a distal collar 1406b, which can be movable relative to one another to transform the disruptor from a collapsed state to an expanded state. As shown in FIG. 14C, a system in accordance with several embodiments of the present technology can comprise an elongated shaft 1408 configured to be positioned over the elongated member 1404 and/or the disruptor 1400. The elongated shaft 1408 can have a generally tubular shape, and/or the elongated shaft 1408 can comprise one or more suitable metals or polymers, for example, polyimide. In some embodiments, the elongated shaft 1408 can have one or more flexibility-enhancing cuts.

In some embodiments, the elongated shaft 1408 can be configured to prevent or limit accumulation of obstructive material within a lumen of the elongated shaft 1408, which could hinder aspiration of the obstructive material. For example, as shown in FIG. 14C, the elongated shaft 1408 can comprise a cutting portion 1410 located at a distal end of the elongated shaft 1408. The cutting portion 1410 can comprise a sharpened edge, a coring edge, a bevel edge, etc.

Figures 15A, 15B, 15C:
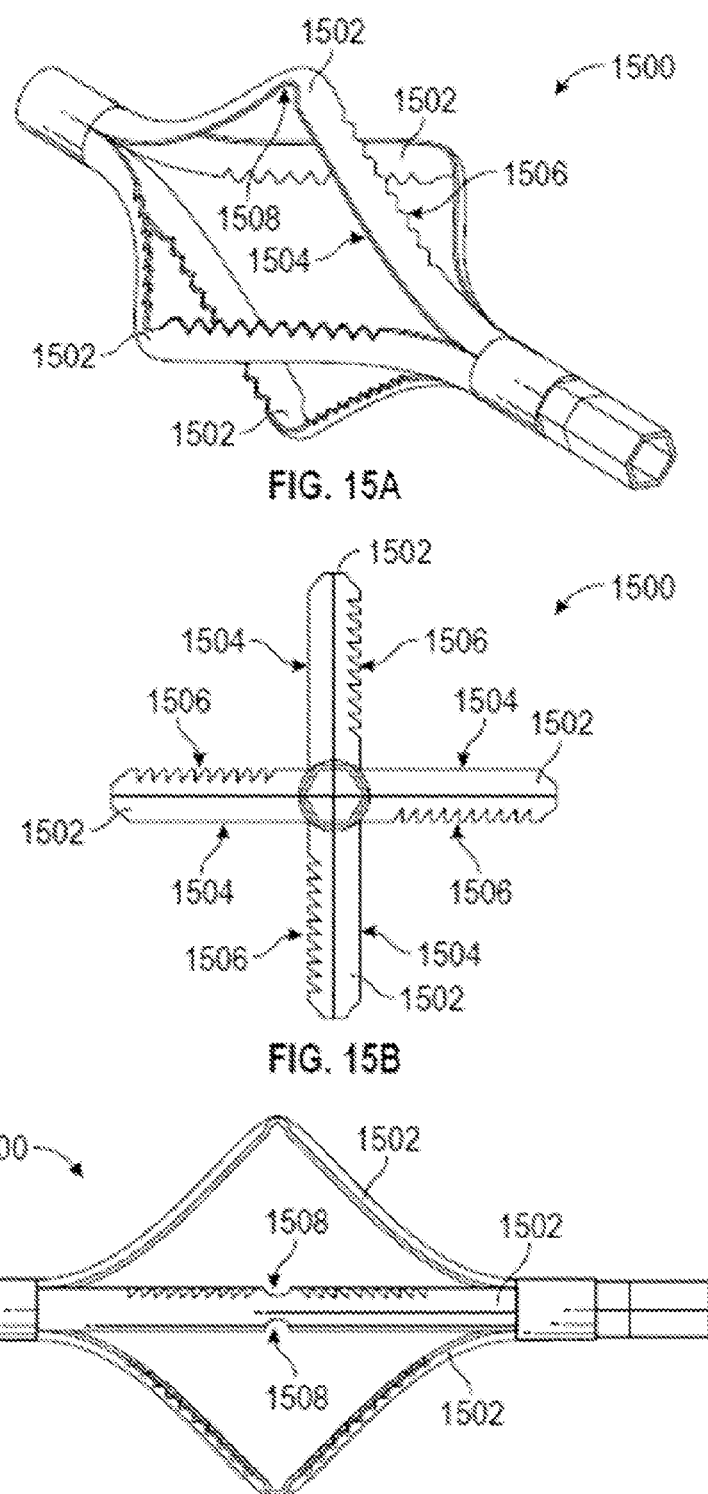
FIGS. 15A-15C are various views of a disrupting element configured in accordance with several embodiments of the present technology.

FIGS. 15A-15C show isometric, end, and side views, respectively, of a disruptor 1500 in accordance with several embodiments of the present technology. The disruptor 1500 can have one or more struts 1502, for example four struts 1502 as shown in FIGS. 15A-15C. Each strut 1502 can comprise a first edge 1504 and a second edge 1506. The first edge 1504 and/or the second edge 1506 can comprise one or more features configured to facilitate disruption of obstructive material engaged by the struts 1502. For example, as shown in FIGS. 15A-15C, the second edge 1506 can be serrated. In these and other embodiments, the second edge 1506 can be a leading edge (e.g., during a rotation of the disruptor 1500, the second edge 1506 can contact the obstructive material before the first edge 1506 contacts the obstructive material). Although not shown in FIGS. 15A-15C, in some embodiments the first edge 1504 is also serrated and/or sharpened. Such configurations may be advantageous for a disruptor 1500 configured to be rotated in two opposing directions.

In some embodiments, the struts 1502 can comprise one or more features configured to facilitate collapse and/or expansion of the disruptor 1500. For example, as shown in FIGS. 15A-15C, the struts 1502 can comprise one or more weakened portions 1508 that facilitate elongation of the struts 1502 as the disruptor 1500 transforms to the collapsed state. The weakened portion 1508 can comprise a recess, an opening, an aperture, a slot, a thinned region, etc.

Figures 16A, 16B, 16C:
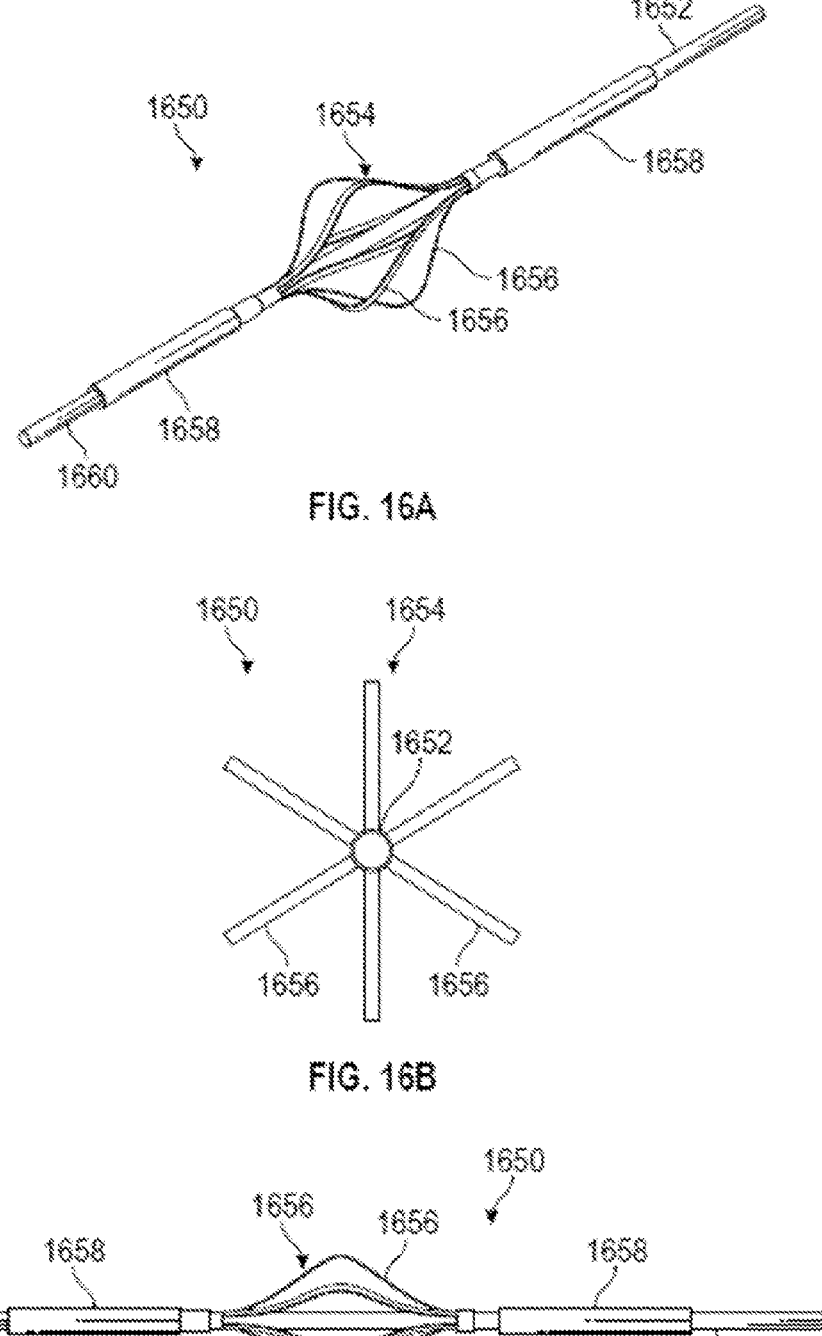
FIGS. 16A-16C are various views of a disrupting element configured in accordance with several embodiments of the present technology.

FIGS. 16A-16C show a disruptor 1650 comprising an elongated member 1652 and a basket 1654 carried by the distal end of the elongated member 1652. The elongated member 1652 can be a tube defining a lumen therethrough or can be a solid member. The basket 1654 may comprise a plurality of expandable struts 1656 (only a few labeled). In some embodiments, the basket 1654 can have an expanded state diameter smaller than the elongated shaft 24 inner diameter (the main lumen and/or a sub-lumen) or even larger since it can actively or passively transform its profile. In some embodiments, such as that shown in FIGS. 16A-16C, the basket 1654 is formed of a tube. The tube may comprise a metal such as, for example, any superelastic or resilient metal (e.g., nitinol, a cobalt-chromium alloy, etc.). In some embodiments the tube has a length of about 0.5 inches. The tube may comprise a plurality of longitudinal slots that create the struts therebetween. The distal and proximal end portions of the tube can remain continuous around their circumference, for example to attach to opposing collars. The tube can be heat set such that the tube self-expands to form a basket when released from a constrained state.

The basket 1654 structure has advantages over the hook embodiments as it has forward and rear edges that will not catch on the elongated shaft 24 (or any constraining structure), while still providing a disrupting and or cutting set of struts 1654. The basket 1654 could be fixed at its distal end while its proximal end is left to slide over the elongated member 24. In this way it could be elongated and compressed for insertion into the elongated shaft 24 lumen and expand to its intended profile in the lumen or in the expanded structure of the elongated shaft 24 at the distal end. In this particular embodiment shown in the figure, the basket 1654 is slidable on the elongated member 1652 in both directions and maintained between two crimped bushings 1658 that govern a finite zone of its sliding. This would allow the basket 1654 to compress as needed while introducing into the elongated shaft 24 or retracting it out of the elongated shaft 24. This embodiment also shows an elongated tip 1660 of about 1 cm length that would be more flexible than the elongated member 1652 to provide an atraumatic, filiform distal end to help guide the device around the clot prior to its retraction and clot agitation.

FIGS. 17A-17C show a disruptor 1700 configured in accordance with several embodiments of the present technology. The disruptor 1700 comprises an elongated shaft 1702 having a hook 1704 at its distal end. The shaft 1702 can be long enough to extend the length of the elongated shaft 22 and/or 24 and the capture structure (such as capture structure 100) and still have enough extra length at the proximal end for holding and imparting motion. The elongated shaft 1702 can be optimized for translation and or rotation but simultaneously minimized to occupy minimal space in the sheath. In some embodiments, the shaft 1702 comprises a nitinol wire having a diameter of from about 0.020 inches to about 0.040 inches. The distal-most tip of the disruptor 1700 can comprise a hook 1704 that extends back proximally. The hook 1704 can have a smaller cross-sectional dimension than the smallest inner diameter of the sheath. The disruptor 1700 can be used to pass through and retract clot material, and in some cases can be rotated to disrupt clot material. In some embodiments, the hook 1704 bends back beyond 180 degrees to reduce the chances of the hook 1704 catching on a portion of an inner surface of the sheath or proximal seal.

FIGS. 18A-18C show a disruptor 1800 configured in accordance with several embodiments of the present technology. The disruptor 1800 includes a shaft 1802 and a plurality of hooks 1804 at the end of the shaft 1802. The hooks 1804 can be arranged in an annular array, similar to a grapple hook. Such an arrangement beneficially provides more surface area for engagement and in more directions, and less rotational direction dependency on engagement.

Figures 19A, 19B, 19C:
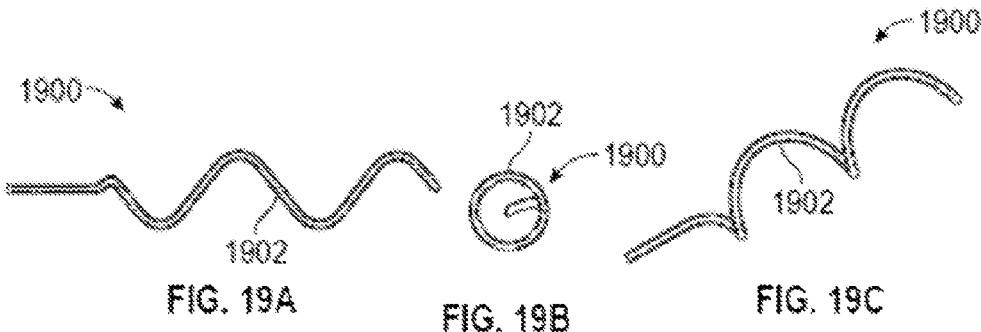
FIGS. 19A-19C are various views of a disrupting element configured in accordance with several embodiments of the present technology.

FIGS. 19A-19C show a disruptor 1900 configured in accordance with several embodiments of the present technology. The disruptor 1900 can comprise an elongated shaft 1902 in the form of a coil. The disruptor 1900 can be configured such that its maximum cross-sectional dimension is approximately the inner diameter of the sheath. Such a configuration can be beneficial for stripping lodged clot off the inner diameter of the sheath lumen. In some embodiments, the elongated shaft 1902 can be rotated about its longitudinal axis to bore into and grab a clot, or to release from the clot in a screw-like fashion. As shown in the end view of FIG. 19B, the projection of the coil can be a hoop with relatively large cross section for engagement. In some embodiments, the loops of the coil can be configured to radially constrict the clot.

Figures 20A, 20B:
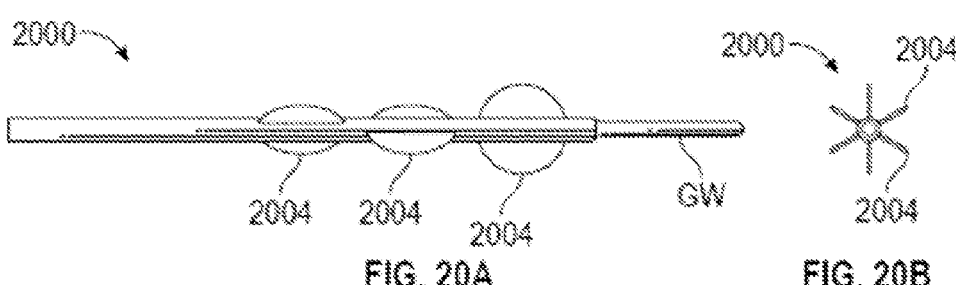
FIGS. 20A-20C are various views of a disrupting element configured in accordance with several embodiments of the present technology.
Figure 20C:
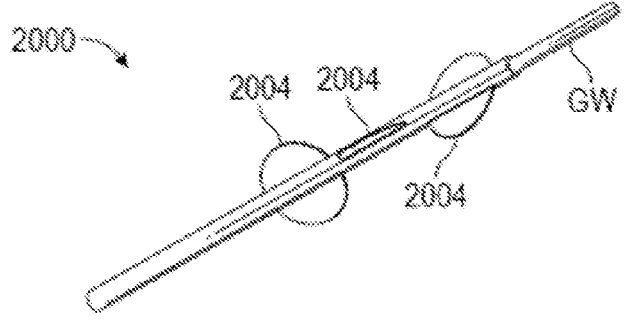

FIGS. 20A-20C show a disruptor 2000 comprising an elongated shaft 2002 and a plurality of curved fins 2004 spaced apart along a distal portion of the shaft 2002. The shaft 2002 can be a solid rod or have a lumen therethrough. In the illustrated embodiment, for example, the shaft 2002 is tubular member defining a lumen and is configured to slidably receive a guidewire GW therethrough. Each of the fins 2004 can have a curved radial surface that presents an atraumatic surface with a low likelihood of catching on the sheath. The shape of the fins 2004 can also be configured to facilitate passage into or through the clot. In some embodiments, all or a portion of the edges of one, some, or all of the fins 2004 are blunt, and in some embodiments, all or a portion of the edges of one, some, or all of the fins 2004 are sharpened. According to several embodiments, a distal-facing edge and/or surface 2008 of one, some, or all of the fins 2004 is a cutting element. In some embodiments, a proximal-facing edge and/or surface 2008 of one, some, or all of the fins 2004 is a cutting element. The individual fins 2004 can have a thickness of from about 0.010 inches to about 0.005 inches and may have a crossing profile just smaller than the inner diameter of the sheath.

In use, the fins 2004 can be translated into or out of a clot via axial movement of the shaft 2002 to provide blunt or cutting clot disruption. In some embodiments, the shaft 2002 and/or fins 2004 can be rotated to bluntly dissect the clot material. Each of the fins 2004 can extend from a different circumferential location about the shaft 2002 such that cumulatively the edges of the fins 2004 are disposed in an annular array about a circumference of the disruptor 2000, as shown in FIG. 20B. In some embodiments, the fins 2004 are positioned at substantially the same longitudinal location on the shaft 2002 but in different orientations, thereby achieving the profile shown in FIG. 20B but without being spaced apart longitudinally along the elongated shaft 2002. The foregoing embodiment reduces a section of maximum material in a discrete location relative to the sheath. This allows an array but minimizes a mechanical "pinch" point that could impede aspiration or physical clot passage.

Figure 21A:
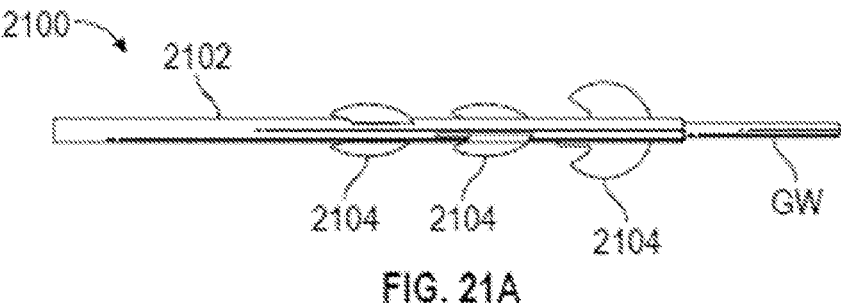
FIGS. 21A-21C are various views of a disrupting element configured in accordance with several embodiments of the present technology.
Figure 21B:
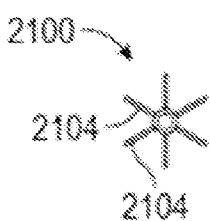
Figure 21C:
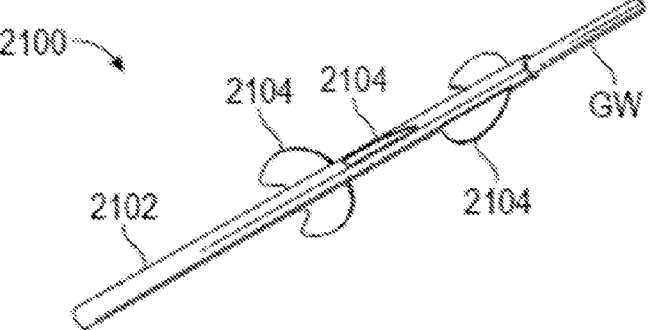

FIGS. 21A-21C show a disruptor 2100 comprising an elongated shaft 2102 and a plurality of curved fins 2104 spaced apart along the shaft 2102. The shaft 2102 can be a solid rod or have a lumen therethrough. In some embodiments, for example, the shaft 2102 defines a lumen and is configured to slidably receive a guidewire GW therethrough. The curvature of the fins 2104 creates an atraumatic surface with a low likelihood of catching on the sheath. The shape of the fins 2104 can also be configured to facilitate passage into or through the clot. In contrast to the fins 1604 of disruptor 1600, the fins 2100 have an arched or curved shape. In some embodiments, all or a portion of the edges of one, some, or all of the fins 2104 are blunt, and in some embodiments, all or a portion of the edges of one, some, or all of the fins 2104 are sharpened. According to several embodiments, a distal-facing edge and/or surface 2108 of one, some, or all of the fins 2104 is a cutting element. In some embodiments, a proximal-facing edge and/or surface 2108 of one, some, or all of the fins 2104 is a cutting element. The individual fins 2104 can have a thickness of from about 0.010 inches to about 0.005 inches and may have a crossing profile just smaller than the inner diameter of the sheath.

In use, the fins 2104 can be translated into or out of a clot to provide blunt or cutting clot disruption. In some embodiments, the shaft 2102 and/or fins 2104 can be rotated to bluntly dissect the clot material. The orientation of the fins 2104 relative to the shaft 2102 can be offset from one another such that cumulatively the edges of the fins 2104 are spaced apart about a circumference of the disruptor 2100, as shown in FIG. 21B. In some embodiments, the fins 2104 are positioned at substantially the same longitudinal location on the shaft 2102 but in different orientations, thereby achieving the profile shown in FIG. 21B but without being spaced apart longitudinally along the elongated shaft 2102. The foregoing embodiment reduces a section of maximum material in a discrete location relative to the sheath. This allows an array but minimizes a mechanical "pinch" point that could impede aspiration or physical clot passage.

Figures 22A, 22B:
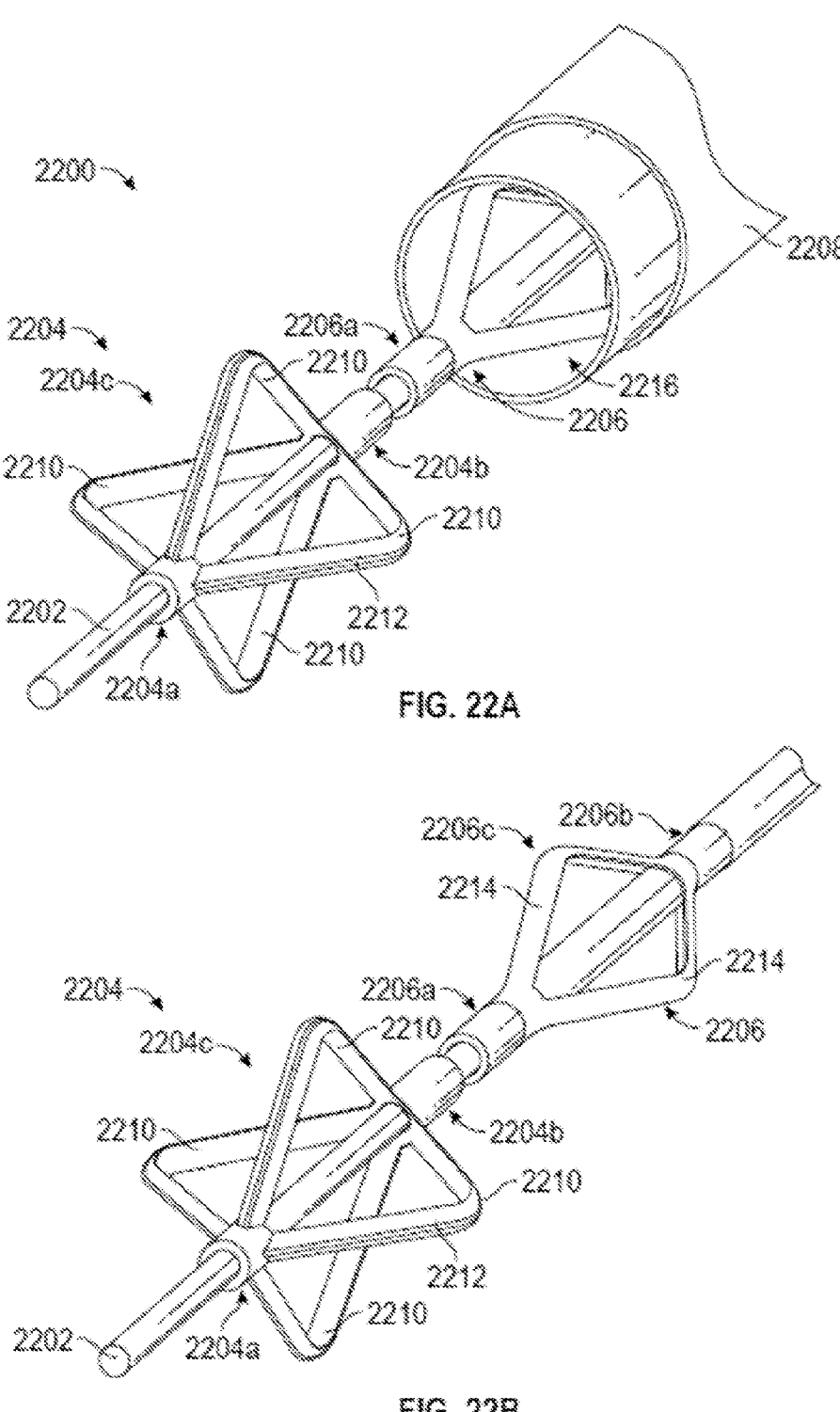
FIGS. 22A and 22B are various views of a disrupting element configured in accordance with several embodiments of the present technology.

In any of the embodiments described herein, a system in accordance with the present technology can include a centering element configured to facilitate alignment of an elongated member carrying a disruptor with a lumen of an elongated shaft configured to receive the elongated member and/or precise and accurate positioning of the disruptor within a distal housing. For example, FIG. 22A depicts a system 2200 comprising an elongated member 2202, a disruptor 2204 carried by the elongated member 2202, a centering element 2206 carried by the elongated member 2202, and an elongated shaft 2208. FIG. 22B depicts the system 2200 without the elongated shaft 2208. As shown in FIGS. 22A and 22B, the disruptor 2204 can have a first end portion 2204a, a second end portion 2204b, and an intermediate portion 2204c. The first and second end portions 2204a, 2204b can be circumferentially continuous while the intermediate portion 2204c is circumferentially discontinuous and comprises a plurality of struts 2210. For example, as shown in FIGS. 22A and 22B, the intermediate portion 2204c of the disruptor 2204 can comprise four struts 2210. In some embodiments, one or more of the struts 2210 can include a cutting feature 2212 (e.g., a blade, a protrusion, etc.) configured to facilitate disruption of the obstructive material. The disruptor 2204 and/or any portion thereof can be similar to any of the disruptors disclosed herein. For example, the disruptor 2204 can comprise a laser cut tube.

In some embodiments, for example as shown in FIGS. 22A and 22B, the centering element 2206 comprises a first end portion 2206a, a second end portion 2206b opposite the first end portion 2206a, and an intermediate portion 2206c between the first and second end portions 2206a, 2206b. The first and second end portions 2206a, 2206b can be circumferentially continuous while the intermediate portion 2206c is circumferentially discontinuous and comprises a plurality of struts 2214. Additionally or alternatively, the intermediate portion 2206c can be circumferentially continuous. A cross-sectional dimension of the centering element 2206 at the intermediate portion 2206c can be greater than a cross-sectional dimension of the centering element 2206 at the first end portion 2206a and/or the second end portion 2206b. In some embodiments, a maximum cross-sectional dimension of the centering element 2206 substantially corresponds to, is slightly less than, or is slightly more than a cross-sectional dimension of a lumen 2216 of the elongated shaft 2208. Accordingly, when the elongated member 2202 carrying the centering element 2206 is positioned within the lumen 2216 of the elongated shaft 2208, the centering element 2206 can contact wall of the elongated shaft 2208, either continuously or intermittently, such that the elongated member 2202 is substantially centered within the lumen 2216.

In certain cases where the obstructive material is harder and/or more difficult to separate, it may be beneficial to utilize a disrupting device configured to shave the obstructive material. Thrombus, for example, can undergo several phases of maturation in which the initial fibrin mesh is infiltrated by inflammatory and mesenchymal cells that gradually lead to a thickening of extant fibrin fibers or replacement with other structural proteins, including collagen. Such remodeling and replacement of structural constituents within a thrombus alters its biomechanical properties and renders certain disruption methods less effective (as compared to these same methods on softer and/or less organized clot). For instance, the disrupting device shown in FIGS. 13A-13E may be less effective when attempting to break apart more organized and/or mature clot material, as the rotational force of the arms may not be sufficient to break apart and/or separate the clot material. As a result, the clot material may simply rotate with the arms (without breaking up) and little (if any) clot material is removed through the aspiration lumen.

Figure 23:
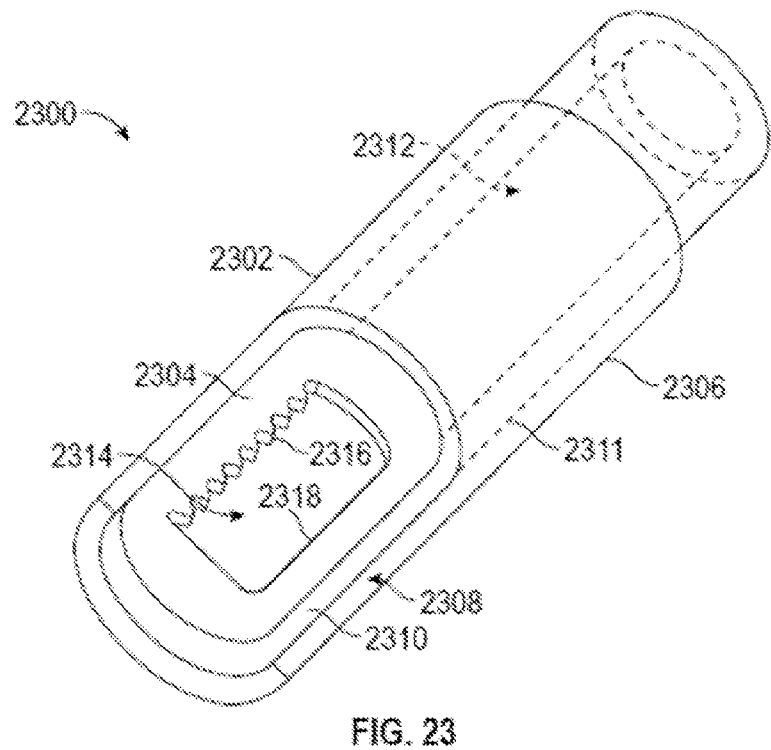
FIGS. 23, 24A, 24B, and 25 are various views of a disrupting device configured in accordance with several embodiments of the present technology.

Several disrupting devices of the present technology address the foregoing challenges by providing an opposing force to the rotational and/or axial motion of the disrupting elements, thereby trapping the obstructive material and enabling the disrupting elements to apply a greater cutting and/or separation force to the obstructive material. FIG. 23, for example, shows such a disrupting device 2300. The disrupting device 2300 comprises a supporting element 2302 and a disrupting element 2304 positioned within a lumen of the supporting element 2302. In some embodiments, the disrupting element 2304 is slidably positioned within the supporting element 2302 such that the disrupting element 2304 can move axially relative to the supporting element 2302, and in some cases the disrupting element 2304 can be completely removed from the lumen of the supporting element 2302. The lumen of the supporting element 2302, for example, can be configured to receive other interventional tools therethrough, such as other types of disruptors and/or disrupting devices.

The supporting element 2302 can comprise a tubular portion 2306 and an open distal end portion 2308 along which the sidewall extends less than 360 degrees, thereby exposing lateral supporting edges 2310. The supporting edges 2310 can be blunt or sharpened. In some embodiments, the supporting element 2302 is a separate piece that is coupled to a distal end of an elongated shaft, such as elongated shaft 24 and/or an aspiration catheter. In some embodiments, the supporting element 2302 is integral with an elongated shaft, such as elongated shaft 24 and/or an aspiration catheter. In several of such embodiments, the elongated shaft and supporting element 2302 can be formed of a hypotube. The hypotube can be laser cut at the distal end to form the open distal end portion 2308. According to several embodiments, the hypotube can also have one or more circumferential slits and/or cuts along the portion of its length coinciding with all or a portion of the supporting element 2302 to increase the flexibility of the supporting element 2302. In any case, the lumen of the supporting element 2302 can be configured to be fluidly coupled to a negative pressure source. In some embodiments, the supporting element 2302 comprises a separate shaft slidably disposed within the elongated shaft 24 and/or sheath.

As shown in FIG. 23, the disrupting element 2304 can comprise an elongated shaft 2311 defining a lumen therethrough 2312. The disrupting element 2304 can have an opening 2314 at its distal end portion that faces away from a longitudinal axis of the device in a radial direction. The opening 2314 can be defined by a surface 2318, at least a portion of which comprises a disrupting edge 2316 having one or more features configured to penetrate, cut, or otherwise disrupt obstructive material. For example, in some embodiments the disrupting edge 2316 can be sharpened and/or serrated. In several embodiments, such as that shown in FIG. 23, the disrupting edge 2316 extends along only a portion of the surface 2318 defining the opening 2314. In some embodiments, the disrupting edge 2316 extends along the entire surface 2318. In some embodiments, the disrupting element 2304 has a proximal end portion configured to be coupled to a negative pressure source to draw captured obstructive material towards and through the opening 2314. In some embodiments, one or both of the supporting element 2302 or disrupting element 2304 is not configured to be fluidly coupled to a negative pressure source.

Figures 24A, 24B:
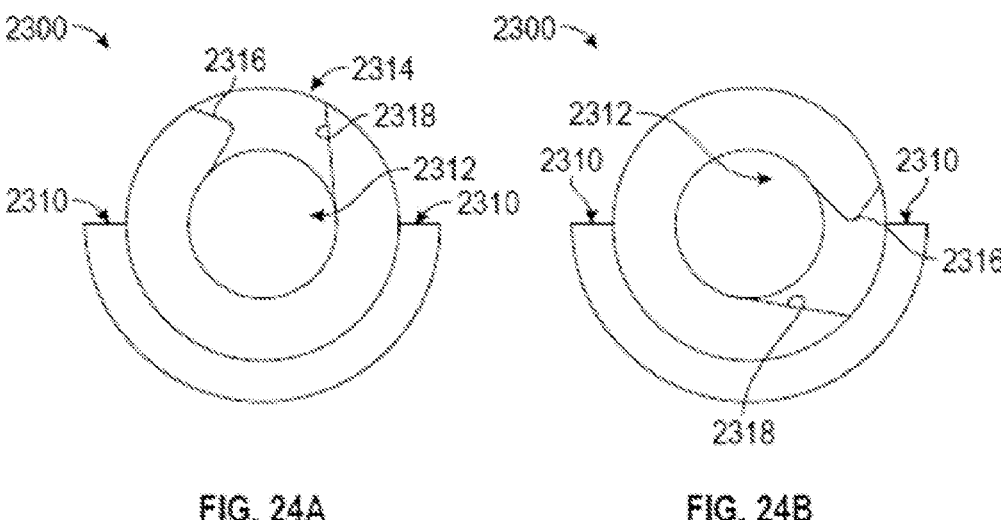

As shown schematically in FIGS. 24A and 24B, the disrupting element 2304 can be configured to rotate relative to the supporting element 2302, thereby bringing the disrupting surface 2316 towards a supporting edge 2310 of the supporting element 2302. In so doing, obstructive material becomes trapped between the disrupting edge 2316 and the supporting edge 2310 such that the supporting edge 2310 provides resistance to rotation of the obstructive material with the disrupting edge 2316 and enables the disrupting edge 2316 to cut through the obstructive material. In some embodiments, both the supporting edge 2310 and disrupting edge 2316 are configured to cut and/or penetrate obstructive material. The separated portions of the obstructive material can then be drawn through the lumen 2312 of the disrupting element 2304 and removed from the body.

Figure 25:
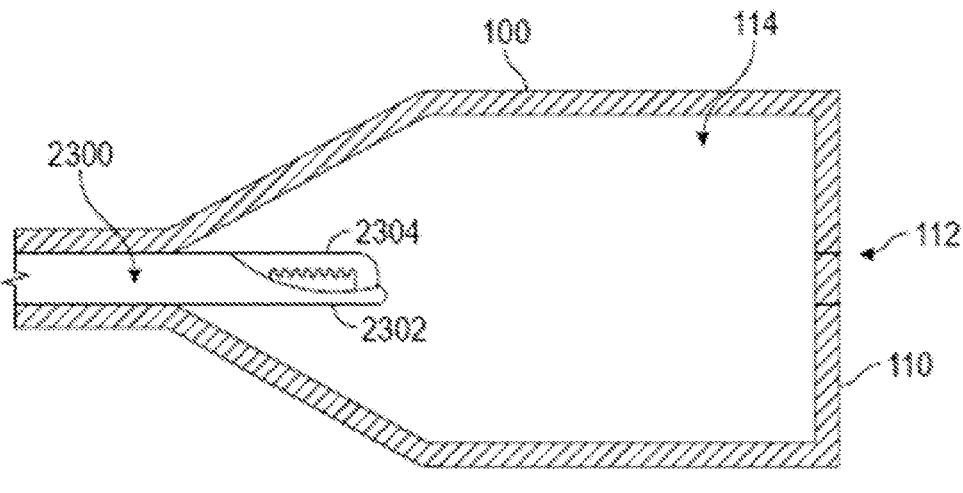

FIG. 25 shows a distal end portion of a treatment system configured in accordance with several embodiments of the present technology, showing the disrupting device 2300 positioned within the capture structure 100. The supporting element 2302 can be positioned within the interior region 114 of the capture structure 100 such that the open distal end region can fully access capture clot (not shown) within the capture structure 100.

Figure 26:
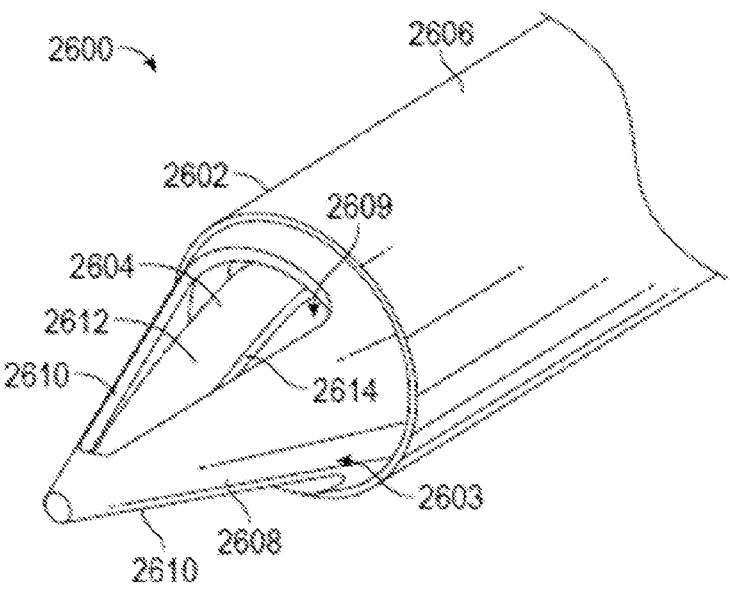
FIGS. 26 and 27 show a disrupting device configured in accordance with several embodiments of the present technology.

FIG. 26 shows a distal portion of a disrupting device 2600 configured in accordance with several embodiments of the present technology. The disrupting device 2600 can comprise a supporting element 2602 and a disrupting element 2604 positioned within a lumen of the supporting element 2602. In some embodiments, the disrupting element 2604 is slidably positioned within the supporting element 2602 such that the disrupting element 2604 can move axially relative to the supporting element 2602, and in some cases the disrupting element 2604 can be completely removed from the lumen of the supporting element 2602. The lumen of the supporting element 2602, for example, can be configured to receive other interventional tools therethrough, such as other types of disruptors and/or disrupting devices.

The supporting element 2602 can comprise a tubular portion 2606 and a conical distal end portion 2603 comprising a plurality of arms 2608 and openings 2609 between the arms 2608. Each of the arms 2608 can extend distally and radially inwardly from the tubular portion 2606. In some embodiments, the distal end portion 2603 can have other shapes and/or may not taper distally. Each of the arms 2608 can have supporting edges 2610 which can be blunt or sharpened.

The supporting element 2602 can be arranged in a variety of ways relative to an elongated shaft (e.g., elongated shaft 24, aspiration catheter, etc.). For example, the supporting element 2602 may comprise only the distal end portion 2603, which may be coupled to the distal end portion of an elongated shaft and/or aspiration catheter. In some embodiments, the supporting element 2602 comprises both the tubular portion 2606 and the distal end portion 2603, but is still a separate piece from the elongated shaft. According to several aspects of the present technology, the tubular portion 2606 extends all the way proximally to the user (i.e., the tubular portion 2606 comprises the elongated shaft), and is slidably disposed within an aspiration catheter (such as elongated shaft 24). In some embodiments, the lumen of the tubular portion 2606 is configured to be coupled to a negative pressure source.

As shown in FIG. 26, the disrupting element 2604 can comprise a plurality of arms 2612 (only one shown) and an elongated member (not visible) extending proximally to the user. The elongated member can be a solid elongated member, or may be an elongated shaft. The arms 2612 can have disrupting edges 2614, at least a portion of which comprises one or more features configured to penetrate, cut, or otherwise disrupt obstructive material. For example, in some embodiments the disrupting edges 2614 can be sharpened and/or serrated. In some embodiments, the disrupting element 2604 has a proximal end portion configured to be coupled to a negative pressure source to draw captured obstructive material towards and through gaps between the arms 2612. In some embodiments, one or both of the supporting element 2602 or disrupting element 2604 is not configured to be fluidly coupled to a negative pressure source.

The arms 2612 of the disrupting element 2604 can be configured to rotate relative to the arms 2608 of the supporting element 2602, thereby bringing the disrupting edges 2614 towards an edge 2610 of the supporting element 2602. In so doing, obstructive material becomes trapped between the disrupting edge 2614 and the supporting edge 2610 such that the supporting edge 2610 provides resistance to rotation of the obstructive material with the disrupting edge 2614 and enables the disrupting edge 2614 to cut through the obstructive material. In some embodiments, both the supporting edge 2610 and disrupting edge 2614 are configured to cut and/or penetrate obstructive material. The separated portions of the obstructive material can then be drawn through the lumen of the supporting element 2602 and/or disrupting element 2604 and removed from the body.

Figure 27:
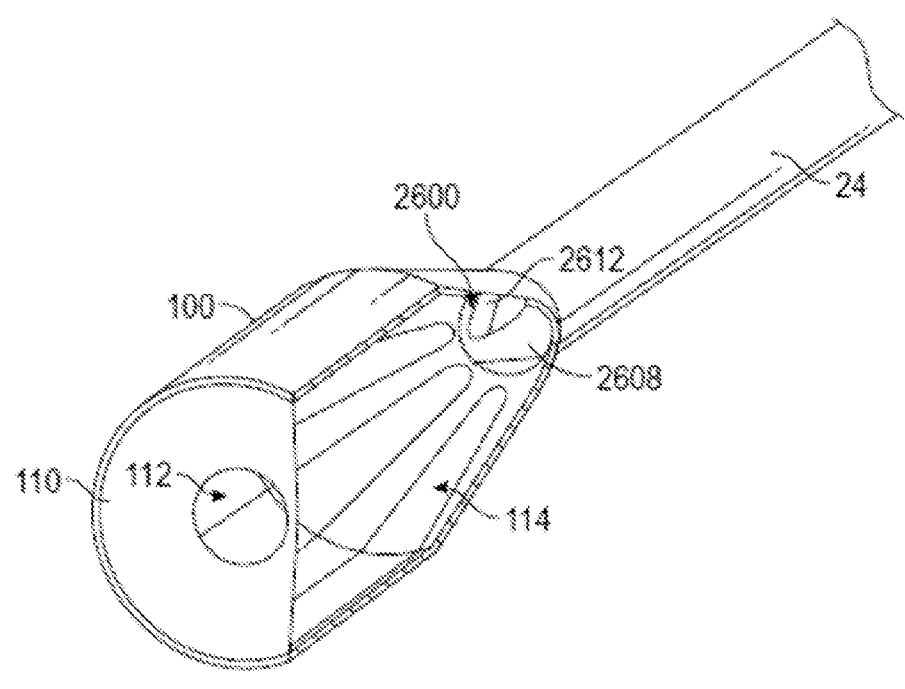

FIG. 27 shows a distal end portion of a treatment system configured in accordance with several embodiments of the present technology, showing the disrupting device 2600 positioned within the capture structure 100. At least a portion of the disrupting device 2600 can be positioned within the interior region 114 of the capture structure 100 such that the arms 2608, 2612 of one or both of the supporting element 2602 and disrupting element 2604 can fully access capture obstructive material (not shown) within the capture structure 100.

Figure 28:
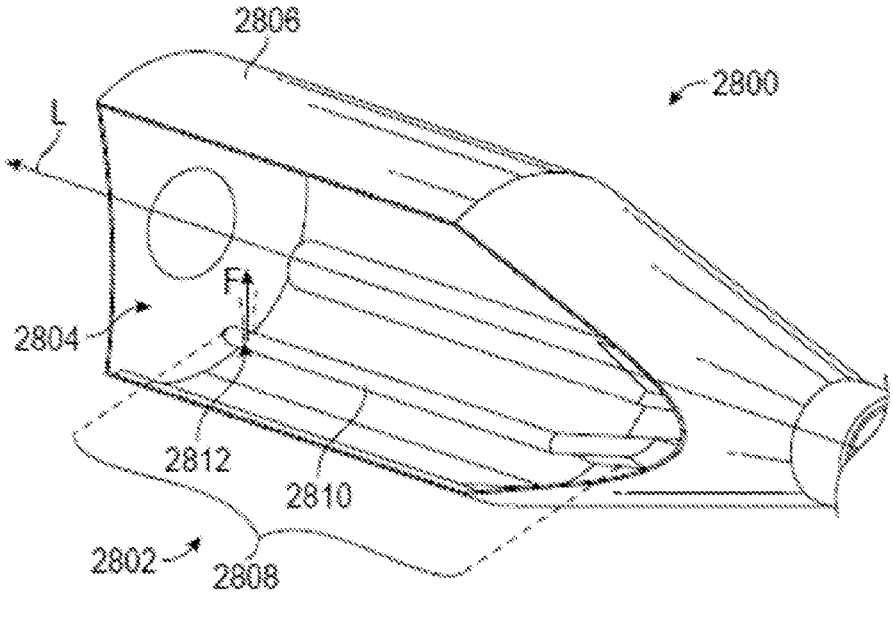
FIG. 28 shows a disrupting device configured in accordance with several embodiments of the present technology.

According to various aspects of the present technology, the treatment system can include a disrupting device configured to hydraulically disrupt obstructive material, rather than (or in addition to) mechanically disrupting the obstructive material. FIG. 28 shows an example distal end of a system 2800 comprising a disruptor 2802 configured to hydraulically disrupt obstructive material. In some embodiments, for example as shown in FIG. 28, a distal region of the disruptor 2802 can be positioned within an interior region 2804 of a capture structure (such as capture structure 100) to deliver fluid to the interior region 2804 and any obstructive material contained therein. The disruptor 2802 can be configured to rotate and/or slide axially relative to the capture structure 100. In some embodiments, an axial and/or rotational position of the disruptor 2802 is fixed relative to the capture structure 100. According to several embodiments, the distal region of the disruptor 2802 can be configured to be positioned within a lumen of the elongated shaft 24 and deliver fluid to the lumen of the elongated shaft 24. In any case, the elongated element 2808 of the disruptor 2802 can be positioned near a sidewall of the capture structure 100 (as shown in FIG. 28) or may extend through the capture structure 100 at a location that is spaced apart from the sidewall.

As shown in FIG. 28, the disruptor 2802 can comprise a hollow elongated element 2808 having a sidewall 2810 defining a lumen and one or more apertures 2812 extending through the sidewall. A proximal portion of the elongated element 2808 can be configured to be coupled to an extracorporeal fluid source, and a distal end of the elongated element 2808 can be closed. In some embodiments, the distal end comprises one or more openings (not shown). In use, fluid flows through the lumen of the elongated element 2808 and into the interior region 2804 through the apertures 2812, thereby disrupting obstructive material within the interior region 2804. The fluid can comprise saline, a lysing agent, a contrast agent, and/or other suitable fluids.

Disruption of obstructive material with fluid can be advantageous in that fewer and/or smaller structural components may be required of the disruptor, thus freeing up more space within the capture structure. Additionally, delivery of pressurized fluid to the interior region 2804 can increase the total pressure acting on obstructive material within the interior region 2804. In some embodiments, the system is configured such that fluid can be delivered to the interior region 2804 of the capture structure 100 while negative pressure is applied to the interior region 2804 to prevent or limit accumulation of the fluid within the interior region 2804. Fluid delivery and aspiration can occur simultaneously and/or independently.

The lumen of the elongated element 2808 can have a diameter of between about 0.01 in and about 0.05 in, between about 0.015 in and about 0.045 in, between about 0.02 in and about 0.04 in, between about 0.025 in and about 0.035 in, less than 0.01 in, about 0.01 in, about 0.015 in, about 0.02 in, about 0.025 in, about 0.03 in, about 0.035 in, about 0.04 in, about 0.045 in, about 0.05 in, or greater than 0.05 in. A thickness of the sidewall of the elongated element 2808 can be between about 0.001 in and about 0.005 in, between about 0.002 in and about 0.004 in, less than 0.001 in, about 0.001 in, about 0.002 in, about 0.003 in, about 0.004 in, about 0.005 in, about 0.003 in or more, or about 0.005 in or more. The elongated element 2808 can comprise a polymer (e.g., polyimide, etc.), a metal, or another suitable material. In some embodiments, the sidewall of the elongated element 2808 can include a reinforcing element such as a braid, a coil, etc.

Fluid can be delivered to the lumen of the elongated element 2808 at a pressure between about 100 psi and about 2000 psi, between about 150 psi and about 1500 psi, between about 200 psi and about 1000 psi, between about 250 psi and about 950 psi, between about 300 psi and about 900 psi, between about 350 psi and about 850 psi, between about 400 psi and about 800 psi, between about 450 psi and about 750 psi, between about 500 psi and about 700 psi, or between about 550 psi and about 650 psi.

The one or more apertures 2812 can have a diameter between about 0.01 in and about 0.05 in, between about 0.015 in and about 0.045 in, between about 0.02 in and about 0.04 in, between about, between about 0.025 in and about 0.035 in, less than 0.01 in, about 0.0.1 in, about 0.02 in, about 0.03 in, about 0.04 in, about 0.05 in, or greater than 0.05 in. Additionally or alternatively, the apertures 2812 can comprise one or more slots and/or slits. The apertures 2812 can have any suitable cross-sectional shape such as, but not limited to, circular, rectangular, triangular, polygonal, etc. In embodiments in which the elongated element 2808 comprises multiple apertures 2812, the apertures 2812 can be separated by a spacing of about 0.01 in, about 0.02 in, about 0.03 in, about 0.04 in, about 0.05 in, or more than 0.05 in.

The longitudinal and circumferential positions of the apertures 2812 along the elongated element 2808 and the angle of the elongated element 2808 relative to the longitudinal axis of the capture structure 100 can be adjusted to direct fluid flow in a desired direction. For example, as shown in FIG. 28, the elongated element 2808 can extend substantially parallel to a longitudinal axis L of the capture structure 100 with at least one aperture 2812 positioned at a circumferential location such that the aperture 2812 faces towards the interior region 2804 of the capture structure 100. Thus, fluid flows away from the aperture 2812 in a direction that is substantially perpendicular to the longitudinal axis L of the capture structure 100. In some embodiments, a distal portion of the elongated element 2808 can be angled relative to the longitudinal axis of the capture structure 100 such that at least some of the fluid flows away from the elongated element 2808 at a non-90 degree angle relative to the longitudinal axis of the capture structure 100. According to several embodiments, the disrupting device 2800 can be configured to deliver fluid into the capture structure 100 and/or elongated shaft 24 along multiple fluid flow paths (see, for example, first fluid flow path F1, second fluid flow path F2, and third fluid flow path F3 in FIG. 29). The fluid flow paths can be spaced apart and/or angled with respect to one another. In some embodiments, the first fluid flow path F1 is angled with respect to the second fluid flow path F2 by about 45 degrees and/or the second fluid flow path F2 is angled with respect to the third fluid flow path F3 by about 45 degrees. In some embodiments, one or more fluid flow paths are directed proximally to facilitate aspiration of obstructive material proximally through the system and out of a patient's body.

Although FIG. 28 depicts one elongated element 2808 with one aperture 2812, the treatment systems of the present technology can comprise any number of elongated elements 2808 (e.g., two elongated elements, three elongated elements, four elongated elements, etc.) or apertures 2812 (e.g., two apertures, three apertures, four apertures, five apertures, six apertures, etc.).

Figure 29:
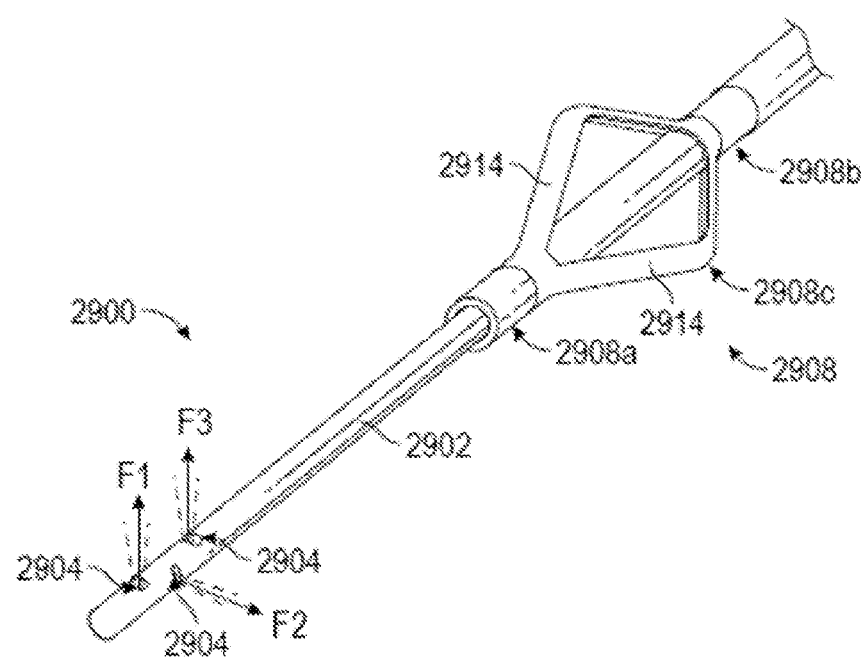
FIGS. 29 and 30 are various views of a disrupting device configured in accordance with several embodiments of the present technology.
Figure 30:
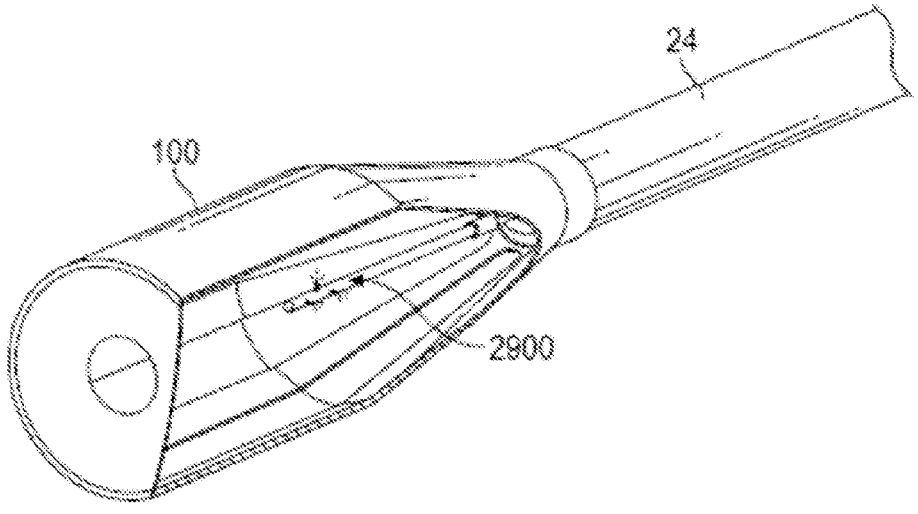

FIG. 29 shows a disrupting device 2900 configured in accordance with the present technology, and FIG. 30 shows the disrupting device 2900 positioned within a capture structure 100. The disrupting device 2900 can comprise an elongated element 2902 having one or more apertures 2904 extending through its sidewall and configured to receive disruptive fluid therethrough. In some embodiments the disrupting device 2900 can include a centering element 2908 slidably or fixedly coupled to the elongated element 2902 of the disrupting device 2900. The centering element 2908 can be configured to facilitate alignment of the disrupting device 2900 with a lumen of the elongated shaft 24 and/or an interior region of the capture structure 100. The centering element 2908 can be similar to any of the centering elements disclosed herein. For example, as shown in FIG. 29, the centering element 2908 can comprise a first end portion 2908a, a second end portion 2908b opposite the first end portion 2908a, and an intermediate portion 2908c, between the first and second end portions 2908a, 2908b. The first and second end portions 2908a, 2908b can be circumferentially continuous while the intermediate portion 2908c can be circumferentially discontinuous such that the intermediate portion 2908c comprises a plurality of struts 2914. Additionally or alternatively, the intermediate portion 2908c can be circumferentially continuous. A cross-sectional dimension of the centering element 2908 at the intermediate portion 2908c can be greater than a cross-sectional dimension of the centering element 2908 at the first end portion 2908a and/or the second end portion 2908b. In some embodiments, a maximum cross-sectional dimension of the centering element 2908 is substantially equivalent to a cross-sectional dimension of the elongated shaft 24. Accordingly, when the centering element 2908 is positioned within the lumen of the elongated shaft 24, the centering element 2908 contacts an inner surface of the elongated shaft 24 such that the disrupting device 2900 is substantially centered within the lumen of the elongated shaft 24 and/or an interior region of the capture structure 100.

It will be appreciated that the centering elements of the present technology can be used with any of the disrupting devices disclosed herein.

Figure 31A:
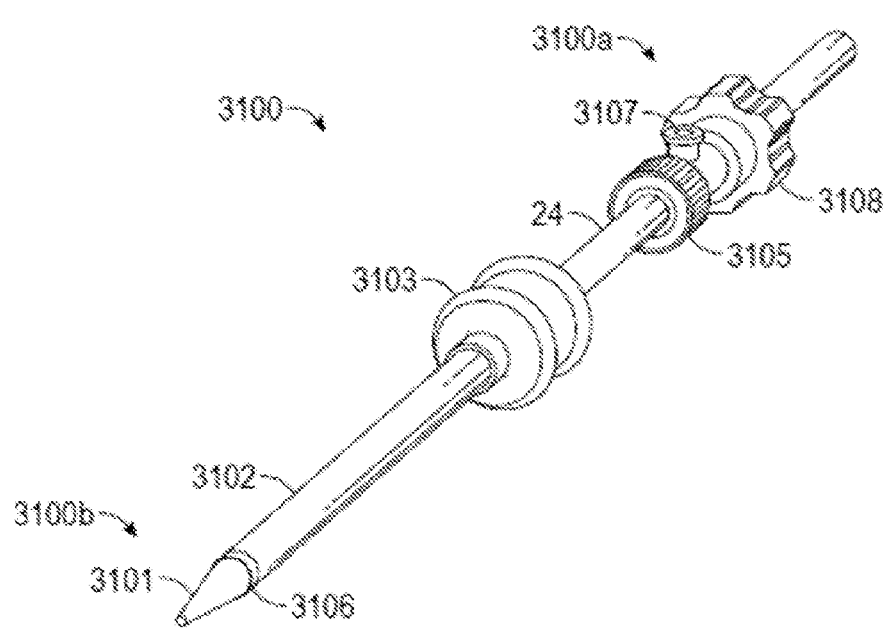
FIG. 31A is an isometric view of a treatment system in a low-profile delivery state configured in accordance with several embodiments of the present technology.

FIGS. 31A-31D show a treatment system 3100 configured in accordance with the present technology. FIG. 31A shows the system 3100 in a low-profile delivery state. The system 3100 has a proximal end portion 3100a and a distal end portion 3100b. The system 3100 can comprise an outer sheath 3102 and an elongated shaft 24 (see FIG. 31B) slidably disposed within a lumen of the sheath 3102. The outer sheath 3102 can have a proximal end region coupled to a slider 3103 and a distal end region. The elongated shaft 3104 can have a proximal end region coupled to a hub or handle 3105 having an aspiration port 3107, a hemostasis valve 3108, and/or other connectors. The system 3100 can further optionally include a dilator 3101, a disrupting device 200 (see FIG. 31C), and a guidewire (not shown). Any of the treatment systems disclosed herein, including treatment systems 1 and 1200, can include a guidewire, a guidewire lumen, and/or a dilator.

In some embodiments, the sheath 3102 comprises a reinforced polymeric shaft. As previously mentioned, the proximal end region of the sheath 3102 can be coupled to a slider 3103 (e.g., thermally or adhesively bonded), and a distal end region of the sheath 3102 can comprise a radiopaque portion 3106. For example, the radiopaque portion 3106 can comprise a radiopaque marker that is coupled (e.g., thermally or adhesively bonded) to an outer surface of the sheath 3102.

Figure 31B:
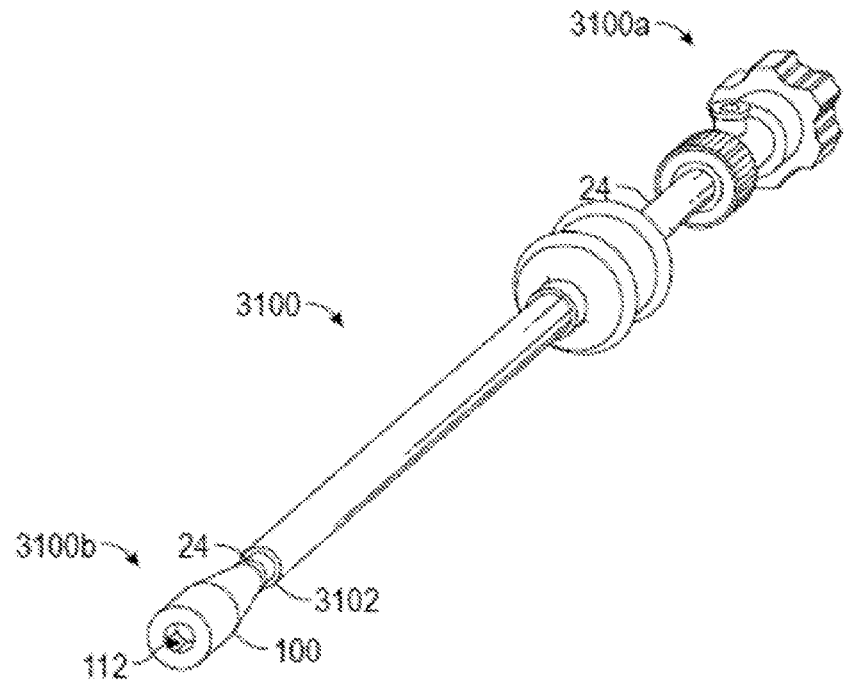
FIG. 31B is an isometric view of the treatment system of FIG. 31A in an expanded state configured in accordance with several embodiments of the present technology.
Figure 31C:
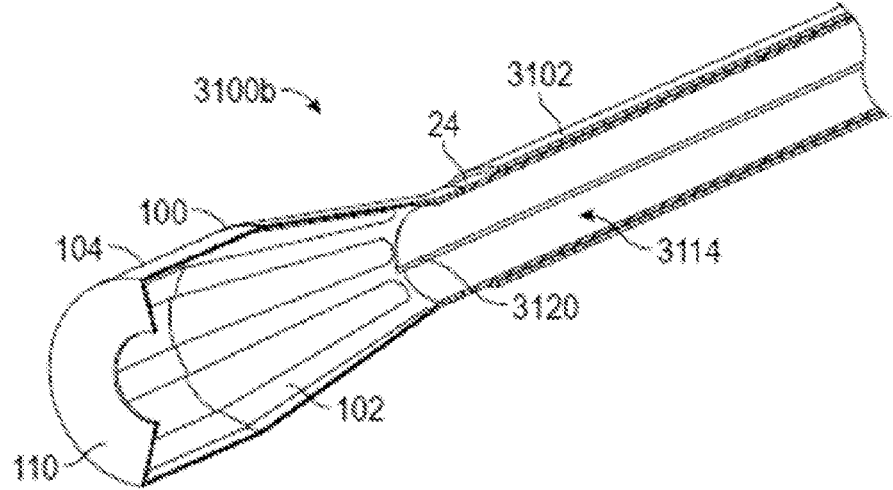
FIG. 31C is an enlarged, cross-sectional view of a distal portion of the treatment system shown in FIG. 31B.

FIG. 31B shows the system 3100 with the dilator 3101 removed and the sheath 3102 withdrawn such that the capture structure 100 is in an expanded state. FIG. 31C shows the orifice 112, the expandable frame 102, the cover 104 comprising the capture structure 100. As is true for any of the expandable frames disclosed herein, the expandable frame 102 can be made from a hypotube (superelastic and/or resilient, or not). In some embodiments, the frame 102 can be made of polymeric or metallic weave or other expandable elements as described herein. As is true for any of the covers disclosed herein, the cover 104 can be a highly conformable material with a wall thickness of less than 0.50 mm, less than 0.40 mm, less than 0.38 mm, less than 0.30 mm, less than 0.20 mm, and others. In some embodiments, the cover 104 is made from a thermal plastic elastomer, such as a thermal plastic polyurethane having a hardness less than 65 Shore D.

FIG. 31C shows an example of a disrupting device 200 having an elongated portion and a disruptor 3120 at the distal end of the elongated portion. The disrupting device 200 can be positioned relative to the elongated shaft 24 such that the disruptor 3120 is located within the interior region of the capture structure 100. Any of the disrupting devices disclosed herein can be used with the system 3100. Moreover, any of the capture structures disclosed herein can be used with the system 3100.

Figures 31D, 32:
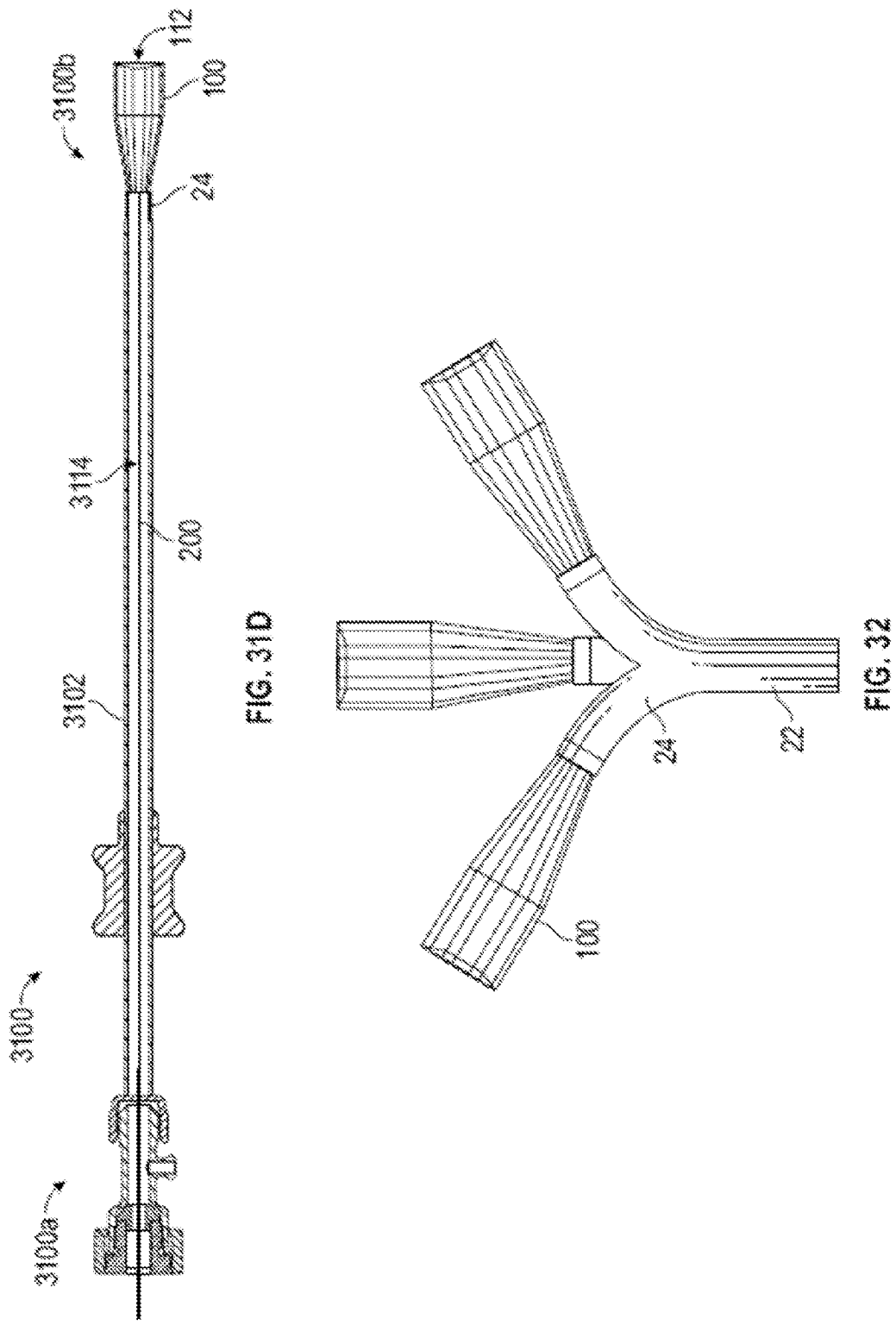
FIG. 31D is a side cross-sectional view of the treatment system shown in FIG. 31B.
FIG. 32 shows an articulating distal portion of a treatment system configured in accordance with several embodiments of the present technology.

FIG. 31D provides a cross-sectional view of the system 3100 and shows the lumen 3114 of the elongated shaft 3102. As previously discussed, the lumen 3114 fluidly connects the stretchable orifice 112 to the channels within the handle.

According to several aspects of the present technology, the elongated shaft 24 and/or sheath 22 can together or separately be configured for directional steering. Such a feature can be beneficial for navigating the tortuous anatomy and/or directing the capture structure 100, engagement wall 110, and/or opening 112 to engage obstructive material in the vessel lumen. The distal portion of any of the elongated shafts disclosed herein, including elongated shaft 24, can be configured to bend, flex, or otherwise articulate in a predetermined manner. For example, in some embodiments the elongated shaft 24 and/or sheath 22 includes a manipulation member having a first end coupled to an actuator at a corresponding handle and a second end coupled to a distal portion of the corresponding elongated shaft 24 and/or sheath 22. The articulation enables the operator to actively steer the distal portion of the elongated shaft 24 and/or sheath 22 through the vascular anatomy as well as span the entire vessel wall of larger vessels, such as the main pulmonary artery. The articulation directs the centerline of at least a portion of the distal section and or orifice at least 5 degrees from the centerline of the proximal section of the central lumen. In some embodiments, a portion of the distal region of the elongated shaft 24 and/or sheath 22 has a preset curve of a desired radius so that, at rest, the centerline of the portion is at least 5 degrees from the centerline of the proximal portion of the corresponding elongated member and less than 270 degrees from the proximal centerline. In such embodiments, the curved distal portion is then covered with an outer sheath to align the centerline of the distal portion with the centerline of the proximal portion. The outer sheath is then retracted axially to expose a portion of the curved distal portion, causing the centerline of the distal portion to angle away from the centerline of the proximal portion of the corresponding elongated shaft 24 and/or sheath 22.

In some embodiments, the elongated shaft 24 and/or sheath 22 is configured to bend at its distal portion. The elongated shaft 24 and/or sheath 22 can be configured to automatically assume a desired bending angle upon release from a restraint, such as a release wire or outer sheath. Such a preset bend in the elongated shaft 24 and/or sheath 22 can be achieved by coldworking, heat treatment, selective etching, and/or selective removal of material from the elongated shaft 24 and/or sheath 22 to impart preferential bending towards the desired angle. In some embodiments, the system can comprise an outer sheath (such as sheath 2602) configured to be translated relative to the elongated shaft 24 and/or sheath 22 to axially to expose more or less of the bendable portion to achieve more or less of a preset bending angle. The sheath 22, for example, can be used to selectively expose portions of the elongated shaft 24 to achieve a desired bending of the elongated shaft 25. In these and other embodiments, the elongated shaft 24 and/or sheath 22 can be configured to be manually manipulated and/or activated into a bent configuration. FIG. 32 depicts an example treatment system having an elongated shaft 24 configured to bend at its distal portion. The bending location is positioned proximal to the capture structure 100, thereby allowing the system to direct the entire capture structure 100 towards the intended target (such as obstructive material).

Figure 33A:
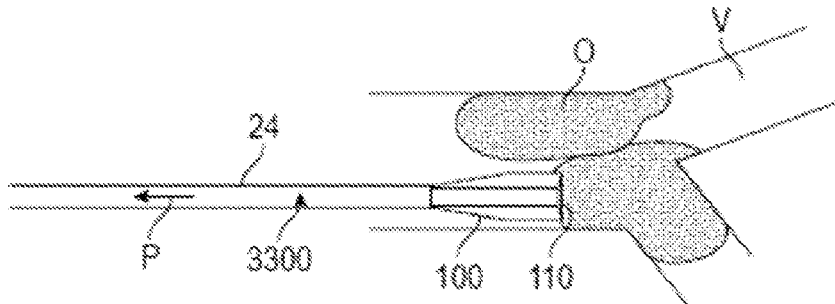
FIGS. 33A-33C illustrates a method for disrupting and/or extracting obstructive material from a vessel lumen using the treatment system shown in FIGS. 31A-31D.
Figure 33B:
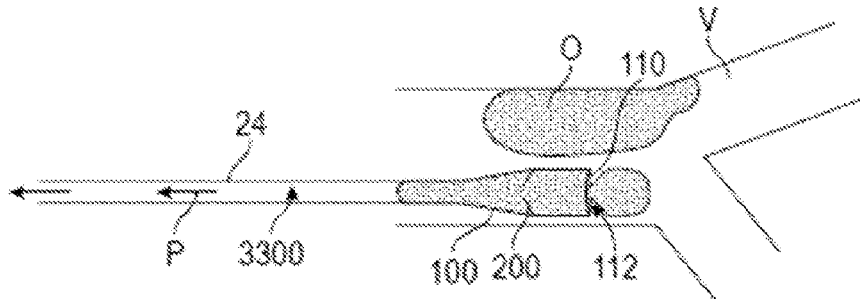
Figure 33C:
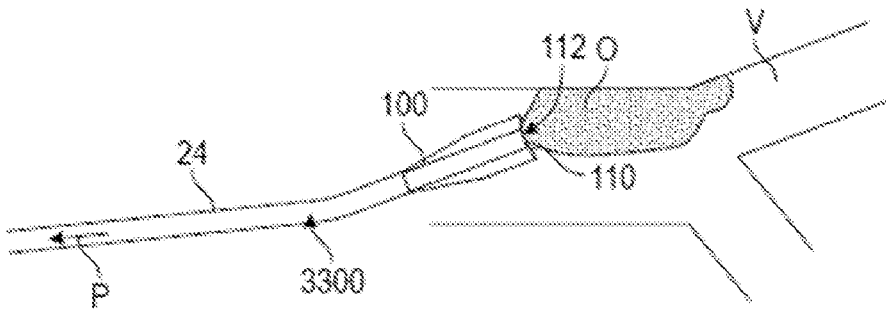

An example method for using a treatment system comprising distal bending is illustrated in FIGS. 33A-33C. The system can be advanced into the vascular anatomy V and positioned proximal to obstructive material, such as obstructive material O. As shown in FIG. 33A, the capture structure 100 can be expanded at the treatment site and engage the thrombus O by (a) advancement of the engagement surface 110 on and over the obstructive material O, by (b) applying negative pressure through the opening 112, or both (a) and (b). In any case, engagement with the obstructive material O causes at least a portion of the obstructive material O to extend through the opening 112 and into the interior region of the capture structure 100, as shown in FIG. 33B. The engagement surface 110 surrounding the opening 112 can apply a radially inward force on the obstructive material O positioned within the opening 112 to retain the obstructive material O within the interior region of the capture structure 100. As shown in FIG. 33B, in some embodiments the system includes a disrupting device comprising a disruptive element and/or disruptor 200 that engages with the obstructive material O. The disrupting device can be configured to disrupt the obstructive material via axial translation of the obstructive material O relative to the disruptor 200 and/or the disruptor 200 relative to the capture structure 100, or both, or by another disruption means and/or using another disrupting device, such as any of the disrupting devices described herein. Such disruption can occur as negative pressure P is applied through a lumen of the elongated shaft 24, thereby urging the obstructive material O proximally through the lumen 3300 and out of the body.

In some methods of use, for example as shown in FIG. 33C, the distal portion of the system, including capture structure 100, can be steered towards additional obstructive material O within the same vascular anatomy V. Once the capture structure 100, engagement surface 110, and/or opening 112 is aligned with the obstructive material O, a negative pressure P can be applied and the process of digesting the obstructive material O and passing it through the lumen 3300 of the elongated shaft 24 of the system can be repeated. The system (and any component thereof) can be repositioned as many times as required.

In any of the embodiments disclosed herein, a proximal portion of the elongated shaft 24 and/or sheath 22 can be stiffer than the distal portion and can have a crossing profile of less than 8 mm. The wall construction can be optimized to withstand a negative pressure of at least 200 mmHg and have a wall thickness of less than 0.5 mm. The proximal portion of the elongated shaft can be constructed from metallic hypotubes, multi-filament braids, and/or flat ribbon and round wire coils encapsulated by polymeric material. The inner layer that surrounds and defines the central lumen can comprise a lubricious material and/or be coated with a hydrophilic or other lubricious coating. The proximal end of the proximal portion is designed to be affixed to a handle. The proximal end can be fluidly connected to at least one port within the handle. In some embodiments, the proximal portion has an additional opening on the side wall and the central lumen is fluidically connected to the central lumen.

Any of the second hubs 44 disclosed herein can include at least two channels that are configured to be fluidically connected to the lumen of the elongated shaft.

In some aspects of the technology, the system includes a vascular access and therapy catheter. It has an outer diameter of less than 30 Fr during insertion and placement to the therapeutic site in the vascular anatomy. It has a length of between 50 and 200 cm. In an initial configuration in maintains an atraumatic insertion profile to minimize/eliminate vascular damage to vessels, vessel walls, valves of the veins, valves and chambers of the heart. A tapered atraumatic removable dilator may be used during placement to augment creating a streamlined insertion profile. The catheter and/or catheter/dilator can accommodate in a slidable and removable fashion guidewires of diameters of 0.020 to 0.038 in. The catheter can accommodate accessory instrumentation in its lumen and to or beyond its distal section during insertion, navigation, or in its therapeutic position. The accessory instrumentation may be for various therapeutic needs. This may include catheters for the delivery of fluids such as saline, lysing agents, and radiological contrast into the sheath, through the sheath, and beyond the catheter. This may include accessories to extend beyond the sheath to help the pushability and or directability of guidewires: for example, an angled tip catheter over and coaxial to the guidewire that would direct the trajectory of the guidewire due to the amount of angled length extended and or twisting of the angled tip catheter, or active angulation or steering. The instrumentation may include accessories to help clear blockages from the sheath lumen or sheath distal tip features. These instruments may be configured to mechanically break up obstructive material, like instruments such as thrombectomy balloons, elongated shafts with bulbous tips that disrupt the clot or de-clog the sheath lumen, elongated shafts with brush-like distal structures, elongated shafts with expanding engagement tips, elongated shafts with cutting or slicing tips, elongated shafts with grasping tips, elongated shafts with suction engagement tips, elongate shafts that supply therapeutic or diagnostic energy such as cryo, ultrasound, radiofrequency, vibration, visualization, heat, electrical sensing, magnetic sensing, impedance sensing, thermal sensing, chemical sensing, and/or other instrumentation. The accessory catheter-like instruments may be disposed coaxially on a guidewire, rapid exchange on a guidewire, or parallel to a guidewire in the sheath lumen. Additionally they may be placed into and/or through the sheath in the absence of a guidewire.

According to some embodiments, one, some, or all of the proximal hubs can have a variable orifice fluid tight seal to maintain hemostasis in the absence of accessories in the sheath lumen and to seal against accessories in the sheath lumen.

The elongated shaft, sheath, and/or dilator (together or individually) can be optimized for pushability, torquability, flexibility, kink/crush resistance to track/navigate from a femoral or jugular percutaneous site, across the vena cava, through the right atrium, through the tricuspid valve, across the right ventricle, through the pulmonary valve, into the pulmonary artery, and into the right and left branches of the pulmonary vasculature from the first and preferably to the secondary and tertiary branches. The elongated shaft, sheath, and/or dilator (together or individually) can be configured resist collapse against internal vacuum pressures of at least 200 mmHg. This can be accomplished by, for example, composite tubular structures such as polymers encapsulating braids, coils, metallic tubes cut with material removal patterns that allow flexibility.

Figures 34A, 34B:
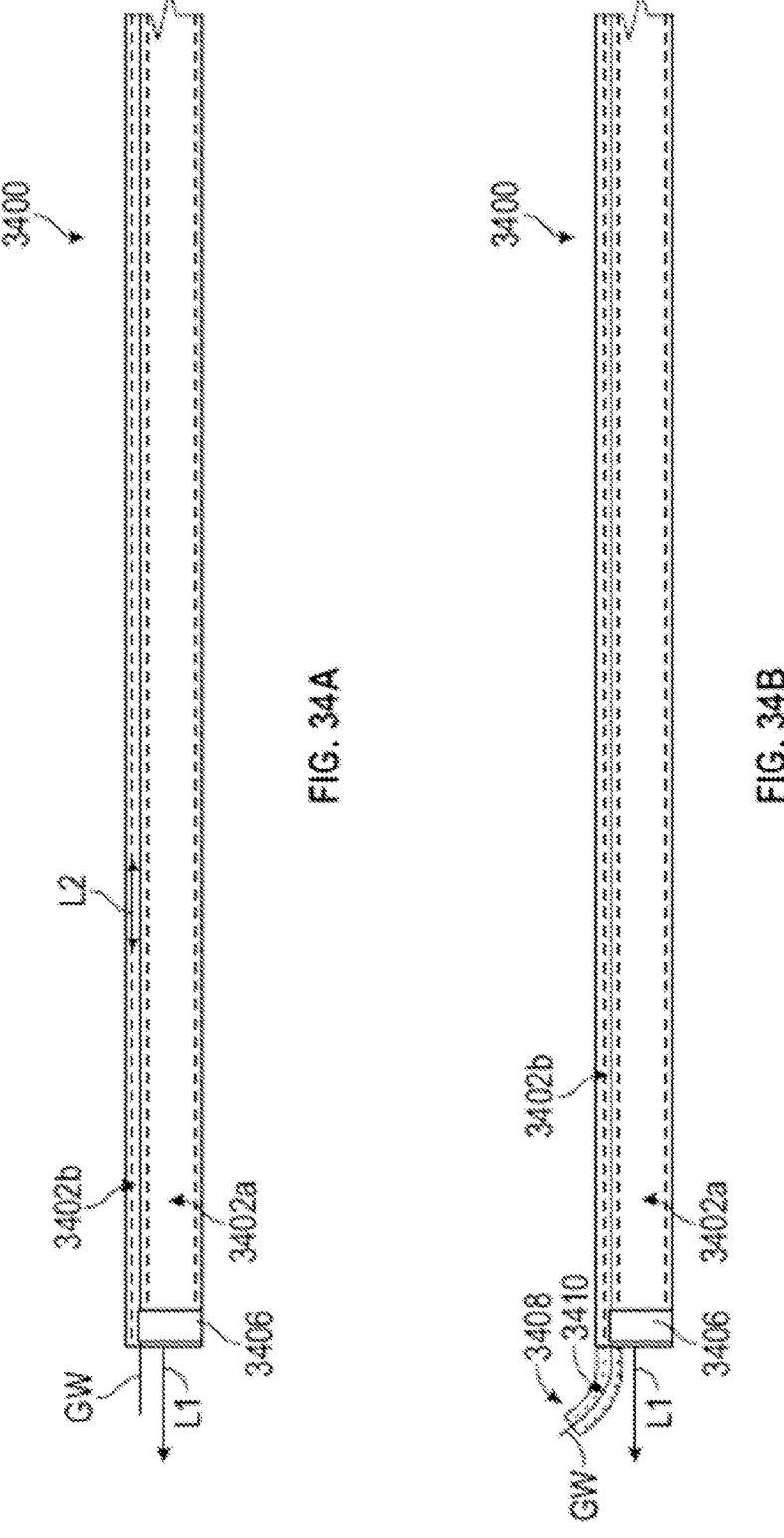
FIGS. 34A and 34B show a treatment system configured in accordance with several embodiments of the present technology.

The capture structure 100, elongated shaft 24, sheath 22, and/or dilator (together or individually) can be passively tracked on a guidewire into position. In some embodiments, the capture structure, elongated shaft, sheath, and/or dilator can have one or more lumens configured to receive the guidewire. For example, FIGS. 34A and 34B show a sheath 3400 having a first lumen 3402*a* and a second lumen 3402*b* (collectively "lumens 3402"). The sheath 3400 can have a first end portion, a second end portion, and a longitudinal axis L1 extending between the first and second end portions. The first lumen 3402*a* can be configured to receive one or more components of the system (e.g., the elongated shaft 24, the sheath 22, an aspiration catheter, a disrupting device, etc.) therethrough, while the second lumen 3402*b* can be configured to receive a guidewire GW therethrough. In some embodiments, a longitudinal axis L2 of the second lumen 3402*b* can be substantially parallel to the longitudinal axis L1 of the sheath 3400 (see FIG. 34A). In some embodiments, the sheath 3400 can include a marker 3406 configured to facilitate visualization of the sheath 3400 once intravascularly positioned.

As shown in FIG. 34B, the first end portion of the sheath 3400 can include a protrusion 3408 having a lumen 3410 extending therethrough that is aligned with and open to the second lumen 3402*b*. Accordingly, the guidewire GW can be inserted into the second lumen 3402*b* and advanced into and through the lumen 3410 of the protrusion 3408 such that the lumen 3410 of the protrusion 3408 guides the guidewire GW along a desired path, thereby enhancing navigability of the system.

Figure 35:
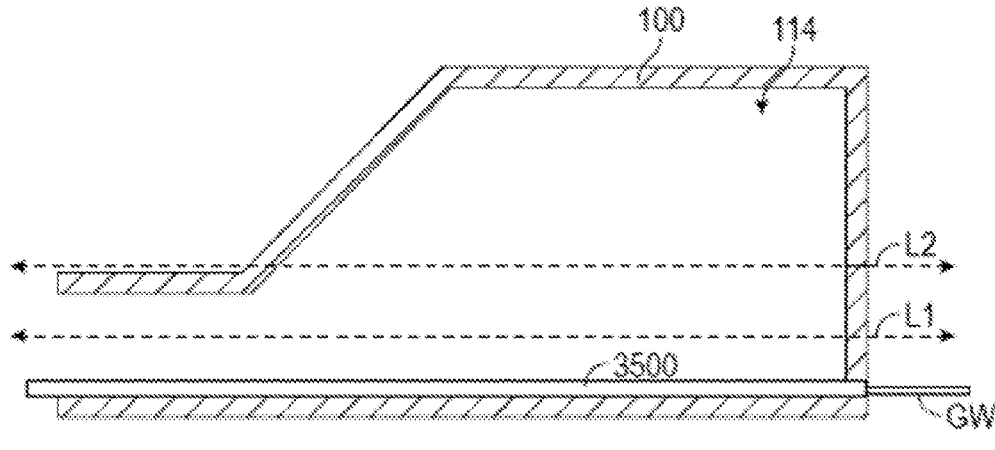
FIG. 35 shows the distal portion of a treatment system configured in accordance with several embodiments of the present technology.
Figure 36:
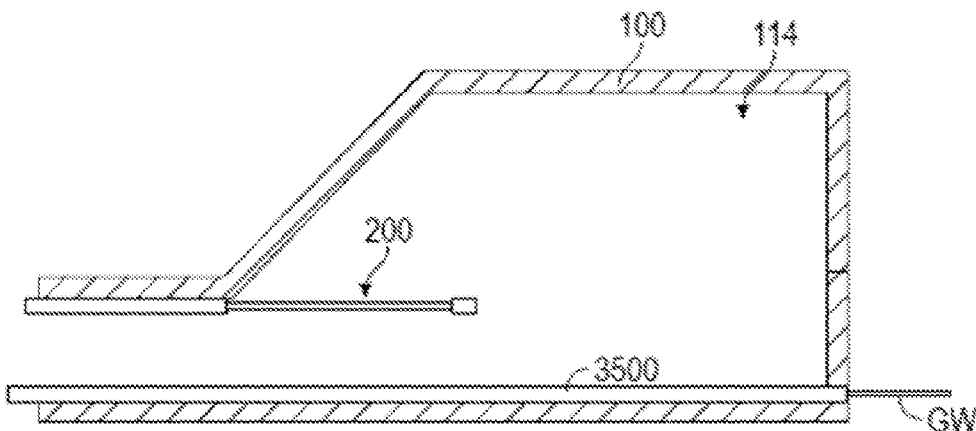
FIG. 36 shows the distal portion of a treatment system configured in accordance with several embodiments of the present technology.

FIG. 35 shows a distal portion of a treatment system including a guidewire channel 3500 extending through the elongated shaft (not shown) and capture structure 100. The guidewire channel 3500 can be positioned within the lumen 114 of the capture structure 100 such that the channel 3500 is offset from the central longitudinal axis L1 of the elongated shaft 24 and the central longitudinal axis L2 of the capture structure 100. In some embodiments, the guidewire channel can extend through the central longitudinal axis of the elongated shaft 24 and/or capture structure 100. In any of the foregoing embodiments, the disrupting device (if used) can be configured to track over the guidewire and/or through the guidewire channel and/or lumen. In some embodiments, for example as shown in FIG. 36, the system includes a separate channel 3600 and/or lumen for the disrupting device 200 (i.e., the disruptive device 200 is not configured to be slidably positioned in the guidewire channel and/or lumen).

Any of the foregoing embodiments, including those with preferential bending and/or directional steering, can be configured for use with a guidewire.

According to several embodiments, the treatment systems of the present technology are configured to extract large thrombi from a pulmonary artery in a patient suffering from pulmonary embolism. In some embodiments, a large thrombus can have a cross-sectional dimension of at least 5 mm.

For example, the large thrombi can have a cross-sectional dimension of between about 8 mm and about 30 mm. Such thrombi may be sufficiently large such that the thrombi cannot be readily aspirated into an interventional device without mechanical disruption. A treatment system can include an elongated shaft and a capture structure carried by a distal region of the elongated shaft and configured to be positioned in a blood vessel lumen proximate the obstructive material. The capture structure can comprise a sidewall that surrounds and defines an interior region that is sized to receive and contain obstructive material. The sidewall can be substantially impermeable to fluids, except for a small orifice extending through the thickness of the sidewall. The capture structure can be fluidly coupled to a negative pressure source (via the elongated shaft) to pull obstructive material through the orifice and into the interior region, and ultimately through the elongated shaft and out of the body. The orifice can have a cross-sectional dimension that is smaller than the cross-sectional dimension of the interior region of the capture structure to prevent escape of obstructive material once the material has been pulled into the interior region. In some embodiments, the treatment system can also include a disruptor configured to be positioned within the interior region of the capture structure to mechanically break up obstructive material that has been pulled or otherwise forced into the interior region for easy extraction through the elongated shaft.

According to several aspects of the present technology, a method for disrupting and/or removing obstructive material (such as a thrombus) from a blood vessel comprises accessing the vascular anatomy at a remote location from the thrombus, navigating and positioning the distal region of the elongated shaft proximal to the thrombus with the capture structure in a collapsed configuration, expanding the capture structure to a second radial profile greater than the first radial profile used for navigating, and engaging the thrombus with the sidewall of the capture structure. Some methods include applying a negative pressure through the lumen of the elongated shaft and interior region of the capture structure to pull the thrombus proximally within the capture structure and elongated shaft. In some embodiments, the method includes deforming at least the portion of the sidewall surrounding the orifice to accommodate movement of the larger thrombus through the smaller orifice.

Several methods of the present technology further include disrupting the thrombus with a disrupting element positioned within the interior region of the capture structure. In some embodiments, the disrupting element mechanically modulates the negative pressure within the lumen of the elongated shaft and interior region of the capture structure. In some embodiments, the disrupting element mechanically macerates the thrombus as it enters the lumen of the elongated shaft and/or interior region of the capture structure. In some embodiments, the disrupting element mechanically engages and pulls the thrombus through the elongated shaft and/or interior region of the capture structure. In some embodiments, the thrombus is advanced through the orifice in the sidewall of the capture structure and at least partially into the interior region of the capture structure prior to the negative pressure being applied. In some embodiments, the capture structure applies a radial compressive force to the thrombus within the interior region. In some embodiments, the capture structure is actively steered through the vascular anatomy using at least one pull wire. In some embodiments, the orifice in the sidewall of the capture structure applies a retaining force on the thrombus as the thrombus is advanced into the lumen of the elongated shaft. In some embodiments, the capture structure is repositioned within the vessel without advancing the elongated shaft.

Although many of the embodiments are described above with respect to systems, devices, and methods for disrupting and/or removing thrombus from a vessel lumen, the technology is applicable to other applications and/or other approaches, such as disruption and/or removal of any obstruction from any body lumen. For example, the devices, systems, and methods disclosed herein can be used for removing thrombus from the peripheral vasculature. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-36.

Macerators

Described herein are macerator apparatuses that may be used to remove tissue from within a vessel, including clot material (e.g., embolus). These apparatuses may be used with or as part of an aspiration catheter. In general, these apparatuses may include an elongate, flexible body that includes a proximal end that may couple with a source of negative pressure (e.g., suction) and a capture device for receiving removed clot material. The distal end of the apparatus may include one or more openings into a suction lumen that extend from the proximal end to the distal end.

The distal end opening may be referred to as a macerator window or macerator opening. In some examples multiple openings (macerator windows) may be included and may be arranged laterally and/or distally. A rotatable, shearing cutter may be positioned within the distal end region and configured to be driven in rotation to shear one or more cutting surfaces relative to a shearing surface on or spanning the distal end opening(s). The rotatable cutter may be driven by rotating a flexible drive shaft.

For example, macerator apparatuses as described herein may have one or more distal-facing opening (e.g., window) and/or one or more multiple side-facing windows. Any of these apparatuses may be driven by a flexible wire drive shaft that may be eccentrically rotated. The entire macerator apparatus may be flexible so that it may bend and navigate through a tortious pathway.

The macerator apparatuses described herein may be any appropriate length and diameter. For example, the macerator apparatus may have a length that is greater than about 20 cm, greater than about 30 cm, greater than about 40 cm, greater than about 50 cm, greater than about 60 cm, greater than about 70 cm, greater than about 80 cm, greater than about 90 cm, greater than about 100 cm, etc. The diameter (e.g., outer diameter) of the macerator apparatus may be configured to fit within a lumen, in some examples, an aspiration lumen, of an aspiration catheter. For example, a macerator apparatus as described herein may be between about 2 mm and about 5 cm in diameter (e.g., between about 3 mm and about 3 cm, between about 4 mm and about 2 cm, etc.).

The apparatuses and methods described herein may be configured to extend the macerator out of the distal end of an aspiration catheter; in some examples, the macerator may be controlled automatically, manually or semi-automatically based on where in the aspiration catheter it is positioned. Methods of controlling the operation of the macerator are also described.

The macerator apparatuses described herein may be used to remove material from a naturally occurring or surgically created body lumen or cavity and/or from within a medical device, such as an aspiration catheter. For example, the macerator apparatuses described herein may be used to remove tumor, plaque, and/or acute or chronic blood clot material. The apparatuses described herein may be used anywhere in a body, including within the vascular system, such as the venous system. For example, these apparatuses may be used in the pulmonary artery to remove pulmonary embolism. These apparatuses may be used in a minimally invasive manner, for example through a laparoscopic or percutaneous access site; for example, these apparatuses may be used through a right femoral percutaneous access. In general, these apparatuses may be configured to have a crossing profile, length, and flexibility to reach the target location.

Any of the methods and apparatuses described herein may be used with one or more imaging techniques, such as with direct vision angioscopy, ultrasound, MRI, impedance mapping (NavX). For example, the apparatuses described herein may be used with fluoroscopic imaging. These apparatuses may be positioned using push/pull and rotation to navigate through a lumen. In some examples these apparatuses may be used with a guidewire (e.g., including placing them over a pre-placed guidewire).

For example, in when in position in the pulmonary artery (e.g., the main branch, right or left branches, secondary branches, tertiary branches) these apparatuses could be used to remove embolism. In one example a macerator apparatus (which may include a mechanical agitator/cutter in conjunction with aspiration) may be used to engage, disrupt then suck material through the device shaft and out of the body.

In general, the macerator apparatuses described herein refer to shearing cutters that reduce larger pieces of (typically unanchored) material, such as embolus material, into smaller pieces. These apparatuses may therefore provide mechanical, shearing disruption of the target material (e.g., clot material). Shearing is provided by moving the rotating cutter, which includes one or more cutters relative to a stationary shearing member (e.g., an edge or transverse portion of an opening through which the target material may be drawn by suction. Thus, these apparatuses may act by mechanical disruption consists of a stationary element and a rotational element.

The stationary element may be an external housing with one or more openings to allow material to be inspired/engage into. In one example this consists of a tubular structure with a single or multiple scythed shaped openings along the tubular wall. Additionally, the tubular housing could have an open or closed distal tip. In some examples the tip is open to allow an additional opening for aspiration and removal of embolism or collateral fluid.

The rotatable cutter may be an internal concentric tubular cutter with a single or multiple scythed shaped openings along the tubular wall. In some examples the cutter (also referred to herein as a "cutter assembly") could have an open or closed distal tip. The tip may be open to allow an additional opening for aspiration and removal of embolism or collateral fluid In use, cutting (macerating) may be achieved by the shearing between stationary and rotational windows as they dynamically change from alignment to mis or complete non-alignment. Cutting may be a combination of these features working in conjunction. For example, the inner rotating element is called the cutter (or cutter assembly).

Cutting may be augmented or achieved with material being aspirated/engaged in the combination of windows by suction.

For example, FIGS. 37A-37F illustrate one example of a macerator apparatus as described herein. In FIG. 37A the distal end region of the macerator 107 is shown. The distal end in this example is shown as a side view, with the apparatus made transparent to allow visualization internal features. In FIG. 37A, the macerator includes an elongate flexible body having an outer housing 135. The macerator also includes a side-facing macerator window 127 at the distal end region of the apparatus. A cutter (cutter assembly 129) is positioned and may be locked or secured within the distal end region so that the macerator window 127 aligns with the cutter window(s) of the cutter assembly 129.

The entire assembly may be actuated by rotation of a drive shaft, e.g., drive wire 147, which is coupled distally to the rotatable cutter 129, and which extends proximally through the suction lumen 133. Rotation of the cutter 129 drive rotation of the cutter window 131 relative to the macerator window 127, as illustrated in FIGS. 37A, 37C and 37E. In this first example the cutter is coupled to the drive shaft (drive wire 147) off-axis, e.g., radially offset from the central axis of rotation of cutter assembly; instead the drive shaft is concentrically coupled, and the cutter may be rotated concentrically around the inner suction luminal wall, as illustrated for each of FIGS. 37A, 37C and 37E; FIGS. 37B, 37D and 37F show examples of end views corresponding to each of FIGS. 37A, 37C and 37D. In this example the open distal end region shows the drive wire 147 coupled distally to the cutter 129 that is contained concentrically within the outer housing 135 of the macerator elongate body.

FIG. 38 illustrates another example of a macerator apparatus 207 including an elongate body having an outer housing 235 enclosing a suction lumen 233. The distal end region may include one or more macerator windows 227 formed through the distal end of the macerator outer housing 235. A cutter assembly 229 (including a cylindrical cutter) is positioned within the suction lumen 233. In FIG. 38, as shown in FIGS. 37A-37F, the drive cable 217 rotates eccentrically around the distal end so that a cutter window 231 aligns with the macerator window to shear a clot material (not shown) that is drawn into the cutter window by suction applied through the suction lumen. Rotation of the cutter 243 to actuate the distal cutter may be driven through the eccentrically mounted drive shaft 217.

The macerator apparatuses described herein may also be referred to macerators, cutters, shaver, or the like. FIGS. 39A-39B show another example of a macerator including a tubular housing 309, a cutter, for which a portion of a cutter window 331 is visible in FIGS. 39A and 39B. This example also includes a positioning ring (also referred to as a fixture 357 in this example). The drive wire (not visible in FIGS. 39A and 39B) may be coupled to the cutter by a crimp or other securement or connector. In operation, the macerator shown in FIGS. 39A and 39B may be driven by rotating the drive wires so that the cutter window 331 moves relative to the macerator window(s) 329 to sheer any material that is drawn into the cutter window by the application of suction through the suction lumen. In FIGS. 39A-39B the distal end 335 of the cutter (and the macerator) is open so that suction may be drawn into the suction lumen of the macerator regardless at all times. In other examples the distal end may be closed, or the rotatable cutter may be configured to cut material entering through the distal end opening(s).

FIGS. 40A and 40B illustrate component parts of an example of a macerator apparatus as described herein. In FIG. 40A, the apparatus includes a rotatable cutter 429 including at least one cutter window 431. The distal end of the cutter may be formed of a cylindrical body forming a stationary housing 409 that includes a plurality macerator windows 427. The cuter may fit within the stationary housing 409 and through the fixture 457 that may couple the distal end of the macerator (e.g., the stationary housing) with the elongate suction lumen formed by the elongate body of the apparatus. In some examples the elongate suction lumen may be coupled to the fixture so that the flexible drive wire 417 is crimped of otherwise secured to the proximal end of the cutter assembly 429.

FIG. 41A shows an exploded view of the cutter assembly of FIG. 39A of a macerator. The cutter assembly includes a drive wire 517 fitted with a crimp 537 on its distal end to the cutter 529; in this example the cutter is configured as a cylindrical or tubular cutter housing including one or more cutter window 531 forming the blade portion of the cutter. The crimp 537 is attached to a connection tab that is integral to the tubular cutter. This can be accomplished by welding or brazing. A positioning ring 545 is attached to the cutter 529 near its distal end and does not overlap with the side openings 531 in the cutter. The cutter-ring-crimp-wire assembly may be slid though the fixture 557 (also referred to as a connector) from a distal end. The macerator housing 535 may then be slid over the cutter 529 from the distal end. The housing may then be secured in place with adhesive, welding, or brazing (e.g., to the fixture 557).

The macerator housing includes side opening(s) 527 forming the macerator window that are configured as shearing surfaces in the stationary housing 535 that at times coincide with the cutter opening(s) 531 in the rotational cutter 529. This may create a maximum aligned opening, aspiration, and material entrapment by aspiration; as rotation of the cutter continues, the passage into the suction lumen would begin to reduce as the openings become out of alignment. As occurs, there is an increased shearing between the stationary macerator opening(s) and the rotating cutter opening(s). This mechanical shearing creates a mechanical disrupting/cutting action on any material engaged by aspiration. The cutting continues until there is complete misalignment and the windows do not have any shared opening.

Any of the macerator apparatuses described herein may include a collar proximal to the cutter assembly to hold the cutter assembly with the distal end region. The collar may ensure that the relationship between the cutter and housing remains even during rotation; the collar may also prevent movement of the cutter during navigation or tension due to rotation.

FIG. 41B shows a side view of the assembled cutter assembly of FIG. 41A, including the distal macerator housing 535 with two macerator openings 527 shown extending from a fixture 557. The cutter (not visible in FIG. 41B is secured distally within the macerator housing and the drive wire 517 extends proximally. A suction lumen (not shown) may be formed by coupling a flexible body (e.g., tube) proximally to the fixture 557 so that it encloses the drive wire 517. FIG. 41C shows a section through the assembly of FIGS. 41A and 41B. In FIG. 41C the cutter 529 is shown concentrically arranged within the macerator housing 535 so that it may rotate and spin the cutter window 531, the edge of which forms the blade. Multiple cutter windows may be included, and they may be offset from each other so that at least one cutter window is at least partially aligned with a macerator window in any position.

The fixture 557 in FIGS. 41A-41C is optional; in some examples the macerators described herein may not include a fixture as shown in FIG. 41. For example, the macerator housing maybe rotationally affixed to the cutter directly, and an elongate body (e.g., flexible tube) may be attached and extend directly from the macerator housing 535. In FIGS. 39A-39B and 41A-41C the fixture may be configured to couple the macerator in a fixed position relative to a catheter, such as an aspiration catheter. The fixture may also include one or more channels 577 for a guidewire, aspiration, etc. In some examples the macerator may be configured to be moved (e.g., into and out of) independently of an aspiration catheter (or other catheter).

FIGS. 42A-42D illustrate one example of the operation of a macerator similar to that shown in FIGS. 39A-39B and 41A-41C. In FIG. 42A a system 600 includes a macerator inserted into an elongate device so that the macerator extends distally. The elongate device may include a distally-extending lumen (not shown) that may form a maceration chamber. The elongate device is not shown to scale; it may extend distally and be configured to flex.

The macerator housing 635 includes a macerator opening (or macerator window) 627 forming a shearing surface against which the inner cutter opening (cutter window) 631 may shear when rotating, as illustrated in FIGS. 42A-42D. In this example the cutter assembly is coupled to a fixture 627. In FIG. 42B the cutter is rotated slightly clockwise by the drive wire (not shown), so that the cutter window 631 is rotated at least partially over the macerator window 627, as is visible through the macerator housing 635. In FIG. 42C, the cutter is rotated even further clockwise, occluding about half of the macerator opening 627, while in FIG. 42D over 80% of the macerator opening into the suction lumen of the macerator is occluded by the cutter. In FIGS. 42A-42D the distal end 680 of the macerator is continuously open even as the lateral macerator opening(s) 627 are partially or completely occluded as the cutter rotates while suction is drawn through the suction lumen of the apparatus. Searing between the cutter window (opening) and the macerator window (opening) results in macerating of material such as clot drawn into the macerator by suction being applied.

FIGS. 43A-43F illustrate concentrically driving rotation of a cutter assembly. In some examples the macerator apparatus includes an elongate tubular flexible body. As described above, in some cases the macerator housing 735 is fixed on the distal end of the tubular body of the macerator. The macerator housing is optional; in some examples the macerator does not include a separate housing. In FIGS. 43A-43F, the cutter rotates inside the macerator housing 735 as the drive wire 717 is rotated, causing the cutter window 731 to shear relative to the macerator window 627. The tubular body allows for aspiration to be applied from external/proximal end to the distal end and for the engagement and transport of macerated material outside of the body.

FIGS. 43B-43F show examples of the position of the drive wire 717 within the suction lumen 733 of the macerator. The rotation of the drive wire that is eccentrically coupled to the cutter as in this example may cause the distal end region of the drive wire 717 to move around the suction lumen 733 as it rotates the cutter. FIGS. 43C and 43E show examples of different rotational positions of the cutter, resulting in movement of the cutter window 731 relative to the macerator window 727. FIGS. 43D and 43F show end-on views of the distal end of the macerator as the cutter is rotated by rotation of the drive wire 717. The drive wire may be rotated from the proximal end and may transmit the torque to the distal end. The drive wire transmits torque and remains flexible.

Alternatively, in some examples a tubular drive is used instead of a drive wire, which may be coupled concentrically to the cutter; for example, a drive tube may be a fluid-tight (e.g., sealed against gas and liquid) and aspiration may be provided through it to the openings in the cutter, and through the macerator housing openings, to entrap/transport material and fluid. In some examples a secondary rotational drive tube may be used, which may not necessarily be fluid-tight, and may allow aspiration to be applied around its OD, through its wall, and out the cutter and housing to entrap/transport fluid and material. The drive tube could consist of a polymer such as nylon, pebax, peek with a durometer high enough to allow torque transmission but still maintain flexibility (e.g., shore 0D to 80D). The drive tube may be a composite with a torque transmitting braided element as part of its wall construction. Alternatively, the drive tube may be a stainless steel hypodermic tubing with a laser cut slotted pattern to allow flexibility and torque transmission. This laser cut tube could have an inner, outer, or encapsulating polymer jacket.

In some examples it may be helpful for the torque transmitting drive member (e.g., a drive tube) to have a larger ID/OD proximal of the diameter constraints of the cutter so that its elongated length did not create an elongated constriction the full length of the device. The drive tube may neck down; this may prevent the cutter from flaring up to the maximum tube size and/or for a secondary drive tube to fit inside the tubular body.

In some examples, the drive member is a drive wire, as described above. Alternatively the drive member may be a drive rod. The drive wire or drive rod may be flexible and less prone to kink, eliminates kink occlusion, may minimize the material cross section within the tubular body, and/or may maximize the aspiration cross section in the tubular body. In some examples the drive wire may attach to the cutter at a concentric location to its distal end. The cutter distal end may include a cap or spoked cover for attachment to the drive wire; the cap or spoked cover may impinge on the ID of the cutter (including the cutter openings) but may also provide additional shearing (cutting). As described above, in some examples the drive wire may attach to the rotatable cutter at a non-concentric location; this may allow the cutter lumen (and suction lumen) to remain maximally open for the aspiration and transport of fluid/embolism material. The drive wire may rotate in an orbit in the confines of the tubular body (e.g., within the suction lumen). This may assist in mechanical disruption and/or agitation of fluid/embolism material as it is being transported through and out of the tubular body.

For example, FIGS. 44A and 44B illustrate rotation of the drive wire 817 within the suction lumen 833 of the macerator in an example in which the drive wire is coupled to the cutter at a non-concentric location (e.g., off of the center axis of rotation of the cutter). In FIGS. 44A-44B a portion of the wall of the elongate body has been cut away to show the suction lumen 833 with the drive wire 817 therein. FIG. 44A shows the cutter without rotation; while FIG. 44B shows the cutter rotated by rotation of the drive wire by 30 degrees. As the drive wire 817 rotates in its orbit it will create a non-concentric agitation along its length. In some examples the drive wire will take an orbital path around the internal perimeter of the tubular body and any additional coaxial structures, wires, components, features inside the tubular body. Thus, the drive wire 817 may act as a coring/wiper element along the tubular body inside diameter where embolic material that has been engaged and cut by the shaver end effector is being transported proximal by aspiration. This may be useful to prevent embolic material from impacting (e.g., becoming wedged or stuck) within the lumen if the aspiration force becomes insufficient to draw it further proximal. It may also mitigate a static blockage.

Figure 45A:
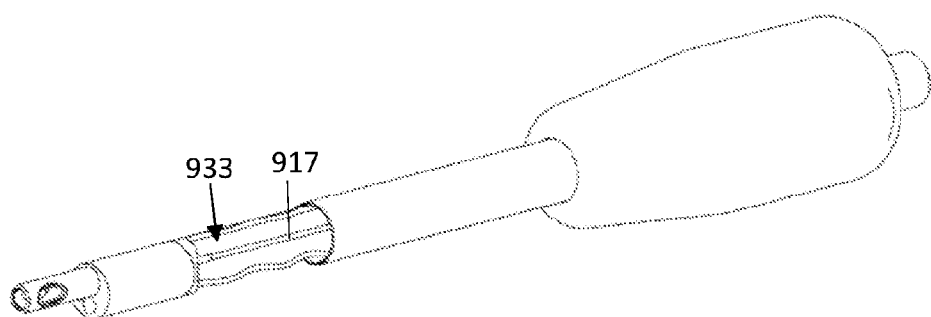
FIGS. 45A-45B illustrate examples of a macerator with a region removed to show the suction lumen and drive member.
Figure 45B:
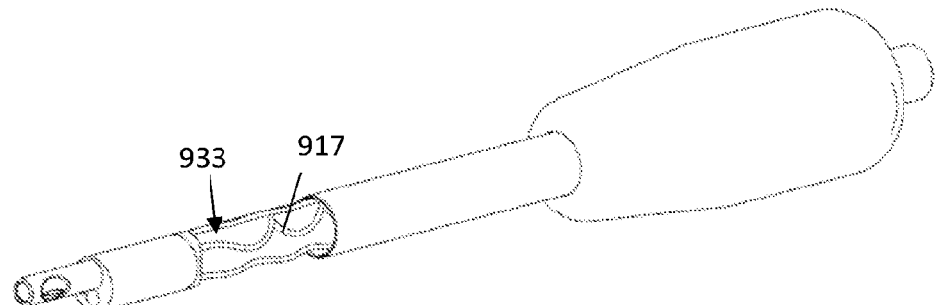

The drive wire may also agitate the inside diameter perimeter. The elongate body of the macerator including the suction lumen may will make multiple bends at various curvatures along its length. This may cause the drive wire to arc across, flex, conform, relax, be pulled towards some ID portions and/or be flexed away from some ID portions. Thus, the drive wire may act as an agitator along its orbital path at these various bend or curving regions. This has the benefit of further agitating embolism in transport down the tubular body lumen. For example, FIGS. 45A-45B illustrate an example of the drive wire 917 taking a variable/semi random orbital pathway within the suction lumen 933 as it is rotated to drive the rotatable cutter. In FIG. 45A the drive wire is shown in a straight orbital path while in FIG. 45B (which has been exaggerated to show bending of the drive wire) the orbital path may include multiple bends and turns that may move within the lumen 933. This may impart an additional agitation on material as it is transported throughout the length of the tubular body.

Any of the macerator apparatuses described herein may have one or more openings in the sidewall of the stationary housing that provide a shearing surface for blades (including the edges of one or more openings) of the rotating cutter. In some examples, during cutter rotation, the lateral (e.g., sidewall) openings may have a maximum alignment position that then reduces to minimal or no aligned openings. Aspiration flow may reduce and or become zero during the non-alignment position. To mitigate the reduction or elimination of aspiration flow the tip of the stationary housing and the rotating cutter may be open-ended, as described in FIGS. 42A-42D. This may guarantee that the internal diameter (e.g., the suction lumen) of the assembly is always open and available for aspiration flow no matter the position of the side openings in housing and cutter. This may also allow an additional opening for the aspiration embolism and blood.

Figure 46A:
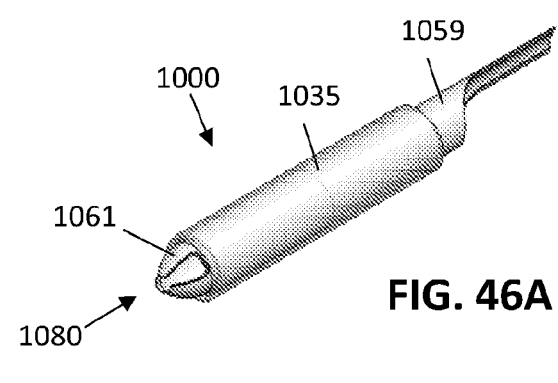
FIGS. 46A-46B show an example of a distal end of a macerator including a protective region over a distal end opening.
Figure 46B:
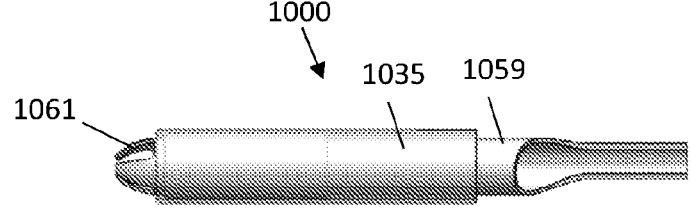

One or more features may be located the open tip of the housing, the cutter, or both, that may provide a disruption and/or cutting function without occluding the open tip. For example, the distal tip region may include an annular array of small teeth or struts directed inward at the housing and cutter tip directed at the axis of rotation or some angle. FIGS. 46A-46B illustrate one example of a macerator 1000 having an open distal end with a plurality of static projections 1061 over the open distal end 1080. In this example the projections 1061 are referred to as static because they do not rotate (e.g., with the cutter). The macerator includes a macerator housing region 1035 and a rotating cutter 1059.

In general, the macerators described herein may include a plurality of macerator openings (e.g., windows). For example, FIGS. 47A-47B shows an example with 3 macerator windows having open and closed distal ends, respectively. The examples shown in FIGS. 47A and 47B include a macerator housing 1135 with the windows 1127, 1127' (only two of the three are visible) extending through the macerator housing and forming a shearing surface that the cutter 1159 may rotate the cutter windows to shear against. In FIG. 47A the distal end 1180 is open, while in FIG. 47B the distal end 1180' is closed. FIGS. 47C and 47D illustrate examples of macerators having four macerator windows 1127, 1127', 1127" (only three are visible) and open and closed distal ends; FIG. 47C shows an example with an open distal end 1180, and FIG. 47D shows an example with a closed distal end 1180'.

In general, the macerator apparatuses described herein may be configured to maintain a minimal/functional amount of aspiration during operation by preventing the cutter assembly from occluding all of the openings of the apparatus. For example, when the cutter rotation is stopped, the cutter blades may be configured so that they do not occlude the openings. In some examples the housing and cutter openings have a desired amount of opening clearance available even in the most mis-aligned configuration. For example, the opening on the housing and the cutter may be configured so that the total available cross sectional area for aspiration between the components is at least a minimal dimension. A desired minimum cross sectional area between the housing and cutter openings would be at least the cross section of the lumen of the tubular cutter. For example, the cutter assembly may be configured so that even when the cutter(s) is/are maximally occluding the opening(s) at the distal end region (lateral or distal-facing) the openings are less than 75% occluded (e.g., less than 70% occluded, less than 65% occluded, less than 60% occluded, less than 55% occluded, less than 50% occluded, less than 45% occluded, less than 40% occluded, less than 30% occluded, etc.). windows maintain an opening cross section always equal to or greater than the circular cross section of the cutter tubing ID. For example, the cutter may have a diameter that is less than the diameter of the opening and/or one or more openings may be configured so remain un-occluded when the cutter(s) is/are in front of other openings. Thus, the quantity, positioning, ratio, size of the openings and cutters may be configured to maintain a minimal aspiration flow path in any position.

In some examples the macerator may include a rotating cutter at the distal facing opening or opening instead of, or in addition to the lateral or side-facing openings. Any of the rotatable cutters described above may include one or more blades or cutters (shavers) at the distal end of the rotatable cutter to generate a sharing force with a stational shearing surface at the distal end of the macerator. FIG. 48 illustrates one example of a macerator apparatus including three distal-facing opening formed by dividing up a distal opening into three regions 1227, 1227', 1227" (e.g., by three projections 1252 forming shearing surfaces). The cutter 1229 includes a propeller-shaped structure that is rotatably coupled to the macerator housing 1235. The cutter is also coupled to the drive wire 1217 at a central region in order to drive rotation of the cutter 1229.

In the example shown in FIG. 48, suction may be applied through the suction lumen to draw clot material into the distal end openings 1227, 1227', 1227", where the cutter 1229 may be rotated to shear the clot material, macerating it so that it may be drawn into the suction lumen and removed.

In some examples the macerator includes a very narrow macerator housing, which may also be referred to as a macerator frame or support. A narrow macerator housing (macerator frame, or equivalently macerator support) and narrow cutter that may rotatably couple to the macerator housing (frame or support) may minimize the rigidity of the distal end of the macerator. Generally the cutter portion must be in a fixed alignment with the shearing surfaces of the macerator housing (or macerator frame/macerator support), and thus this region may generally be limiting on the ability of the distal end region of the macerator to be narrow or compact along a length of the macerator.

In some examples, the width of the macerator and its component portions may be significantly shortened, e.g., by maintaining the width of the macerator frame and the cutter housing (or, equivalently cutter frame) as substantially low, such as less than about the diameter of the suction lumen of the macerator (e.g., 95% or less than the diameter of the suction lumen, 90% or less than the diameter of the suction lumen, 85% or less than the diameter of the suction lumen, 80% or less than the diameter of the suction lumen, etc.). This had the surprisingly effective benefit of enhancing navigation as compared to other macerators.

For example, FIGS. 49A-49B illustrated one example of a macerator apparatus distal end region including a very short thickness in the longitudinal direction 1360. For example, FIG. 49A shows a distal-facing end of the macerator including the macerator frame 1336 (e.g., macerator housing) formed as a circular region that includes three projections forming shearing surfaces 1352 that divides the distal-facing opening into three openings 1327, 1327', 1327''. The projections in this example form three spokes that may have a flat bottom surface (facing into the suction lumen) and squared or acute-angled edges that form a shearing edge. The cutter 1328 may include one or more blades that may also have squared or acute-angled edges for shearing tissue that is drawn into the openings. In FIGS. 49A-49B the cutter is formed as a propeller-like structure to which a drive wire (not shown) may be attached at the center of the axis of rotation. Alternatively the drive wire may be coupled eccentrically, off of this axis of rotation as illustrated in FIGS. 49B and 42A-52B, below.

FIG. 49B shows a side perspective view of a distal end of the macerator apparatus of FIG. 49B, showing the relative thickness 1360 of the macerator frame 1336 and cutter frame. The cutter (not visible) may include a circular or annular frame that include the cutter blade surface extending across it and is coupled to a drive wire 1317 within the suction lumen 1333 so that the drive wire is coupled eccentrically to a peripheral region of the cutter frame. In this example the diameter of the macerator frame and cutter (e.g., cutter frame) is much smaller than the diameter of the suction lumen 1367. In some examples the width or thickness (in the longitudinal direction) is about the same as the diameter of the suction lumen or is less than the diameter of the suction lumen (e.g., about 95% or less, about 90% or less, about 85% or less, about 80% or less, etc.).

Figure 50A:
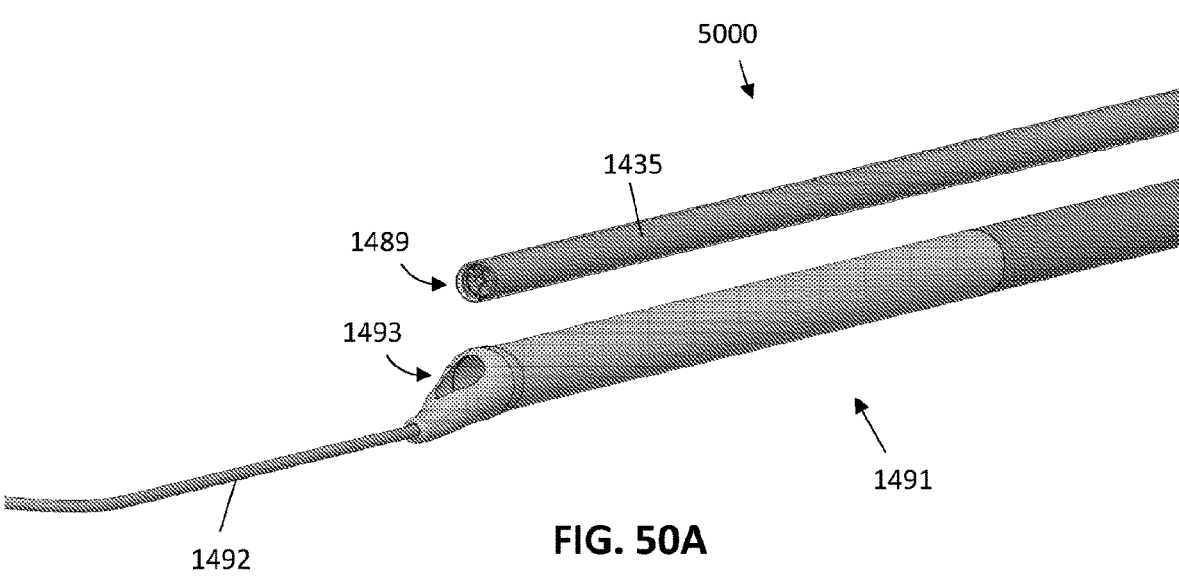
FIG. 50A shows an example of an apparatus including an aspiration catheter and a macerator.
Figure 50B:
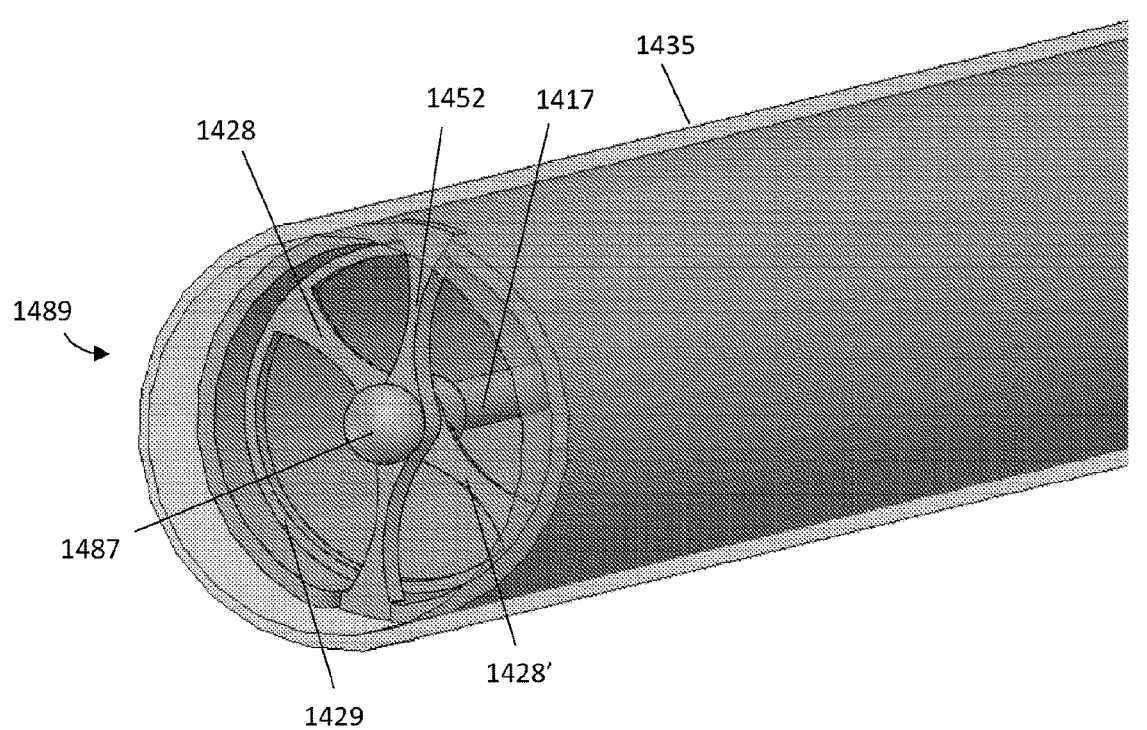
FIG. 50B shows an enlarged view of a distal end of the macerator of FIG. 50A.

FIGS. 50A-50B illustrate one example of an apparatus including a macerator 5000 that may be used with an aspiration catheter 1491. The aspiration catheter 1491 may be guided over a guidewire or guide catheter 1492 and includes a suction lumen 1493. The aspiration catheter may be flexible and configured to navigate through the body. In this example the macerator 5000 may be inserted through the aspiration catheter 1491 either after it has been positioned (e.g., steered into position with the body using a guide wire or guide catheter or steerable guide catheter), or may be inserted as it is positioned or moved within the body. The macerator may be configured to extend out of the aspiration lumen of the aspiration catheter distally or it may be configured to be prevented from extending distally beyond the distal end of the suction lumen of the aspiration catheter. In some examples the apparatus may prevent the macerator from macerating (e.g., from driving the cutter) when the macerator extends distally beyond the distal opening of the aspiration catheter suction lumen.

In use, the macerator may be used to remove material from within the suction lumen of the aspiration catheter either as it is advanced through the aspiration catheter or once it is in predetermine region (e.g., a "maceration chamber" region) of the aspiration catheter. For example, in FIG.

50A the maceration chamber maybe just before the distal end opening into the suction lumen of the aspiration chamber.

Figure 50C:
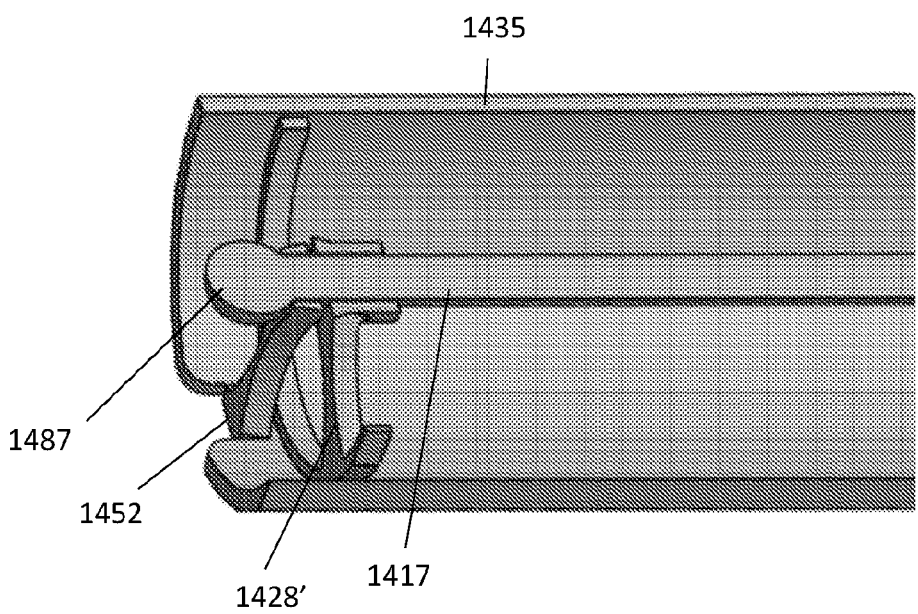
FIG. 50C shows a sectioned view through the distal end of the macerator of FIG. 50A.

FIG. 50B illustrates an example of a macerator including a distal-facing cutter 1489. In this example the macerator includes an elongate, flexible body 1435 extending proximally from a distal end region that includes a macerator frame 1452 including a strut extending across the distal end of the macerator forming two openings. A rotatable cutter formed from a round cutter frame 1429 that includes a pair of propellor-like blades 1428, 1428' is coupled to a drive wire 1417 and is rotatably mounted to the macerator frame via a ball connector 1487. A spacer may be positioned between the blades and the macerator frame struts to maintain the shearing distance. FIG. 50C shows an example of a section through the macerator of FIG. 50B. In this example the drive wire 1417 may be flexibly connected to the central axis of rotation of the cutter (e.g., between the cutters 1428, 1428'). The ball connection 1487 may allow the wire to flex when navigating turns or bends. Alternatively in some examples the drive wire may be coupled to the rotatable cutter via one or more flexible connectors.

Figure 51:
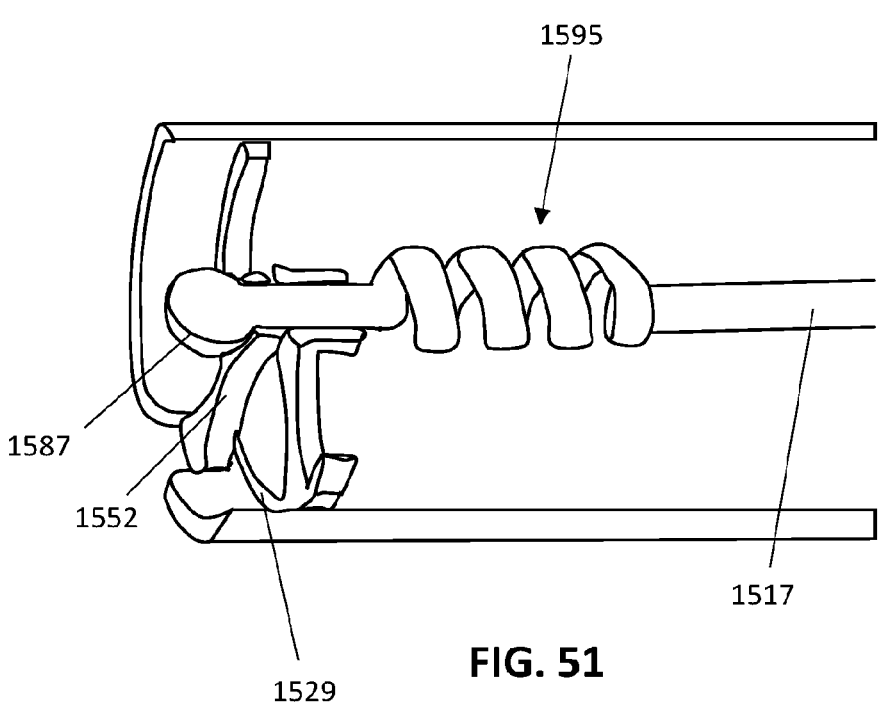
FIG. 51 schematically illustrates another example of a section through a macerator distal end.

FIG. 51 shows a section through one example of a macerator including a flexible connector 1595 coupling the cutter to the drive wire 1517. The drive wire may be locked against the macerator frame 1552 via the ball connector 1587 at the distal end, or a via a crimp, or other locking mechanism that allows rotation of the drive wire relative to the macerator frame. In FIG. 51 the example of the flexible connector includes a coil region; the coil (spring) region may be formed of the same material as the drive wire (e.g., stainless steel, Nitinol™, etc.), or it may be formed of a different material and bonded to the drive wire. A flexible connector may also be used in variations in which the connection to the cutter is eccentric.

Figures 52A, 52B, 52C, 52D:
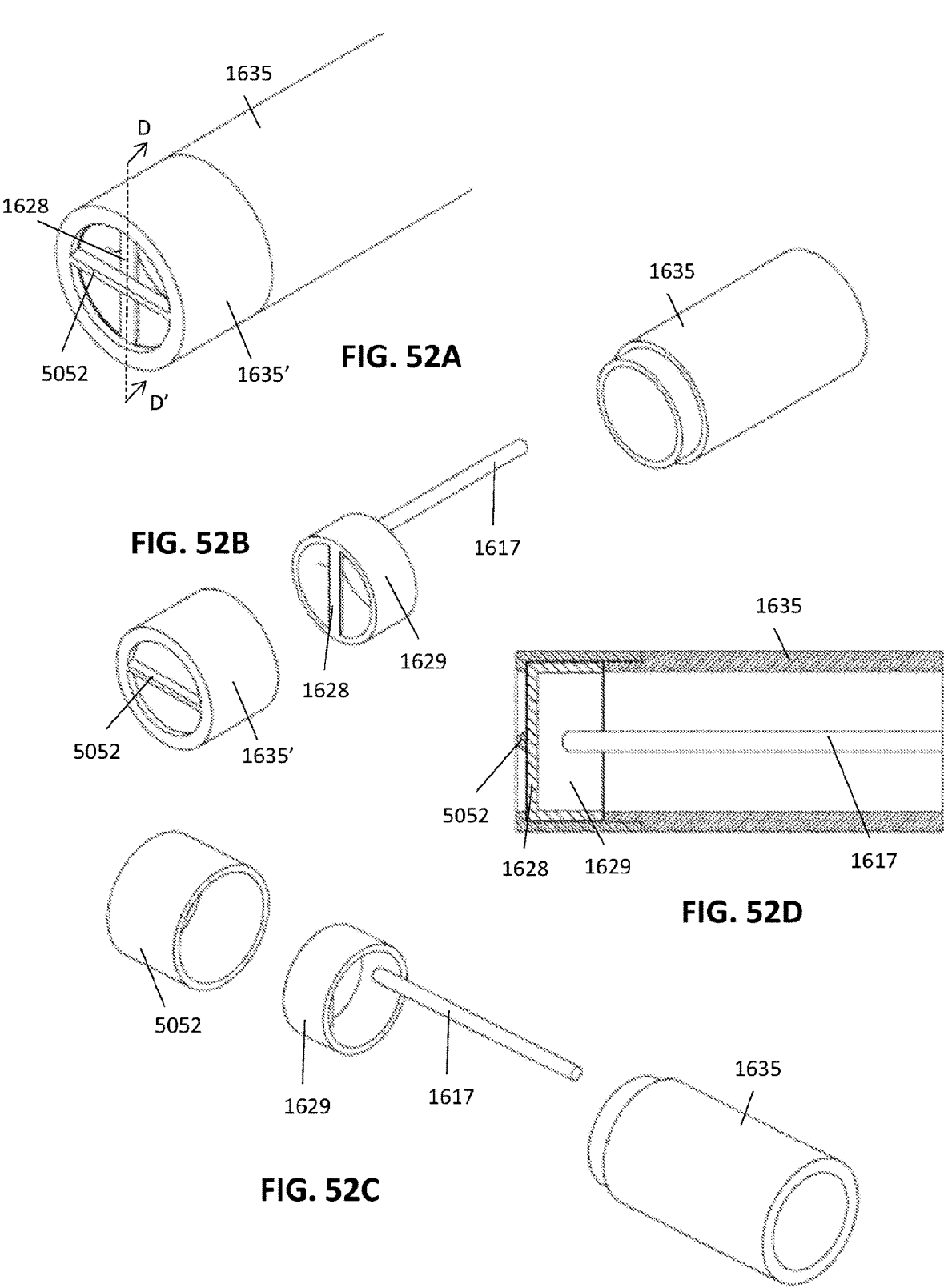
FIGS. 52A-52D illustrate perspective (FIG. 52A), exploded first perspective (FIG. 52B), exploded second perspective (FIG. 52C) and section (FIG. 52D) view of another example of a macerator.

FIGS. 52A-52D illustrate an example of a macerator having a distal-facing cutter that includes an eccentric connection to the drive member (e.g., drive wire). FIG. 52A shows the assembled macerator including a short distal macerator frame region that includes a crossbar diving the distal opening into two openings. The crossbar 5052 forms a shearing surface for the cutter blade 1628 portion of the cutter housed within the distal end of the macerator. FIGS. 52B and 52C show exploded views of the distal end of the macerator apparatus of FIG. 52A, showing the assembly of the macerator frame 1635 including the shearing surface formed by the crossbar 5052, the cutter frame 1629 including a cutter blade 1638 extending across the cutter frame. A drive member (drive wire 1617) is eccentrically coupled to the cutter frame to drive rotation of the cutter frame relative to the macerator frame, as shown. In this example the elongate body 1635 of the macerator forming the macerator suction lumen is attached to the macerator frame 1635' (in some examples the elongate body may be continuous with the macerator frame, so that a separate macerator frame is not necessary). FIG. 52D shows a section through the macerator distal end of FIGS. 52A-52C, taken along line D-D'.

In general, the cutters (and blades of the cutters) described herein may be configured to be used "blind" (e.g., with minimal imaging or targeting) in the removal of material such as pulmonary embolism material. For example, the macerators described herein may have multiple windows in the housing to entrap and cut material around its circumference. This may allow more material cut per rotation and also does not require a specific orientation (e.g., on a particular surface) relative to the lumen or to the material to be removed. Multiple openings (windows) can be a series of scythed openings around the wall of the tubular housing, as described above. Although the macerators described herein may be used as part of a system that minimizes the blood loss, in some cases multiple openings may also allow collateral fluid (e.g., blood) to be aspirated. There is a benefit from some collateral fluid entrained during the aspiration. A small amount of entrained fluid in conjunction with the cut solid material may aid in creating a fluid-like slurry that may be easier to aspirate. Additionally fluid pockets interspersed with the solid material may allow for easier aspiration because the aspirated mass may not be a continuous solid column.

Any of the apparatuses described herein may be used with or as part of an aspiration catheter or aspiration system that may allow the apparatus to be used within the lumen of the aspiration catheter. In some examples it may be useful to have a cover/guard over the macerator if it is used blind. This may mitigate the possibility of the cutter engaging a vessel wall or material not intended to be cut. In some examples, a strutted cage may surround the shaver tip so that the openings may be contained central to the cage but may still allow embolic material to flow into the cage.

In some examples the macerator may be used within a maceration chamber of an aspiration catheter. For example, a maceration chamber may be an expandable, non-permeable, funnel like shroud (e.g., capture containment chamber) surrounding the macerator. The distal face of the chamber may be open or may be at least partially (or fully) covered with a cover, such as a membrane having an opening. The opening may be, e.g., a slit to allow embolic material into the chamber. In some examples the membrane may be a deformable membrane that may be driven open by drawing the clot material into the chamber (e.g., by suction). The membrane may hold the clot material within the chamber even when suction decreases. Once in the chamber, the macerator may draw the clot material in to cut and macerator it; even if fragments are not immediately drawn into the suction channel for removal, the chamber may prevent loss of clot material that is capture. The chamber may also prevent the vessel wall from being drawn in and cut by the macerator.

Any of the macerators described herein may be configured for use within the suction lumen of an aspiration catheter and may be configured so that they do not include a macerator suction lumen; in some examples suction is applied through just the suction lumen of the aspiration catheter and may pass through the macerator cutter assembly when the cutter is within the suction lumen with suction being applied through the aspiration suction lumen.

For example, FIGS. 53A-53B show a first example of a macerator apparatus without a suction lumen, e.g., without an elongate body forming the suction lumen of the macerator. In FIG. 53A the macerator is shown as a distal-facing cutter that includes a concentric connection to the drive member (e.g., drive wire 1717). The macerator may also include side cutting regions (not shown). In this example the drive member is a flexible drive wire that is housed within a sheath or sleeve 1730. The inner lumen of the sheath may be lubricious or may include a lubricant and the drive wire may rotate within the flexible sheath or sleeve. The sheath or sleeve may generally be flexible but may provide sufficient column strength so that the distal end of the macerator may be driven into and through the suction lumen by applying proximal force to drive the macerator distally in the suction catheter. For example the sheath may be formed of a semi-flexible polymeric material or composite material (e.g., NYLON, PEBAX with coil, PEEK, Polyimide etc.). The sheath 1730 may be rigidly affixed to the macerator frame 1735' (in some examples the elongate body may be continuous with the macerator frame, so that a separate macerator frame is not necessary). The sheath in FIG. 53A may be affixed to one or more struts 1741, 1741' (e.g., 3 or more struts) connected to the macerator frame. The assembled macerator includes the short distal macerator frame 1735' that includes a crossbar 1752 diving the distal opening into two openings (more than one crossbar may be used). The crossbar 1752 forms a shearing surface for the cutter blade 1728 portion of the cutter housed within the distal end of the macerator. FIGS. 52B and 52C show exploded views of the distal end of the macerator apparatus of FIG. 52A, showing the assembly of the macerator frame 1635 including the shearing surface formed by the crossbar 5052, the cutter frame 1629 including a cutter blade 1738 extending across the cutter frame. The drive member (drive wire 1717) is rigidly coupled to the cutter blade 1738 and rotatably coupled to the crossbar 1752 in this example. Rotation of the drive wire drives rotation of the cutter blade (and in some case a cutter frame to which the cutter blade(s) are attached) relative to the macerator frame 1735. The apparatus does not include an elongate body of the macerator forming a macerator suction lumen. FIG. 53B shows a distal (enface) view of the macerator distal end of FIG. 53A.

FIGS. 53C-53C show another example of a macerator apparatus without a suction lumen, e.g., without an elongate body forming the suction lumen of the macerator. In FIG. 53C the macerator is shown as a distal-facing cutter that includes an eccentric connection to the drive member (e.g., drive wire 1717) to a rotatable cutter frame 1729 that rotates relative to eh macerator frame 1735'. A separate flexible positioning shaft 1734 is rigidly coupled to the macerator frame 1735' and may be used to steer or position the distal end of the macerator within the suction lumen of the aspiration catheter. The positioning shaft may be solid or hollow (e.g., tubular), and may generally have sufficient column strength and/or torsional stiffness so that proximal manipulation (e.g., advancement) of the positioning shaft may position the distal end of the macerator with generally high fidelity. In any of these examples the macerator frame may be solid or may include openings (e.g., increasing its longitudinal flexibility and decreasing the weight. The positioning shaft may be generally flexible.

The dive wire 1717 may be rigidly coupled 1742 to the cutter assembly (e.g., cutter blade 1738 and/or cutter frame 1729), or it may be rotatably coupled to the cutter assembly. Rotation of the drive wire therefore rotates the distal cutter assembly to shear against the shear plane formed by the crossbar 1752, as described above.

In any of these apparatuses the outer diameter of the macerator distal end region may be comparable with the inner diameter of the suction lumen of the aspiration catheter in which the macerator is used. For example, the outer diameter of the macerator distal end region (e.g., the maximum OD) may be between about 50% and 99% of the ID of the suction lumen in which it is used. For example, the OD of the macerator distal end may be, e.g., between about 60-95%, between about 65-95%, between about 70-95%, between about 75-95%, between about 80%-95%, between about 85%-95%, between about 90-95%, etc. of the ID of the suction lumen. In some examples macerator may be oversized relative to the inner diameter of the suction lumen and may include a compressible sealing skirt or rim (not shown in FIGS. 53A-53D) that may compress or collapse to allow passage within the suction lumen while forming at least a partial seal or occlusion between the outer diameter of the macerator and the inner diameter of the suction lumen. This may help guide suction through macerator rather than around the macerator. Alternatively, the macerator may be undersized relative to the inner diameter of the suction lumen, and may allow some (e.g., smaller) material through the region adjacent to the macerator distal end.

Figure 54A:
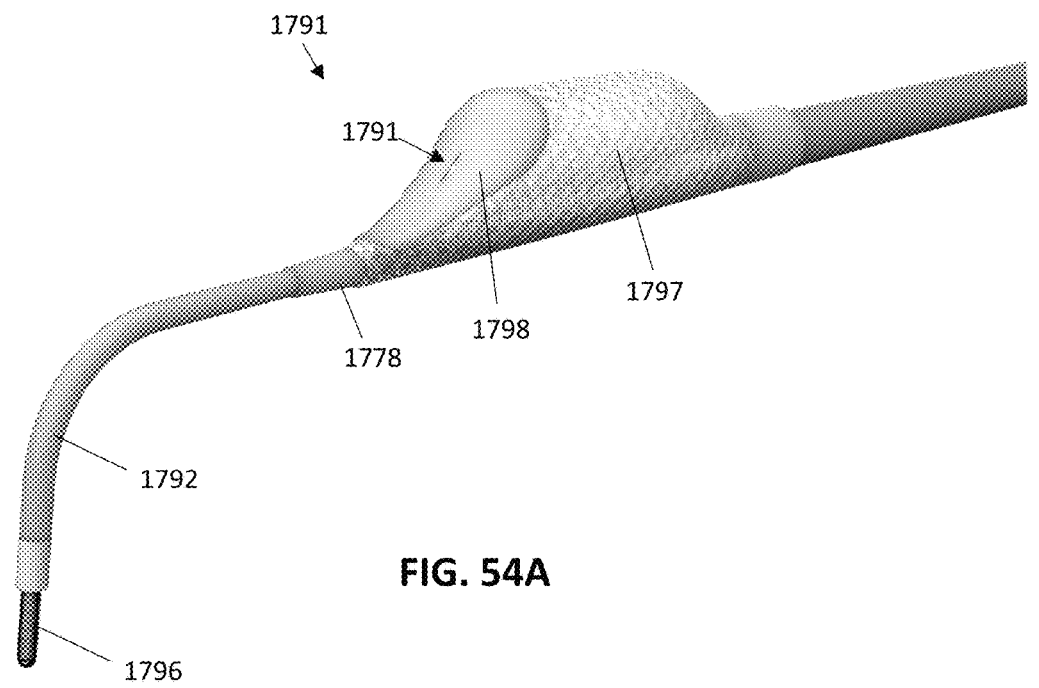
FIG. 54A illustrates one example of an aspiration catheter including a maceration chamber.

FIG. 54A shows an example of an aspiration catheter that may be used with any of the macerators described herein. In this example the aspiration catheter 1791 includes a channel 1778 for a guide wire 1796 and/or guide catheter 1792. The aspiration catheter also includes a maceration chamber 1797 at a distal end region of the aspiration catheter in fluid communication with a suction lumen. In this example, the maceration chamber is configured to have a larger cross-sectional area that the suction lumen; in some examples it may expand. The maceration chamber may be open or, as shown in FIG. 54A, covered with a membrane 1798. The membrane includes an aperture (e.g., a slit 1791 in this example) that may expand open to allow thrombus material into the maceration chamber and/or suction lumen. For example, the membrane covering the maceration chamber may be deformable (e.g., elastically deformable) and suction may open the aperture to allow clot to enter, while minimizing the blood flow into the chamber.

Figure 54B:
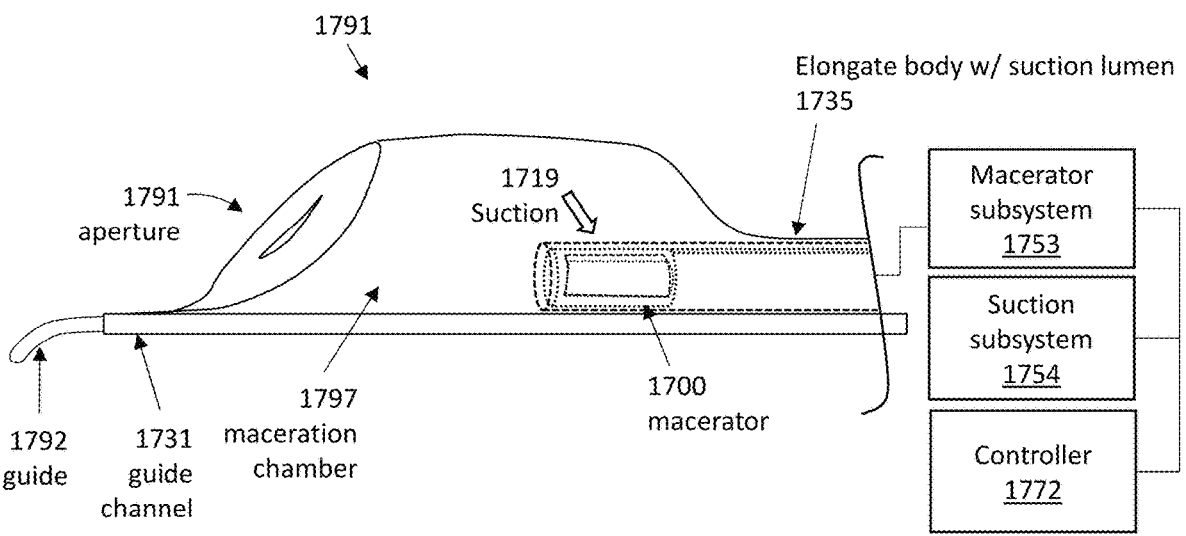
FIG. 54B shows a partially transparent view of the aspiration catheter of FIG. 54A.

FIG. 54B is a partially transparent schematic of an apparatus including an aspiration catheter 1791 similar to that shown in FIG. 54A, as well as a macerator 1700. In FIG. 54B the macerator is shown extended through the suction lumen of the aspiration catheter so that the elongate body 1735 of the macerator passes through the suction lumen. The system apparatus also includes a controller 1772 for controlling the aspiration and/or the macerator drive. For example the system may also include a suction subsystem 1754 and a macerator subsystem 1753. The suction subsystem may coordinate the application of suction so that it is applied to either or both the suction lumen of the aspiration catheter and/or to the suction lumen of the macerator or both. In some cases the suction subsystem may coordinate the application of suction 1719 so that it applied during a portion of the cardiac and/or respiratory cycle. For example the suction subsystem may be configured to receive input indicating the respiration of the patient and may apply suction 1719 (or may increase suction) only when the respiration cycle is at a point in which the blood flow near the distal end of the aspiration catheter is at a minimum. Similarly the suction subsystem may receive input from one or more cardiac (e.g., pulse, ECG, etc.) sensors and may apply suction 1719 (or may increase suction) only when the cardiac cycle is at a point in which the blood flow near the distal end of the aspiration catheter is at a minimum.

The apparatus may also include a macerator subsystem that may coordinate drive of the macerator with the position of the macerator within the lumen of the aspiration catheter, as descried in greater detail below. The controller 1772 may include or control the macerator subsystem 1753 and/or the suction subsystem 1754. The controller may include one or more inputs and one or more outputs (e.g. display, etc.).

Figure 55A:
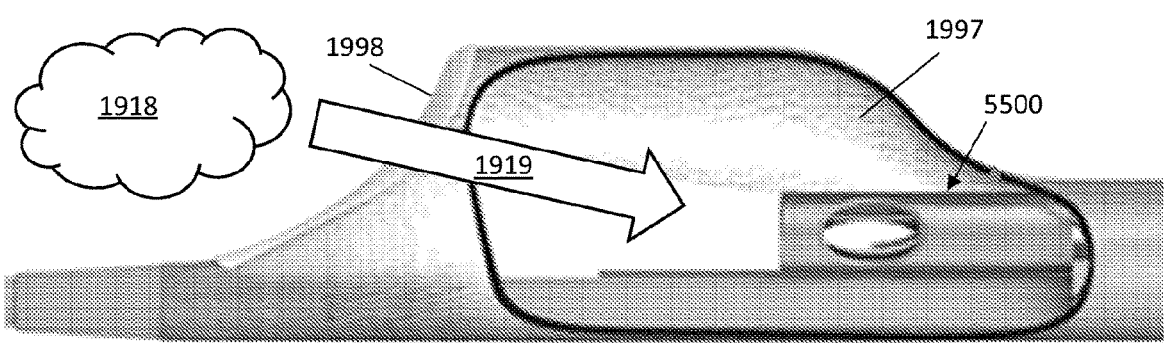
FIGS. 55A-55C illustrates use of an apparatus including an aspiration catheter with a maceration chamber and a macerator.
Figure 55B:
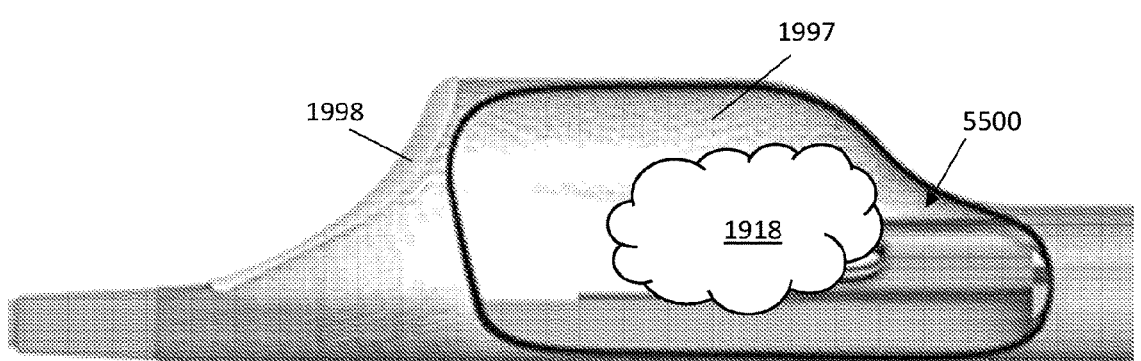
Figure 55C:
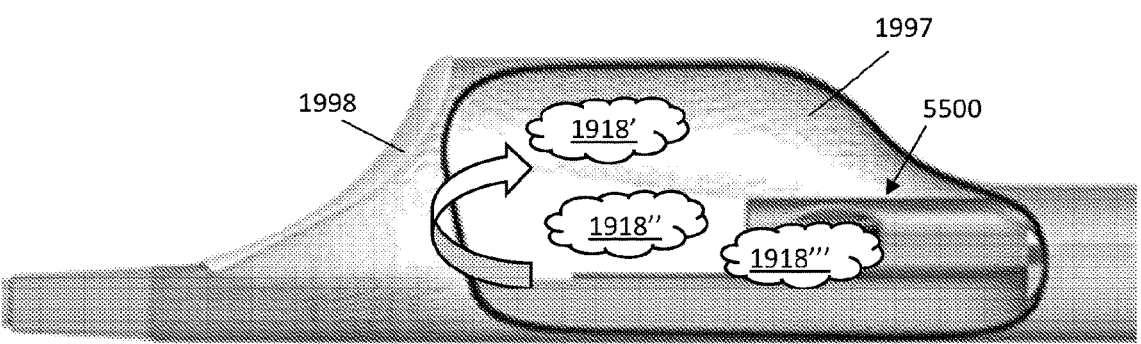

FIGS. 55A-55C illustrate one example of the operation of an apparatus as described herein including an aspiration catheter having a maceration chamber and a macerator. In FIG. 55A, the macerator is shown with the distal end extended into the maceration chamber 1997 of the aspiration catheter. The aspiration catheter has been positioned adjacent a clot material 1918. Suction 1919 is applied through the suction lumen of the macerator (or the suction lumen of the aspiration catheter and the suction lumen of the macerator) to draw the clot material into the aspiration catheter, through an aperture in the membrane 1998 covering the maceration chamber. The macerator 5500 may be operated to drive rotation of the macerator while applying suction, pulling the clot material into the macerator as shown in FIG. 55B. The clot material may be macerated by the shearing force applied between the rotating cutter and the macerator housing, breaking the clot material up 1918, 1918', 1918" as shown in FIG. 55C and drawing it into the macerator suction lumen for removal. In this example, the embolic material that may fracture into smaller portions during maceration are maintained in the capture chamber (maceration chamber) because of the aspiration and the membrane with the aperture, which creates a valve-like barrier to prevent distal embolization of the material. The material within the chamber is also protected or shielded from external venous distal flow.

Figure 56:
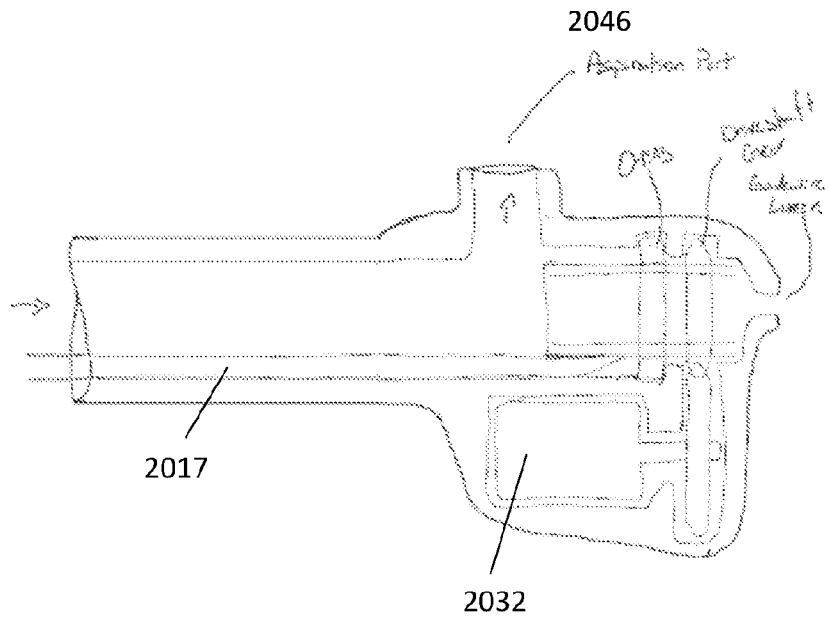
FIG. 56 schematically shows one example of a handle of a macerator.

Any of the apparatuses described herein may include a handle at the proximal end. For example, FIG. 56 illustrates one example of a proximal handle region. The proximal end may include an aspiration port 2046 that may couple to a source of negative pressure and may be regulated by a controller and/or a suction sub-subsystem. The proximal end of the device may also include or may couple to a drive for driving rotation of the drive member (e.g., drive wire) 2017. In FIG. 56 the proximal end includes a motor 2032. The proximal handle region may also include one or more gears (e.g., driveshaft gears) to drive rotation of the drive member (e.g., drive wire or drive tube). In variations including a drive tube, the proximal end may be sealed for rotation and have openings distal of the seal to allow aspirated material to exit. In variations with a drive wire, the drive wire may be sealed via a valve at the proximal end (e.g., a hemostatic valve). The macerator proximal end may also allow a guidewire to be inserted through the suction lumen.

As described above, any of the macerators described herein may be used with a maceration chamber, which may be configured as a soft, dip coated chamber (maceration chamber) of the aspiration catheter, which may allow for easy trackability inside the human anatomy and may ensure that the cutter will not contact any material besides the clot that enters the balloon. For example, an aspiration catheter including a maceration chamber may taper at the proximal end to ensure the clot is focused at the two points of maceration upon capture of the clot. An aspiration catheter may feature a small opening (aperture) in a membrane which acts as a gate allowing clot to enter upon contact, as well as keeps clot close to the shaver so there is minimal blood loss.

In general, the macerators described herein may be configured to rotate the cutter assembly so that the cutter spins, e.g., at between 1000-10,000 RPM (e.g., between about 5000-4500 RPM, between about 1600-4200 RPM, etc.). Any of the apparatuses described herein may include a gearing to step down the rotation of the motor to rotate the cutter assembly at within at desired rotational range. For example, the driver may rotate at greater than 10,000 RPM and may be stepped down to between about 1000-10,000 RPM. The apparatus may be configured so that the drive member (e.g., drive wire) is prevented from spinning if the forces acting on the drive member (e.g., torque) exceed a threshold value. This threshold value, which may be preset or adjustable, may provide a mechanical failure mode which stops the drive member from spinning to allow the apparatus to be cleared safely without harm to the patient.

In general, the apparatuses described herein may allow substantially more clot material to be removed from the patient with less risk, and less blood loss than any other traditional aspiration methods. In particular, the macerators described herein may allow the procedure to take place with virtually no blood loss when used with an aspiration catheter including an enclosed maceration chamber and the cutting mechanism's ability to reduce clot to a liquid-like consistency. Since the maceration chamber only pulls in blood clots on contact, the macerator may work by macerating the clot inside the chamber, not contingent any way on blood flow or blood loss. These techniques improve upon the ways large volume unwanted material such as blood clots may be removed from the vasculature without the use of thrombolytics. Current technologies for removing unwanted material from the vasculature include mechanical thrombectomy via aspiration, physical extraction, physical clot agitation using fluid or a combination of the prior. Such technologies have limitations with navigating tortuous anatomy such as the pulmonary vasculature, reaching distal branches of the vasculature, as well as being able to completely extract the large volumes of clot due to the size of the unwanted material being removed. Because of the size of the unwanted material, mechanical thrombectomy devices typically get clogged in 20-30% of the cases causing the clinician to completely remove the device from the patient, clean out the device, and attempt to reinsert the device back into the patient to attempt to remove more material. Within these cases, the material burden can extend into the distal branches of the vasculature where the vessels reduce in size and become highly bifurcated requiring the clinician to insert and advance another smaller device into the body to attempt to retrieve the material from the distal branches. Due to one limitation or another, there hasn't been a procedure or a device that has fully met the needs of removing large volume of unwanted material from the vasculature in a single pass; therefore, there remains a need for the development of new systems that address these limitations.

The methods and apparatuses described herein may permit high flowrate aspirations of unwanted material through a large bore aspiration lumen catheter and may allow for an insertable distal facing macerator to be safely advanced through that aspiration lumen while under vacuum if the aspiration lumen gets clogged. The macerator may macerate unwanted material within the lumen allowing the macerated unwanted material to pass through the lumen of the macerator and out the body. If the macerator is used within the aspiration catheter, the clinician can continue to aspirate through the macerating catheter to pull unwanted material to the catheter system and macerate the unwanted material as it enters the aspiration orifice, or the clinician can continue to advance the macerator distal through the aspiration orifice of the aspiration catheter extending into the smaller vessels of the vasculature to physically engage with the unwanted material. As the distal end of the macerator passes through the aspiration orifice of the aspiration catheter, the macerating element of the catheter may be deactivated, allowing the clinician to safely pass through the vessels with the macerator to engage with unwanted material using aspiration or other mechanical means. Once the macerator has engaged with the unwanted material, the macerator can be retracted proximal towards the aspiration catheter, pulling the unwanted material with the catheter. Once the distal end of the macerator passes through the aspiration orifice and is safely inside the aspiration lumen of the aspiration catheter, the cutter of the macerator may be reactivated, to macerate the unwanted material, allowing the unwanted material particles to pass through the aspiration lumen of the macerator and out of the body. If the user (e.g., clinician, doctor, surgeon, etc.) desires, the aspiration catheter with the macerator may be positioned proximal to the aspiration orifice of the aspiration catheter to navigate the catheters as a system aspirating and macerating the unwanted material as the unwanted material enters the aspiration orifice of the aspiration catheter.

The apparatuses described herein may enable the aspiration catheter and macerator to be navigated together by having an integrated guidewire lumen and/or navigation catheter lumen offset but adjacent to the longitudinal axis of the aspiration lumen (suction lumen) of the aspiration catheter. This navigation lumen may be concentric with the aspiration lumen, but for removing large volume of unwanted material such as venous clot, an offset navigation lumen may be desirable as the unwanted material is typically soft and may not be adherent to the vessel wall. The offset lumen may allow for a larger aspiration orifice area for engaging the unwanted material and allowing for the navigation catheter or guidewire to pass between the unwanted material and the vessel wall without obstructing the space between the unwanted material and the aspiration orifice. The offset, adjacent navigation lumen also allows the aspiration orifice to be rotated around the longitudinal axis of the navigation lumen giving the apparatus the ability to effectively cover the entire blood luminal area of vessels larger than the catheter area. The offset, adjacent navigation lumen may allow for an aspiration orifice to be directionally positioned towards the unwanted material. This is beneficial when the unwanted material is stuck within a bend of a vessel or on the inside wall of the vessel after a bend. The guidewire that is used to guide the catheters through the vasculature may track on the outside wall of the vessel after coming out of a bend causing aspiration catheters with concentric guidewire lumens or no guidewire lumen to hug the outside wall of the vessel not allowing the device to get close to the unwanted material and when these types of devices go to aspirate to pull the unwanted material towards its aspiration orifice the orifice sucks onto the wall preventing aspiration and potential harm to the vessel wall. If the navigation lumen is offset to the longitudinal axis of the aspiration orifice, the aspiration system can be rotated proximally causing the aspiration orifice to rotate around the guidewire and point towards the inside wall of the vessel.

The offset (e.g., off of the axis of the midline of the apparatus) of the guide lumen may therefore enable the removal of large volumes of unwanted material within a single session by allowing pivoting to position the aspiration catheter (and/or macerator) within the body, which may lead to improved efficiency and safety especially when having to navigate through vital anatomy to get to the unwanted material such as the heart.

FIGS. 57-61B described below illustrate non-limiting examples of apparatuses as described herein and in particular, illustrate the control of the macerator Macerator Control Any of the apparatuses described herein may control the operation of the macerator so that the rotation of the cutter of the macerator is coordinated automatically or semi-automatically during operation. In particular, the controller and/or macerator subsystem and/or suction subsystem may be configured to control operation of the apparatus by limiting the activation of the cutter so that it is on only when the macerator is within the lumen and/or maceration chamber of the aspiration catheter.

Figure 57:
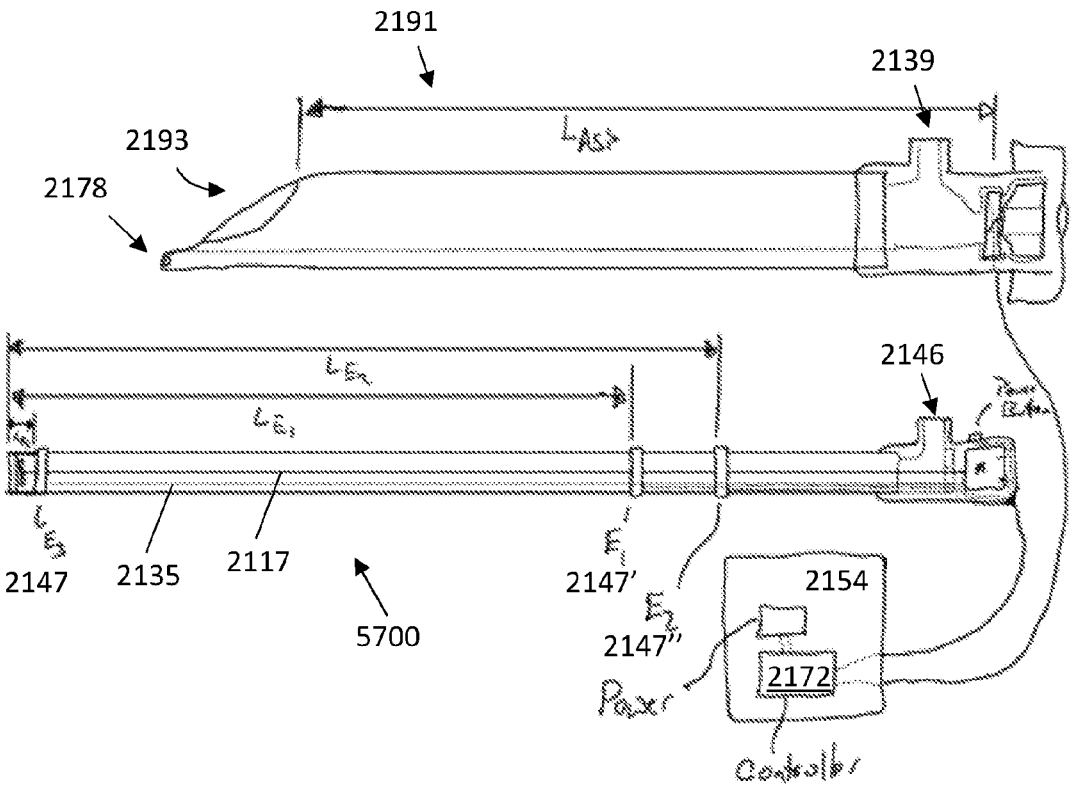
FIG. 57 schematically illustrates an example of an apparatus including an aspiration catheter and a macerator configured to detect relative position of the macerator to the aspiration catheter for controlling the macerator.

For example, FIG. 57 illustrates one example of an apparatus including an aspiration catheter 2191 and a macerator 5700. The aspiration catheter includes an off-axis channel for guidance 2178, and a suction lumen 2193. The aspiration catheter has a length (Lasp), and a portion for coupling to a source of negative pressure (aspiration port 2139), which may be controlled by an aspiration (or suction) sub-system as described above. The macerator may be any of the macerators described herein, including a distal-facing macerator and/or a side facing macerator. In FIG. 57, the macerator 5700 includes an elongate body 2135 has an overall length (from the distal end cutting region to the proximal handle region) that is typically longer than the length of the aspiration catheter. The macerator may also include an aspiration (suction) port 2146 that may couple to the same source of negative pressure as the aspiration catheter or a different source of negative pressure that may also be controlled by the controller 2172 and/or an aspiration (or suction) sub-system 2154.

In any of the apparatuses described herein the apparatus may sense, detect or determine the position of the macerator within the aspiration lumen, and in particular, the position of the macerator distal end relative to the position of the aspiration catheter, including a macerator chamber and/or may sense, detect or determine when the macerator exits distally from the aspiration catheter, and may turn off or disable maceration until unless and until the macerator distal end (including the cutter) is within the lumen and/or maceration chamber of the aspiration catheter.

For example, either or both the macerator and the aspiration catheter may include an encoder that encodes the length and/or position of the macerator within the aspiration catheter. Any appropriate sensor and/or encoder may be used, including mechanical, optical and/or electrical sensors and/or encoders. For example, an apparatus may optically determine the position from the proximal end, and/or may electrically determine the position of the distal end of the macerator relative to the aspiration catheter.

In FIG. 57, the apparatus (e.g., configured as a clot extraction system) shown include a variable stiffness elongated aspiration catheter 2191 having a distal end, a luminal body having a distal segment, a proximal segment, at least one inner (suction) lumen 2193, and a proximal end that is affixed to a hub having at least an aspiration port 2139, a navigation lumen port, and a hemostatic orifice that is normally closed and allows for the insertion of other elongated medical accessories known to be used in a minimally invasive catheter based procedure. The apparatus also include an insertable, flexible elongated macerator 5700 (e.g., macerator catheter) having an atraumatic distal end, an elongate luminal body having at least one inner lumen (e.g., suction lumen), a proximal end, a shearing macerating assembly (e.g., cutting assembly) positioned within a predetermined distance (e.g., within about 10 mm, about 8 mm, about 7 mm, about 6 mm, about 5 mm, about 4 mm, etc.) from the distal orifice of the distal end, a flexible macerating drive element (e.g., drive wire 2117) that runs throughout the inner lumen of the body, and a handle affixed to the proximal end of the elongate body 2135 having at least an aspiration port 2146 and a driving element (e.g., motor). The apparatus also includes a controller 2172 having or controlling a vacuum pump, power source (e.g., DC power source), and one or more sensors, such as a means of monitoring electrical signals. The controller may generally receive input from the one or more sensors and may modulate negative pressure (suction) to the macerator and/or aspiration catheter and/or the macerator, e.g., by controlling the power (e.g., DC power) to the macerator.

In this example, the elongated aspiration catheter has a luminal body of at least two inner lumens longitudinally running throughout. In some examples, the luminal body will have three or more inner lumen throughout and the two of the inner lumen may terminate more distal and more proximal to one of the lumens (e.g., the suction lumen). The shortest of the lumen may be referred to as the suction or aspiration lumen 2193 and may have a cross-section area greater than the other lumens taking up 50% or more of the total area of the luminal body. One of the other lumens may be referred to as the navigation lumen 2178 and may extend and terminate distally to the center of the aspiration orifice at the distal end of the aspiration (suction) lumen. In this example the navigation lumen 2178 is spatially located adjacent to but offset from the longitudinal axis of the of the aspiration lumen. The construction of the luminal body may be done in a way that makes at least the distal region (e.g., distal 20 cm or more, distal 25 cm or more, distal 30 cm more, distal 35 cm or more, etc.) more flexible than the proximal section. In some examples the variable stiffness luminal body will have three segments to accommodate the different anatomical regions the elongated catheter will transverse through. An example of a three segmented variable stiffness elongated catheter may include a most flexible distal segment being, e.g., between about 3 to 10 cm long, a middle segment being stiffer than the distal segment, but more flexible than the proximal segment starting just proximal the distal segment and continuing proximal, e.g., until about 20 to 40 cm from the distal end, and a proximal segment being the stiffest section and starting just proximal to the middle segment and continuing to the proximal end where the handle is affixed. This three segmented variable stiffness elongated catheter may enable the catheter to transverse from a proximal access site. A segmented variable stiffness catheter may be particularly useful when navigating from an access site, e.g., within the leg of a patient, and traversing through the vasculature up through the heart into the pulmonary arteries. A three (3) segmented variable stiffness elongated catheter may provide a flexible distal segment of the catheter to navigate the segmental branches of the pulmonary vasculature, a semi-flexible middle segment that has the flexibility to navigate through the atrium and ventricle but the stiffness and pushability to ensure the catheter doesn't prolapse or fall back into the ventricle as the distal segment is moved within the pulmonary vasculature, and a stiff proximal section that allows good pushability and stability within the larger iliac and vena cava near the leg of the patient.

In FIG. 57, the apparatus includes three electrical contacts that are positioned at specific, predefined position on the length of the macerator's elongate body. These electrical contacts may be annular (e.g., rings) and may comprise a conductive material 2147, 2147', 2147" that may be detected by one or more detection circuits on the port and/or the aspiration catheter for determining when the macerator is inserted into the aspiration catheter and/or the position of the macerator assembly at the distal end region of the macerator.

Figure 58A:
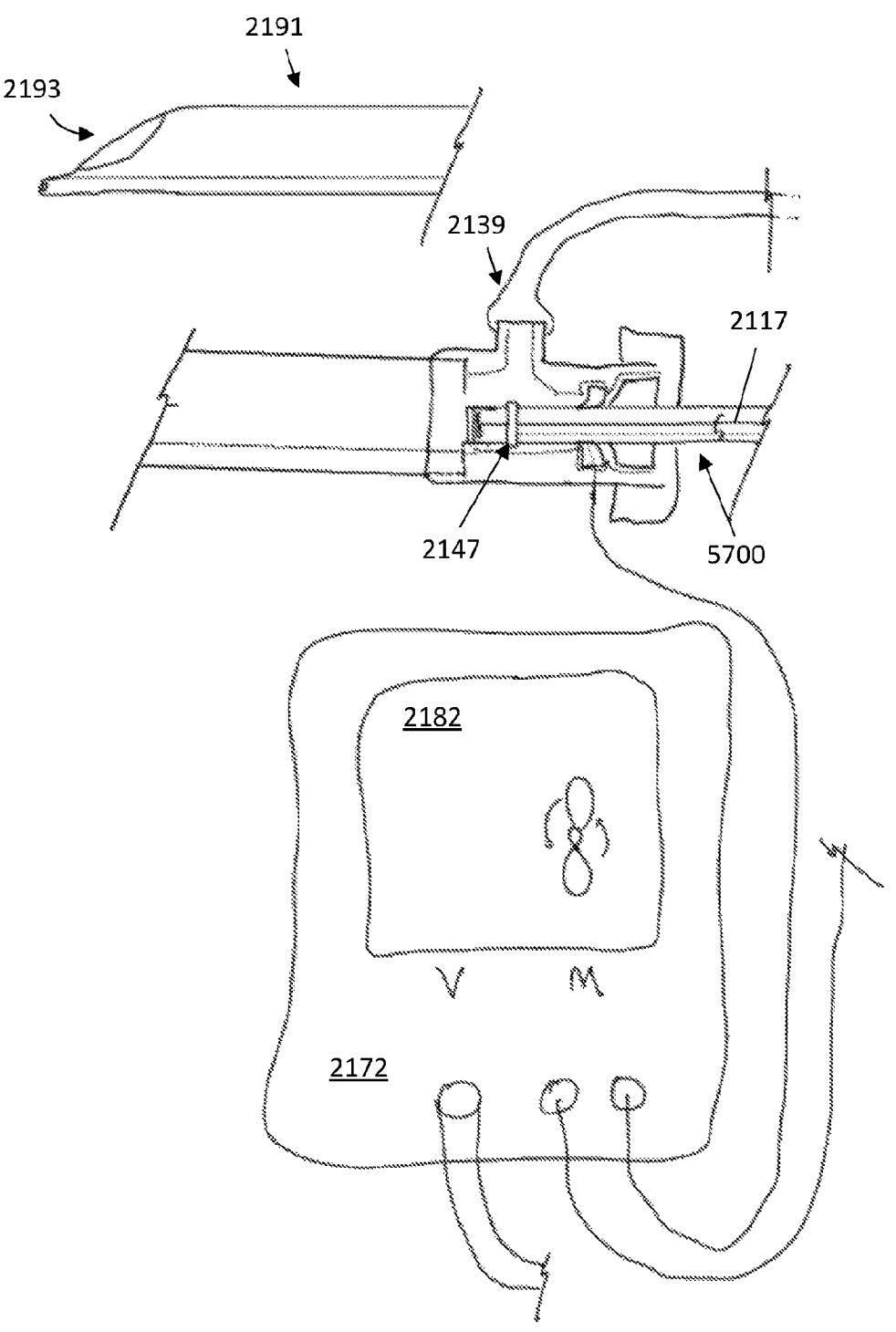
FIGS. 58A-58C illustrate operation of an apparatus including an aspiration catheter and a macerator.
Figure 58B:
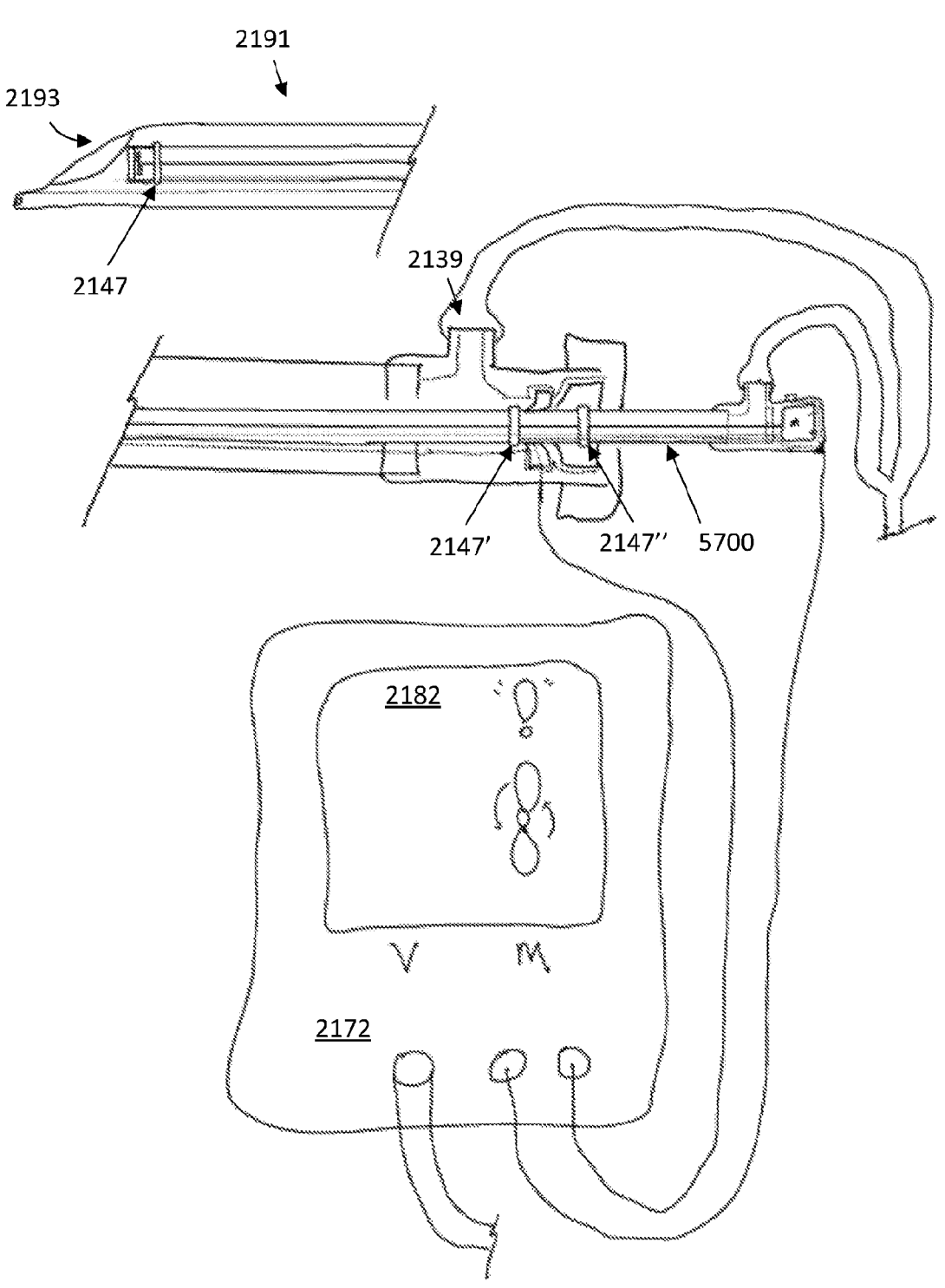
Figure 58C:
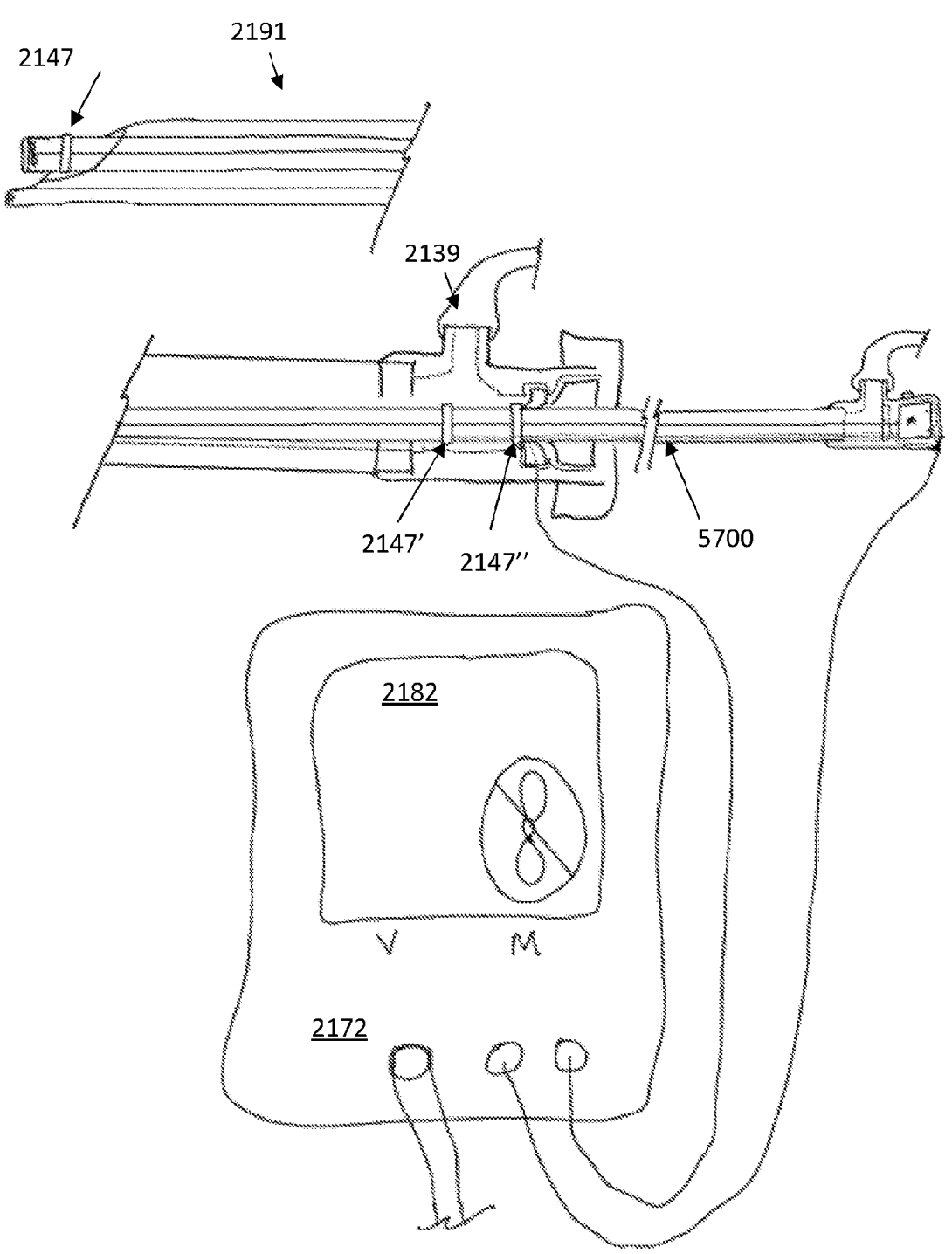

FIGS. 58A-58C illustrate the use of the electrical contacts for determining the position of the macerator within (or extending distally from) the aspiration catheter and therefore controlling operation of the macerator and/or aspiration. In FIG. 58A, the controller 2172 may receive input from one or more electrical circuits that detect contact with the first annual conductive region 2147 on the macerator 5700 as it is inserted into the suction lumen 2193 of the aspiration catheter 2191. For example, the controller may detect the closing of a circuit as the electrically conducive annulus contacts electrodes on the valve of the aspiration catheter or a proximal handle region coupled to the aspiration catheter. The controller 2172 may include a user interface and/or display 2182. The display shows the status of the macerator ("M") showing an icon in FIG. 58A indicating that the macerator is on or is enabled (able to be manually turned on). A second indicator may indicate that suction (vacuum, "V") is on or able to be turned on, and/or may indicate and/or allow control of the level of suction to be applied. The suction may be controlled or regulated independently of the macerator. In some examples, the macerator may only be enabled when suction is on; in some examples activation of the macerator may automatically turn on suction.

FIG. 58B shows the apparatus of FIG. 58B in which the macerator has been inserted so that the second (but not the third) annular conductive region has been detected by the detection circuit indicating that the macerator is within the distal end region, e.g., within a maceration chamber, but has not extended distally out of the aspiration catheter.

In FIG. 58C the third annular conductive region 2147" has been detected by the detection circuit, indicating that the macerator is extending distally from the aspiration catheter, and disabling the macerator.

Figure 59A:
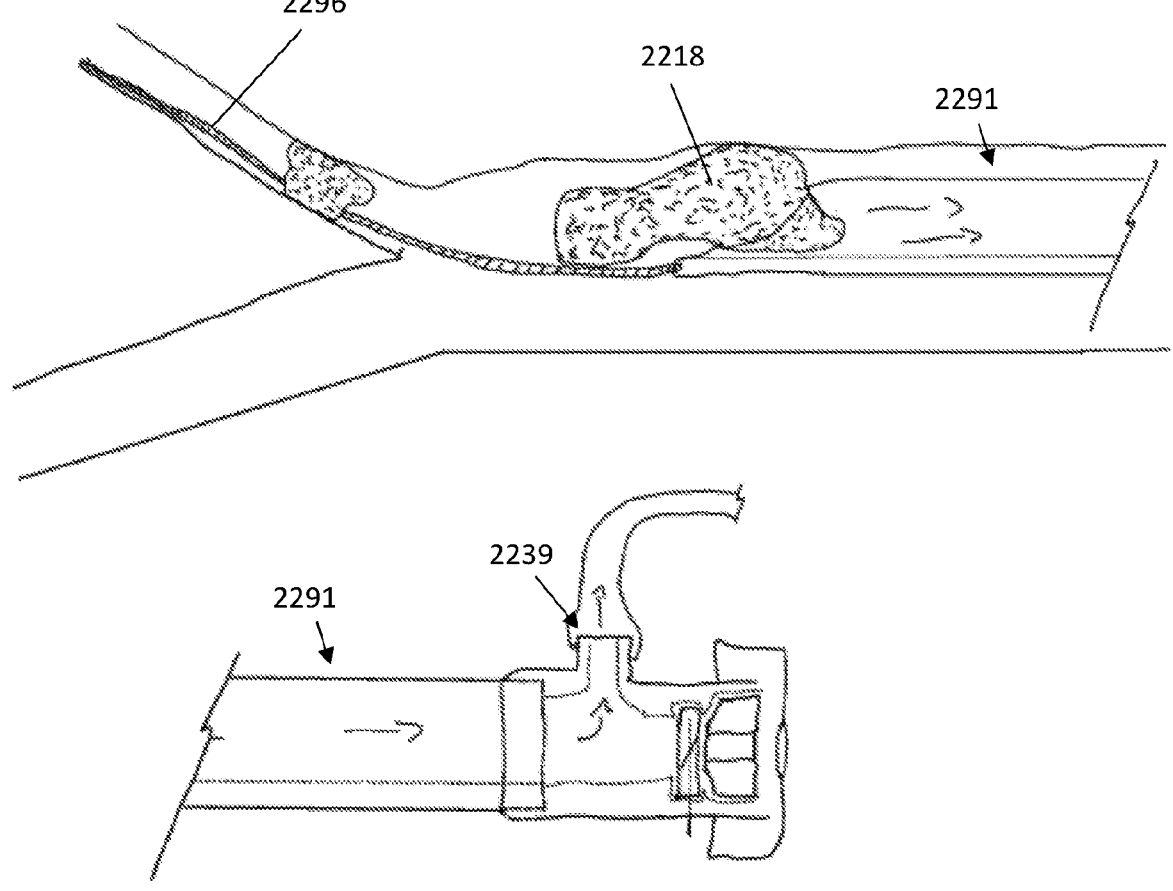
FIGS. 59A-59D illustrate operation of an apparatus including an aspiration catheter and a macerator.

FIGS. 59A-59D illustrate another example of the apparatus of FIGS. 58A-58C in use. In FIG. 59A the aspiration catheter is shown removing clot material within a vessel. The aspiration catheter 2291 may be guided over a guidewire 2296 in position to remove clot material by applying suction through the suction lumen of the aspiration catheter from a suction port 2239, as shown.

Figure 59B:
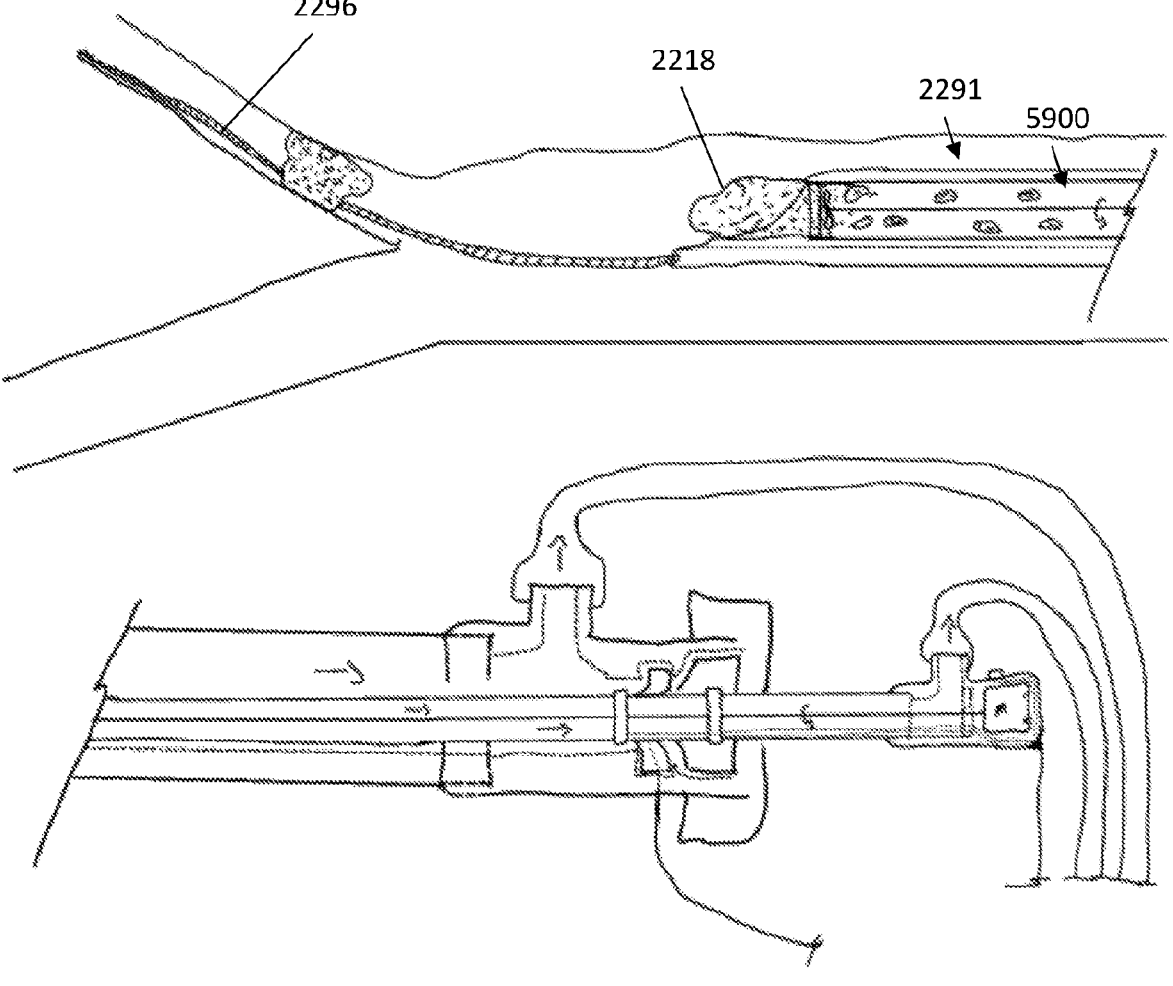
Figure 59C:
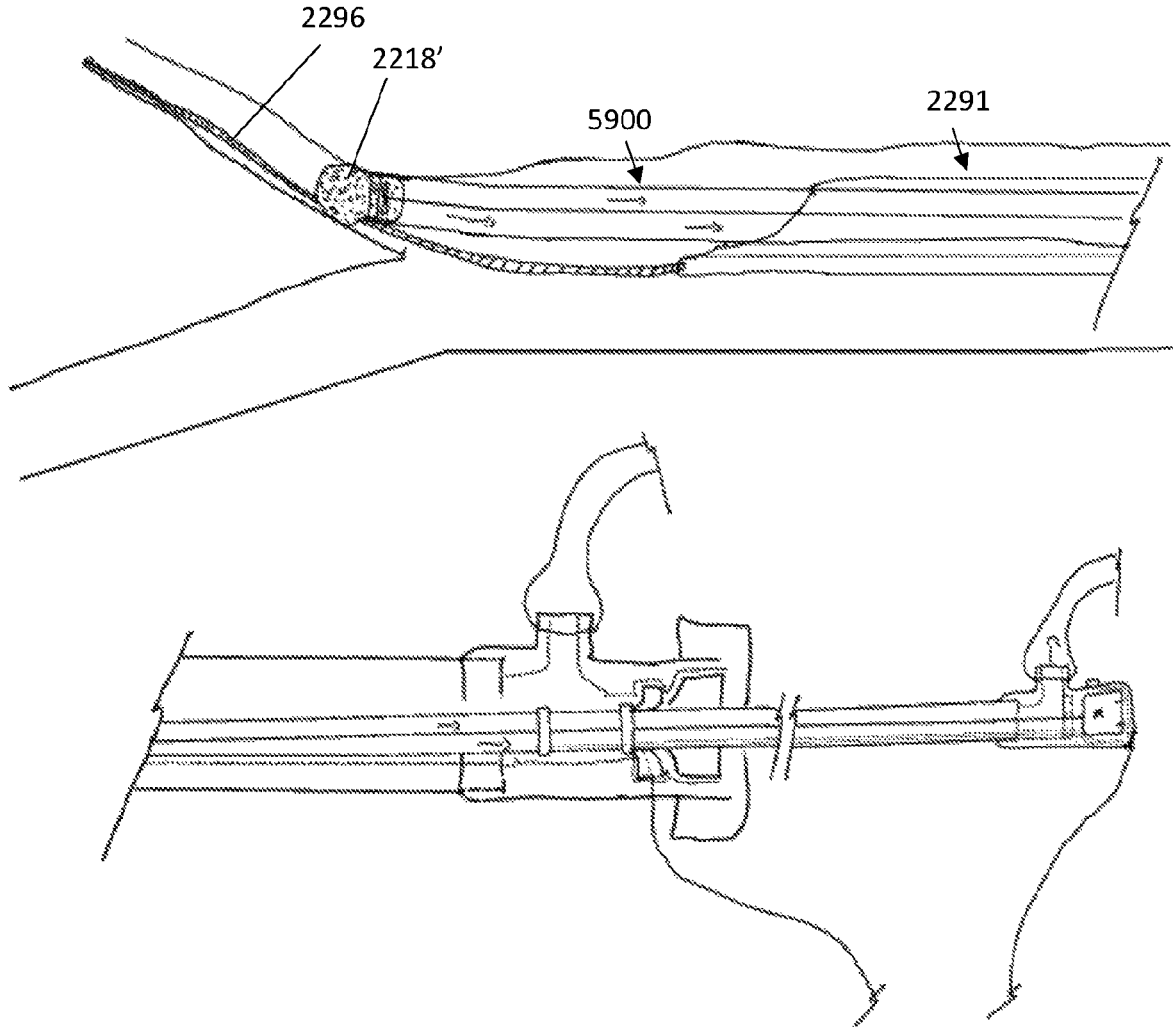
Figure 59D:
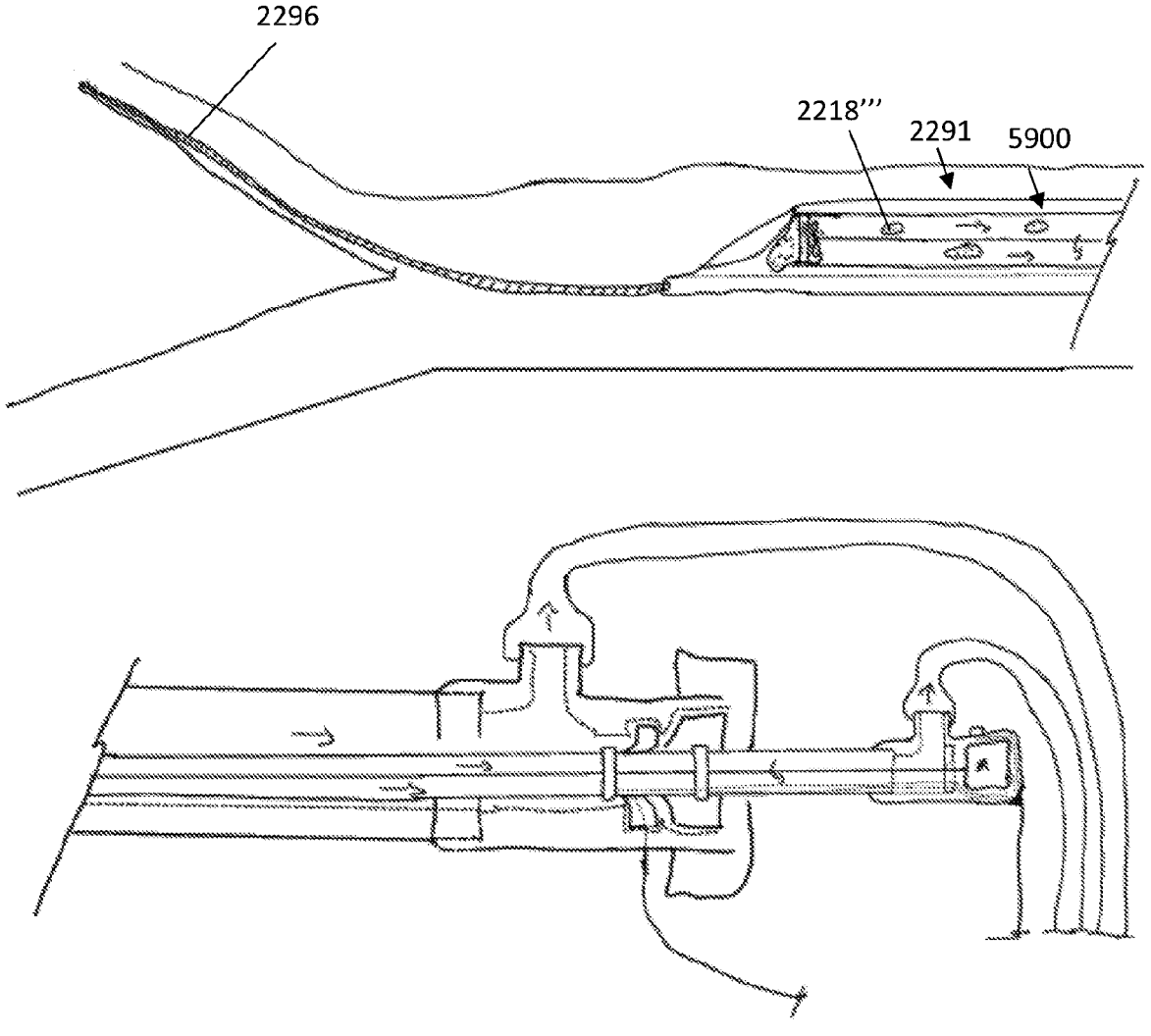

In FIG. 59B the macerator 5900 has been inserted into the suction lumen of the aspiration catheter so that clot material within the distal end of the aspiration catheter may be macerated by the distal facing cutter, as shown. Suction may be applied through either the macerator or both the macerator and the suction lumen of the aspiration catheter (as in FIG. 59B). As in FIG. 57B, the apparatus may detect or sense that the macerator is within the aspiration catheter, enabling maceration. In FIG. 57C, the macerator has been extended distally from the aspiration catheter into a branch of the vessel. The apparatus may sense that the macerator has extended distally out of the aspiration catheter and may disable the macerator but may continue suction. The macerator 5900 may therefore act as an independently extendable suction catheter, and may engage with clot material 2218', which may be pulled back into the lumen of the aspiration catheter 2291 where it may be macerated and removed, as shown in FIG. 58D. The macerator 5900 has been withdrawn back into the aspiration catheter and maceration enabled and/or automatically turned on to macerate the clot material 2218'".

Figure 60:
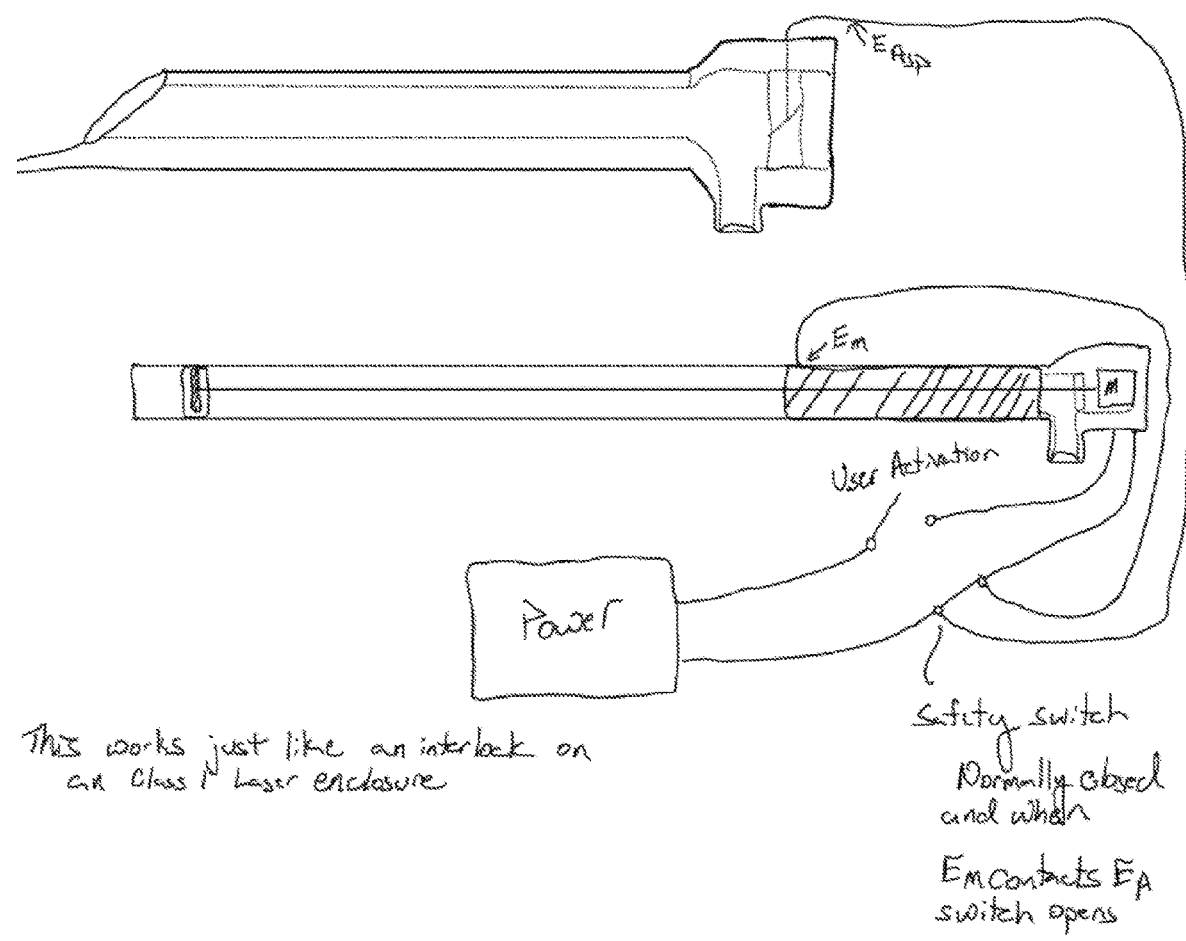
FIG. 60 schematically illustrates an example of an apparatus including an aspiration catheter and a macerator.

FIG. 60 illustrates one example of a control system for an apparatus as shown in FIGS. 57A-57C and 58A-58D in which active electrode circuits may be within the aspiration catheter and may detect the presence or absence of a conductive material on the macerator, which may be used to control the macerator, as described above.

Figure 61A:
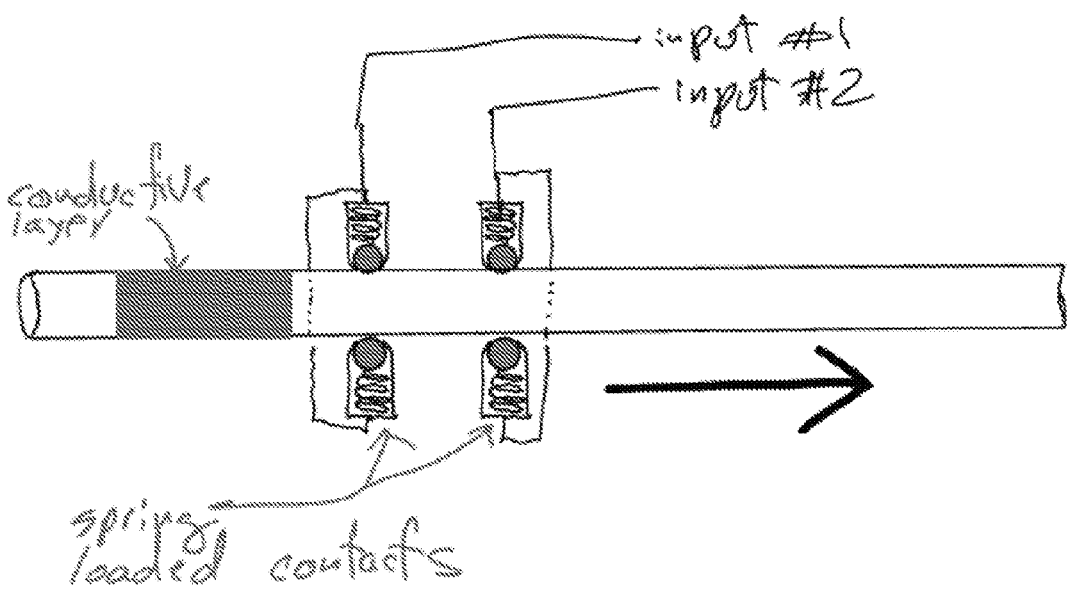
FIGS. 61A-61B schematically illustrate an example of sensing or determining relative position of a macerator and an aspiration catheter.
Figure 61B:
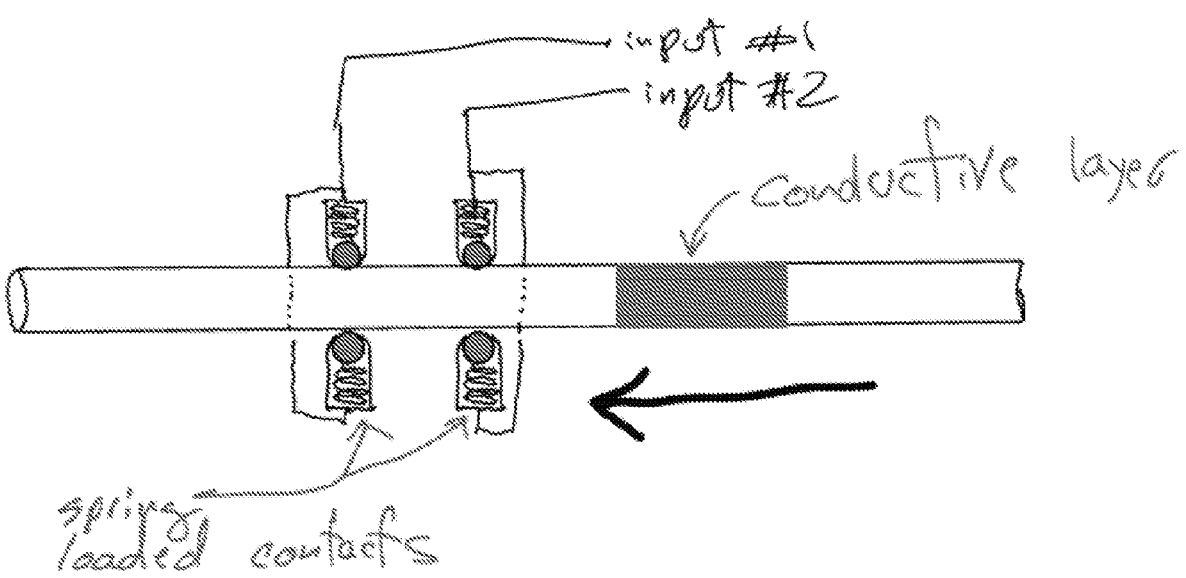

Similarly, FIGS. 61A-61B illustrate another example of an apparatus in which one or more conductive regions (e.g., annular bands) may be detected by sensors and/or circuits on a handle and/or the aspiration catheter. As the macerator is advanced distally, the conductive regions may contact the conductive sensors (which may include spring-loaded, e.g., biased, contacts) that sense the longitudinal position of the macerator. Having two or more sets of contacts may allow redundancy and may provide directionality in sensing the position of the macerator. The apparatus may therefore determine that the macerator has been inserted and advanced; the apparatus may determine the direction of movement (advancing/withdrawing) and/or the relative position of the distal end of the macerator relative to the aspiration catheter. Alternatively, in some examples the apparatus may optically sense one or more markers on the elongate body of the macerator.

Conical, Distal-Facing Macerator

Any of the macerator apparatuses described herein may be configured to include a conical, distal-facing end. These macerators may be referred to herein as conical macerators or conical, distal-facing macerators. A conical distal-facing macerator may include one or more macerator windows forming a shearing surface with a rotating cutter having a conical shape. Any number of macerator windows through the conical macerator housing or macerator frame may be included (e.g., one, two, three, four, etc.). The rotating cutter may include one or more blades that rotate across the macerator windows of the conical macerator housing. The rotating cutter may be part of a rotating cutter assembly including a cutter blade or blades and a cutter frame or housing. The cutter frame or housing may be configured as a conical shape complementary to the conical macerator housing or macerator frame. As in any of the macerator examples shown above for side-facing and/or distal-facing cutters, the blades may be formed from a wire, from one or more cutter windows through a cutter frame or housing, etc. The cutter assembly (e.g., cutter frame/housing, cutter blades, etc.) may be eccentrically or concentrically coupled to a drive member, such as a drive wire. As in any of the macerators described herein, the cutter blades may be on the inside (e.g., behind the macerator window or crossbar, etc., forming the shearing surface) or outside (e.g., in front of the macerator window or crossbar, etc. forming the shearing surface).

Figure 62:
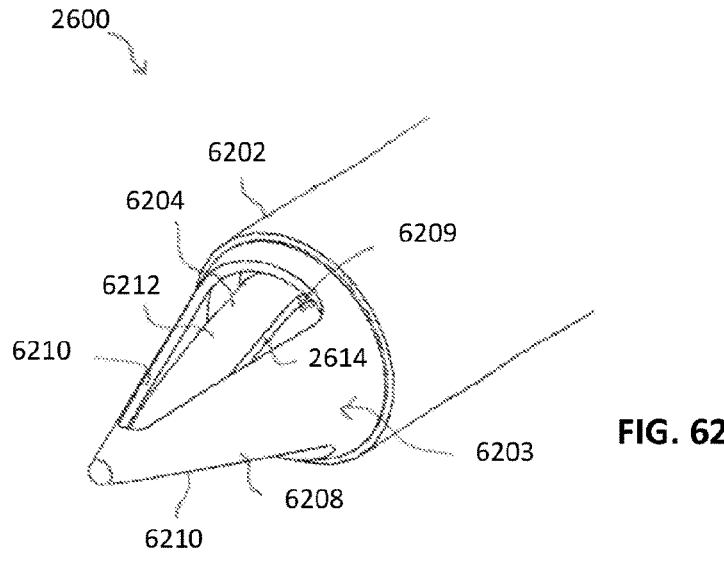
FIG. 62 illustrates another example of a macerator as described herein, including a distal-facing cutter that is conical.

For example, FIG. 62 shows a first example of a conical distal-facing macerator 2600. In FIG. 62, the distal portion of a conical macerator apparatus 2600 includes an elongate housing 6202 forming a suction lumen (which may be optional, in variations that do not include a macerator suction lumen). The elongate body (e.g., supporting element 6202) may be flexible. The conical macerator in FIG. 62 may also include a cutter assembly including a rotatable cutting blade 6204 that may be formed as part of or attached to a cutter frame or housing (not visible in FIG. 62). In the example shown in FIG. 62, the cutter assembly, including the blade, is positioned within the lumen of the macerator frame or macerator housing 6203. The cutter assembly 6212 may include a plurality of cutter blades 6204. In some examples, the cutter assembly including cutter blades 6204 may be rotatably positioned within the macerator housing 6203 and the cutter blades and/or cutter frame or housing may be coupled eccentrically or concentrically to a drive wire (not visible in FIGS. 62, such that the cutter blade(s) 6204 can rotate relative to the macerator frame or macerator housing 6203 causing a shearing force between the shearing surface 6210 of the macerator window 6209 or openings. The cutting blade 6204 may have a sharpened and/or beveled cutting edge 6214.

In any of the macerators described herein, the cutter assembly can be completely removed from the lumen of the elongate body 6202 and/or macerator housing. The In FIG. 62, the macerator 2600 includes a tubular elongate body 6202 that is attached to the conical macerator housing 6203 (macerator frame) and may form a suction lumen therethrough. The macerator housing 6203 at the distal end of the macerator may include plurality of arms 6208 and openings (windows 6209) between the arms. Each of the arms 6208 can extend distally and radially inwardly. The distal macerator housing (macerator frame) 6203 can have other shapes and/or may not taper distally. Each of the arms 6208 can have edges 6210 (e.g., on the macerator openings/macerator windows) which can be blunt or sharpened and may form a shearing surface when the cutter blades are operational.

Figure 63A:
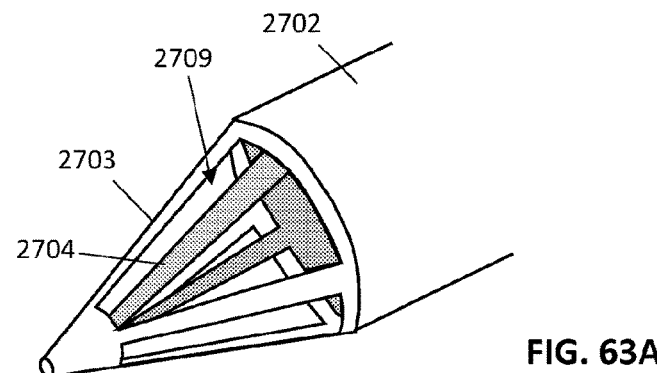
FIGS. 63A-63C illustrate another example of a conical, distal-facing cutter as described herein.
Figures 63B, 63C:
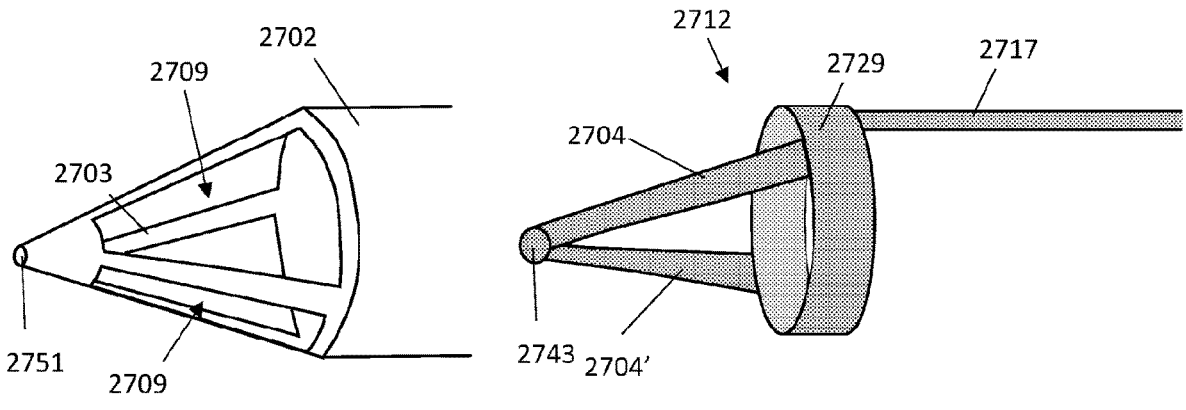

Another example of a conical macerator is shown in FIGS. 63A-63C. FIG. 63A shows an assembled conical macerator including a conical distal-facing macerator housing 2703 configured as a conical macerator frame that has a plurality of openings 2709 (e.g., 4 openings are shown) formed by windows of the macerator frame. In general, the distal facing region may be configured to maximize the opening size(s) of the macerator frame/macerator housing. FIG. 63B shows an isolate view of the macerator frame coupled to a portion of the elongate body 2702 (e.g., forming a suction lumen through which suction may be applied). The distal tip 2751 of the macerator frame may be rounded (as shown) or may be sharp. The macerator apparatus in FIGS. 63A-63C also includes a rotatable cutter assembly 2712, as shown in FIG. 63C. The cutter assembly 2712 in this example may fit into the macerator housing at the distal end of the device and may be configured to rotate relative to the macerator housing, either by concentric attachment to a drive member (e.g., drive wire 2717) or by eccentric attachment to a drive member (e.g., drive wire 2717), as shown in FIG. 63C. The cutter assembly includes a cutter frame 2729 and one or more cutter blades 2704 attached to form a conical shape. The distal end 2743 of the cutter assembly may be configured to rotatably engage with the inside of the distal end of the macerator assembly. As in any of the apparatuses described herein, the cutter assembly may be retained within or coupled to the macerator frame/macerator housing so that it may rotate within a fixed distance from the shearing surface(s) of the macerator housing, such as the macerator window(s).

The conical macerators described herein may include any of the features described above.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An apparatus, the apparatus comprising:

an elongated shaft having a proximal end portion, a distal end portion, and a lumen extending therebetween, wherein the distal end portion of the elongated shaft is configured to expand from a collapsed delivery state to a funnel-shaped expanded state for engaging and capturing an obstructive material, and wherein, at least in the expanded state, an average cross-sectional dimension of the distal end portion of the shaft is greater than the average cross-sectional dimension of the rest of the shaft;

a disrupter configured to extend through the elongate shaft so that a distal end of the disrupter is positioned and rotatable within the expanded funnel-shaped distal end portion of the elongate shaft, wherein the distal end of the disrupter comprises an elongate longitudinal member having a bend or hook that is configured to be prevented from extending distally beyond the distal end of the distal end portion of the shaft, wherein the disrupter is configured to extend through the elongate shaft so that the distal end of the disrupter is positioned and rotatable off-axis within the expanded funnel-shaped distal end portion of the elongate shaft.

2. The apparatus of claim 1, wherein a proximal portion of the elongated shaft is configured to be fluidly coupled to a negative pressure source to apply a suction force through the lumen.

3. The apparatus of claim 1, wherein a maximum cross-sectional dimension of an interior region of the distal end portion is at least two times greater than a cross-sectional dimension of the lumen of the rest of the elongated shaft.

4. The apparatus of claim 1, wherein the disrupter comprises a macerator positioned within an interior capture region.

5. The apparatus of claim 1, further comprising a control configured to apply suction through the lumen of the elongate shaft.

6. The apparatus of claim 1, wherein the disrupter is coupled to a rotatable drive shaft.

7. The apparatus of claim 1, further comprising a guide lumen extending adjacent to the lumen.

8. The apparatus of claim 1, further comprising a distal wall extending across a distal face of the distal end portion and at least partially covering the distal end portion, the distal wall having an aperture extending therethrough wherein the aperture provides exclusive access into an interior capture region from a body lumen into which the apparatus is inserted.

9. The apparatus of claim 1, wherein a distal-facing end of the distal end portion of the shaft is tapered as it extends distally.

10. The apparatus of claim 1, wherein the funnel-shaped distal end region is configured to self-expand radially outwards into a deployed configuration.

11. The apparatus of claim 1, wherein the disrupter comprises an elongate rod extending proximally to distally.

12. An apparatus, the apparatus comprising:

an elongated shaft having a proximal end portion, a distal end portion, and a lumen extending therebetween, wherein the distal end portion of the elongated shaft is configured to expand from a collapsed delivery state to a funnel-shaped expanded state for engaging and capturing an obstructive material, and wherein, at least in the expanded state, an average cross-sectional dimension of the distal end portion of the shaft is greater than the average cross-sectional dimension of the rest of the shaft, wherein the distal end portion is configured to be steered by bending at distal portion proximal to the distal end portion; and a disrupter configured to extend through the elongate shaft so that a distal end of the disrupter is positioned and rotatable off-axis within the expanded funnel-shaped distal end portion of the elongate shaft, wherein the distal end of the disrupter comprises an elongate longitudinal member having a bend or hook that is configured to be prevented from extending distally beyond the distal end portion of the shaft wherein the disrupter comprises a strut comprising the bend or hook at the distal end configured to strip lodged clot off of an inner diameter of the apparatus.

13. The apparatus of claim 1, wherein the disrupter comprises a strut comprising the bend or hook at the distal end configured to strip lodged clot off of an inner diameter of the apparatus.

* * * * *